US011066481B2

(12) United States Patent
Mikita et al.

(10) Patent No.: US 11,066,481 B2
(45) Date of Patent: Jul. 20, 2021

(54) ANTIBODIES TO COAGULATION FACTOR XIA AND USES THEREOF

(71) Applicants: THE REGENTS OF THE UNIVERSITY OF CALIFORNIA, Oakland, CA (US); PFIZER INC., New York, NY (US)

(72) Inventors: Thomas Mikita, Sausalito, CA (US); Lauren K. Ely, Palo Alto, CA (US); Huilan Gao, West Roxbury, MA (US); Yun Kim, Walnut Creek, CA (US); Isaac J. Rondon, San Francisco, CA (US); Tovo David, San Francisco, CA (US); Shaun R. Coughlin, Tiburon, CA (US)

(73) Assignees: The Regents of the University of California, Oakland, CA (US); Pfizer, Inc., New York, NY (US)

( * ) Notice: Subject to any disclaimer, the term of this patent is extended or adjusted under 35 U.S.C. 154(b) by 541 days.

(21) Appl. No.: 15/746,305

(22) PCT Filed: Jul. 22, 2016

(86) PCT No.: PCT/US2016/043703
§ 371 (c)(1),
(2) Date: Jan. 19, 2018

(87) PCT Pub. No.: WO2017/015619
PCT Pub. Date: Jan. 26, 2017

(65) Prior Publication Data
US 2020/0095334 A1  Mar. 26, 2020

Related U.S. Application Data

(60) Provisional application No. 62/196,037, filed on Jul. 23, 2015.

(51) Int. Cl.
*C07K 16/36* (2006.01)

(52) U.S. Cl.
CPC .......... *C07K 16/36* (2013.01); *C07K 2299/00* (2013.01); *C07K 2317/52* (2013.01); *C07K 2317/622* (2013.01); *C07K 2317/76* (2013.01); *C07K 2317/92* (2013.01); *C07K 2319/00* (2013.01)

(58) Field of Classification Search
None
See application file for complete search history.

(56) References Cited

U.S. PATENT DOCUMENTS

| 7,217,794 | B2 | 5/2007 | Abdel-Meguid et al. | |
| 8,236,316 | B2 * | 8/2012 | Gruber | A61P 11/00 424/145.1 |
| 8,388,959 | B2 * | 3/2013 | Gruber | C07K 16/36 424/133.1 |
| 8,568,724 | B2 * | 10/2013 | Hack | C07K 16/36 424/145.1 |
| 8,859,254 | B2 | 10/2014 | Morant | |
| 2003/0235587 | A1 | 12/2003 | Feuerstein | |
| 2005/0143317 | A1 | 6/2005 | Abdel-Meguid et al. | |
| 2005/0181978 | A1 | 8/2005 | Rojkjaer et al. | |
| 2011/0020349 | A1 | 1/2011 | Gruber et al. | |
| 2011/0217284 | A1 | 9/2011 | Seifried et al. | |
| 2014/0194600 | A1 | 7/2014 | Hack et al. | |
| 2014/0275225 | A1 | 9/2014 | Sullenger et al. | |
| 2015/0099298 | A1 | 4/2015 | Jörissen et al. | |

FOREIGN PATENT DOCUMENTS

| WO | 2010080623 A2 | 7/2010 | |
| WO | WO-2013167669 A1 * | 11/2013 | ............ C07K 16/36 |
| WO | 2014075045 A1 | 5/2014 | |
| WO | 2016207858 A1 | 12/2016 | |
| WO | WO-2016207858 A1 * | 12/2016 | ............ A61K 45/06 |
| WO | 2017015558 A1 | 1/2017 | |

OTHER PUBLICATIONS

Janeway et al., Immunobiology, 3rd edition, 1997 Garland Publishing Inc., pp. 3:1-3:11.*
Rudikoff et al., Proc Natl Acad Sci USA. Mar. 1982;79(6):1979-83.*
Edwards et al., J Mol Biol. Nov. 14, 2003;334(1):103-18.*
Lloyd et al., Protein Eng Des Sel. Mar. 2009;22(3):159-68. doi: 10.1093/protein/gzn058. Epub Oct. 29, 2008.*
Goel et al., J Immunol. Dec. 15, 2004;173(12)7358-67.*
Kanyavuz et al., Nat Rev Immunol. Jun. 2019;19(6):355-368. doi: 10.1038/S41577-019-0126-7.*
Sinha et al., J Biol Chem. Sep. 5, 1985;260(19):10714-9.*
PCT/US2016/043555, "International Search Report and Written Opinion", dated Oct. 14, 2016, 9 pages.
PCT/US2016/043703, "International Search Report and Written Opinion", dated Oct. 28, 2016, 10 pages.
The Signal Peptide Database, Accession ID. 7428, 1986, 4 pages.
U.S. Appl. No. 15/746,269, Final Office Action dated Jun. 16, 2020, 23 pages.

(Continued)

*Primary Examiner* — Michael Szperka
(74) *Attorney, Agent, or Firm* — Kilpatrick Townsend & Stockton LLP

(57) ABSTRACT

In one aspect, antibodies, or antigen-binding fragments thereof, that specifically bind to activated Factor XI (FXIa) are provided. Also provided are methods of obtaining such antibodies and nucleic acids encoding the same. In another aspect, compositions and therapeutic prevention of thrombotic diseases, disorders or conditions are provided. In another aspect, anti-idiotype antibodies that bind anti-FXIa antibodies of the disclosure, as well as compositions comprising the anti-idiotype antibodies, methods of obtaining the antibodies and nucleic acids encoding the same, are also provided.

19 Claims, 38 Drawing Sheets

Specification includes a Sequence Listing.

(56) References Cited

OTHER PUBLICATIONS

U.S. Appl. No. 15/746,269, Non-Final Office Action dated Nov. 20, 2019, 26 pages.
De La Lastra et al., Epitope Mapping of 10 Monoclonal Antibodies Against the Pig Analogue of Human Membrane Cofactor Protein (MCP), Immunology, vol. 96, No. 4, XP55572134, Apr. 1, 1999, pp. 663-670.
Depalma, Poly-His Tags Improve Protein Purification, Genetic Engineering and Biotechnology News, Available online: https://www.genengnews.com/insights/poly-his-tags-improve-protein-purification/, Nov. 20, 2019, 7 pages.
European Application No. EP16828607.8, Office Action dated Mar. 20, 2020, 5 pages.
European Application No. EP16828654.0, Office Action dated Jun. 9, 2020, 5 pages.
Gailani et al., Factor XI and Contact Activation as Targets for Antithrombotic Therapy, Journal of Thrombosis and Haemostasis, vol. 13, No. 8, 2015, pp. 1383-1395.
International Application No. PCT/US2016/043555, International Preliminary Report on Patentability dated Feb. 1, 2018, 6 pages.
Su et al., The Role of Factor XIa (FXIa) Catalytic Domain Exosite Residues in Substrate Catalysis and Inhibition by the Kunitz Protease Inhibitor Domain of Protease Nexin 2*, The Journal of Biological Chemistry, vol. 286, No. 36, 2011, pp. 31904-31914.
Aktimur et al., "The Factor IX γ-Carboxyglutamic Acid (Gla) Domain Is Involved in Interactions between Factor IX and Factor XI a", The Journal of Biological Chemistry, vol. 278, No. 10, Mar. 7, 2003, pp. 7981-7987.

Al-Horani et al., "Designing Allosteric Inhibitors of Factor XIa. Lessons from the Interactions of Sulfated Pentagalloylglucopyranosides", Journal of Medicinal Chemistry, vol. 57, No. 11, May 29, 2014, pp. 4805-4818.
David et al., "Factor XIa-Specific Lgg and a Reversal Agent to Probe Fac-tor XI Function in Thrombosis and Hemostasis", Science Translational Medicine, vol. 8, No. 353, Available online at URL:http://stm.sciencemag.orgjcontentjscitransmed/8/353/353ra112.full.pdf, Aug. 24, 2016, vol. 8 Issue 353ra112, pp. 1-15.
Ely et al., "Structural Basis for Activity and Specificity of an Anticoagulant Anti-FXIa Monoclonal Antibody and a Reversal Agent", Structure, vol. 26, No. 2, Feb. 6, 2018, pp. 187-198.e1-e4.
EP16828607.8, "Extended European Search Report", dated Nov. 27, 2018, 10 pages.
EP16828654.0, "Partial Supplementary European Search Report", dated Dec. 17, 2018, 15 pages.
Navaneetham et al., "Structural and Mutational Analyses of the Molecular Interactions between the Catalytic Domain of Factor XIa and the Kunitz Protease Inhibitor Domain of Protease Nexin 2", Journal of Biological Chemistry, vol. 280, No. 43, Aug. 6, 2005, pp. 36165-36175.
Sinha et al., "Functional Characterization of Human Blood Coagulation Factor XIa Using Hybridoma Antibodies", Journal of Biological Chemistry, vol. 260, No. 19, Sep. 5, 1985, pp. 10714-10719.
Van Montfoort et al., "Two Novel Inhibitory Anti-Human Factor XI Antibodies Prevent Cessation of Blood Flow in a Murine Venous Thrombosis Model", Thrombosis and Haemostasis, vol. 110, No. 5, Aug. 8, 2013, pp. 1065-1073.

* cited by examiner

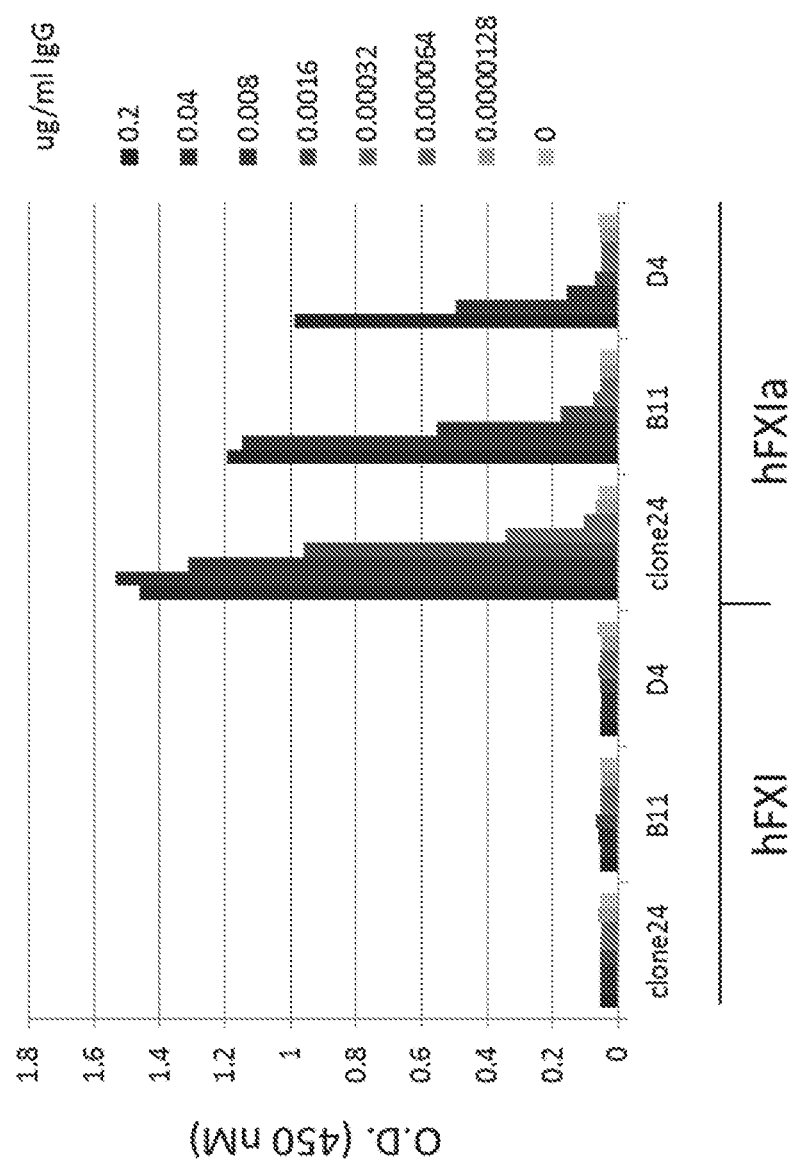

FIG. 4B

| | temperature (°C) | ka (M⁻¹s⁻¹) | kd (s⁻¹) | KD (M) |
|---|---|---|---|---|
| D4 IgG | 25 | 1.28E+05 | 1.18E-04 | 9.30E-10 |
| B11 IgG | 25 | 3.73E+05 | 6.86E-05 | 1.87E-10 |
| C24 Fab | 37 | 2.39E+06 | 3.66E-05 | 1.52E-11 |
| DEF Fab | 37 | 1.60E+06 | 5.38E-05 | 3.39E-11 |

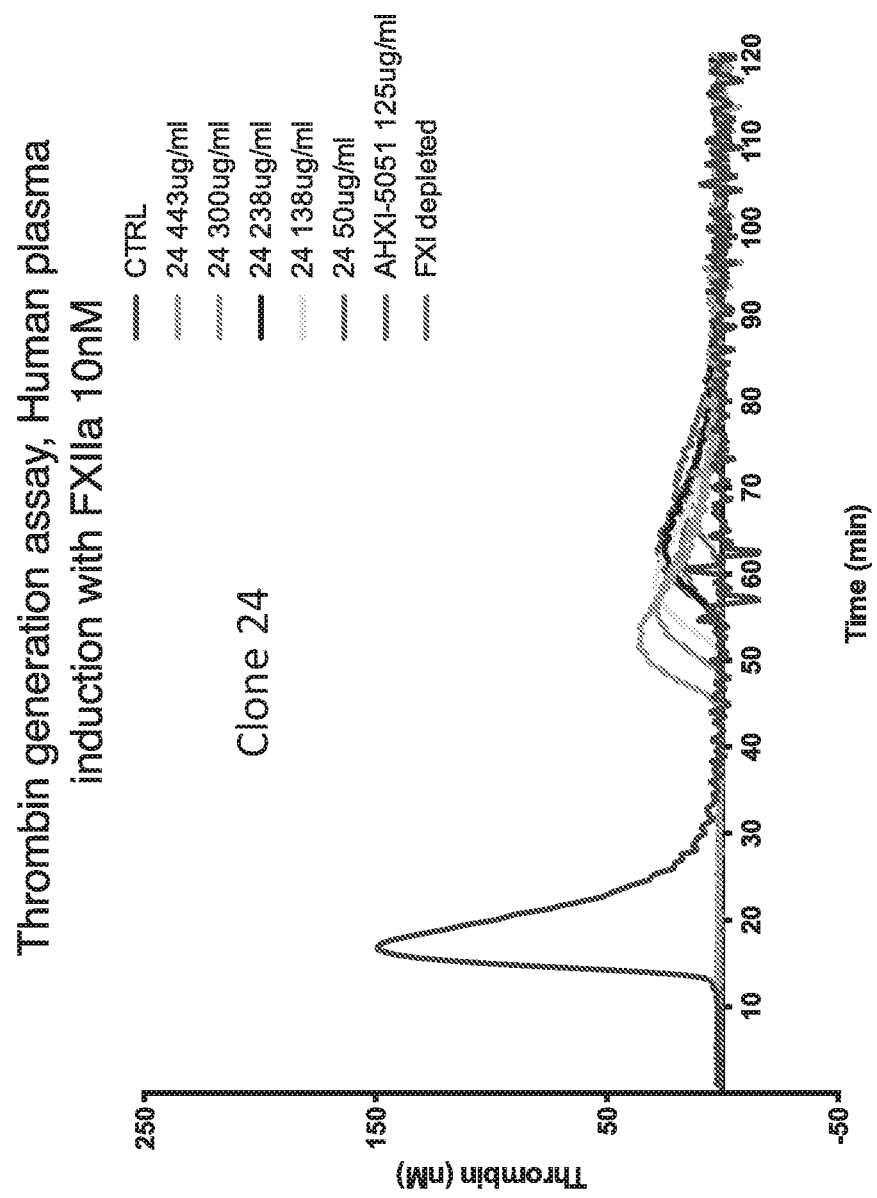

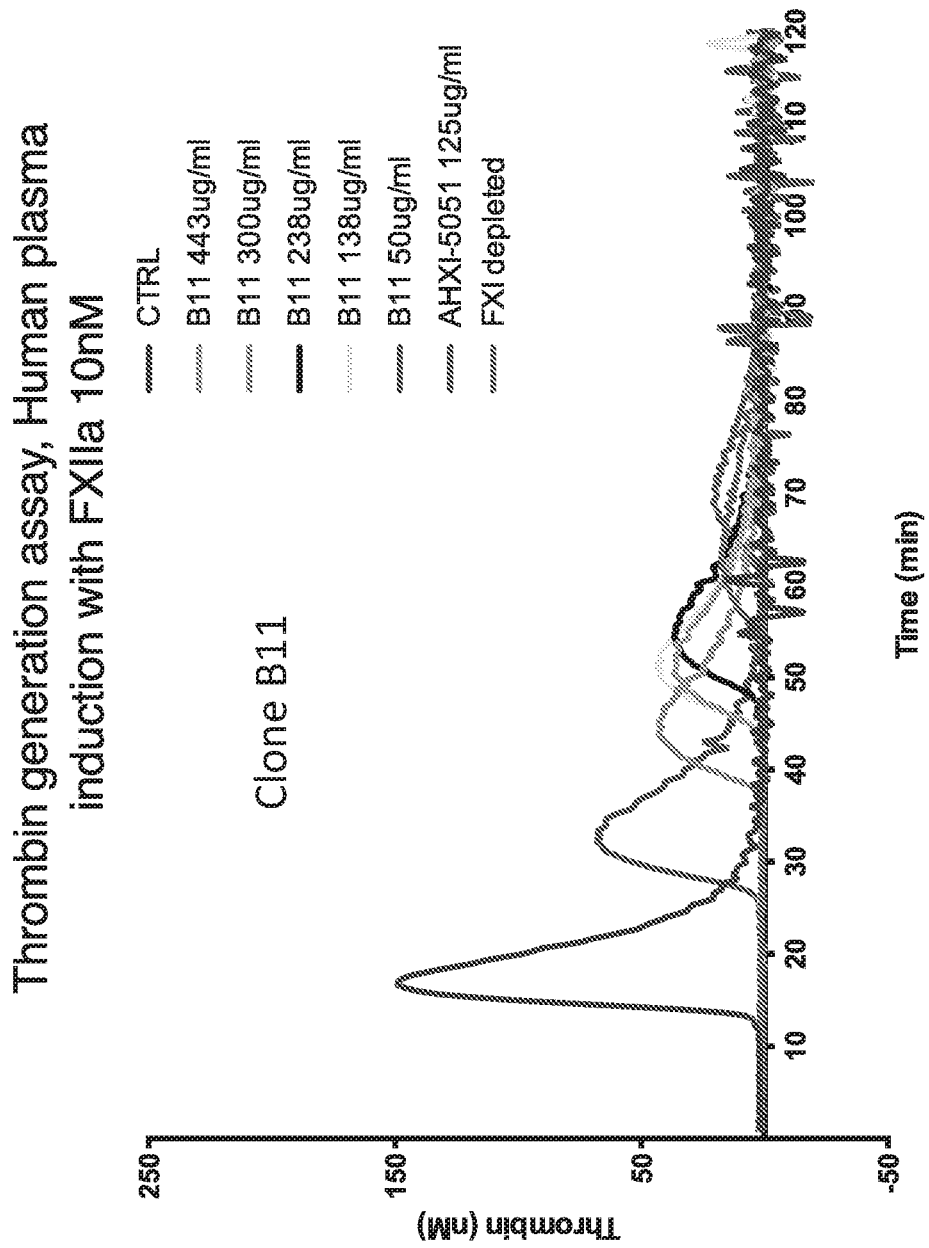

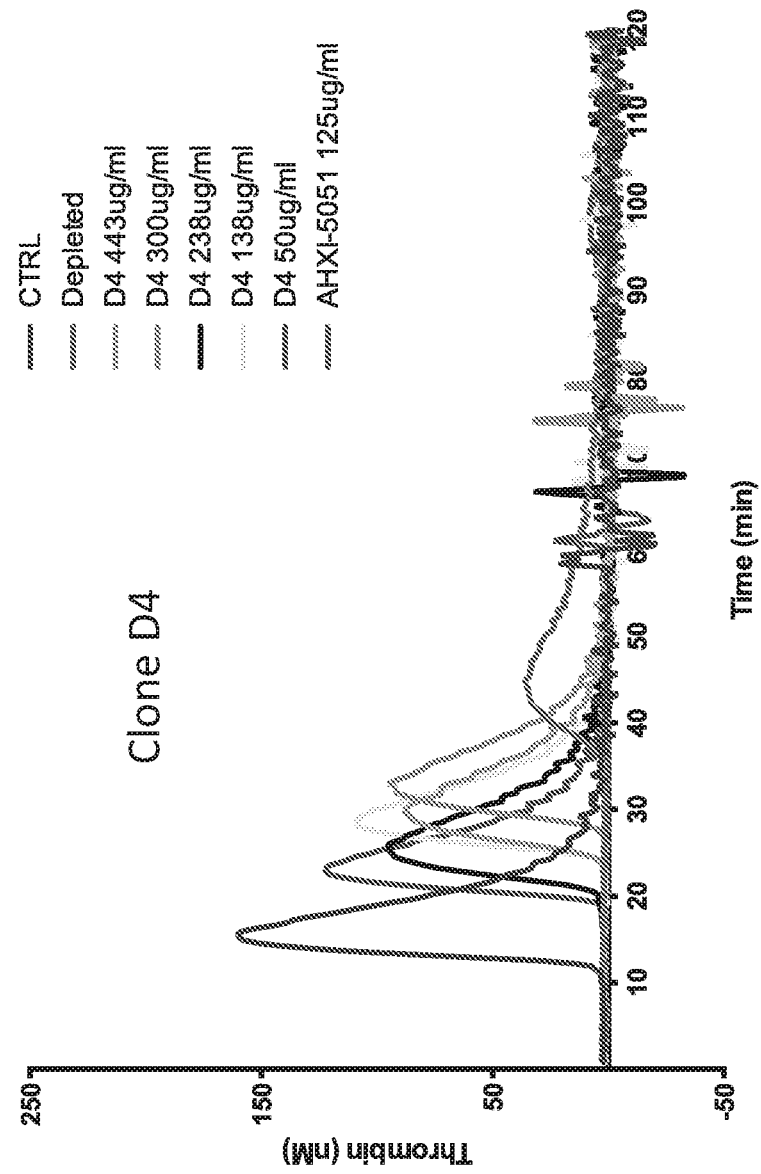

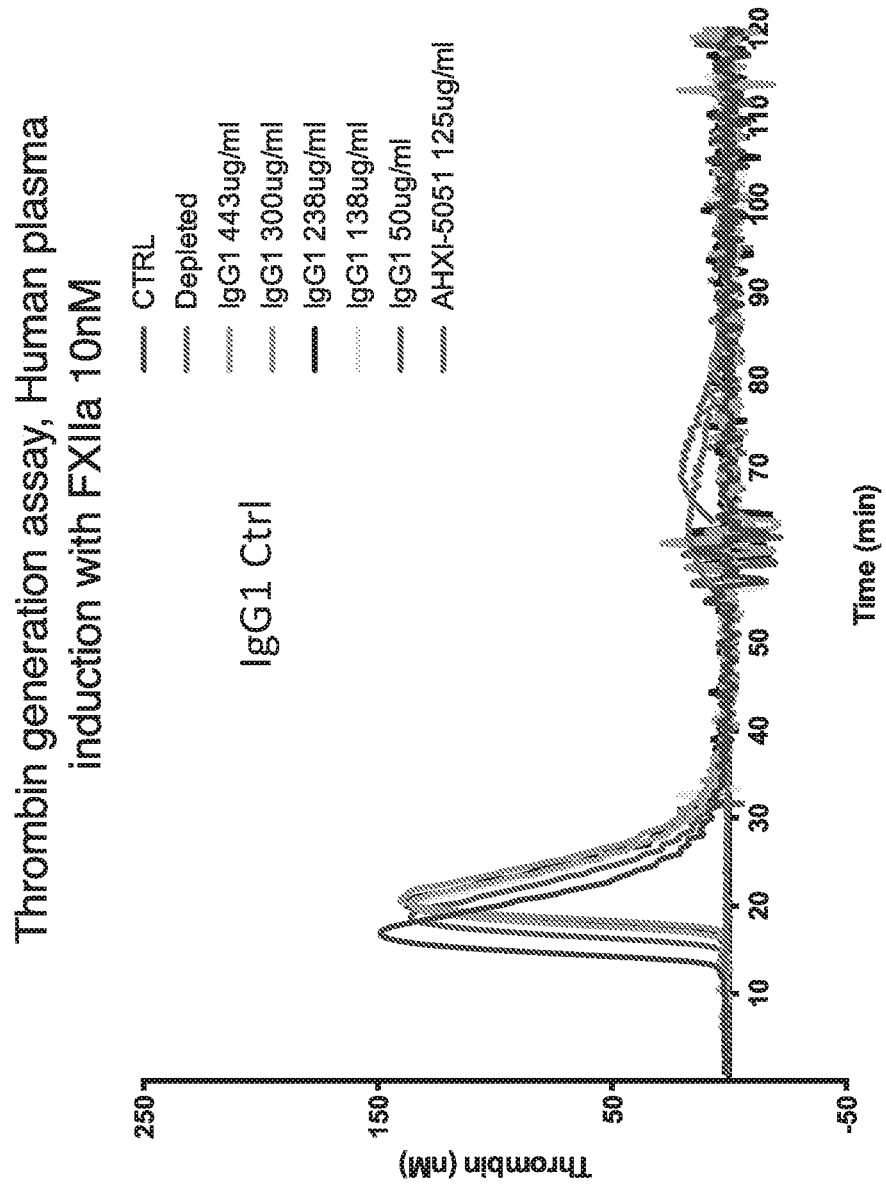

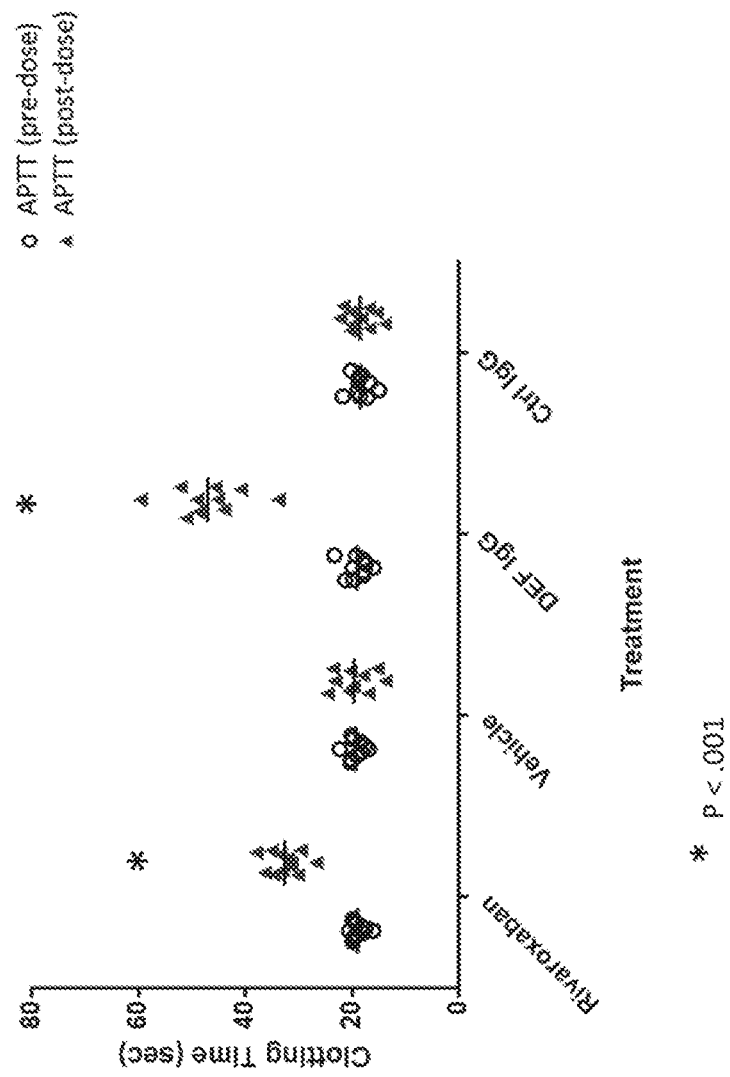

* P < .0001

ANTIBODIES TO COAGULATION FACTOR XIA AND USES THEREOF

CROSS-REFERENCE TO RELATED APPLICATIONS

This application is a U.S. National Phase application under 35 U.S.C. § 371 of International Application No. PCT/US2016/043703, filed Jul. 22, 2016, which claims priority to U.S. Provisional Application No. 62/196,037, filed Jul. 23, 2015, the entire contents of which are incorporated by reference herein.

PARTIES TO A JOINT RESEARCH AGREEMENT

The presently claimed invention was made by or on behalf of the below listed parties to a joint research agreement. The joint research agreement was in effect on or before the date the claimed invention was made and the claimed invention was made as a result of activities undertaken within the scope of the joint research agreement. The parties to the joint research agreement are PFIZER INC, and THE REGENTS OF THE UNIVERSITY OF CALIFORNIA.

REFERENCE TO SUBMISSION OF A SEQUENCE LISTING AS A TEXT FILE

The Sequence Listing written in file 081906-1072797-222210US Sequence Listing.txt created on Jan. 19, 2018, containing 80,444 bytes, machine format IBM-PC, MS-Windows operating system, is hereby incorporated by reference in its entirety for all purposes.

FIELD OF THE INVENTION

The present disclosure relates to antibodies, e.g., full-length antibodies and antigen-binding fragments thereof that specifically bind coagulation Factor XIa (FXIa). The disclosure further relates to compositions comprising antibodies to FXIa, and methods of using the antibodies as a medicament. The FXIa antibodies are useful for, for example, inhibiting the intrinsic pathway of coagulation or increasing clotting time. In addition, the present disclosure relates to anti-idiotype antibodies e.g., full-length antibodies and antigen-binding fragments thereof that specifically bind to the antigen-binding site of an anti-FXIa antibody or antigen-binding portion thereof of the disclosure, compositions comprising such anti-idiotype antibodies, and methods of using such antibodies as a medicament. The anti-idiotype antibodies to anti-FXIa antibodies are useful for, for example, reversing the effects of an anti-FXIa antibody (e.g., decreasing anticoagulant activity or reducing clotting time).

BACKGROUND OF THE INVENTION

Two distinct inputs trigger the coagulation cascade that generates blood clots: (1) the extrinsic pathway comprised of Tissue Factor (TF)/FVIIa and (2) the intrinsic pathway comprised of FXII, FXI and other components. Both feed into a common cascade that triggers conversion of FIX to FIXa, FX to FXa, and prothrombin to thrombin. Thrombin is the effector protease of the cascade that activates platelets and cleaves fibrinogen to generate fibrin. Fibrin actively self-assembles and, in combination with activated platelets, starts formation of a clot (in the context of hemostasis) or thrombus (in the context of thrombosis) (Woodruff, R. S., Sullenger, B., and R. C. Becker. *J. Thromb Thrombolysis.* 2011, 32: 9-20).

The extrinsic pathway is triggered when blood vessels are disrupted and FVII and other coagulation factors in plasma reach tissue factor in the extravascular (or extrinsic) compartment. TF/VIIa cleaves FX to FXa and, as part of an amplification step, FIX to FIXa, which also converts FX to Xa. As above, FXa in turn converts prothrombin to thrombin. All of these extrinsic pathway and common cascade components are necessary for normal hemostasis, and all existing anticoagulants target one or more of these factors.

In contrast to the extrinsic pathway, all of the components of the intrinsic pathway are contained in plasma (i.e., intrinsic to blood). Tissue damage leads to release or exposure of negatively charged surfaces and polymers, which support assembly of intrinsic pathway components and activation of Factor XII to FXIIa. FXIIa in turn converts FXI to FXIa, which connects the intrinsic pathway to the common cascade by activating FIX to FIXa, Thrombin can also convert FXI to FXIa in a positive feedback loop that may be important for thrombus formation in some settings. Unlike the extrinsic and common pathways, the components of the intrinsic pathway are unnecessary for hemostasis.

Recent evidence suggests that intrinsic pathway inhibitors might provide "next generation" anti-thrombotic drugs. Published observations suggest that FXIa inhibition may effect thrombosis while sparing hemostasis. In animal studies, FXI knockout mice show no apparent bleeding defect, yet they are protected against thrombosis in the FeCl3-induced arterial injury model (Wang, X., Cheng, Q., Xu, L., Feuerstain, G. Z., Hsu, M. Y., Smith, P. L., Seiffert, D. A., Schumacher, W. A., Ogletree, M. L., and D. Gailani. *J Thromb Haemost.* 2005: 3 (4): 695-702). Other animal studies have shown that FXI inhibition is protective against thrombosis in non-human primate models, also with minimal increased bleeding events (Crosby J R, Marzec U, Revenko A. S., Zhao C, Gao D, Matafonov A, Gailani D, MacLeod A. R., Tucker E. I., Gruber A, Hanson S. R., and B. P. Monia. *Arterioscler Thromb Vasc Biol.* 2013; 33(7): 1670-8). In the human population, FXI deficiency is known to exist, and while some surgeries are associated with a higher bleeding risk, there is little association with serious spontaneous bleeding in this population (Scligsohn, U. *J. Thromb Haemost.* 2009: 7 suppl. 1: 84-87). In addition, case-controlled studies suggest FXI-deficient humans have less ischemic stroke and venous thromboembolism (VTE), with the converse being true for individuals with elevated FXI (He, R., Chen, D., and H. Shilin. *Thrombosis Research.* 2012; 129: 541-550). A recent Phase 2 trial in humans supports the hypothesis that a FXI antisense molecule may be safe and effective in preventing VTE after total knee replacement (Biller H. R., Bethune C, Bhanot S, Gailani D, Monia B. P., Raskob G. E., Segers A., Verhamme P., Weitz J. I.; FXI-ASO TKA Investigators. *N Engl J Med.* 2015. 15; 372(3):232-40).

Efforts to create selective small molecule inhibitors against FXIa have yet to achieve adequate potency, selectivity, and pharmacokinetics (Schumacher, W. A., Luettgen, J. M., Quan, M. L., and D. A. Seiffert. *Arterioscler Thromb Vasc Biol.* 2010; 30: 388-392). Limitations also exist, from a treatment standpoint, with the FXI antisense inhibitor currently in clinical development as multiple weeks of pre-dosing are required before the treatment becomes effective.

Thus, the current state of need for a high affinity, high potency, high selectivity, and fast acting IgG inhibitor of the coagulation cascade serine protease FXIa is great. Further, there is a great and long-felt need for fast-acting reversal agents for anticoagulants to increase their safety, in this case, an agent to reverse the action of an inhibitor of FXIa.

BRIEF SUMMARY OF THE INVENTION

This application discloses isolated antibodies, or antigen-binding portions thereof, that specifically bind FXIa. This application also discloses isolated anti-idiotype antibodies, or antigen-binding portions thereof, that specifically bind to the antigen-binding site of an anti-FXIa antibody or antigen-binding portion thereof of the disclosure.

In certain aspects, the disclosure relates to an isolated monoclonal antibody, or an antigen-binding portion thereof, that specifically binds the Factor XIa catalytic domain, wherein the antibody or antigen-binding portion thereof has at least one of the following properties:
 (a) prolongs activated partial thromboplastin time (APTT) without significantly increasing prothrombin time (PT);
 (b) has an increased dissociation rate from FXIa in the presence of a serine protease inhibitor;
 (c) has an increased dissociation rate from FXIa after treatment of the latter with an agent that chemically modifies the active site serine of a serine protease (e.g., phenylmethylsulfonyl fluoride (PMSF)); and
 (d) binds to, and has its anticoagulant activity decreased by, a recombinant FXIa protease-domain in which the active site serine is changed to alanine.

In some embodiments, the antibody or antigen-binding portion thereof has properties (a) and (b). In some embodiments, the antibody or antigen-binding portion thereof has properties (a) and (c). In some embodiments, the antibody or antigen-binding portion thereof has properties (a) and (d). In some embodiments, the antibody or antigen-binding portion thereof has properties (b) and (c). In some embodiments, the antibody or antigen-binding portion thereof has properties (b) and (d). In some embodiments, the antibody or antigen-binding portion thereof has properties (c) and (d). In some embodiments, the antibody or antigen-binding portion thereof has properties (a), (b), and (c). In some embodiments, the antibody or antigen-binding portion thereof has properties (a), (b), and (d). In some embodiments, the antibody or antigen-binding portion thereof has properties (a), (c), and (d). In some embodiments, the antibody or antigen-binding portion thereof has properties (b), (c), and (d). In some embodiments, the antibody or antigen-binding portion thereof has properties (a), (b), (c), and (d).

In certain aspects, the disclosure relates to an isolated monoclonal antibody, or an antigen-binding portion thereof, that specifically binds Factor XIa, where the antibody comprises: a) a heavy chain (H) complementarity region (CDR) 1 comprising the amino acid sequence of SEQ ID NO: 2 or 5; b) an HCDR2 comprising the amino acid sequence of SEQ ID NO: 3, 6, 94 or 95; c) an HCDR3 comprising the amino acid sequence of SEQ ID NO: 4; d) a light chain (L) CDR1 comprising the amino acid sequence of SEQ ID NO: 8, 11, 32, or 33; e) an LCDR2 comprising the amino acid sequence of SEQ ID NO: 9 or 12; and/or f) an LCDR3 comprising the amino acid sequence of SEQ ID NO: 10 or 13.

In certain aspects, the disclosure relates to an isolated monoclonal antibody, or an antigen-binding portion thereof, that specifically binds Factor XIa, wherein the antibody, or antigen-binding portion thereof, comprises HCDR1-3 and LCDR1-3 comprising the amino acid sequences of:
 a) SEQ ID NOs: 2, 3, 4, 8, 9, and 10, respectively;
 b) SEQ ID NOs: 5, 6, 4, 11, 12, and 13, respectively;
 c) SEQ ID NOs: 2, 94, 4, 8, 9, and 10, respectively;
 d) SEQ ID NOs: 5, 95, 4, 11, 12, and 13, respectively;
 e) SEQ ID NOs: 2, 15, 4, 8, 9, and 10, respectively;
 f) SEQ ID NOs: 5, 16, 4, 11, 12, and 13, respectively;
 g) SEQ ID NOs: 2, 66, 4, 8, 9, and 10, respectively; or
 h) SEQ ID NOs: 5, 67, 4, 11, 12, and 13, respectively.

In certain aspects, the disclosure relates to an isolated monoclonal antibody, or an antigen-binding portion thereof, that specifically binds Factor XIa, wherein the antibody comprises: a heavy chain variable domain (VH) comprising the amino acid sequence of SEQ ID NO: 1 and/or a light chain variable domain (VL) comprising the amino acid sequence of SEQ ID NO: 7.

In certain aspects, the disclosure relates to an isolated monoclonal antibody, or an antigen-binding portion thereof, that specifically binds Factor XIa, wherein the antibody comprises: a heavy chain variable domain (VH) comprising the amino acid sequence of SEQ ID NO: 65 and/or a light chain variable domain (VL) comprising the amino acid sequence of SEQ ID NO: 68.

In certain aspects, the disclosure relates to an isolated monoclonal antibody, or an antigen-binding portion thereof, that specifically binds Factor XIa, wherein the antibody comprises: a heavy chain variable domain (VH) comprising the amino acid sequence of SEQ ID NO: 14 and/or a light chain variable domain (VL) comprising the amino acid sequence of SEQ ID NO: 17.

In certain aspects, the disclosure relates to an isolated monoclonal antibody, or antigen-binding portion thereof, that specifically binds Factor XIa, wherein the antibody comprises:
 a) a heavy chain variable domain (VH) sequence comprising the amino acid sequence of SEQ ID NOs: 1, 14, 18, 22, 24, 26, 28, 34, 38, 40, 43, 47, 51, 55, 59, 63, 65, or 96; and/or
 b) a light chain variable domain (VL) sequence comprising the amino acid sequence of SEQ ID NOs: 7, 17, 21, 23, 27, 31, 37, 39, 42, 46, 50, 54, 58, 62, 64, 68, or 97.

In certain aspects, the disclosure relates to an isolated monoclonal antibody, or an antigen-binding portion thereof, that specifically binds Factor XIa, wherein the antibody comprises a heavy chain variable domain and a light chain variable domain comprising the following amino acid sequences, respectively:
 SEQ ID NOs: 18 and 21,
 SEQ ID NOs: 22 and 23,
 SEQ ID NOs: 24 and 25,
 SEQ ID NOs: 26 and 27,
 SEQ ID NOs: 28 and 31,
 SEQ ID NOs: 34 and 37,
 SEQ ID NOs: 38 and 39,
 SEQ ID NOs: 40 and 42,
 SEQ ID NOs: 43 and 46,
 SEQ ID NOs: 47 and 50,
 SEQ ID NOs: 51 and 54,
 SEQ ID NOs: 55 and 58,
 SEQ ID NOs: 59 and 62, or
 SEQ ID NOs: 63 and 64.

In certain aspects, the disclosure relates to an isolated monoclonal antibody, or an antigen-binding portion thereof, that specifically binds Factor XIa, wherein the antibody is chimeric, humanized, or human. In some embodiments, the isolated monoclonal antibody, or an antigen-binding portion thereof, that specifically binds Factor XIa comprises a human IgG heavy chain constant region. In some embodiments, the isolated monoclonal antibody, or an antigen-binding portion thereof, that specifically binds Factor XIa comprises a human IgG$_1$ heavy chain constant region.

In certain aspects, the disclosure relates to an isolated monoclonal antibody, or an antigen-binding portion thereof, that specifically binds Factor XIa, comprises a heavy chain constant domain comprising the amino acid sequence of SEQ ID NO:82 or SEQ ID NO: 103 and/or a light chain constant domain comprising the amino acid sequence of SEQ ID NO:83.

In certain aspects, the disclosure relates to an isolated monoclonal antibody, or an antigen-binding portion thereof, that specifically binds Factor XIa, wherein the antibody comprises: a heavy chain variable domain (VH) comprising the amino acid sequence encoded by the cDNA insert of the plasmid deposited under ATCC accession number PTA-122090 and/or a light chain variable domain (VL) comprising the amino acid sequence encoded by the cDNA insert of the plasmid deposited under ATCC accession number PTA-122091.

In certain aspects, the disclosure relates to an isolated monoclonal antibody that competes for binding to FXIa and/or binds the same epitope as an isolated monoclonal antibody, or an antigen-binding portion thereof, that specifically binds Factor XIa.

In certain aspects, the disclosure relates to an isolated monoclonal antibody, or an antigen-binding portion thereof, that specifically binds Factor XIa, wherein the dissociation rate of the antibody, or antigen-binding portion thereof, from FXIa is increased in the presence of a serine protease inhibitor. In some embodiments, the serine protease inhibitor is PMSF (phenylmethylsulfonyl fluoride).

In certain aspects, the disclosure relates to an isolated monoclonal antibody, or an antigen-binding portion thereof, that specifically binds Factor XIa, wherein the antibody, or antigen-binding portion thereof, prolongs activated partial thromboplastin time (APTT). In some embodiments, the antibody, or antigen-binding portion thereof, does not increase prothrombin time (PT).

In certain aspects, the disclosure relates to an isolated monoclonal antibody that binds an antibody variable region formed by SEQ ID NO: 69 and SEQ ID NO: 75.

In certain aspects, the disclosure relates to an isolated nucleic acid molecule comprising a nucleotide sequence encoding a monoclonal antibody, or an antigen-binding portion thereof, that specifically binds Factor XIa.

In certain aspects, the disclosure relates to an isolated nucleic acid molecule comprising a nucleotide sequence encoding an antibody, or an antigen-binding portion thereof, that specifically binds to Factor XIa, wherein the nucleic acid molecule comprises:
 a) the nucleotide sequence of SEQ ID NO: 84, 86, or 88;
 b) the nucleotide sequence of SEQ ID NO: 85, 87, or 89; or
 c) both a) and b).

In certain aspects, the disclosure relates to a vector comprising an isolated nucleic acid molecule comprising a nucleotide sequence encoding a monoclonal antibody, or an antigen-binding portion thereof, that specifically binds Factor XIa.

In certain aspects, the disclosure relates to a vector comprising an isolated nucleic acid molecule comprising a nucleotide sequence encoding an antibody, or an antigen-binding portion thereof, that specifically binds to Factor XIa, wherein the nucleic acid molecule comprises:
 a) the nucleotide sequence of SEQ ID NO: 84, 86, or 88;
 b) the nucleotide sequence of SEQ ID NO: 85, 87, or 89; or
 c) both a) and b).

In certain aspects, the disclosure relates to an isolated host cell comprising a vector comprising an isolated nucleic acid molecule comprising a nucleotide sequence encoding a monoclonal antibody, or an antigen-binding portion thereof, that specifically binds Factor XIa.

In certain aspects, the disclosure relates to an isolated host cell comprising a vector comprising an isolated nucleic acid molecule comprising a nucleotide sequence encoding an antibody, or an antigen-binding portion thereof, that specifically binds to Factor XIa, wherein the nucleic acid molecule comprises:
 a) the nucleotide sequence of SEQ ID NO: 84, 86, or 88;
 b) the nucleotide sequence of SEQ ID NO: 85, 87, or 89; or
 c) both a) and b).

In certain aspects, the disclosure relates to an isolated host cell that produces an antibody, or an antigen-binding portion thereof, that specifically binds to Factor XIa.

In certain aspects, the disclosure relates to a method of producing an antibody or antigen-binding portion thereof, comprising culturing a host cell comprising a vector comprising an isolated nucleic acid molecule comprising a nucleotide sequence encoding a monoclonal antibody, or an antigen-binding portion thereof, that specifically binds Factor XIa, under conditions that result in production of the antibody, and isolating the antibody, or antigen-binding portion thereof, from the host cell or culture.

In certain aspects, the disclosure relates to a method of producing an antibody or antigen-binding portion thereof, comprising culturing a host cell comprising a vector comprising an isolated nucleic acid molecule comprising a nucleotide sequence encoding an antibody, or an antigen-binding portion thereof, that specifically binds to Factor XIa, wherein the nucleic acid molecule comprises:
 a) the nucleotide sequence of SEQ ID NO: 84, 86, or 88;
 b) the nucleotide sequence of SEQ ID NO: 85, 87, or 89; or
 c) both a) and b),
under conditions that result in production of the antibody, and isolating the antibody, or antigen-binding portion thereof, from the host cell or culture.

In certain aspects, the disclosure relates to a method of producing an antibody or antigen-binding portion thereof, comprising culturing a host cell that produces an antibody, or an antigen-binding portion thereof, that specifically binds to Factor XIa under conditions that result in production of the antibody, and isolating the antibody, or antigen-binding portion thereof, from the host cell or culture.

In certain aspects, the disclosure relates to a method for inhibiting the intrinsic pathway of coagulation in a subject, comprising administering to said subject an antibody, or an antigen-binding portion thereof, that specifically binds to Factor XIa.

In certain aspects, the disclosure relates to a method for increasing clotting time in a subject, comprising administering to said subject an antibody, or an antigen-binding portion thereof, that specifically binds to Factor XIa, wherein the clotting time is increased compared to the clotting time in the subject prior to administration of the antibody, or antigen-binding portion thereof.

In certain aspects, the disclosure relates to an antibody, or an antigen-binding portion thereof, that specifically binds to Factor XIa for use in inhibiting the intrinsic pathway of coagulation in a subject.

In certain aspects, the disclosure relates to an antibody, or an antigen-binding portion thereof, that specifically binds to Factor XIa for use in increasing clotting time in a subject.

In certain aspects, the disclosure relates to use of an isolated antibody, or an antigen-binding portion thereof, that specifically binds to Factor XIa in the manufacture of a medicament for inhibiting the intrinsic pathway of coagulation in a subject.

In certain aspects, the disclosure relates to use of an isolated antibody, or an antigen-binding portion thereof, that specifically binds to Factor XIa in the manufacture of a medicament for increasing clotting time in a subject.

In certain aspects, the disclosure relates to a pharmaceutical composition comprising an isolated antibody, or an antigen-binding portion thereof, that specifically binds to Factor XIa, and a pharmaceutically acceptable excipient.

In certain aspects, the disclosure relates to an isolated monoclonal antibody, or an antigen-binding portion thereof, that specifically binds to the antigen-binding site of an anti-Factor XIa antibody, or antigen-binding portion thereof, that specifically binds to Factor XIa, wherein the antibody comprises: a) an HCDR1 comprising the amino acid sequence of SEQ ID NO: 70 or 73; b) an HCDR2 comprising the amino acid sequence of SEQ ID NO: 71 or 74; c) an HCDR3 comprising the amino acid sequence of SEQ ID NO: 72; d) an LCDR1 comprising the amino acid sequence of SEQ ID NO: 76 or 79; e) an LCDR2 comprising the amino acid sequence of SEQ ID NO: 77 or 80; and/or f) an LCDR3 comprising the amino acid sequence of SEQ ID NO: 78 or 81, 37. In some embodiments, the monoclonal antibody comprises: a heavy chain variable domain (VH) comprising the amino acid sequence of SEQ ID NO: 69 and/or a light chain variable domain (VL) comprising the amino acid sequence of SEQ ID NO: 75. In some embodiments, the isolated monoclonal antibody, or an antigen-binding portion thereof, that specifically binds to the antigen-binding site of an anti-Factor XIa antibody, or antigen-binding portion thereof, that specifically binds to Factor XIa is chimeric, humanized, or human. In some embodiments, the isolated monoclonal antibody, or an antigen-binding portion thereof, that specifically binds to the antigen-binding site of an anti-Factor XIa antibody, or antigen-binding portion thereof, that specifically binds to Factor XIa comprises a human IgG heavy chain constant region. In some embodiments, the isolated monoclonal antibody, or an antigen-binding portion thereof, that specifically binds to the antigen-binding site of an anti-Factor XIa antibody, or antigen-binding portion thereof, that specifically binds to Factor XIa comprises a human $IgG_1$, heavy chain constant region.

In certain aspects, the disclosure relates to an isolated monoclonal antibody, or an antigen-binding portion thereof, that specifically binds to the antigen-binding site of an anti-Factor XIa antibody, or antigen-binding portion thereof, that specifically binds to Factor XIa, wherein the antibody comprises three HCDR sequences from the heavy chain variable domain (VH) comprising the amino acid sequence of SEQ ID NO: 69 and/or three LCDR sequences from a light chain variable domain (VL) comprising the amino acid sequence of SEQ ID NO: 75. In some embodiments, the antibody, or antigen-binding portion thereof, comprises HCDR1-3 and LCDR1-3 comprising the amino acid sequences of SEQ ID NOs: 70, 71, 72, 76, 77 and 78, respectively. In some embodiments, the antibody or antigen-binding portion comprises HCDR1-3 and LCDR1-3 comprising the amino acid sequences of SEQ ID NOs: 73, 74, 72, 79, 80 and 81, respectively. In some embodiments, the isolated monoclonal antibody, or an antigen-binding portion thereof, that specifically binds to the antigen-binding site of an anti-Factor XIa antibody, or antigen-binding portion thereof, that specifically binds to Factor XIa is chimeric, humanized, or human. In some embodiments, the isolated monoclonal antibody, or an antigen-binding portion thereof, that specifically binds to the antigen-binding site of an anti-Factor XIa antibody, or antigen-binding portion thereof, that specifically binds to Factor XIa comprises a human IgG heavy chain constant region. In some embodiments, the isolated monoclonal antibody, or an antigen-binding portion thereof, that specifically binds to the antigen-binding site of an anti-Factor XIa antibody, or antigen-binding portion thereof, that specifically binds to Factor XIa comprises a human $IgG_1$ heavy chain constant region.

In certain aspects, the disclosure relates to an isolated monoclonal antibody, or an antigen-binding portion thereof, that specifically binds to the antigen-binding site of an anti-Factor XIa antibody, or antigen-binding portion thereof, that specifically binds to Factor XIa, wherein the antibody comprises a heavy chain constant domain comprising the amino acid sequence of SEQ ID NO: 82 and/or a light chain constant domain comprising the amino acid sequence of SEQ ID NO: 83.

In certain aspects, the disclosure relates to an isolated monoclonal antibody that competes for binding to FXIa and/or binds the same epitope as an isolated monoclonal antibody, or an antigen-binding portion thereof, that specifically binds to the antigen-binding site of an anti-Factor XIa antibody, or antigen-binding portion thereof, that specifically binds to Factor XIa.

In certain aspects, the disclosure relates to an isolated nucleic acid molecule comprising a nucleotide sequence encoding an isolated monoclonal antibody, or an antigen-binding portion thereof, that specifically binds to the antigen-binding site of an anti-Factor XIa antibody or antigen-binding portion thereof that specifically binds to Factor XIa.

In certain aspects, the disclosure relates to an isolated nucleic acid molecule comprising a nucleotide sequence encoding an antibody, or an antigen-binding portion thereof, that specifically binds to an antigen-binding site of an anti-Factor XIa antibody, or antigen-binding portion thereof, that specifically binds to Factor XIa, wherein the nucleic acid molecule comprises:
  a) the nucleotide sequence of SEQ ID NO: 90;
  b) the nucleotide sequence of SEQ ID NO: 91; or
  c) both a) and b).

In certain aspects, the disclosure relates to a vector comprising an isolated nucleic acid molecule comprising a nucleotide sequence encoding an isolated monoclonal antibody, or an antigen-binding portion thereof, that specifically binds to the antigen-binding site of an anti-Factor XIa antibody, or antigen-binding portion thereof, that specifically binds to Factor XIa.

In certain aspects, the disclosure relates to a vector comprising an isolated nucleic acid molecule comprising a nucleotide sequence encoding an antibody, or an antigen-binding portion thereof, that specifically binds to an antigen-binding site of an anti-Factor XIa antibody, or antigen-binding portion thereof, that specifically binds to Factor XIa, wherein the nucleic acid molecule comprises:
  a) the nucleotide sequence of SEQ ID NO: 90;
  b) the nucleotide sequence of SEQ ID NO: 91; or
  c) both a) and b).

In certain aspects, the disclosure relates to a host cell comprising a vector comprising an isolated nucleic acid molecule comprising a nucleotide sequence encoding an isolated monoclonal antibody, or an antigen-binding portion thereof, that specifically binds to the antigen-binding site of an anti-Factor XIa antibody, or antigen-binding portion thereof, that specifically binds to Factor XIa.

In certain aspects, the disclosure relates to a host cell comprising a vector comprising an isolated nucleic acid molecule comprising a nucleotide sequence encoding an antibody, or an antigen-binding portion thereof, that specifically binds to an antigen-binding site of an anti-Factor XIa antibody, or antigen-binding portion thereof, that specifically binds to Factor XIa, wherein the nucleic acid molecule comprises:

a) the nucleotide sequence of SEQ ID NO: 90;

b) the nucleotide sequence of SEQ ID NO: 91; or c) both a) and b).

In certain aspects, the disclosure relates to an isolated host cell that produces a monoclonal antibody, or an antigen-binding portion thereof, that specifically binds to the antigen-binding site of an anti-Factor XIa antibody, or antigen-binding portion thereof, that specifically binds to Factor XIa.

In certain aspects, the disclosure relates to a method of producing an antibody, or antigen-binding portion thereof, comprising culturing a host cell comprising a vector comprising an isolated nucleic acid molecule comprising a nucleotide sequence encoding an isolated monoclonal antibody, or an antigen-binding portion thereof, that specifically binds to the antigen-binding site of an anti-Factor XIa antibody, or antigen-binding portion thereof, that specifically binds to Factor XIa, under conditions that result in production of the antibody, and isolating the antibody or antigen-binding portion thereof from the host cell or culture.

In certain aspects, the disclosure relates to a method of producing an antibody, or antigen-binding portion thereof, comprising culturing a host cell comprising a vector comprising an isolated nucleic acid molecule comprising a nucleotide sequence encoding an antibody, or an antigen-binding portion thereof, that specifically binds to an antigen-binding site of an anti-Factor XIa antibody, or antigen-binding portion thereof, that specifically binds to Factor XIa, wherein the nucleic acid molecule comprises:

a) the nucleotide sequence of SEQ ID NO: 90;

b) the nucleotide sequence of SEQ ID NO: 91; or c) both a) and b), under conditions that result in production of the antibody, and isolating the antibody or antigen-binding portion thereof from the host cell or culture.

In certain aspects, the disclosure relates to a method of producing an antibody or antigen-binding portion thereof, comprising culturing a host cell that produces a monoclonal antibody, or an antigen-binding portion thereof, that specifically binds to the antigen-binding site of an anti-Factor XIa antibody, or antigen-binding portion thereof, that specifically binds to Factor XIa, under conditions that result in production of the antibody, and isolating the antibody or antigen-binding portion thereof from the host cell or culture.

In certain aspects, the disclosure relates to a method for decreasing anticoagulant activity in a subject being administered a first antibody or antigen-binding portion thereof, wherein said first antibody, or an antigen-binding portion thereof, specifically binds to Factor XIa, comprising administering to said subject a second antibody or antigen-binding portion thereof, wherein said second antibody, or an antigen-binding portion thereof, specifically binds to the antigen-binding site of an anti-Factor XIa antibody, or antigen-binding portion thereof, that specifically binds to Factor XIa, wherein the anticoagulant activity is reduced compared with the anticoagulant activity in the subject prior to administration of the second antibody or antigen-binding portion thereof.

In certain aspects, the disclosure relates to a method for reducing clotting time in a subject being administered a first antibody or antigen-binding portion thereof, wherein said first antibody, or an antigen-binding portion thereof, specifically binds to Factor XIa, comprising administering to said subject a second antibody or antigen-binding portion thereof, wherein said second antibody, or an antigen-binding portion thereof, specifically binds to the antigen-binding site of an anti-Factor XIa antibody, or antigen-binding portion thereof, that specifically binds to Factor XIa, wherein the clotting time is reduced compared with the clotting time in the subject prior to administration of the second antibody or antigen-binding portion thereof.

In certain aspects, the disclosure relates to an antibody or antigen-binding portion thereof, wherein said antibody, or an antigen-binding portion thereof, specifically binds to the antigen-binding site of an anti-Factor XIa antibody, or antigen-binding portion thereof, that specifically binds to Factor XIa, for use in decreasing anticoagulant activity in a subject being administered a first antibody or antigen-binding portion, wherein said first antibody, or an antigen-binding portion thereof, specifically binds to Factor XIa, wherein the anticoagulant activity is reduced compared with the anticoagulant activity in the subject prior to administration of the antibody or antigen-binding portion thereof.

In certain aspects, the disclosure relates to an isolated antibody or antigen-binding portion thereof, wherein said antibody, or an antigen-binding portion thereof, specifically binds to the antigen-binding site of an anti-Factor XIa antibody, or antigen-binding portion thereof, that specifically binds to Factor XIa, for use in reducing clotting time in a subject being administered a first antibody or antigen-binding portion thereof, wherein said first antibody, or an antigen-binding portion thereof, specifically binds to Factor XIa, wherein the clotting time is reduced compared with the clotting time in the subject prior to administration of the antibody or antigen-binding portion thereof.

In certain aspects, the disclosure relates to use of an isolated antibody or antigen-binding portion thereof, wherein said antibody, or an antigen-binding portion thereof, specifically binds to the antigen-binding site of an anti-Factor XIa antibody, or antigen-binding portion thereof, that specifically binds to Factor XIa, in the manufacture of a medicament for use in decreasing anticoagulant activity in a subject being administered a first antibody or antigen-binding portion thereof, wherein said first antibody, or an antigen-binding portion thereof, specifically binds to Factor XIa, wherein the anticoagulant activity is reduced compared with the anticoagulant activity in the subject prior to administration of the antibody or antigen-binding portion thereof.

In certain aspects, the disclosure relates to use of an isolated antibody or antigen-binding portion thereof, wherein said antibody, or an antigen-binding portion thereof, specifically binds to the antigen-binding site of an anti-Factor XIa antibody, or antigen-binding portion thereof, that specifically binds to Factor XIa, in the manufacture of a medicament for use in reducing clotting time in a subject being administered a first antibody or antigen-binding portion thereof, wherein said first antibody, or an antigen-binding portion thereof, specifically binds to Factor XIa, wherein the clotting time is reduced compared with the clotting time in the subject prior to administration of the antibody or antigen-binding portion thereof.

In certain aspects, the disclosure relates to a pharmaceutical composition comprising an isolated antibody or antigen-binding portion, wherein said antibody, or an antigen-binding portion thereof, specifically binds to the antigen-binding site of an anti-Factor XIa antibody, or antigen-binding portion thereof, that specifically binds to Factor XIa, and a pharmaceutically acceptable excipient.

BRIEF DESCRIPTION OF THE DRAWINGS

The foregoing summary, as well as the following detailed description of the invention, will be better understood when read in conjunction with the appended drawings. For the purpose of illustrating the invention there are shown in the drawings embodiment(s). It should be understood, however, that the invention is not limited to the precise arrangements and instrumentalities shown.

FIG. 1A and

FIG. 1B depict the binding response of positive scFv clones, after reformatting to IgG, to human FXIa (A) and cynomolgus (B) FXIa. FIG. 1C and FIG. 1D depict the human (C) and cynomolgus (D) FXIa inhibitory activity of the positive scFV clones, after reformatting to IgG, as measured by half-maximal inhibitory concentration ($IC_{50}$) values.

FIG. 3A-3D depict the generation of improved versions of the D4 anti-FXIa mAb as determined by selective binding to and activity against FXIa. FIG. 3A shows the binding of D4 variants to hFXI and hFXIa. FIG. 3B-3D show the inhibitory activity of D4 and its variants clone 24, DEF, and 24F, against human FXIa (B), cynomolgus FXIa (C), and rabbit FXIa (D), as measured by $IC_{50}$ values.

FIG. 4A-4B show the FXIa affinity and binding kinetics for selected mAbs and Fabs. FIG. 4A shows the binding response versus time for D4 IgG, B11 IgG, clone 24 ("C24") Fab and DEF Fab over a series of antibody/Fab concentrations. FIG. 4B summarizes the kinetic rate constant data.

FIG. 6A-6F depict the dose-dependent inhibition of thrombin generation by anti-FXIa mAbs in a human plasma assay. FXIIa was used to trigger the activation of FXI to FXIa to drive the overall coagulation cascade downstream to the final step of thrombin activation. FIGS. 6A-6D depict the results of the thrombin generation assay for clone 24 (A), clone B 1 (B), clone D4 (C), and IgG1 control (D). FIGS. 6E and 6F depict the decreases in peak thrombin activity (E) and lag time to peak thrombin activity (F).

FIG. 10A-10C show the effects of anti-FXIa mAb DEF in a rabbit cuticle bleeding study. Rivaroxaban, vehicle, and a control IgG were included for comparison. FIGS. 10A-10C show the pre- and post-dose bleeding amount (A), pre- and post-dose APTT (B), and pre- and post-dose PT (C).

FIG. 13A shows the mean APTT values while FIG. 13B shows the mean PT values.

FIG. 15A shows the binding response versus time for C4 mAb at various DEF Fab concentrations. FIG. 15B summarizes the kinetic rate constant data.

FIG. 19A shows the effect of sequential addition of DEF, ctrl IgG, and C4 mAb on ex vivo APTT coagulation time, with FIG. 19B showing PT coagulation time effects.

DETAILED DESCRIPTION OF THE INVENTION

I. Introduction

Figures 1A, 1B:
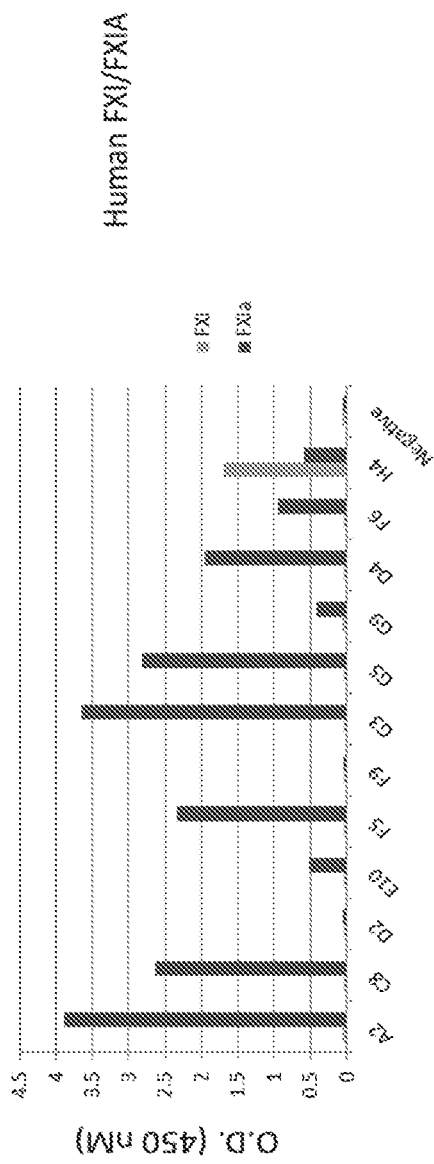
FIG. 1A-1D depict the production and selection of anti-FXIa mAbs.

Current anticoagulants still suffer from efficacy versus safety limitations (Tahir, F., Riaz, H., Riaz, T., Maaz, Badshah, B., Riaz, I. R., Hamza, A., and H. Mohiuddin. *Thromb J.* 2013; 11: 18). If they are under-dosed, the anti-thrombotic effects are not realized and patients with a wide range of thrombotic disease complications fail to be adequately managed, resulting in a higher incidence of dangerous blood clots. If patients are over-treated or have conditions that predispose them to bleeding, then dangerous bleeding events result. While the current thrombin and FXa small molecule inhibitors have shown improved efficacy versus safety results over older medications like warfarin in many anti-thrombotic disease indications (for example, atrial fibrillation (AF) or venous thromboembolism (VTE)), there are other indications that would benefit from a novel anti-thrombotic treatment with an improved efficacy versus safety profile, such as mechanical heart valve replacement, VTE in the medically ill, VTE prophylaxis in the medically ill, VTE prophylaxis in knee or hip surgery, Afib in the renal disease population and/or patients previously identified as bleeders, acute coronary syndromes, use of extracorporeal circulations, and devices in which blood contacts artificial surfaces. See, e.g., Ortel, T. L., and G. M. Arepally. *Annu. Rev. Med.* 2015; 66: 241-253; Flaumenhaft, R. *N Engl J Med.* 2015, 15; 372(3):277-8.

Disclosed herein are antibodies that specifically bind to Factor XIa (e.g., human FXIa). In some embodiments, anti-FXIa antibodies are useful for inhibiting the intrinsic pathway of coagulation or increasing clotting time, and preventing or treating thrombosis with less bleeding risk than existing coagulants, which inhibit the extrinsic and common pathways of coagulation. Methods of making FXIa antibodies, compositions comprising these antibodies, and methods of using these antibodies are also provided. FXIa antibodies can be used in the prevention, treatment, and/or amelioration of diseases, disorders or conditions caused by and/or associated with FXIa activity. Such diseases, disorders or conditions include, but are not limited to, thrombotic conditions such as AF, VTE, mechanical heart valve replacement. VTE in the medically ill, VTE prophylaxis in the medically ill, VTE prophylaxis in knee or hip surgery, Afib in the renal disease population and/or patients previously identified as bleeders, acute coronary syndromes, and use of extracorporeal circulations and devices in which blood contacts artificial surfaces, as would be appreciated by one skilled in the art provided with the teachings disclosed herein.

Also disclosed herein are anti-idiotype antibodies that specifically bind to the antigen-binding site of an anti-FXIa antibody or antigen-binding portion thereof of the disclosure and that act as reversal agents of the anti-FXIa anticoagulant antibodies to improve their safety. Methods of making such anti-idiotype antibodies, compositions comprising these antibodies, and methods of using these antibodies are provided. The anti-idiotype antibodies to anti-FXIa antibodies are useful for, for example, reversing the effects of an anti-FXIa antibody (e.g., decreasing anticoagulant activity or reducing clotting time).

II. Definitions

Unless otherwise defined herein, scientific and technical terms used herein shall have the meanings that are commonly understood by those of ordinary skill in the art. Further, unless otherwise required by context, singular terms shall include pluralities and plural terms shall include the singular. Generally, nomenclatures used in connection with, and techniques of, cell and tissue culture, molecular biology, immunology, microbiology, genetics and protein and nucleic acid chemistry and hybridization described herein are those well-known and commonly used in the art.

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-1998) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel et al., eds., 1987); PCR: The Polymerase Chain Reaction, (Mullis et al., eds., 1994); Current Protocols in Immunology (J. E. Coligan et al., eds., 1991); Sambrook and Russell, Molecular Cloning: A Laboratory Manual, 3rd. ed., Cold Spring Harbor Laboratory Press, Cold Spring Harbor, N.Y. (2001); Ausubel et al., Current Protocols in Molecular Biology, John Wiley & Sons, NY (2002): Harlow and Lane Using Antibodies: A Laboratory Manual, Cold Spring Harbor Laboratory Press, Cold Spring Harbor, N.Y. (1998); Coligan et al., Short Protocols in Protein Science. John Wiley & Sons, NY (2003); Short Protocols in Molecular Biology (Wiley and Sons, 1999); Immunobiology (C. A. Janeway and P. Travers, 1997); Antibodies (P. Finch, 1997); Antibodies: a practical approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999): The Antibodies (M. Zanetti and J. D. Capra, eds., Harwood Academic Publishers, 1995).

Enzymatic reactions and purification techniques are performed according to manufacturer's specifications, as commonly accomplished in the art or as described herein. The nomenclatures used in connection with, and the laboratory procedures and techniques of, analytical chemistry, biochemistry, immunology, molecular biology, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

The term "FXIa" refers to Factor XIa, a serine protease that is activated from a zymogen form (Factor XI, or "FXI") during coagulation as part of the coagulation cascade. FXI is a homodimer in which each subunit contains four apple domains (A1-A4) and a catalytic domain (CD). FXI subunits are activated by cleavage of a bond between A4 and the catalytic domain. See, Gailani et al., *J. Thromb Haemost.*, 2009, 7 (Suppl 1):75-78, incorporated by reference herein. As used herein. "FXIa" refers to any naturally occurring form of activated Factor XI, whether monomeric or multimeric, including dimers, trimers, etc., which may be derived from any suitable organism. In some embodiments, "FXIa" refers to a mammalian FXIa, such as human, rat or mouse, as well as non-human primate, bovine, ovine, or porcine FXIa. In some embodiments, the FXIa is human (see, e.g., Genbank Accession Number M13142, SEQ ID NO: 98) or from cynomolgus monkey. The term "FXIa" also encompasses fragments, variants, isoforms, and other homologs of such FXIa molecules. Variant FXIa molecules will generally be characterized by having the same type of activity as naturally occurring FXIa, such as the ability to bind FIX, thrombin or platelets, and the ability to activate the coagulation cascade.

As used herein, the term "isolated molecule" (where the molecule is, for example, a polypeptide, a polynucleotide, or an antibody or fragment thereof) refers to a molecule that by virtue of its origin or source of derivation (1) is not associated with naturally associated components that accompany it in its native state, (2) is substantially free of other molecules from the same species (3) is expressed by a cell from a different species, or (4) does not occur in nature. Thus, for example, a non-naturally occurring molecule that is chemically synthesized, or expressed in a cellular system different from the cell from which it naturally originates, will be "isolated" from its naturally associated components. A molecule also may be rendered substantially free of naturally associated components by isolation, using purification techniques well known in the art. Molecule purity or homogeneity may be assayed by a number of means well known in the art. For example, the purity of a polypeptide sample may be assayed using polyacrylamide gel electrophoresis and staining of the gel to visualize the polypeptide using techniques well known in the art. For certain purposes, higher resolution may be provided by using HPLC or other means well known in the art for purification.

As used herein, "substantially pure" means an object species is the predominant species present (i.e., on a molar basis it is more abundant than any other individual species in the composition), and preferably a substantially purified fraction is a composition wherein the object species (e.g., a glycoprotein, including an antibody or receptor) comprises at least about 50 percent (on a molar basis) of all macromolecular species present. Generally, a substantially pure composition will have the object species as at least about 80% of all macromolecular species present in the composition, more preferably more than about 85%, 90%, 95%, or 99%. Most preferably, the object species is purified to essential homogeneity (contaminant species cannot be detected in the composition by conventional detection methods) wherein the composition consists essentially of a single macromolecular species. In certain embodiments a substantially pure material is at least 50% pure (i.e., free from contaminants), more preferably, at least 90% pure, at least 95% pure, at least 96% pure, at least 97% pure, least 98% pure, or at least 99% pure.

As used herein, the term "antibody" refers to an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term encompasses not only intact polyclonal or monoclonal antibodies, but also, unless otherwise specified, any antigen binding portion thereof that competes with the intact antibody for specific binding, fusion proteins comprising an antigen binding portion, and any other modified configuration of the immunoglobulin molecule that comprises an antigen recognition site. Antigen binding portions include, for example. Fab, Fab', F(ab')$_2$. Fd, Fv, domain antibodies (dAbs, e.g., shark and camelid antibodies), fragments including complementarity determining regions (CDRs), single chain variable fragment antibodies (scFv), maxibodies, minibodies, intrabodies, diabodies, triabodies, tetrabodies, v-NAR and bis-scFv, and polypeptides that contain at least a portion of an immunoglobulin that is sufficient to confer specific antigen binding to the polypeptide. An antibody includes an antibody of any class, such as IgG, IgA, or IgM (or sub-class thereof), and the antibody need not be of any particular class. Depending on the antibody amino acid sequence of the constant region of its heavy chains, immunoglobulins can be assigned to different classes. There are five major classes of immunoglobulins: IgA, IgD, IgE, IgG, and IgM, and several of these may be further divided into subclasses (isotypes), e.g., IgG$_1$, IgG$_2$, IgG$_3$, IgG$_4$, IgA$_1$ and IgA$_2$. The heavy-chain constant regions that correspond to the different classes of immunoglobulins are called alpha, delta, epsilon, gamma, and mu, respectively. The subunit structures and three-dimensional configurations of different classes of immunoglobulins are well known.

The terms "antigen-binding portion" or "antigen-binding fragment" of an antibody or "antibody portion," as used interchangeably herein, refer to one or more fragments of an antibody that retain the ability to specifically bind to an antigen (e.g., FXIa). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR), disulfide-linked Fvs (dsFv), and anti-idiotypic (anti-Id) antibodies and intrabodies. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv)); see e.g., Bird et al. *Science* 242:423-426 (1988) and Huston et al. *Proc. Natl. Acad. Sci. USA* 85:5879-5883 (1988)). Such single chain antibodies are also intended to be encompassed within the term "antigen-binding portion" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger et al. *Proc. Natl. Acad. Sci. USA* 90:6444-6448 (1993); Poljak et al., 1994, *Structure* 2:1121-1123).

Antibodies may be derived from any mammal, including, but not limited to, humans, monkeys, pigs, horses, rabbits, dogs, cats, mice, etc., or other animals such as birds (e.g. chickens), fish (e.g., sharks) and camelids (e.g., llamas).

A "variable region" of an antibody refers to the variable region of the antibody light chain (VL) or the variable region of the antibody heavy chain (VH), either alone or in combination. As known in the art, the variable regions of the heavy and light chains each consist of four framework regions (FRs) connected by three complementarity determining regions (CDRs) also known as hypervariable regions, and contribute to the formation of the antigen binding site of antibodies. If variants of a subject variable region are desired, particularly with substitution in amino acid residues outside of a CDR region (i.e., in the framework region), appropriate amino acid substitution, preferably, conservative amino acid substitution, can be identified by comparing the subject variable region to the variable regions of other antibodies which contain CDR1 and CDR2 sequences in the same canonical class as the subject variable region (Chothia and Lesk. *J. Mol. Biol.* 196(4): 901-917, 1987).

In certain embodiments, definitive delineation of a CDR and identification of residues comprising the binding site of an antibody is accomplished by solving the structure of the antibody and/or solving the structure of the antibody-ligand complex. In certain embodiments, that can be accomplished by any of a variety of techniques known to those skilled in the art, such as X-ray crystallography. In certain embodiments, various methods of analysis can be employed to identify or approximate the CDR regions. In certain embodiments, various methods of analysis can be employed to identify or approximate the CDR regions. Examples of such methods include, but are not limited to, the Kabat definition, the Chothia definition, the AbM definition, the contact definition, and the conformational definition.

The Kabat definition is a standard for numbering the residues in an antibody and is typically used to identify CDR regions. See, e.g., Johnson & Wu, 2000, *Nucleic Acids Res.*, 28: 214-8. The Chothia definition is similar to the Kabat definition, but the Chothia definition takes into account positions of certain structural loop regions. See, e.g., Chothia et al., 1986, *J. Mol. Biol.*, 196: 901-17; Chothia et al., 1989, Nature, 342: 877-83. The AbM definition uses an integrated suite of computer programs produced by Oxford Molecular Group that model antibody structure. See, e.g., Martin et al., 1989, *Proc Natl Acad Sci (USA)*, 86:9268-9272; "AbM™, A Computer Program for Modeling Variable Regions of Antibodies," Oxford, UK; Oxford Molecular, Ltd. The AbM definition models the tertiary structure of an antibody from primary sequence using a combination of knowledge databases and ab initio methods, such as those described by Samudrala et al., 1999, "Ab Initio Protein Structure Prediction Using a Combined Hierarchical Approach," in PROTEINS, Structure, Function and Genetics Suppl., 3:194-198. The contact definition is based on an analysis of the available complex crystal structures. See, e.g., MacCallum et al., 1996, *J. Mol. Biol.*, 5:732-45. In another approach, referred to herein as the "conformational definition" of CDRs, the positions of the CDRs may be identified as the residues that make enthalpic contributions to antigen binding. See, e.g., Makabe et al., 2008, *Journal of Biological Chemistry*, 283:1156-1166. Still other CDR boundary definitions may not strictly follow one of the above approaches, but will nonetheless overlap with at least a portion of the Kabat CDRs, although they may be shortened or lengthened in light of prediction or experimental findings that particular residues or groups of residues do not significantly impact antigen binding. As used herein, a CDR may refer to CDRs defined by any approach known in the art, including combinations of approaches. The methods used herein may utilize CDRs defined according to any of these approaches. For any given embodiment containing more than one CDR, the CDRs may be defined in accordance with any of Kabat, Chothia, extended, AbM, contact, and/or conformational definitions.

The term "contact residue," as used herein with respect to an antibody or the antigen specifically bound thereby, refers to an amino acid residue present on an antibody/antigen comprising at least one heavy atom (i.e., not hydrogen) that is within 4 Å or less of a heavy atom of an amino acid residue present on the cognate antibody/antigen.

As used herein, a "constant region" of an antibody refers to the constant region of the antibody light chain or the constant region of the antibody heavy chain, either alone or in combination.

As used herein, "monoclonal antibody" refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. Furthermore, in contrast to polyclonal antibody preparations, which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present disclosure may be made by the hybridoma method first described by Kohler and Milstein, 1975, *Nature* 256:495, or may be made by recombinant DNA methods such as described in U.S. Pat. No. 4,816,567. The monoclonal antibodies may also be isolated from phage libraries generated using the techniques described in McCafferty et al., 1990, *Nature* 348:552-554, for example. As used herein, "humanized" antibody refers to forms of non-human (e.g. murine) antibodies that are chimeric immunoglobulins, immunoglobulin chains, or fragments thereof (such as Fv, Fab, Fab', F(ab')$_2$ or other antigen-binding subsequences of antibodies) that contain minimal sequence derived from non-human immunoglobulin. Preferably, humanized antibodies are human immunoglobulins (recipient antibody) in which residues from a CDR of the recipient are replaced by residues from a CDR of a non-human species (donor antibody) such as mouse, rat, or rabbit having the desired specificity, affinity, and capacity. The humanized antibody may comprise residues that are found neither in the recipient antibody nor in the imported CDR or framework sequences, but are included to further refine and optimize antibody performance.

As used herein, a "human antibody" refers to an antibody having an amino acid sequence that corresponds to that of an antibody produced by a human and/or that has been made using any of the techniques for making human antibodies as disclosed herein. This definition of a human antibody specifically excludes a humanized antibody comprising non-human antigen binding residues.

As used herein, the term "chimeric antibody" refers to antibodies in which the variable region sequences are derived from one species and the constant region sequences are derived from another species, such as an antibody in which the variable region sequences are derived from a mouse antibody and the constant region sequences are derived from a human antibody or vice versa. The term also encompasses an antibody comprising a V region from one individual from one species (e.g., a first mouse) and a constant region from another individual from the same species (e.g., a second mouse).

As used herein, the term "antigen" ("Ag") refers to the molecular entity used for immunization of an immunocompetent vertebrate to produce the antibody (Ab) that recognizes the Ag or to screen an expression library (e.g., phage, yeast or ribosome display library, among others). As used herein, the term "antigen" or "Ag" includes target molecules that are specifically recognized by the Ab, thus including fragments or mimics of the molecule used in an immunization process for raising the Ab or in library screening for selecting the Ab. Thus, for antibodies of the disclosure binding to FXIa, full-length FXIa from mammalian species (e.g., human, monkey, mouse and rat FXIa), including monomers and multimers, such as dimers, trimers, etc. thereof, as well as truncated and other variants of FXIa, are referred to as an antigen.

As used herein, the term "epitope" refers to the area or region of an antigen to which an antibody specifically binds, i.e., an area or region in physical contact with the antibody. Thus, the term "epitope" refers to that portion of a molecule capable of being recognized by and bound by an antibody at one or more of the antibody's antigen-binding regions. Typically, an epitope is defined in the context of a molecular interaction between an "antibody or antigen-binding fragment thereof" ("Ab") and its corresponding antigen. Epitopes often consist of a surface grouping of molecules such as amino acids or sugar side chains and have specific three-dimensional structural characteristics as well as specific charge characteristics. In some embodiments, the epitope can be a protein epitope. Protein epitopes can be linear or conformational. In a linear epitope, all of the points of interaction between the protein and the interacting molecule (such as an antibody) occur linearly along the primary amino acid sequence of the protein. A "nonlinear epitope" or "conformational epitope" comprises noncontiguous polypeptides (or amino acids) within the antigenic protein to which an antibody specific to the epitope binds. The term "antigenic epitope" as used herein, is defined as a portion of an antigen to which an antibody can specifically bind as determined by any method well known in the art, for example, by conventional immunoassays. Alternatively, during the discovery process, the generation and characterization of antibodies may elucidate information about desirable epitopes. From this information, it is then possible to competitively screen antibodies for binding to the same epitope. An approach to achieve this is to conduct competition and cross-competition studies to find antibodies that compete or cross-compete with one another for binding to FXIa, e.g., the antibodies compete for binding to the antigen. Similarly, in the case of the anti-idiotype antibodies of the disclosure, competition and cross-competition studies can be conducted to find antibodies that compete or cross-compete with one another for binding to an anti-FXIa antibody, e.g., the antibodies compete for binding to the antigen-binding site of an anti-FXIa antibody of the disclosure.

As used herein, the terms "wild-type amino acid," "wild-type IgG," "wild-type antibody," or "wild-type mAb," refer to a sequence of amino or nucleic acids that occurs naturally within a certain population (e.g., human, mouse, rats, cell, etc.).

As outlined elsewhere herein, certain positions of the antibody molecule can be altered. By "position" as used herein is meant a location in the sequence of a protein. Positions may be numbered sequentially, or according to an established format, for example the EU index and Kabat index can be used to number amino acid residues of an antibody. For example, position 297 is a position in the human antibody IgG1. Corresponding positions are determined as outlined above, generally through alignment with other parent sequences.

By "residue" as used herein is meant a position in a protein and its associated amino acid identity. For example, Asparagine 297 (also referred to as Asn297, also referred to as N297) is a residue in the human antibody IgG1.

The terms "polynucleotide" or "nucleic acid," as used interchangeably herein, refer to chains of nucleotides of any length, and include DNA and RNA. The nucleotides can be deoxyribonucleotides, ribonucleotides, modified nucleotides or bases, and/or their analogs, or any substrate that can be incorporated into a chain by DNA or RNA polymerase. A polynucleotide may comprise modified nucleotides, such as methylated nucleotides and their analogs. If present, modification to the nucleotide structure may be imparted before or after assembly of the chain. The sequence of nucleotides may be interrupted by non-nucleotide components. A polynucleotide may be further modified after polymerization, such as by conjugation with a labeling component. Other types of modifications include, for example, "caps," substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, alpha- or beta-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), (O)NR$_2$ ("amidate"), P(O)R, P(O)OR', CO or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

As used herein, a molecule "preferentially binds" or "specifically binds" (used interchangeably herein) to a cell or to a substance (e.g., a protein, polypeptide, or antibody, e.g., a protein, polypeptide, or antibody comprising an epitope) if the molecule reacts or associates more frequently, more rapidly, with greater duration and/or with greater affinity with a particular cell or substance than it does with alternative cells or substances. An antibody "specifically binds" or "preferentially binds" to a target if it binds with greater affinity, avidity, more readily, and/or with greater duration than it binds to other substances. Also, an antibody "specifically binds" or "preferentially binds" to a target if it binds with greater affinity, avidity, more readily, and/or with greater duration to that target in a sample than it binds to other substances present in the sample. For example, an antibody that specifically or preferentially binds to a FXIa epitope is an antibody that binds this epitope with greater affinity, avidity, more readily, and/or with greater duration than it binds to other FXIa epitopes or non-FXIa epitopes. It will be understood by a person of ordinary skill in the art reading this definition, for example, that an antibody (or moiety or epitope) that specifically or preferentially binds to a first target may or may not specifically or preferentially bind to a second target. As such, "specific binding" or "preferential binding" does not necessarily require (although it can include) exclusive binding. Generally, but not necessarily, reference to binding means preferential binding. "Specific binding" or "preferential binding" includes a compound, e.g., a protein, a nucleic acid, an antibody, and the like, which recognizes and binds to a specific molecule, but does not substantially recognize or bind other molecules in a sample. For instance, an antibody that recognizes and binds to a binding partner (e.g., an anti-FXIa antibody that binds FXIa) in a sample, but does not substantially recognize or bind other molecules in the sample, specifically binds to that cognate ligand or binding partner. Thus, under designated assay conditions, the specified binding moiety (e.g., an antibody or an antigen-binding portion thereof) binds preferentially to a particular target molecule and does not bind in a significant amount to other components present in a test sample.

A variety of assay formats may be used to select an antibody or peptide that specifically binds a molecule of interest. For example, solid-phase ELISA immunoassay, immunoprecipitation, Biacore™ (GE Healthcare. Piscataway, N.J.), kinetic exclusion assay (KinExA®, Sapidyne Instruments, Inc., Boise, Id.)), fluorescence-activated cell sorting (FACS), Octet™ (ForteBio, Inc., Menlo Park, Calif.) and Western blot analysis are among many assays that may be used to identify an antibody that specifically reacts with an antigen or a receptor, or ligand binding portion thereof, that specifically binds with a cognate ligand or binding partner. Typically, a specific or selective reaction will be at least twice the background signal or noise, more typically more than 10 times background, even more typically, more than 50 times background, more typically, more than 100 times background, yet more typically, more than 500 times background, even more typically, more than 1000 times background, and even more typically, more than 10,000 times background. In some embodiments, an antibody is said to "specifically bind" an antigen when the equilibrium dissociation constant ($K_D$) is ≤7 nM.

The term "binding affinity" is herein used as a measure of the strength of a non-covalent interaction between two molecules, e.g., an antibody, or fragment thereof, and an antigen. The term "binding affinity" is used to describe monovalent interactions (intrinsic activity).

Binding affinity between two molecules, e.g. an antibody, or fragment thereof, and an antigen, through a monovalent interaction may be quantified by determination of the dissociation constant ($K_D$). In turn. $K_D$ can be determined by measurement of the kinetics of complex formation and dissociation using, e.g., the surface plasmon resonance (SPR) method (Biacore™). The rate constants corresponding to the association and the dissociation of a monovalent complex are referred to as the association rate constants $k_a$ (or $k_{on}$) and dissociation rate constant $k_d$ (or $k_{off}$), respectively. $K_D$ is related to $k_a$ and $k_d$ through the equation $K_D=k_d/k_a$. The value of the dissociation constant can be determined directly by well-known methods, and can be computed even for complex mixtures by methods such as those, for example, set forth in Caceci et al. (1984, *Byte* 9: 340-362). For example, the $K_D$ may be established using a double-filter nitrocellulose filter binding assay such as that disclosed by Wong & Lohman (1993, *Proc. Natl. Acad. Sci. USA* 90: 5428-5432). Other standard assays to evaluate the binding ability of ligands such as antibodies towards target antigens are known in the art, including for example, ELISAs, Western blots, RIAs, and flow cytometry analysis, and other assays exemplified elsewhere herein. The binding kinetics and binding affinity of the antibody also can be assessed by standard assays known in the art, such as Surface Plasmon Resonance (SPR), e.g. by using a Biacore™ system, or KinExA®.

A competitive binding assay can be conducted in which the binding of the antibody to the antigen is compared to the binding of the target by another ligand of that target, such as another antibody or a soluble receptor that otherwise binds the target. The concentration at which 50% inhibition occurs is known as the $K_i$. Under ideal conditions, the $K_i$ is equivalent to $K_D$. The $K_i$ value will never be less than the $K_D$, so measurement of $K_i$ can conveniently be substituted to provide an upper limit for $K_D$.

Following the above definition, binding affinities associated with different molecular interactions, e.g., comparison of the binding affinity of different antibodies for a given antigen, may be compared by comparison of the $K_D$ values for the individual antibody/antigen complexes. $K_D$ values for antibodies or other binding partners can be determined using methods well established in the art. One method for determining the $K_D$ is by using surface plasmon resonance, typically using a biosensor system such as a Biacore® system.

Similarly, the specificity of an interaction may be assessed by determination and comparison of the $K_D$ value for the interaction of interest, e.g., a specific interaction between an antibody and an antigen, with the $K_D$ value of an interaction not of interest, e.g., a control antibody known not to bind FXIa.

An antibody that specifically binds its target may bind its target with a high affinity, that is, exhibiting a low $K_D$ as discussed above, and may bind to other, non-target molecules with a lower affinity. For example, the antibody may bind to non-target molecules with a $K_D$ of $1 \times 10^{-6}$ M or more, more preferably $1 \times 10^{-5}$ M or more, more preferably $1 \times 10^{-4}$ M or more, more preferably $1 \times 10^{-3}$ M or more, even more preferably $1 \times 10^{-2}$ M or more. An anti-FXIa antibody of the disclosure is preferably capable of binding to its target with an affinity that is at least two-fold, 10-fold, 50-fold, 100-fold, 200-fold, 500-fold, 1,000-fold or 10,000-fold or greater than its affinity for binding to another non-FXIa molecule. Similarly, an anti-idiotype antibody of the disclosure is preferably capable of binding to its target with an affinity that is at least two-fold, 10-fold, 50-fold, 100-fold, 200-fold, 500-fold, 1,000-fold or 10,000-fold or greater than its affinity for binding to another non-anti-FXIa antibody molecule.

A "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected and/or transformed in vivo with a polynucleotide of this disclosure.

As used herein, the term "Fc region" refers to a C-terminal region of an immunoglobulin heavy chain. The "Fc region" may be a native sequence Fc region or a variant Fc region. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The numbering of the residues in the Fc region is that of the EU index as described in Kabat et al., Sequences of Proteins of Immunological Interest, 5th Ed. Public Health Service, National Institutes of Health, Bethesda, Md., 1991. The Fc region of an immunoglobulin generally comprises two constant domains, CH2 and CH3. As is known in the art, an Fc region can be present in dimer or monomeric form.

As used herein, the term "Fc receptor" or "FcR" refers to a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. FcRs are reviewed in Ravetch and Kinet, 1991, *Ann. Rev. Immunol.*, 9:457-92; Capel et al., 1994, *Immunomethods*, 4:25-34; and de Haas et al., 1995, *J. Lab. Clin. Med.*, 126:330-41. "FcR" also includes the neonatal receptor, FcRn, which is responsible for the transfer of maternal IgGs to the fetus (Guyer et al., 1976, *J. Immunol.*, 117:587; and Kim et al., 1994, *J. Immunol.*, 24:249).

The term "compete," as used herein with regard to an antibody, means that a first antibody, or an antigen-binding portion thereof, binds to an epitope in a manner sufficiently similar to the binding of a second antibody, or an antigen-binding portion thereof, such that the result of binding of the first antibody with its cognate epitope is detectably decreased in the presence of the second antibody compared to the binding of the first antibody in the absence of the second antibody. The alternative, where the binding of the second antibody to its epitope is also detectably decreased in the presence of the first antibody, can, but need not be the case. That is, a first antibody can inhibit the binding of a second antibody to its epitope without that second antibody inhibiting the binding of the first antibody to its respective epitope. However, where each antibody detectably inhibits the binding of the other antibody with its cognate epitope or ligand, whether to the same, greater, or lesser extent, the antibodies are said to "cross-compete" with each other for binding of their respective epitope(s). Both competing and cross-competing antibodies are encompassed by the present disclosure. Regardless of the mechanism by which such competition or cross-competition occurs (e.g., steric hindrance, conformational change, or binding to a common epitope, or portion thereof), the skilled artisan would appreciate, based upon the teachings provided herein, that such competing and/or cross-competing antibodies are encompassed and can be useful for the methods disclosed herein.

A "functional Fc region," as used herein, possesses at least one effector function of a native sequence Fc region. Exemplary "effector functions" include C1q binding; complement dependent cytotoxicity; Fc receptor binding; antibody-dependent cell-mediated cytotoxicity; phagocytosis; down-regulation of cell surface receptors (e.g. B cell receptor), etc. Such effector functions generally require the Fc region to be combined with a binding domain (e.g. an antibody variable domain or antigen-binding portion thereof) and can be assessed using various assays known in the art for evaluating such antibody effector functions.

A "native sequence Fc region," as used herein, comprises an amino acid sequence identical to the amino acid sequence of an Fc region found in nature. A "variant Fc region," as used herein, comprises an amino acid sequence that differs from that of a native sequence Fc region by virtue of at least one amino acid modification, yet retains at least one effector function of the native sequence Fc region. Preferably, the variant Fc region has at least one amino acid substitution compared to a native sequence Fc region or to the Fc region of a parent polypeptide, e.g. from about one to about ten amino acid substitutions, and preferably, from about one to about five amino acid substitutions in a native sequence Fc region or in the Fc region of the parent polypeptide. The variant Fc region herein will preferably possess at least about 80% sequence identity with a native sequence Fc region and/or with an Fc region of a parent polypeptide, and most preferably, at least about 90% sequence identity therewith, more preferably, at least about 95%, at least about 96%, at least about 97%, at least about 98%, at least about 99% sequence identity therewith.

As used herein, "treatment" is an approach for obtaining beneficial or desired clinical results. For purposes of this disclosure, beneficial or desired clinical results include, but are not limited to, one or more of the following: improved survival rate (reduced mortality), decrease in the occurrence of disease (e.g., thrombosis or thromboembolism), decreased extent of damage from the disease, decreased duration of the disease, and/or reduction in the number, extent, or duration of symptoms related to the disease. The term includes the administration of the compounds or agents of the present disclosure to prevent or delay the onset of the symptoms, complications, or biochemical indicia of a disease, alleviating the symptoms or arresting or inhibiting further development of the disease, condition, or disorder. Treatment may be prophylactic (to prevent or delay the onset of the disease, or to prevent the manifestation of clinical or subclinical symptoms thereof) or therapeutic suppression or alleviation of symptoms after the manifestation of the disease.

"Ameliorating," as used with respect to administering an anti-FXIa antibody as described herein, means a lessening or improvement of one or more symptoms as compared to not administering an anti-FXIa antibody. "Ameliorating" also includes shortening or reduction in duration of a symptom.

As used herein, an "effective dosage" or "effective amount" of a drug, compound, or pharmaceutical composition is an amount sufficient to affect any one or more beneficial or desired results. In more specific aspects, an effective amount prevents, alleviates or ameliorates symptoms of disease or infection, and/or prolongs the survival of the subject being treated. For prophylactic use, beneficial or desired results include eliminating or reducing the risk, lessening the severity, or delaying the outset of the disease, including biochemical, histological and/or behavioral symptoms of the disease, its complications and intermediate pathological phenotypes presenting during development of the disease. For therapeutic use, beneficial or desired results include clinical results such as reducing one or more symptoms of a FXIa-mediated disease, disorder or condition, decreasing the dose of other medications required to treat the disease, enhancing the effect of another medication, and/or delaying the progression of the disease of patients. An effective dosage can be administered in one or more administrations. For purposes of this disclosure, an effective dosage of drug, compound, or pharmaceutical composition is an amount sufficient to accomplish prophylactic or therapeutic treatment either directly or indirectly. As is understood in the clinical context, an effective dosage of a drug, compound, or pharmaceutical composition may or may not be achieved in conjunction with another drug, compound, or pharmaceutical composition. Thus, an "effective dosage" may be considered in the context of administering one or more therapeutic agents, and a single agent may be considered to be given in an effective amount if, in conjunction with one or more other agents, a desirable result may be or is achieved.

An "individual" or a "subject" is a mammal, in some embodiments, a human. Mammals also include, but are not limited to, farm animals (e.g., cows, pigs, horses, chickens, etc.), sport animals, pets, primates, horses, dogs, cats, mice and rats. In some embodiments, the individual is considered to be at risk for a disease, disorder or condition mediated by or associated with FXIa. In certain embodiments, the subject has a thrombotic condition. In certain embodiments, the subject is being administered an anti-FXIa antibody and is in need of a reversal agent.

As used herein, "vector" means a construct, which is capable of delivering, and, preferably, expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

As used herein, "expression control sequence" means a nucleic acid sequence that directs transcription of a nucleic acid. An expression control sequence can be a promoter, such as a constitutive or an inducible promoter, or an enhancer. The expression control sequence is operably linked to the nucleic acid sequence to be transcribed.

As used herein, "pharmaceutically acceptable carrier" or "pharmaceutical acceptable excipient" includes any material which, when combined with an active ingredient, allows the ingredient to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents. Preferred diluents for aerosol or parenteral administration are phosphate buffered saline (PBS) or normal (0.9%) saline. Compositions comprising such carriers are formulated by well-known conventional methods (see, for example, Remington's Pharmaceutical Sciences, 18th edition, A. Gennaro, ed., Mack Publishing Co., Easton, Pa., 1990; and Remington, The Science and Practice of Pharmacy 20th Ed. Mack Publishing, 2000).

Reference to "about" a value or parameter herein includes (and describes) embodiments that are directed to that value or parameter per se. For example, description referring to "about X" includes description of "X." Numeric ranges are inclusive of the numbers defining the range.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a stated range of "1 to 10" should be considered to include any and all subranges between (and inclusive of) the minimum value of 1 and the maximum value of 10; that is, all subranges beginning with a minimum value of 1 or more, e.g. 1 to 6.1, and ending with a maximum value of 10 or less, e.g., 5.5 to 10.

Unless otherwise defined, all technical and scientific terms used herein have the same meaning as commonly understood by one of ordinary skill in the art to which this invention belongs. In case of conflict, the present specification, including definitions, will control. Throughout this specification and claims, the word "comprise," or variations such as "comprises" or "comprising" will be understood to imply the inclusion of a stated integer or group of integers but not the exclusion of any other integer or group of integers. Unless otherwise required by context, singular terms shall include pluralities and plural terms shall include the singular. Any example(s) following the term "e.g." or "for example" is not meant to be exhaustive or limiting.

It is understood that wherever embodiments are described herein with the language "comprising," otherwise analogous embodiments described in terms of "consisting of" and/or "consisting essentially of" are also provided.

Where aspects or embodiments of the disclosure are described in terms of a Markush group or other grouping of alternatives, the present disclosure encompasses not only the entire group listed as a whole, but each member of the group individually and all possible subgroups of the main group, but also the main group absent one or more of the group members. The present invention also envisages the explicit exclusion of one or more of any of the group members in the claimed invention.

Exemplary methods and materials are described herein, although methods and materials similar or equivalent to those described herein can also be used in the practice or testing of the present invention. The materials, methods, and examples are illustrative only and not intended to be limiting.

III. Antibodies to FXIa and Anti-Idiotype Antibodies that Bind Anti-FXIa Antibodies In one aspect, the present disclosure relates to antibodies, e.g., full-length antibodies and antigen-binding fragments thereof, that specifically bind to Factor XIa (FXIa) or a target molecule comprising an epitope from FXIa. In some embodiments, an anti-FXIa antibody specifically binds to a mammalian FXIa, such as human, rat or mouse, as well as non-human primate, bovine, ovine, or porcine FXIa. In some embodiments, the anti-FXIa antibody specifically binds a full-length human FXIa (e.g., the human FXIa protein of SEQ ID NO: 98) or or a full-length cynomolgus monkey FXIa. In some embodiments, the anti-FXIa antibody specifically binds a fragment, variant, isoform, or homolog of such an FXIa molecule. In some embodiments, a variant FXIa molecule is characterized by having the same type of activity as a naturally occurring FXIa, such as the ability to bind FIX, thrombin or platelets, and the ability to activate the coagulation cascade.

In some embodiments, the FXIa variant or fragment may comprise one or more, two or more, three or more, four or more, five or more, six or more, seven or more, eight or more, nine or more, ten or more, twelve or more or fifteen or more solvent accessible residues of FXIa. Where the FXIa comprises a homomultimeric form of FXIa, the FXIa variant or fragment may comprise one or more, two or more, three or more, four or more, five or more, six or more, seven or more, eight or more, nine or more, ten or more, twelve or more, or fifteen or more solvent accessible residues of a first subunit of FXIa, and one or more, two or more, three or more, four or more, five or more, six or more, seven or more, eight or more, nine or more, ten or more, twelve or more, or fifteen or more solvent accessible residues of a second subunit of FXIa.

In some embodiments, an antibody or antigen-binding fragment thereof specifically binds to FXIa or to a target molecule comprising an epitope from FXIa. In some embodiments, the target molecule may comprise the catalytic domain of FXIa.

In another aspect, the present disclosure relates to anti-idiotype antibodies that specifically bind to anti-FXIa antibodies as described herein.

In another aspect, the disclosure also relates to compositions comprising anti-FXIa antibodies or anti-idiotype antibodies that specifically bind to anti-FXIa antibodies as described herein, as well as uses for such antibodies, including therapeutic and pharmaceutical uses.

As detailed herein, the antibodies useful in the present disclosure (e.g. anti-FXIa antibodies and anti-idiotype antibodies that specifically bind to the antigen-binding site of an anti-FXIa antibody) can encompass monoclonal antibodies, polyclonal antibodies, antibody fragments (e.g., Fab, Fab', F(ab')$_2$, Fv, Fc, etc.), chimeric antibodies, bispecific antibodies, heteroconjugate antibodies, single chain (ScFv), mutants thereof, fusion proteins comprising an antibody portion (e.g., a domain antibody), humanized antibodies, and any other modified configuration of the immunoglobulin molecule that comprises an antigen recognition site of the required specificity, including glycosylation variants of antibodies, amino acid sequence variants of antibodies, and covalently modified antibodies. The antibodies may be murine, rat, human, or any other origin (including chimeric or humanized antibodies). In some embodiments, the FXIa antibody is a monoclonal antibody. In some embodiments, the FXIa antibody is a human or humanized antibody. In some embodiments, the anti-idiotype antibody is a monoclonal antibody. In some embodiments, the anti-idiotype antibody is a human or humanized antibody.

Anti-FXIa Antibodies

In one aspect, the present disclosure relates to antibodies that bind to FXIa. The antibodies preferably specifically bind to FXIa, i.e., they bind to FXIa but they do not detectably bind, or bind at a lower affinity, to other molecules. In particular, in some embodiments, the disclosure relates to antibodies that specifically bind to FXIa but not the zymogen FXI. In some embodiments, the anti-FXIa antibodies of the disclosure specifically bind the FXIa catalytic domain and/or adjacent residues.

In some embodiments, the anti-FXIa antibodies of the disclosure prolong activated partial thromboplastin time (APTT) without significantly increasing prothrombin time (PT). This finding reflects inhibition of the intrinsic pathway but not the extrinsic or common pathways of coagulation by the antibody and was associated with anti-thrombotic protection without increased bleeding risk, as shown in the Examples (e.g., FIGS. 9 and 10). As used herein, the term "prolong activated partial thromboplastin time" refers to a measurement of the length of time it takes for plasma to clot after addition of an intrinsic pathway activator such as ellagic acid or kaolin, and the term "increasing prothrombin time" refers to a measurement of the length of time it takes for plasma to clot after addition of an extrinsic pathway activator such as Tissue Factor or thromboplastin. Thus, APTT is a measurement of the intrinsic pathway of coagulation, while PT is a measurement of the extrinsic pathway of coagulation. Both can also be prolonged by sufficient inhibition of the common pathway.

In some embodiments, an anti-FXIa antibody prolongs activated partial thromboplastin time (APTT) if the length of time it takes for a sample of plasma to clot after addition of an intrinsic pathway activator (e.g., ellagic acid or kaolin) in the presence of an anti-FXIa antibody is greater than the length of time it takes for a sample of plasma to clot after addition of the intrinsic pathway activator in the absence of the anti-FXIa antibody. In some embodiments, an anti-FXIa antibody prolongs APTT by at least 10%, at least 20%, at least 30%, at least 40%, at least 50%, at least 60%, at least 70%, at least 80%, at least 90%, at least 100%, at least 150%, or more. In some embodiments, an anti-FXIa antibody does not "significantly increase prothrombin time" if the length of time it takes for a sample of plasma to clot after addition of an extrinsic pathway activator (e.g., Tissue Factor or thromboplastin) in the presence of an anti-FXIa antibody is no more than 20% longer, no more than 15% longer, no more than 10% longer, no more than 5% longer, or no longer than the length of time it takes for a sample of plasma to clot after addition of the extrinsic pathway activator in the absence of the anti-FXIa antibody. APTT and PT can be measured at a predetermined time after administration of an anti-FXIa antibody (e.g., 15 mins, 20 mins, 30 mins, 40 mins, 45 mins, 50 mins, 60 mins or more after administration of an anti-FXIa antibody). Methods of measuring APTT and PT are known in the art and are also described herein in the Examples section.

In some embodiments, the anti-FXIa antibodies of the disclosure have an increased dissociation rate from FXIa in the presence of a serine protease inhibitor. In some embodiments, the anti-FXIa antibodies of the disclosure have an increased dissociation rate from FXIa after treatment of the latter with an agent that chemically modifies the active site serine of a serine protease. In some embodiments, the serine protease inhibitor or agent is phenylmethylsulfonyl fluoride (PMSF). Methods of measuring the dissociation rate of an anti-FXIa antibody from FXIa are known in the art and are also described in the Examples section below. In some embodiments, dissociate rate is measured using Surface Plasmon Resonance (SPR), e.g. by using a Biacore™ system. In some embodiments, an anti-FXIa antibody has an increased dissociation rate from FXIa in the presence of a serine protease inhibitor or after treatment of FXIa with an agent that chemically modifies the active site serine of a serine protease if the dissociation rate is increased at least about 20%, 30%, 40%, 50%, 60%, 70%, 80%, 90%, 95%, 100%, 1.5 fold, 2-fold, 3-fold, 4-fold, 5-fold, or more as compared to the dissociation rate of the anti-FXIa antibody from FXIa in the absence of the serine protease inhibitor or agent.

In some embodiments, the anti-FXIa antibodies of the disclosure bind to, and have their anticoagulant activity decreased by, a recombinant FXIa protease-domain in which the active site serine is changed to alanine (e.g., as described in U.S. Provisional Patent Application "Reversal Agents for FXIa Inhibitors," No. 62/196,085, incorporated by reference herein). Methods of measuring specific binding and binding affinity are known in the art and include, but are not limited to, solid-phase binding assays, immunoprecipitation, surface plasmon resonance (e.g., Biacore™ (GE Healthcare, Piscataway, N.J.)), kinetic exclusion assay, fluorescence-activated cell sorting (FACS). Octet™ (ForteBio, Inc., Menlo Park, Calif.), and Western blot analysis. Methods of measuring anticoagulant activity are known in the art and include, but are not limited to, measuring clotting time (e.g., APTT and/or PT) and measuring thrombin production (e.g., using a thrombin generation assay (TGA)). Methods of measuring specific binding and binding affinity and anticoagulant activity are also described in U.S. Provisional Patent Application No. 62/196,085. In some embodiments, the binding activity of an anti-FXIa antibody to a recombinant FXIa protease-domain in which the active site serine is changed to alanine, and the anticoagulant activity of an anti-FXIa antibody in the presence of a recombinant FXIa protease-domain in which the active site serine is changed to alanine, are measured using a recombinant FXIa protease-domain that is disclosed in U.S. Provisional Patent Application No. 62/196, 085 and that has the amino acid sequence of SEQ ID NO:2 in U.S. Provisional Patent Application No. 62/196,085.

Preferably, an anti-FXIa antibody of the disclosure has at least one of these features. In some embodiments, the anti-FXIa antibody has two or more of these features. In some embodiments, the anti-FXIa antibody has all of these features.

In one embodiment, the disclosure provides an antibody having a light chain sequence, or a portion thereof, and a heavy chain, or a portion thereof, derived from any of the following antibodies: D4, DEF, QCA11, B1D2, B10H2, B10E6, B10F6, B10D8, B10B12, S1D4, S10H9, Clone 8, Clone 16, Clone 20, Clone 22, Clone 32, or Clone 24; or a composition (including pharmaceutical compositions) comprising such an antibody. The amino acid sequences of the light chain variable domain (VL) and heavy chain variable domains (VH) of the anti-FXIa antibodies DEF, D4, QCA11, B1D2, B10H2, B10E6, B10F6, B10D8, B10B12, S1D4, S10H9, Clone 8, Clone 16, Clone 20, Clone 22, Clone 32, and Clone 24 are set forth in Table 5 below.

In some embodiments, an anti-FXIa antibody of the disclosure comprises both:

a) a VH comprising the amino acid sequence of SEQ ID NO:1, and a VL comprising the amino acid sequence of SEQ ID NO:7;

b) a VH comprising the amino acid sequence of SEQ ID NO: 14, and a VL comprising the amino acid sequence of SEQ ID NO: 17;

c) a VH comprising the amino acid sequence of SEQ ID NO: 18, and a VL comprising the amino acid sequence of SEQ ID NO:21;

d) a VH comprising the amino acid sequence of SEQ ID NO:22, and a VL comprising the amino acid sequence of SEQ ID NO:23;

e) a VH comprising the amino acid sequence of SEQ ID NO:24, and a VL comprising the amino acid sequence of SEQ ID NO:25;

f) a VH comprising the amino acid sequence of SEQ ID NO:26, and a VL comprising the amino acid sequence of SEQ ID NO:27;

g) a VH comprising the amino acid sequence of SEQ ID NO:28, and a VL comprising the amino acid sequence of SEQ ID NO:31;

h) a VH comprising the amino acid sequence of SEQ ID NO:34, and a VL comprising the amino acid sequence of SEQ ID NO:37;

i) a VH comprising the amino acid sequence of SEQ ID NO:38, and a VL comprising the amino acid sequence of SEQ ID NO:39;

j) a VH comprising the amino acid sequence of SEQ ID NO:40, and a VL comprising the amino acid sequence of SEQ ID NO:42;

k) a VH comprising the amino acid sequence of SEQ ID NO:43, and a VL comprising the amino acid sequence of SEQ ID NO:46;

l) a VH comprising the amino acid sequence of SEQ ID NO:47, and a VL comprising the amino acid sequence of SEQ ID NO:50;

m) a VH comprising the amino acid sequence of SEQ ID NO:51, and a VL comprising the amino acid sequence of SEQ ID NO:54 n) a VH comprising the amino acid sequence of SEQ ID NO:55, and a VL comprising the amino acid sequence of SEQ ID NO:58;

o) a VH comprising the amino acid sequence of SEQ ID NO:59, and a VL comprising the amino acid sequence of SEQ ID NO:62;

p) a VH comprising the amino acid sequence of SEQ ID NO:63, and a VL comprising the amino acid sequence of SEQ ID NO:64; or q) a VH comprising the amino acid sequence of SEQ ID NO:65, and a VL comprising the amino acid sequence of SEQ ID NO:68.

In some embodiments, an anti-FXIa antibody of the disclosure comprises both a VH comprising the consensus amino acid sequence of SEQ ID NO:96, and a VL comprising the consensus amino acid sequence of SEQ ID NO:97. The consensus VH sequence of SEQ ID NO:96 and the consensus VL sequence of SEQ ID NO:97 are described in Table 5 below.

In another aspect, the antibody comprises a variant of any one or more of these sequences, wherein such variants can include both conservative and non-conservative substitutions, deletions, and/or additions, and typically include peptides that share at least 60%, at least 65%, at least 70%, at least 75%, at least 80%, at least 85%, at least 87%, at least 89%, at least 90%, at least 91%, at least 92%, at least 93%, at least 94%, at least 95%, at least 96%, at least 97%, at least 98%, or at least 99% sequence identity to any of the specific sequences disclosed herein.

For example, in one aspect, the disclosure provides an isolated antibody or antigen-binding portion thereof that comprises a VL chain amino acid sequence as set forth in SEQ ID NO: 7, SEQ ID NO: 17, SEQ ID NO:21, SEQ ID NO:23, SEQ ID NO:25, SEQ ID NO:27, SEQ ID NO:31, SEQ ID NO:37, SEQ ID NO:39, SEQ ID NO:42, SEQ ID NO:46, SEQ ID NO:50, SEQ ID NO:54, SEQ ID NO:58, SEQ ID NO:62, SEQ ID NO:64, SEQ ID NO:68, or SEQ ID NO:97 or a variant thereof. In one aspect, said antibody variant comprises 1, 2, 3, 4, 5, 6, 7, 8, 9, 10, 11, 12, 13, 14, or 15 conservative or non-conservative substitutions, and/or 1, 2, 3, 4, 5, 6, 7, 8, 9, 10, 11, 12, 13, 14, or 15 additions and/or deletions to SEQ ID NO: 7, SEQ ID NO:17, SEQ ID NO:21, SEQ ID NO:23, SEQ ID NO:25, SEQ ID NO:27, SEQ ID NO:31, SEQ ID NO:37, SEQ ID NO:39, SEQ ID NO:42, SEQ ID NO:46, SEQ ID NO:50, SEQ ID NO:54, SEQ ID NO:58, SEQ ID NO:62, SEQ ID NO:64, SEQ ID NO:68, or SEQ ID NO:97. In a further aspect, said variant shares at least 65%, at least 75%, at least 85%, at least 90%, at least 95%, at least 96%, at least 97%, at least 98%, or at least 99% sequence identity with SEQ ID NO: 7, SEQ ID NO: 17, SEQ ID NO:21, SEQ ID NO:23, SEQ ID NO:25, SEQ ID NO:27, SEQ ID NO:31, SEQ ID NO:37, SEQ ID NO:39, SEQ ID NO:42, SEQ ID NO:46, SEQ ID NO:50, SEQ ID NO:54, SEQ ID NO:58, SEQ ID NO:62, SEQ ID NO:64, SEQ ID NO:68, or SEQ ID NO:97 and wherein said antibody or antigen-binding portion specifically binds FXIa.

In a further aspect, the disclosure provides an isolated antibody or antigen-binding portion thereof that comprises a $V_H$ chain amino acid sequence as set forth in SEQ ID NO: 1, SEQ ID NO:14, SEQ ID NO: 18, SEQ ID NO:22, SEQ ID NO:24, SEQ ID NO:26, SEQ ID NO:28, SEQ ID NO:34, SEQ ID NO:38, SEQ ID NO:40, SEQ ID NO:43, SEQ ID NO:47, SEQ ID NO:51, SEQ ID NO:55, SEQ ID NO:59, SEQ ID NO:63, SEQ ID NO:65, or SEQ ID NO:96, or a variant thereof. In one aspect, said antibody variant comprises 1, 2, 3, 4, 5, 6, 7, 8, 9, 10, 11, 12, 13, 14, or 15 conservative or non-conservative substitutions, and/or 1, 2, 3, 4, 5, 6, 7, 8, 9, 10, 11, 12, 13, 14, or 15 additions and/or deletions to SEQ ID NO: 1, SEQ ID NO: 14, SEQ ID NO: 18, SEQ ID NO:22, SEQ ID NO:24, SEQ ID NO:26, SEQ ID NO:28, SEQ ID NO:34, SEQ ID NO:38, SEQ ID NO:40, SEQ ID NO:43, SEQ ID NO:47, SEQ ID NO:51, SEQ ID NO:55, SEQ ID NO:59, SEQ ID NO:63, SEQ ID NO:65, or SEQ ID NO:96. In a further aspect, said variant shares at least 65%, at least 75%, at least 85%, at least 90%, at least 95%, at least 96%, at least 97%, at least 98%, or at least 99% sequence identity with SEQ ID NO: 1, SEQ ID NO:14, SEQ ID NO: 18, SEQ ID NO:22, SEQ ID NO:24, SEQ ID NO:26, SEQ ID NO:28, SEQ ID NO:34, SEQ ID NO:38, SEQ ID NO:40, SEQ ID NO:43, SEQ ID NO:47, SEQ ID NO:51, SEQ ID NO:55, SEQ ID NO:59, SEQ ID NO:63, SEQ ID NO:65, or SEQ ID NO:96, and wherein said antibody or antigen-binding portion specifically binds FXIa.

An anti-FXIa antibody of the disclosure may comprise a heavy chain comprising a VH comprising the amino acid sequence of SEQ ID NO: 1, SEQ ID NO: 14, SEQ ID NO: 18, SEQ ID NO:22, SEQ ID NO:24, SEQ ID NO:26, SEQ ID NO:28, SEQ ID NO:34, SEQ ID NO:38, SEQ ID NO:40, SEQ ID NO:43, SEQ ID NO:47, SEQ ID NO:51, SEQ ID NO:55, SEQ ID NO:59, SEQ ID NO:63, SEQ ID NO:65, or SEQ ID NO:96, wherein the antibody further comprises a heavy chain constant domain. As more fully set forth elsewhere herein, the antibody heavy chain constant domain can be selected from an $IgG_1$, $IgG_2$, $IgG_3$, $IgG_4$, IgA, IgE, IgM or IgD constant region, but most preferably is an $IgG_1$ or $IgG_2$ constant region. The IgG constant region sequence can be any of the various alleles or allotypes known to occur among different individuals, such as Gm(1), Gm(2), Gm(3), and Gm(17). For a Fab fragment heavy chain gene, the VH-encoding DNA can be operatively linked to another DNA molecule encoding only the heavy chain CH1 constant region. The CH1 heavy chain constant region may be derived from any of the heavy chain genes.

In one aspect, the antibody may comprise a heavy chain comprising a VH selected from a VH comprising the amino acid sequence of SEQ ID NO: 1, SEQ ID NO: 14, SEQ ID NO:18, SEQ ID NO:22, SEQ ID NO:24, SEQ ID NO:26, SEQ ID NO:28, SEQ ID NO:34, SEQ ID NO:38, SEQ ID NO:40, SEQ ID NO:43, SEQ ID NO:47, SEQ ID NO:51, SEQ ID NO:55, SEQ ID NO:59, SEQ ID NO:63, SEQ ID NO:65, or SEQ ID NO:96, and further comprising the IgG1 constant domain comprising a triple mutation decreasing or abolishing Fc effector function. In one aspect, said antibody variant comprises 1, 2, 3, 4, 5, 6, 7, 8, 9, 10, 11, 12, 13, 14, or 15 conservative or non-conservative substitutions, and/or 1, 2, 3, 4, 5, 6, 7, 8, 9, 10, 11, 12, 13, 14, or 15 additions and/or deletions to the full length heavy chain. In a further aspect, said variant shares at least 65%, at least 75%, at least 85%, at least 90%, at least 95%, at least 96%, at least 97%, at least 98%, or at least 99% sequence identity with the full length heavy chain, and wherein said antibody or antigen-binding portion specifically binds FXIa. In some embodiments, the antibody comprises a heavy chain constant domain comprising the amino acid sequence of SEQ ID NO:82 or SEQ ID NO: 103.

An antibody of the disclosure may comprise a light chain comprising a VL comprising the amino acid sequence of SEQ ID NO: 7, SEQ ID NO: 17, SEQ ID NO:21, SEQ ID NO:23, SEQ ID NO:25, SEQ ID NO:27, SEQ ID NO:31, SEQ ID NO:37, SEQ ID NO:39, SEQ ID NO:42, SEQ ID NO:46, SEQ ID NO:50, SEQ ID NO:54, SEQ ID NO:58, SEQ ID NO:62, SEQ ID NO:64, SEQ ID NO:68, or SEQ ID NO:97, wherein the antibody further comprises a light chain constant domain. The antibody light chain constant domain can be selected from a Cκ or Cλ constant region, for example the constant region of SEQ ID NO:83. In one aspect, said antibody variant comprises 1, 2, 3, 4, 5, 6, 7, 8, 9, 10, 11, 12, 13, 14, or 15 conservative or non-conservative substitutions, and/or 1, 2, 3, 4, 5, 6, 7, 8, 9, 10, 11, 12, 13, 14, or 15 additions and/or deletions to the full length light chain. In a further aspect, said variant shares at least 65%, at least 75%, at least 85%, at least 90%, at least 95%, at least 96%, at least 97%, at least 98%, or at least 99% sequence identity with the full length light chain, and wherein said antibody or antigen-binding portion specifically binds FXIa. In some embodiments, the antibody comprises a light chain constant domain comprising the amino acid sequence of SEQ ID NO:83.

An antibody of the disclosure may comprise a fragment of one of the VL or VH amino acid sequences shown in Table 5. For example, an antibody of the disclosure may comprise a fragment of at least 7, at least 8, at least 9, at least 10, at least 12, at least 15, at least 18, at least 20 or at least 25 consecutive amino acids from a VH comprising SEQ ID NO: 1, SEQ ID NO: 14, SEQ ID NO: 18, SEQ ID NO:22, SEQ ID NO:24, SEQ ID NO:26, SEQ ID NO:28, SEQ ID NO:34, SEQ ID NO:38, SEQ ID NO:40, SEQ ID NO:43, SEQ ID NO:47, SEQ ID NO:51, SEQ ID NO:55, SEQ ID NO:59, SEQ ID NO:63, SEQ ID NO:65, or SEQ ID NO:96, and/or from a VL comprising SEQ ID NO: 7, SEQ ID NO: 17, SEQ ID NO:21, SEQ ID NO:23, SEQ ID NO:25, SEQ ID NO:27, SEQ ID NO:31, SEQ ID NO:37, SEQ ID NO:39, SEQ ID NO:42, SEQ ID NO:46, SEQ ID NO:50, SEQ ID NO:54, SEQ ID NO:58, SEQ ID NO:62, SEQ ID NO:64, SEQ ID NO:68, or SEQ ID NO:97. Such a fragment will preferably retain one or more of the functions discussed above, such as the ability to bind to FXIa.

A suitable fragment or variant of any of these VH or VL sequences will retain the ability to bind to FXIa. In some embodiments, it will retain the ability to specifically bind to FXIa. In some embodiments, it will retain the ability to specifically bind to the same or similar epitope or region of the FXIa molecule as the antibody from which it is derived.

An antibody of the disclosure may comprise a CDR region from the specific antibody identified herein, such as a CDR region from within SEQ ID NOs: 7, 17, 21, 23, 25, 27, 31, 37, 39, 42, 46, 50, 54, 58, 62, 64, 68, or 97 or within SEQ ID NOs: 1, 14, 18, 22, 24, 26, 28, 34, 38, 40, 43, 47, 51, 55, 59, 63, 65, or 96. Such an antibody will preferably retain the ability to bind to FXIa as described herein. For example, the CDR sequences of the antibodies D4, DEF, QCA11, B1D2, B10H2, B10E6, B10F6, B10D8, B10B12, S1D4, S10H9, Clone 8, Clone 16, Clone 20, Clone 22, Clone 32, or Clone 24 are shown in Table 5 and in the accompanying Sequence Listing.

In one aspect, the disclosure provides an antibody variant comprising 1, 2, 3, 4, 5, 6, 7, 8, 9, 10, 11, 12, 13, 14, or 15 conservative or non-conservative substitutions, and/or 1, 2, 3, 4, 5, 6, 7, 8, 9, 10, 11, 12, 13, 14, or 15 additions and/or deletions to a CDR listed herein (e.g., a CDR sequence as shown in Table 5). In a further aspect, the variant shares at least 65%, at least 75%, at least 85%, at least 90%, at least 95%, at least 96%, at least 97%, at least 98%, or at least 99% sequence identity with a CDR sequence listed herein (e.g., a CDR sequence as shown in Table 5), and wherein the antibody or antigen-binding portion specifically binds FXIa.

In some embodiments, an anti-FXIa antibody binds to the active site of the catalytic domain of FXIa (e.g., human FXIa). In some embodiments, an anti-FXIa antibody binds to the active site of the catalytic domain of FXIa near the FXIa catalytic triad (e.g., His 431, Asp 480, and Ser 575 in human FXIa). In some embodiments, the anti-FXIa antibody binds to FXIa at one or more of the following residues of FXIa: His 414, Tyr 434, Met 474, Ala 475, Ser 477, Asp 480, Tyr 521, Arg 525, Asp 526, Asp 569, Lys 572, Ser 594, and Gly 598, wherein the FXIa is numbered with reference to the full-length FXIa sequence of SEQ ID NO:98. In some embodiments, the anti-FXIa antibody binds two or more (e.g., 2, 3, 4, 5, 6, 7, 8, 9, 10 or more) of the residues His 414, Tyr 434, Met 474, Ala 475, Ser 477, Asp 480, Tyr 521, Arg 525, Asp 526, Asp 569, Lys 572, Ser 594, and Gly 598 in FXIa, wherein the residues are numbered with reference to the full-length FXIa sequence of SEQ ID NO:98. In some embodiments, the anti-FXI antibody binds to all of the residues His 414, Tyr 434, Met 474, Ala 475. Ser 477, Asp 480, Tyr 521, Arg 525, Asp 526, Asp 569, Lys 572, Ser 594, and Gly 598 of FXIa, wherein the residues are numbered with reference to the full-length FXIa sequence of SEQ ID NO:98 (e.g., a full-length FXIa sequence that includes the native signal peptide). When these residues are instead numbered with reference to a truncated FXIa catalytic domain (i.e., Ile370 to Ala606, for example as shown in SEQ ID NO: 100), the residues are numbered His 27, Tyr 47, Met 87, Ala 88, Ser 90, Asp 93, Tyr 134, Arg 138, Asp 139, Asp 182, Lys 185, Ser 207, and Gly 211, respectively.

In some embodiments, an anti-FXIA antibody can be defined by its paratopes. The definition of the term "paratope" is derived from the above definition of "epitope" by reversing the perspective. Thus, the term "paratope" refers to the area or region on the antibody which specifically binds an antigen, i.e., the amino acid residues on the antibody which make contact with the antigen (FXIa or anti-FXIa antibody) as "contact" is defined elsewhere herein.

In some embodiments, an anti-FXIa antibody comprises a paratope comprising one or more of the residues Leu 99 or Tyr 33, wherein the residues are numbered with reference to the sequence of SEQ ID NO: 101; and or comprises a paratope comprising one or more (e.g., 1, 2, 3, 4, 5, 6, 7, 8, 9 or more) of the residues Ala 25, Gln 27, Arg 30, Asp 32, Ser 67, Thr 69, His 91, Asp 92, Il3 93, or Tyr 94, wherein the residues are numbered with reference to the sequence of SEQ ID NO: 102.

Anti-Idiotipe Antibodies that Specifically Bind to Anti-FXIa Antibodies

In another aspect, the present disclosure relates to anti-idiotype antibodies that specifically bind to an anti-FXIa antibody, such as the anti-FXIa antibodies described herein. In some embodiments, an anti-idiotype antibody specifically binds to the antigen-binding site of the anti-FXIa antibody.

In one embodiment, the disclosure provides an anti-idiotype antibody that binds to the antigen binding site of an anti-FXIa antibody, wherein the anti-idiotype antibody has a light chain sequence, or a portion thereof, and a heavy chain, or a portion thereof, derived from the antibody C4; or a composition (including pharmaceutical compositions) comprising such an antibody. The amino acid sequences of the light chain variable domain (VL) and heavy chain variable domains (VH) of the anti-idiotype antibodies C4 are set forth in Table 5 below.

In some embodiments, an anti-idiotype antibody of the disclosure that specifically binds to the antigen-binding site of an anti-FXIa antibody or antigen-binding portion thereof of the disclosure may comprise both a VH comprising the amino acid sequence of SEQ ID NO:69, and a VL comprising the amino acid sequence of SEQ ID NO:75.

In another aspect, the anti-idiotype antibody comprises a variant of these sequences, wherein such variants can include both conservative and non-conservative substitutions, deletions, and/or additions, and typically include peptides that share at least 60%, at least 65%, at least 70%, at least 75%, at least 80%, at least 85%, at least 87%, at least 89%, at least 90%, at least 91%, at least 92%, at least 93%, at least 94%, at least 95%, at least 96%, at least 97%, at least 98%, or at least 99% sequence identity to any of the specific sequences disclosed herein.

For example, in one aspect, the disclosure provides an isolated antibody or antigen-binding portion thereof that comprises a $V_L$ chain amino acid sequence as set forth in SEQ ID NO:75 or a variant thereof. In one aspect, said antibody variant comprises 1, 2, 3, 4, 5, 6, 7, 8, 9, 10, 11, 12, 13, 14, or 15 conservative or non-conservative substitutions, and/or 1, 2, 3, 4, 5, 6, 7, 8, 9, 10, 11, 12, 13, 14, or 15 additions and/or deletions to SEQ ID NO:75. In a further aspect, said variant shares at least 65%, at least 75%, at least 85%, at least 90%, at least 95%, at least 96%, at least 97%, at least 98%, or at least 99% sequence identity with SEQ ID NO:75 and wherein said antibody or antigen-binding portion specifically binds an anti-FXIa antibody of the disclosure (e.g., DEF).

In a further aspect, the disclosure provides an isolated antibody or antigen-binding portion thereof that comprises a $V_H$ chain amino acid sequence as set forth in SEQ ID NO:69 or a variant thereof. In one aspect, said antibody variant comprises 1, 2, 3, 4, 5, 6, 7, 8, 9, 10, 11, 12, 13, 14, or 15 conservative or non-conservative substitutions, and/or 1, 2, 3, 4, 5, 6, 7, 8, 9, 10, 11, 12, 13, 14, or 15 additions and/or deletions to SEQ ID NO:69. In a further aspect, said variant shares at least 65%, at least 75%, at least 85%, at least 90%, at least 95%, at least 96%, at least 97%, at least 98%, or at least 99% sequence identity with SEQ ID NO:69, and wherein said antibody or antigen-binding portion specifically binds specifically binds an anti-FXIa antibody of the disclosure.

An anti-idiotype antibody of the disclosure may comprise a heavy chain comprising a VH comprising the amino acid sequence of SEQ ID NO:69, wherein the antibody further comprises a heavy chain constant domain. The antibody heavy chain constant domain can be selected from an $IgG_1$, $IgG_2$, $IgG_3$, $IgG_4$, IgA, IgE, IgM or IgD constant region, but most preferably is an IgG or $IgG_2$ constant region. The IgG constant region sequence can be any of the various alleles or allotypes known to occur among different individuals, such as Gm(1), Gm(2). Gm(3), and Gm(17). For a Fab fragment heavy chain gene, the VH-encoding DNA can be operatively linked to another DNA molecule encoding only the heavy chain CH1 constant region. The CH1 heavy chain constant region may be derived from any of the heavy chain genes.

In one aspect, the antibody may comprise a heavy chain comprising a VH comprising the amino acid sequence of SEQ ID NO:69, and further comprising the IgG1 constant domain comprising a triple mutation decreasing or abolishing Fc effector function. In one aspect, said antibody variant comprises 1, 2, 3, 4, 5, 6, 7, 8, 9, 10, 11, 12, 13, 14, or 15 conservative or non-conservative substitutions, and/or 1, 2, 3, 4, 5, 6, 7, 8, 9, 10, 11, 12, 13, 14, or 15 additions and/or deletions to the full length heavy chain. In a further aspect, said variant shares at least 65%, at least 75%, at least 85%, at least 90%, at least 95%, at least 96%, at least 97%, at least 98%, or at least 99% sequence identity with the full length heavy chain, and wherein said antibody or antigen-binding portion specifically binds an anti-FXIa antibody of the disclosure.

An antibody of the disclosure may comprise a light chain comprising a VL comprising the amino acid sequence of SEQ ID NO:75, wherein the antibody further comprises a light chain constant domain. The antibody light chain constant domain can be selected from a Cκ or Cλ constant region, for example the constant region of SEQ ID NO:83. In one aspect, said antibody variant comprises 1, 2, 3, 4, 5, 6, 7, 8, 9, 10, 11, 12, 13, 14, or 15 conservative or non-conservative substitutions, and/or 1, 2, 3, 4, 5, 6, 7, 8, 9, 10, 11, 12, 13, 14, or 15 additions and/or deletions to the full length light chain. In a further aspect, said variant shares at least 65%, at least 75%, at least 85%, at least 90%, at least 95%, at least 96%, at least 97%, at least 98%, or at least 99% sequence identity with the full length light chain, and wherein said antibody or antigen-binding portion specifically binds an anti-FXIa antibody of the disclosure.

An anti-idiotype antibody of the disclosure may comprise a fragment of SEQ ID NO:69 or SEQ ID NO:75 shown in Table 5. For example, an antibody of the disclosure may comprise a fragment of at least 7, at least 8, at least 9, at least 10, at least 12, at least 15, at least 18, at least 20 or at least 25 consecutive amino acids from a VH comprising SEQ ID NO:69, or from a VL comprising SEQ ID NO:75. Such a fragment will preferably retain one or more of the functions discussed above, such as the ability to bind to an anti-FXIa antibody of the disclosure.

A suitable fragment or variant of any of these VH or VL sequences will retain the ability to bind to an anti-FXIa antibody of the disclosure. In some embodiments, it will retain the ability to specifically bind to an anti-FXIa antibody of the disclosure. In some embodiments, it will retain the ability to specifically bind to the same or similar epitope or region of the anti-FXIa antibody (e.g. variable domain) as the antibody from which it is derived.

An antibody of the disclosure may comprise a CDR region from the specific antibody identified herein such as a CDR region from within SEQ ID NO: 69 or within SEQ ID NO:75. Such an antibody will preferably retain the ability to bind to an anti-FXIa antibody of the disclosure as described herein. For example, the CDR sequences of the anti-idiotype antibody C4 are shown in Table 5 and in the accompanying Sequence Listing.

In one aspect, the disclosure provides an antibody variant comprising 1, 2, 3, 4, 5, 6, 7, 8, 9, 10, 11, 12, 13, 14, or 15 conservative or non-conservative substitutions, and/or 1, 2, 3, 4, 5, 6, 7, 8, 9, 10, 11, 12, 13, 14, or 15 additions and/or deletions to the CDRs listed above. In a further aspect, the variant shares at least 65%, at least 75%, at least 85%, at least 90%, at least 95%, at least 96%, at least 97%, at least 98%, or at least 99% sequence identity with the CDR sequences listed above, and wherein the antibody or antigen-binding portion specifically binds an anti-FXIa antibody of the disclosure.

Identification and Characterization of Anti-FXIa Antibodies and Anti-Idiotype Antibodies that Specifically Bind to Anti-F17a Antibodies FXIa antibodies can be identified or characterized using methods known in the art, whereby binding to FXIa is required for selection, and reduction, amelioration, or neutralization of FXIa activity is detected and/or measured, for example, in an in vitro activity assay with a substrate. In some embodiments, an FXIa antibody is identified by incubating a candidate agent (e.g., FXIa) with a substrate and monitoring binding and/or attendant reduction or inhibition of a biological activity of FXIa (e.g. catalytic activity). The binding assay may be performed with, e.g., purified FXIa polypeptide(s) or with human plasma. In one embodiment, the binding assay is a competitive binding assay, where the ability of a candidate antibody to compete with a known FXIa antibody for FXIa binding is evaluated. The assay may be performed in various formats, including the ELISA format. In some embodiments, a FXIa antibody is identified by incubating a candidate antibody with FXIa and monitoring binding.

Anti-idiotype antibodies that specifically bind to the antigen-binding site of an anti-FXIa antibody can be identified or characterized using methods known in the art, whereby reduction, amelioration, or neutralization of anti-FXIa antibody activity (e.g. FXIa inhibitory activity) is detected and/or measured.

Following initial identification, the activity of a candidate FXIa antibody or anti-idiotype antibody specifically binds to the antigen-binding site of an anti-FXIa antibody can be further confirmed and refined by bioassays, known to test the targeted biological activities. In some embodiments, an in vitro biochemical assay is used to further characterize a candidate FXIa antibody or anti-idiotype antibody specifically binds to the antigen-binding site of an anti-FXIa antibody. For example, bioassays can be used to screen candidates directly. Some of the methods for identifying and characterizing FXIa antibody or anti-idiotype antibody are described in detail in the Examples.

FXIa antibodies or anti-idiotype antibodies that specifically bind to the antigen-binding site of an anti-FXIa antibody may be characterized using methods well known in the art. For example, one method is to identify the epitope to which it binds, or "epitope mapping." There are many methods known in the art for mapping and characterizing the location of epitopes on proteins, including solving the crystal structure of an antibody-antigen complex, competition assays, gene fragment expression assays, and synthetic peptide-based assays, as described, for example, in Chapter 11 of Harlow and Lane, Using Antibodies, a Laboratory Manual, Cold Spring Harbor Laboratory Press, Cold Spring Harbor, N.Y., 1999. In an additional example, epitope mapping can be used to determine the sequence to which a FXIa antibody or anti-idiotype antibody of the disclosure binds. Epitope mapping is commercially available from various sources, for example, Pepscan Systems (Edelhertweg 15, 8219 PH Lelystad, The Netherlands). The epitope can be a linear epitope, i.e., contained in a single stretch of amino acids, or a conformational epitope formed by a three-dimensional interaction of amino acids that may not necessarily be contained in a single stretch. Peptides of varying lengths (e.g., at least 4-6 amino acids long) can be isolated or synthesized (e.g., recombinantly) and used for binding assays with a FXIa antibody or anti-idiotype antibody of the disclosure. In another example, the epitope to which the FXIa antibody binds can be determined in a systematic screening by using overlapping peptides derived from the FXIa sequence and determining binding by the antibody. According to the gene fragment expression assays, the open reading frame encoding FXIa can be fragmented either randomly or by specific genetic constructions and the reactivity of the expressed fragments of FXIa with the antibody to be tested is determined. The gene fragments may, for example, be produced by PCR and then transcribed and translated into protein in vitro, in the presence of radioactive amino acids. The binding of the antibody to the radioactively labeled FXIa fragments is then determined by immunoprecipitation and gel electrophoresis. Certain epitopes can also be identified by using large libraries of random peptide sequences displayed on the surface of phage particles (phage libraries) or yeast (yeast display). Alternatively, a defined library of overlapping peptide fragments can be tested for binding to the test antibody in simple binding assays. In an additional example, mutagenesis of an antigen, domain swapping experiments and alanine scanning mutagenesis can be performed to identify residues required, sufficient, and/or necessary for epitope binding. For example, alanine scanning mutagenesis experiments can be performed using a mutant FXIa in which various residues of the FIXa polypeptide have been replaced with alanine. By assessing binding of the antibody to the mutant FXIa, the importance of the particular FXIa residues to antibody binding can be assessed.

In another example, the epitope to which the anti-idiotype antibody binds can be determined in a systematic screening by using overlapping peptides derived from the anti-FXIa antibody sequence and determining binding by the anti-idiotype antibody. According to the gene fragment expression assays, the open reading frame encoding the anti-FXIa antibody can be fragmented either randomly or by specific genetic constructions and the reactivity of the expressed fragments of the anti-FXIa antibody with the antibody to be tested is determined. The gene fragments may, for example, be produced by PCR and then transcribed and translated into protein in vitro, in the presence of radioactive amino acids. The binding of the antibody to the radioactively labeled anti-FXIa antibody fragments is then determined by immunoprecipitation and gel electrophoresis. Certain epitopes can also be identified by using large libraries of random peptide sequences displayed on the surface of phage particles (phage libraries) or yeast (yeast display). Alternatively, a defined library of overlapping peptide fragments can be tested for binding to the test antibody in simple binding assays. In an additional example, mutagenesis of an antigen, domain swapping experiments and alanine scanning mutagenesis can be performed to identify residues required, sufficient, and/or necessary for epitope binding. For example, alanine scanning mutagenesis experiments can be performed using a mutant anti-FXIa antibody in which various residues of the anti-FXIa antibody (e.g. variable domain residues) have been replaced with alanine. By assessing binding of the anti-idiotype antibody to the mutant anti-FXIa antibody, the importance of the particular the anti-FXIa antibody residues to anti-idiotype antibody binding can be assessed.

Yet another method that can be used to characterize an anti-FXIa antibody is to use competition assays with other antibodies known to bind to the same antigen, i.e., various fragments on FXIa, to determine if the anti-FXIa antibody binds to the same epitope as other antibodies. Competition assays are well known to those of skill in the art. Similarly, another method which can be used to characterize an anti-idiotype antibody that specifically binds to the antigen-binding site of an anti-FXIa antibody is to use competition assays with other antibodies known to bind to the same antigen, i.e., various fragments of the anti-FXIa antibody, to determine if the anti-idiotype antibody binds to the same epitope as other antibodies. Competition assays are well known to those of skill in the art.

Further, the epitope for a given antibody/antigen binding pair can be defined and characterized at different levels of detail using a variety of experimental and computational epitope mapping methods. The experimental methods include mutagenesis, X-ray crystallography, Nuclear Magnetic Resonance (NMR) spectroscopy, hydrogen/deuterium exchange Mass Spectrometry (H/D-MS) and various competition binding methods well-known in the art. As each method relies on a unique principle, the description of an epitope is intimately linked to the method by which it has been determined. Thus, the epitope for a given antibody/antigen pair will be defined differently depending on the epitope mapping method employed.

At its most detailed level, the epitope for the interaction between the antigen ("Ag") and the antibody ("Ab") can be defined by the spatial coordinates defining the atomic contacts present in the Ag-Ab interaction, as well as information about their relative contributions to the binding thermodynamics. At a less detailed level the epitope can be characterized by the spatial coordinates defining the atomic contacts between the Ag and Ab. At a further less detailed level the epitope can be characterized by the amino acid residues that it comprises as defined by a specific criterion, e.g., by distance between atoms (e.g., heavy, i.e., non-hydrogen atoms) in the Ab and the Ag. At a further less detailed level the epitope can be characterized through function, e.g. by competition binding with other Abs. The epitope can also be defined more generically as comprising amino acid residues for which substitution by another amino acid will alter the characteristics of the interaction between the Ab and Ag (e.g. using alanine scanning).

From the fact that descriptions and definitions of epitopes, dependent on the epitope mapping method used, are obtained at different levels of detail, it follows that comparison of epitopes for different Abs on the same Ag can similarly be conducted at different levels of detail.

Epitopes described at the amino acid level, e.g., determined from an X-ray structure, are said to be identical if they contain the same set of amino acid residues. Epitopes are said to overlap if at least one amino acid is shared by the epitopes. Epitopes are said to be separate (unique) if no amino acid residue is shared by the epitopes.

Epitopes characterized by competition binding are said to be overlapping if the binding of the corresponding antibodies are mutually exclusive, i.e., binding of one antibody excludes simultaneous or consecutive binding of the other antibody. The epitopes are said to be separate (unique) if the antigen is able to accommodate binding of both corresponding antibodies simultaneously.

The epitope and paratope for a given antibody/antigen pair may be identified by routine methods. For example, in the case of the anti-FXIa antibodies of the disclosure, the general location of an epitope may be determined by assessing the ability of an antibody to bind to different fragments or variant FXIa polypeptides. Similarly, in the case of the anti-idiotype antibodies of the disclosure, the general location of an epitope may be determined by assessing the ability of an antibody to bind to different fragments or variant anti-FXIa antibodies or antigen-binding fragments thereof. The specific amino acids within FXIa that make contact with a FXIa antibody (epitope) and the specific amino acids in an antibody that make contact with FXIa (paratope) may also be determined using routine methods, such as those described in the examples. Similarly, the specific amino acids within the anti-FXIa antibody that make contact with an anti-idiotype antibody (epitope) and the specific amino acids in an anti-idiotype antibody that make contact with the anti-FXIa antibody (paratope) may also be determined using routine methods, such as those described in the examples. For example, the antibody and target molecule may be combined and the antibody/antigen complex may be crystallized. The crystal structure of the complex may be determined and used to identify specific sites of interaction between the antibody and its target.

A FXIa antibody according to the current disclosure may bind to the same epitope or domain of FXIa as the antibodies of the disclosure that are specifically disclosed herein. For example, other as yet unidentified antibodies of the disclosure may be identified by comparing their binding to FXIa with that of any of the following monoclonal antibodies: D4, DEF, QCA11, B1D2, B10H2, B10E6, B10F6, B10D8, B10B12, S1D4, S10H9, Clone 8, Clone 16, Clone 20, Clone 22, Clone 32, Clone 24, and variants thereof; or by comparing the function of yet unidentified antibodies with that of the antibodies described herein; and/or by comparing the epitope/contact residues on FXIa of yet unidentified antibodies with those of the antibodies of the disclosure. Analyses and assays that may be used for the purpose of such identification include assays assessing the competition for binding of FXIa between the antibody of interest and FXIa substrate, in biological activity assays as described in Examples 1-13 and 20-22, and in analysis of the crystal structure of the antibody, such as described in Example 23.

An anti-idiotype antibody antibody according to the disclosure that specifically binds to the antigen-binding site of an anti-FXIa antibody may bind to the same epitope or domain of an anti-FXIa antibody as the anti-idiotype antibodies of the disclosure that are specifically disclosed herein. For example, other as yet unidentified anti-idiotype antibodies of the disclosure may be identified by comparing their binding to an anti-FXIa antibody with that of the monoclonal antibody C4, and variants thereof; or by comparing the function of yet unidentified anti-idiotype antibodies with that of the anti-idiotype antibodies described herein; and/or by comparing the epitope/contact residues on the anti-FXIa antibody of yet unidentified antibodies with those of the anti-idiotype antibodies of the disclosure. Analyses and assays that may be used for the purpose of such identification include assays assessing the competition for binding of anti-FXIa antibody between the anti-idiotype antibody of interest and FXIa, in biological activity assays as described in Examples 14-19, and in analysis of the crystal structure of the antibody.

An anti-FXIa antibody of the disclosure may have the ability to compete or cross-compete with another antibody of the disclosure for binding to FXIa as described herein. For example, an antibody of the disclosure may compete or cross-compete with antibodies described herein for binding to FXIa, or to a suitable fragment or variant of FXIa that is bound by the antibodies disclosed herein.

That is, if a first anti-FXIa antibody competes with a second antibody for binding to FXIa, but it does not compete where the second antibody is first bound to FXIa, it is deemed to "compete" with the second antibody (also referred to as unidirectional competition). Where an antibody competes with another antibody regardless of which antibody is first bound to FXIa, then the antibody "cross-competes" for binding to FXIa with the other antibody. Such competing or cross-competing antibodies can be identified based on their ability to compete/cross-compete with a known antibody of the disclosure in standard binding assays. For example, SPR, e.g. by using a Biacore™ system, ELISA assays or flow cytometry may be used to demonstrate competition/cross-competition. Such competition/cross-competition may suggest that the two antibodies bind to identical, overlapping or similar epitopes.

An anti-idiotype antibody of the disclosure may have the ability to compete or cross-compete with another antibody of the disclosure for binding to an anti-FXIa antibody as described herein. For example, an anti-idiotype antibody of the disclosure may compete or cross-compete with anti-idiotype antibodies described herein for binding to an anti-FXIa antibody, or to a suitable fragment or variant of an anti-FXIa antibody that is bound by the anti-idiotype antibodies disclosed herein.

That is, if a first anti-idiotype antibody competes with a second anti-idiotype antibody for binding to an anti-FXIa antibody, but it does not compete where the second anti-idiotype antibody is first bound to the anti-FXIa antibody, it is deemed to "compete" with the second anti-idiotype antibody (also referred to as unidirectional competition). Where an anti-idiotype antibody competes with another anti-idiotype antibody regardless of which antibody is first bound to the anti-FXIa antibody, then the anti-idiotype antibody "cross-competes" for binding to the anti-FXIa antibody with the other anti-idiotype antibody. Such competing or cross-competing anti-idiotype antibodies can be identified based on their ability to compete/cross-compete with a known anti-idiotype antibody of the disclosure in standard binding assays. For example, SPR, e.g. by using a Biacore™ system, ELISA assays or flow cytometry may be used to demonstrate competition/cross-competition. Such competition/cross-competition may suggest that the two anti-idiotype antibodies bind to identical, overlapping or similar epitopes.

An anti-FXIa antibody of the disclosure may therefore be identified by a method that comprises a binding assay which assesses whether or not a test antibody is able to compete/cross-compete with a reference antibody of the disclosure (e.g., D4, DEF, QCA11, B1D2, B10H2, B10E6, B10F6, B10D8, B10B12, S1D4, S10H9, Clone 8, Clone 16, Clone 20, Clone 22, Clone 32, Clone 24) for a binding site on the target molecule. Similarly, an anti-idiotype antibody of the disclosure may be identified by a method that comprises a binding assay which assesses whether or not a test antibody is able to compete/cross-compete with a reference antibody of the disclosure (e.g., C4). Methods for carrying out competitive binding assays are disclosed herein and/or are well known in the art. For example they may involve binding a reference antibody of the disclosure to a target molecule using conditions under which the antibody can bind to the target molecule. The antibody/target complex may then be exposed to a test/second antibody and the extent to which the test antibody is able to displace the reference antibody of the disclosure from antibody/target complexes may be assessed. An alternative method may involve contacting a test antibody with a target molecule under conditions that allow for antibody binding, then adding a reference antibody of the disclosure that is capable of binding that target molecule and assessing the extent to which the reference antibody of the disclosure is able to displace the test antibody from antibody/target complexes or to simultaneously bind to the target (i.e., non-competing antibody).

The ability of a test antibody to inhibit the binding of a reference antibody of the disclosure to the target demonstrates that the test antibody can compete with a reference antibody of the disclosure for binding to the target and thus that the test antibody binds to the same, or substantially the same, epitope or region on the FXIa protein as the reference antibody of the disclosure. A test antibody that is identified as competing with a reference antibody of the disclosure in such a method is also an antibody of the present disclosure. The fact that the test antibody can bind FXIa in the same region as a reference antibody of the disclosure and can compete with the reference antibody of the disclosure suggests that the test antibody may act as an inhibitor at the same binding site as the antibody of the disclosure and that the test antibody may therefore mimic the action of the reference antibody and is, thus, an antibody of the disclosure. This can be confirmed by comparing the activity of FXIa in the presence of the test antibody with the activity of FXIa in the presence of the reference antibody under otherwise identical conditions, using an assay as more fully described elsewhere herein.

The reference antibody of the disclosure may be an antibody as described herein, such as D4, DEF, QCA11, B1D2, B10H2, B10E6, B10F6, B10D8, B10B12, S1D4, S10H9, Clone 8, Clone 16, Clone 20, Clone 22, Clone 32, Clone 24, or any variant, or fragment thereof, as described herein that retains the ability to bind to FXIa. An antibody of the disclosure may bind to the same epitope as the reference antibodies described herein or any variant or fragment thereof as described herein that retains the ability to bind to FXIa.

The ability of a test anti-idiotype antibody to inhibit the binding of a reference anti-idiotype antibody of the disclosure to the target demonstrates that the test antibody can compete with a reference antibody of the disclosure for binding to the target and thus that the test antibody binds to the same, or substantially the same, epitope or region on the anti-FXIa antibody as the reference antibody of the disclosure. A test antibody that is identified as competing with a reference antibody of the disclosure in such a method is also an antibody of the present disclosure. The fact that the test antibody can bind an anti-FXIa antibody in the same region as a reference antibody of the disclosure and can compete with the reference antibody of the disclosure suggests that the test antibody may act as an inhibitor at the same binding site as the antibody of the disclosure and that the test antibody may therefore mimic the action of the reference antibody and is, thus, an antibody of the disclosure. This can be confirmed by comparing the activity of the anti-FXIa antibody in the presence of the test antibody with the activity of the anti-FXIa antibody in the presence of the reference antibody under otherwise identical conditions, using an assay as more fully described elsewhere herein.

The reference antibody of the disclosure may be an antibody as described herein, such as C4, or any variant, or fragment thereof, as described herein that retains the ability to bind to an anti-FXIa antibody. An antibody of the disclosure may bind to the same epitope as the reference antibodies described herein or any variant or fragment thereof as described herein that retains the ability to bind to an anti-FXIa antibody.

As stated previously elsewhere herein, specific binding may be assessed with reference to binding of the antibody to a molecule that is not the target. This comparison may be made by comparing the ability of an antibody to bind to the target and to another molecule. This comparison may be made as described above in an assessment of $K_D$ or $K_i$. The other molecule used in such a comparison may be any molecule that is not the target molecule. Preferably, the other molecule is not identical to the target molecule. Preferably the target molecule is not a fragment of the target molecule.

The other molecule used to determine specific binding may be unrelated in structure or function to the target. For example, the other molecule may be an unrelated material or accompanying material in the environment.

The other molecule used to determine specific binding may be another molecule involved in the same in vivo pathway as the target molecule, i.e., FXIa, in the case of an anti-FXIa antibody of the disclosure. By ensuring that the antibody of the disclosure has specificity for FXIa over another such molecule, unwanted in vivo cross-reactivity may be avoided. For example, in some embodiments, the anti-FXIa antibody of the disclosure fails to inhibit the ability of human plasma kallikrein, a protease closely related to human factor XIa, to cleave small fluorogenic substrates. Similarly, in the case of an anti-idiotype antibody of the disclosure, the other molecule used to determine specific binding may be another anti-FXIa antibody. By ensuring that the antibody of the disclosure has specificity for one anti-FXIa antibody over another such molecule, unwanted in vivo cross-reactivity may be avoided.

In some embodiments, the antibody of the disclosure may retain the ability to bind to some molecules that are related to the target molecule.

Alternatively, the anti-FXIa antibody of the disclosure may have specificity for a particular target molecule. For example, it may bind to one target molecule as described herein, but may not bind, or may bind with significantly reduced affinity to a different target molecule as described herein. For example, a full length mature human FXIa may be used as the target, but the antibody that binds to that target may be unable to bind to or may bind with lesser affinity to, e.g. other FXIa proteins from other species, such as other mammalian FXIa. In some embodiments, the antibody binds to both human and cynomolgus FXIa. In some embodiments, the antibody binds to one or more of human, cynomolgus, and rabbit FXIa.

The anti-idiotype antibody of the disclosure may have specificity for a particular anti-FXIa antibody (e.g. D4, DEF, QCA11, B1D2, B10H2, B10E6, B10F6, B10D8, B10B12, S1D4, S10H9, Clone 8, Clone 16, Clone 20, Clone 22, Clone 32, Clone 24). In some embodiments, the anti-idiotype antibody of the disclosure may have specificity for DEF.

Antibody Fragments and Variants

In some embodiments, an antibody comprises an antibody fragment, e.g., an antigen-binding fragment (Fab) or a single chain variable fragment (scFv). Polypeptide or antibody "fragments" or "portions" according to the disclosure may be made by truncation, e.g. by removal of one or more amino acids from the N and/or C-terminal ends of a polypeptide. Up to 10, up to 20, up to 30, up to 40 or more amino acids may be removed from the N and/or C terminal in this way. Fragments may also be generated by one or more internal deletions.

An anti-FXIa antibody of the disclosure may be, or may comprise, a fragment of, any one of antibodies D4, DEF, QCA11, B1D2, B10H2, B10E6, B10F6, B10D8, B10B12, S1D4, S10H9, Clone 8, Clone 16, Clone 20, Clone 22, Clone 32, Clone 24, or a variant thereof. The FXIa antibody of the disclosure may be or may comprise an antigen-binding portion of this antibody or a variant thereof. For example, the antibody of the disclosure may be a Fab fragment of this antibody or a variant thereof or may be a single chain antibody derived from this antibody or a variant thereof.

An anti-idiotype antibody of the disclosure may be, or may comprise, a fragment of, antibody C4, or a variant thereof. The anti-idiotype antibody of the disclosure may be or may comprise an antigen-binding portion of this antibody or a variant thereof. For example, the antibody of the disclosure may be a Fab fragment of this antibody or a variant thereof or may be a single chain antibody derived from this antibody or a variant thereof.

A variant antibody may comprise 1, 2, 3, 4, 5, up to 10, up to 20, up to 30 or more amino acid substitutions and/or deletions and/or insertions from the specific sequences and fragments discussed above. "Deletion" variants may comprise the deletion of individual amino acids, deletion of small groups of amino acids such as 2, 3, 4 or 5 amino acids, or deletion of larger amino acid regions, such as the deletion of specific amino acid domains or other features. "Insertion" variants may comprise the insertion of individual amino acids, insertion of small groups of amino acids such as 2, 3, 4 or 5 amino acids, or insertion of larger amino acid regions, such as the insertion of specific amino acid domains or other features. "Substitution" variants preferably involve the replacement of one or more amino acids with the same number of amino acids and making conservative amino acid substitutions. For example, an amino acid may be substituted with an alternative amino acid having similar properties, for example, another basic amino acid, another acidic amino acid, another neutral amino acid, another charged amino acid, another hydrophilic amino acid, another hydrophobic amino acid, another polar amino acid, another aromatic amino acid or another aliphatic amino acid. Some properties of the 20 main amino acids which can be used to select suitable substituents are as described below.

Substitution variants have at least one amino acid residue in the antibody molecule removed and a different residue inserted in its place. The sites of greatest interest for substitutional mutagenesis include the hypervariable regions, but framework alterations are also contemplated. Conservative substitutions are shown in Table 1 under the heading of "conservative substitutions." If such substitutions result in a change in biological activity, then more substantial changes, denominated "exemplary substitutions" shown below, or as further described below in reference to amino acid classes, may be introduced and the products screened.

TABLE 1

Amino Acid Substitutions

| Original Residue | Conservative Substitutions | Exemplary Substitutions |
| --- | --- | --- |
| Ala (A) | Val | Val; Leu; Ile |
| Arg (R) | Lys | Lys; Gln; Asn |
| Asn (N) | Gln | Gln; His; Asp, Lys; Arg |
| Asp (D) | Glu | Glu; Asn |
| Cys (C) | Ser | Ser; Ala |
| Gln (Q) | Asn | Asn; Glu |
| Glu (E) | Asp | Asp; Gln |
| Gly (G) | Ala | Ala |
| His (H) | Arg | Asn; Gln; Lys; Arg |
| Ile (I) | Leu | Leu; Val; Met; Ala; Phe; Norleucine |
| Leu (L) | Ile | Norleucine; Ile; Val; Met; Ala; Phe |
| Lys (K) | Arg | Arg; Gln; Asn |
| Met (M) | Leu | Leu; Phe; Ile |
| Phe (F) | Tyr | Leu; Val; Ile; Ala; Tyr |
| Pro (P) | Ala | Ala |
| Ser (S) | Thr | Thr |
| Thr (T) | Ser | Ser |
| Trp (W) | Tyr | Tyr; Phe |
| Tyr (Y) | Phe | Trp; Phe; Thr; Ser |
| Val (V) | Leu | Ile; Leu; Met; Phe; Ala; Norleucine |

Substantial modifications in the biological properties of the antibody are accomplished by selecting substitutions that differ significantly in their effect on maintaining (a) the structure of the polypeptide backbone in the area of the substitution, for example, as a β-sheet or helical conformation, (b) the charge or hydrophobicity of the molecule at the target site, or (c) the bulk of the side chain. Naturally occurring residues are divided into groups based on common side-chain properties:

(1) Non-polar: Norleucine, Met, Ala, Val, Leu, Ile;
(2) Polar without charge: Cys, Ser, Thr, Asn, Gln;
(3) Acidic (negatively charged): Asp, Glu;
(4) Basic (positively charged): Lys, Arg;
(5) Residues that influence chain orientation: Gly, Pro; and
(6) Aromatic: Trp, Tyr, Phe, His.

Non-conservative substitutions are made by exchanging a member of one of these classes for another class.

One type of substitution, for example, that may be made is to change one or more cysteines in the antibody, which may be chemically reactive, to another residue, such as, without limitation, alanine or serine. For example, there can be a substitution of a non-canonical cysteine. The substitution can be made in a CDR or framework region of a variable domain or in the constant region of an antibody. In some embodiments, the cysteine is canonical. Any cysteine residue not involved in maintaining the proper conformation of the antibody also may be substituted, generally with serine, to improve the oxidative stability of the molecule and prevent aberrant cross-linking. Conversely, cysteine bond(s) may be added to the antibody to improve its stability, particularly where the antibody is an antibody fragment such as an Fv fragment.

Generation and Modification of Anti-FXIa Antibodies and Anti-Idiotype Antibodies The disclosure also provides methods of generating, selecting, and making anti-FXIa antibodies and anti-idiotype antibodies. The antibodies of this disclosure (e.g. anti-FXIa antibodies, anti-idiotype antibodies that specifically bind to the antigen-binding site of an anti-FXIa antibody) can be made by procedures known in the art. In some embodiments, antibodies may be made recombinantly and expressed using any method known in the art. General techniques for production of human and mouse antibodies are known in the art and/or are described herein.

In some embodiments, antibodies may be prepared and selected by phage display technology. See, for example, U.S. Pat. Nos. 5,565,332; 5,580,717; 5,733,743; and 6,265,150; and Winter et al., Annu. Rev. Immunol. 12:433-455, 1994. Alternatively, the phage display technology (McCafferty et al., Nature 348:552-553, 1990) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B cell. Phage display can be performed in a variety of formats; for review see, e.g., Johnson, Kevin S, and Chiswell, David J., *Current Opinion in Structural Biology* 3:564-571, 1993. Several sources of V-gene segments can be used for phage display. Clackson et al., *Nature* 352:624-628, 1991, isolated a diverse array of anti-oxazolone antibodies from a small random combinatorial library of V genes derived from the spleens of immunized mice. A repertoire of V genes from human donors can be constructed and antibodies to a diverse array of antigens (including self-antigens) can be isolated essentially following the techniques described by Mark et al., 1991, *J. Mol. Biol.* 222:581-597, or Griffith et al., 1993, *EMBO J.* 12:725-734. In a natural immune response, antibody genes accumulate mutations at a high rate (somatic hypermutation). Some of the changes introduced will confer higher affinity, and B cells displaying high-affinity surface immunoglobulin are preferentially replicated and differentiated during subsequent antigen challenge. This natural process can be mimicked by employing the technique known as "chain shuffling." (Marks et al., 1992, *Bio/Technol.* 10:779-783). In this method, the affinity of "primary" human antibodies obtained by phage display can be improved by sequentially replacing the heavy and light chain V region genes with repertoires of naturally occurring variants (repertoires) of V domain genes obtained from unimmunized donors. This technique allows the production of antibodies and antibody fragments with affinities in the pM-nM range. A strategy for making very large phage antibody repertoires (also known as "the mother-of-all libraries") has been described by Waterhouse et al., *Nucl. Acids Res.* 21:2265-2266, 1993. Gene shuffling can also be used to derive human antibodies from rodent antibodies, where the human antibody has similar affinities and specificities to the starting rodent antibody. According to this method, which is also referred to as "epitope imprinting," the heavy or light chain V domain gene of rodent antibodies obtained by phage display technique is replaced with a repertoire of human V domain genes, creating rodent-human chimeras. Selection on antigen results in isolation of human variable regions capable of restoring a functional antigen-binding site, i.e., the epitope governs (imprints) the choice of partner. When the process is repeated in order to replace the remaining rodent V domain, a human antibody is obtained (see PCT Publication No. WO 93/06213). Unlike traditional humanization of rodent antibodies by CDR grafting, this technique provides completely human antibodies, which have no framework or CDR residues of rodent origin.

In some embodiments, antibodies may be made using hybridoma technology. It is contemplated that any mammalian subject including humans or antibody producing cells therefrom can be manipulated to serve as the basis for production of mammalian, including human, hybridoma cell lines. The route and schedule of immunization of the host animal are generally in keeping with established and conventional techniques for antibody stimulation and production, as further described herein. Typically, the host animal is inoculated intraperitoneally, intramuscularly, orally, subcutaneously, intraplantar, and/or intradermally with an amount of immunogen, including as described herein.

Hybridomas can be prepared from the lymphocytes and immortalized myeloma cells using the general somatic cell hybridization technique of Kohler, B, and Milstein, C., 1975, Nature 256:495497 or as modified by Buck, D. W., et al., *In Vitro*, 18:377-381, 1982. Available myeloma lines, including but not limited to X63-Ag8.653 and those from the Salk Institute, Cell Distribution Center, San Diego, Calif., USA, may be used in the hybridization. Generally, the technique involves fusing myeloma cells and lymphoid cells using a fusogen such as polyethylene glycol, or by electrical means well known to those skilled in the art. After the fusion, the cells are separated from the fusion medium and grown in a selective growth medium, such as hypoxanthine-aminopterin-thymidine (HAT) medium, to eliminate unhybridized parent cells. Any of the media described herein, supplemented with or without serum, can be used for culturing hybridomas that secrete monoclonal antibodies. As another alternative to the cell fusion technique, EBV immortalized B cells may be used to produce the anti-FXIa monoclonal antibodies and/or the anti-idiotype antibodies of the disclosure. The hybridomas or other immortalized B-cells are expanded and subcloned, if desired, and supernatants are assayed for anti-immunogen activity by conventional immunoassay procedures (e.g., radioimmunoassay, enzyme immunoassay, or fluorescence immunoassay).

Hybridomas that may be used as source of anti-FXIa antibodies encompass all derivatives, progeny cells of the parent hybridomas that produce monoclonal antibodies specific for FXIa, or a portion thereof. Hybridomas that may be used as source of anti-idiotype antibodies encompass all derivatives, progeny cells of the parent hybridomas that produce monoclonal anti-idiotype antibodies specific for an anti-FXIa antibody, or a portion thereof.

Hybridomas that produce such anti-FXIa antibodies or anti-idiotype antibodies may be grown in vitro or in vivo using known procedures. The monoclonal antibodies may be isolated from the culture media or body fluids, by conventional immunoglobulin purification procedures such as ammonium sulfate precipitation, gel electrophoresis, dialysis, chromatography, and ultrafiltration, if desired. Undesired activity, if present, can be removed, for example, by running the preparation over adsorbents made of the immunogen attached to a solid phase and eluting or releasing the desired antibodies off the immunogen. Immunization of a host animal with FXIa polypeptide, or a fragment containing the target amino acid sequence conjugated to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$ where R and $R^1$ are different alkyl groups, can yield a population of antibodies (e.g., monoclonal anti-FXIa antibodies). Immunization of a host animal with an anti-FXIa polypeptide, or a fragment containing the target amino acid sequence (e.g. variable domain sequence) conjugated to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups, can yield a population of antibodies (e.g., monoclonal anti-idiotype antibodies).

If desired, the anti-FXIa antibody or anti-idiotype antibody (monoclonal or polyclonal) of interest may be sequenced and the polynucleotide sequence may then be cloned into a vector for expression or propagation. The sequence encoding the antibody of interest may be maintained in vector in a host cell and the host cell can then be expanded and frozen for future use. Production of recombinant monoclonal antibodies in cell culture can be carried out through cloning of antibody genes from B cells by means known in the art. See, e.g. Tiller et al., 2008, J. Immunol. Methods 329, 112. U.S. Pat. No. 7,314,622.

In some embodiments, the polynucleotide sequence may be used for genetic manipulation to "humanize" the antibody or to improve the affinity, or other characteristics of the antibody. Antibodies may also be customized for use, for example, in dogs, cats, primate, equines and bovines.

In some embodiments, fully human antibodies may be obtained by using commercially available mice that have been engineered to express specific human immunoglobulin proteins. Transgenic animals that are designed to produce a more desirable (e.g., fully human antibodies) or more robust immune response may also be used for generation of humanized or human antibodies. Examples of such technology are Xenomouse™ from Abgenix, Inc. (Fremont, Calif.) and HuMAb-Mouse® and TC Mouse™ from Medarex, Inc. (Princeton, N.J.).

Antibodies may be made recombinantly by first isolating the antibodies and antibody producing cells from host animals, obtaining the gene sequence, and using the gene sequence to express the antibody recombinantly in host cells (e.g., CHO cells). Another method which may be employed is to express the antibody sequence in plants (e.g., tobacco) or transgenic milk. Methods for expressing antibodies recombinantly in plants or milk have been disclosed. See, for example, Peeters, et al. Vaccine 19:2756, 2001; Lonberg, N, and D. Huszar Int. Rev. Immunol 13:65, 1995, and Pollock, et al., J Immunol Methods 231:147, 1999. Methods for making derivatives of antibodies, e.g., domain, single chain, etc. are known in the art.

Immunoassays and flow cytometry sorting techniques such as fluorescence activated cell sorting (FACS) can also be employed to isolate antibodies that are specific for FXIa. These assays can also be employed to isolate antibodies that are specific for an anti-FXIa antibody (e.g., DEF).

DNA encoding the monoclonal antibodies is readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into expression vectors (such as expression vectors disclosed in PCT Publication No. WO 87/04462), which are then transfected into host cells such as E. coli cells, simian COS cells, Chinese hamster ovary (CHO) cells, or myeloma cells that do not otherwise produce immunoglobulin protein, to obtain the synthesis of monoclonal antibodies in the recombinant host cells. See, e.g., PCT Publication No. WO 87/04462. The DNA also may be modified, for example, by substituting the coding sequence for human heavy and light chain constant domains in place of the homologous murine sequences, Morrison et al., Proc. Nat. Acad. Sci. 81:6851, 1984, or by covalently joining to the immunoglobulin coding sequence all or part of the coding sequence for a non-immunoglobulin polypeptide. In that manner, "chimeric" or "hybrid" antibodies are prepared that have the binding specificity of for example, an anti-FXIa antibody herein or an anti-idiotype antibody herein.

Antibody fragments can be produced by proteolytic or other degradation of the antibodies, by recombinant methods (i.e., single or fusion polypeptides) as described above or by chemical synthesis. Polypeptides of the antibodies, especially shorter polypeptides up to about 50 amino acids, are conveniently made by chemical synthesis. Methods of chemical synthesis are known in the art and are commercially available. For example, an antibody could be produced by an automated polypeptide synthesizer employing the solid phase method. See also, U.S. Pat. Nos. 5,807,715; 4,816,567; and 6,331,415.

In some embodiments, a polynucleotide comprises a sequence encoding the heavy chain and/or the light chain variable regions of an anti-FXIa antibody of the present disclosure. The sequence encoding the antibody of interest may be maintained in a vector in a host cell and the host cell can then be expanded and frozen for future use. Vectors (including expression vectors) and host cells are further described herein.

In some embodiments, a polynucleotide comprises a sequence encoding the heavy chain and/or the light chain variable regions of an anti-idiotype antibody of the present disclosure. The sequence encoding the antibody of interest may be maintained in a vector in a host cell and the host cell can then be expanded and frozen for future use. Vectors (including expression vectors) and host cells are further described herein.

The disclosure includes affinity-matured embodiments. For example, affinity matured antibodies can be produced by procedures known in the art (Marks et al., 1992, *Bio/Technology*, 10:779-783: Barbas et al., 1994, *Proc Nat. Acad. Sci, USA* 91:3809-3813; Schier et al., 1995, *Gene*, 169:147-155: Yelton et al., 1995, *J. Immunol.*, 155:1994-2004; Jackson et al., 1995, *J. Immunol.*, 154(7):3310-9; Hawkins et al., 1992, *J. Mol. Biol.*, 226:889-896; and PCT Publication No. WO2004/058184).

The following methods may be used for adjusting the affinity of an antibody and for characterizing a CDR. One way of characterizing a CDR of an antibody and/or altering (such as improving) the binding affinity of a polypeptide, such as an antibody, termed "library scanning mutagenesis." Generally, library scanning mutagenesis works as follows. One or more amino acid positions in the CDR are replaced with two or more (such as 3, 4, 5, 6, 7, 8, 9, 10, 11, 12, 13, 14, 15, 16, 17, 18, 19, or 20) amino acids using art recognized methods. This generates small libraries of clones (in some embodiments, one for every amino acid position that is analyzed), each with a complexity of two or more members (if two or more amino acids are substituted at every position). Generally, the library also includes a clone comprising the native (unsubstituted) amino acid. A small number of clones, e.g., about 20-80 clones (depending on the complexity of the library), from each library are screened for binding affinity to the target polypeptide (or other binding target), and candidates with increased, the same, decreased, or no binding are identified. Methods for determining binding affinity are well-known in the art. Binding affinity may be determined using, for example, Biacore™ surface plasmon resonance analysis, which detects differences in binding affinity of about 2-fold or greater, Kinexa® Biosensor, scintillation proximity assays, ELISA, ORIGEN® immunoassay, fluorescence quenching, fluorescence transfer, and/or yeast display. Binding affinity may also be screened using a suitable bioassay. Biacore™ is particularly useful when the starting antibody already binds with a relatively high affinity, for example a $K_D$ of about 10 nM or lower.

In some embodiments, every amino acid position in a CDR is replaced (in some embodiments, one at a time) with all 20 natural amino acids using art recognized mutagenesis methods (some of which are described herein). This generates small libraries of clones (in some embodiments, one for every amino acid position that is analyzed), each with a complexity of 20 members (if all 20 amino acids are substituted at every position).

In some embodiments, the library to be screened comprises substitutions in two or more positions, which may be in the same CDR or in two or more CDRs. Thus, the library may comprise substitutions in two or more positions in one CDR. The library may comprise substitution in two or more positions in two or more CDRs. The library may comprise substitution in 3, 4, 5, or more positions, said positions found in two, three, four, five or six CDRs. The substitution may be prepared using low redundancy codons. See, e.g., Table 2 of Balint et al., 1993, *Gene* 137(1):109-18.

The CDR may be heavy chain variable region (VH) CDR3 and/or light chain variable region (VL) CDR3. The CDR may be one or more of VH CDR1, VH CDR2, VH CDR3, VL CDR1, VL CDR2, and/or VL CDR3. The CDR may be a Kabat CDR, a Chothia CDR, an extended CDR, an AbM CDR, a contact CDR, or a conformational CDR.

Candidates with improved binding may be sequenced, thereby identifying a CDR substitution mutant which results in improved affinity (also termed an "improved" substitution). Candidates that bind may also be sequenced, thereby identifying a CDR substitution which retains binding.

Multiple rounds of screening may be conducted. For example, candidates (each comprising an amino acid substitution at one or more position of one or more CDR) with improved binding are also useful for the design of a second library containing at least the original and substituted amino acid at each improved CDR position (i.e., amino acid position in the CDR at which a substitution mutant showed improved binding). Preparation, and screening or selection of this library is discussed further below.

Library scanning mutagenesis also provides a means for characterizing a CDR, in so far as the frequency of clones with improved binding, the same binding, decreased binding or no binding also provide information relating to the importance of each amino acid position for the stability of the antibody-antigen complex. For example, if a position of the CDR retains binding when changed to all 20 amino acids, that position is identified as a position that is unlikely to be required for antigen binding. Conversely, if a position of CDR retains binding in only a small percentage of substitutions, that position is identified as a position that is important to CDR function. Thus, the library scanning mutagenesis methods generate information regarding positions in the CDRs that can be changed to many different amino acids (including all 20 amino acids), and positions in the CDRs which cannot be changed or which can only be changed to a few amino acids. Candidates with improved affinity may be combined in a second library, which includes the improved amino acid, the original amino acid at that position, and may further include additional substitutions at that position, depending on the complexity of the library that is desired, or permitted using the desired screening or selection method. In addition, if desired, adjacent amino acid position can be randomized to at least two or more amino acids. Randomization of adjacent amino acids may permit additional conformational flexibility in the mutant CDR, which may in turn, permit or facilitate the introduction of a larger number of improving mutations. The library may also comprise substitution at positions that did not show improved affinity in the first round of screening.

The second library is screened or selected for library members with improved and/or altered binding affinity using any method known in the art, including screening using Biacore™, Kinexa™ biosensor analysis, and selection using any method known in the art for selection, including phage display, yeast display, and ribosome display.

To express the anti-FXIa antibodies of the present disclosure, DNA fragments encoding VH and VL regions can first be obtained using any of the methods described above. Various modifications, e.g. mutations, deletions, and/or additions can also be introduced into the DNA sequences using standard methods known to those of skill in the art. For example, mutagenesis can be carried out using standard methods, such as PCR-mediated mutagenesis, in which the mutated nucleotides are incorporated into the PCR primers such that the PCR product contains the desired mutations or site-directed mutagenesis. In some embodiments, a dNTP pool biased mutagenesis may be carried out.

To express the anti-idiotype antibodies of the present disclosure, DNA fragments encoding VH and VL regions can first be obtained using any of the methods described above. Various modifications, e.g. mutations, deletions, and/or additions can also be introduced into the DNA sequences using standard methods known to those of skill in the art. For example, mutagenesis can be carried out using standard methods, such as PCR-mediated mutagenesis, in which the mutated nucleotides are incorporated into the PCR primers such that the PCR product contains the desired mutations or site-directed mutagenesis. In some embodiments, a dNTP pool biased mutagenesis may be carried out.

The disclosure encompasses modifications to the variable regions and the CDRs indicated in Table 3. For example, the disclosure includes antibodies comprising functionally equivalent variable regions and CDRs which do not significantly affect their properties as well as variants which have enhanced or decreased activity and/or affinity. For example, the amino acid sequence may be mutated to obtain an antibody with the desired binding affinity to FXIa. In the case of an anti-idiotype antibody, the amino acid sequence may be mutated to obtain an antibody with the desired binding affinity to an anti-FXIa antibody. Examples of modified polypeptides include polypeptides with conservative substitutions of amino acid residues, one or more deletions or additions of amino acids which do not significantly deleteriously change the functional activity, or which mature (enhance) the affinity of the polypeptide for its ligand, or use of chemical analogs.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to an epitope tag. Other insertional variants of the antibody molecule include the fusion to the N- or C-terminus of the antibody of an enzyme or a polypeptide that increases the half-life of the antibody in the blood circulation.

The antibodies may also be modified, e.g., in the variable domains of the heavy and/or light chains, e.g., to alter a binding property of the antibody. Changes in the variable region can alter binding affinity and/or specificity. In some embodiments, no more than one to five conservative amino acid substitutions are made within a CDR domain. In other embodiments, no more than one to three conservative amino acid substitutions are made within a CDR domain. For example, a mutation may be made in one or more of the CDR regions to increase or decrease the $K_D$ of the anti-FXIa antibody for FXIa, to increase or decrease $k_{off}$, or to alter the binding specificity of the antibody. Similarly, a mutation may be made in one or more of the CDR regions to increase or decrease the $K_D$ of the anti-idiotype antibody for an anti-FXIa antibody, to increase or decrease $k_{off}$, or to alter the binding specificity of the antibodyTechniques in site-directed mutagenesis are well-known in the art. See, e.g., Sambrook et al, and Ausubel et al., supra.

A modification or mutation may also be made in a framework region or constant region to increase the half-life of an an-FXIa antibody or an anti-idiotype antibody. See, e.g., PCT Publication No. WO 00/09560. A mutation in a framework region or constant region can also be made to alter the immunogenicity of the antibody, to provide a site for covalent or non-covalent binding to another molecule, or to alter such properties as complement fixation, FcR binding and antibody-dependent cell-mediated cytotoxicity. A mutation in a framework region can also be made to alter the affinity and potency of the antibody. In some embodiments, the mutation may be a Q->K substitution in the framework region (e.g., in FR1). According to the disclosure, a single antibody may have mutations in any one or more of the CDRs or framework regions of the variable domain or in the constant region.

Modifications also include glycosylated and nonglycosylated polypeptides, as well as polypeptides with other post-translational modifications, such as, for example, glycosylation with different sugars, acetylation, and phosphorylation. Antibodies are glycosylated at conserved positions in their constant regions (Jefferis and Lund, 1997, Chem. Immunol. 65:111-128; Wright and Morrison, 1997, TibTECH 15:26-32). The oligosaccharide side chains of the immunoglobulins affect the protein's function (Boyd et al., 1996, Mol. Immunol. 32:1311-1318; Wittwe and Howard, 1990, Biochem. 29:4175-4180) and the intramolecular interaction between portions of the glycoprotein, which can affect the conformation and presented three-dimensional surface of the glycoprotein (Jefferis and Lund, supra: Wyss and Wagner, 1996, Current Opin. Biotech. 7:409-416). Oligosaccharides may also serve to target a given glycoprotein to certain molecules based upon specific recognition structures. Glycosylation of antibodies has also been reported to affect antibody-dependent cellular cytotoxicity (ADCC). In particular, antibodies produced by CHO cells with tetracycline-regulated expression of β(1,4)-N-acetylglucosaminyltransferase III (GnTIII), a glycosyltransferase catalyzing formation of bisecting GlcNAc, was reported to have improved ADCC activity (Umana et al., 1999, Nature Biotech. 17:176-180).

Glycosylation of antibodies is typically either N-linked or O-linked. N-linked refers to the attachment of the carbohydrate moiety to the side chain of an asparagine residue. The tripeptide sequences asparagine-X-serine, asparagine-X-threonine, and asparagine-X-cysteine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

The glycosylation pattern of antibodies may also be altered without altering the underlying nucleotide sequence. Glycosylation largely depends on the host cell used to express the antibody. Since the cell type used for expression of recombinant glycoproteins. e.g. antibodies, as potential therapeutics is rarely the native cell, variations in the glycosylation pattern of the antibodies can be expected (see, e.g. Hse et al., 1997, J. Biol. Chem. 272:9062-9070).

In addition to the choice of host cells, factors that affect glycosylation during recombinant production of antibodies include growth mode, media formulation, culture density, oxygenation, pH, purification schemes and the like. Various methods have been proposed to alter the glycosylation pattern achieved in a particular host organism including introducing or overexpressing certain enzymes involved in oligosaccharide production (U.S. Pat. Nos. 5,047,335; 5,510,261 and 5,278,299). Glycosylation, or certain types of glycosylation, can be enzymatically removed from the glycoprotein, for example, using endoglycosidase H (Endo H), N-glycosidase F, endoglycosidase F1, endoglycosidase F2, endoglycosidase F3. In addition, the recombinant host cell can be genetically engineered to be defective in processing certain types of polysaccharides. These and similar techniques are well known in the art.

Other methods of modification include using coupling techniques known in the art, including, but not limited to, enzymatic means, oxidative substitution and chelation. Modifications can be used, for example, for attachment of labels for immunoassay. Modified polypeptides are made using established procedures in the art and can be screened using standard assays known in the art, some of which are described below and in the Examples.

In some embodiments, the antibody comprises a modified constant region that has increased or decreased binding affinity to a human Fc gamma receptor, is immunologically inert or partially inert, e.g., does not trigger complement mediated lysis, does not stimulate antibody-dependent cell mediated cytotoxicity (ADCC), or does not activate microglia; or has reduced activities (compared to the unmodified antibody) in any one or more of the following: triggering complement mediated lysis, stimulating ADCC, or activating microglia. Different modifications of the constant region may be used to achieve optimal level and/or combination of effector functions. See, for example, Morgan et al., *Immunology* 86:319-324, 1995; Lund et al., *J. Immunology* 157: 4963-9 157:4963-4969, 1996; Idusogie et al., *J. Immunology* 164:4178-4184, 2000; Tao et al., *J. Immunology* 143: 2595-2601, 1989; and Jefferis et al., *Immunological Reviews* 163:59-76, 1998. In some embodiments, the constant region is modified as described in *Eur. J Immunol.*, 1999, 29:2613-2624; PCT Application No. PCT/GB99/01441; and/or UK Patent Application No. 9809951.8.

In some embodiments, an antibody constant region can be modified to avoid interaction with Fc gamma receptor and the complement and immune systems. The techniques for preparation of such antibodies are described in WO 99/58572. For example, the constant region may be engineered to more resemble human constant regions to avoid immune response if the antibody is used in clinical trials and treatments in humans. See, e.g., U.S. Pat. Nos. 5,997,867 and 5,866,692.

In some embodiments, the constant region is modified as described in *Eur. J. Immunol.*, 1999, 29:2613-2624; PCT Application No. PCT/GB99/01441; and/or UK Patent Application No. 9809951.8. In such embodiments, the Fc can be human IgG$_2$ or human IgG$_4$. The Fc can be human IgG$_2$ containing the mutation A330P331 to S330S331 (IgG$_{2\Delta a}$), in which the amino acid residues are numbered with reference to the wild type IgG$_2$ sequence. *Eur. J. Immunol.*, 1999, 29:2613-2624. In some embodiments, the antibody comprises a constant region of IgG$_4$ comprising the following mutations (Armour et al., 2003, *Molecular Immunology* 40 585-593): E233F234L235 to P233V234A235 (IgG$_{4\Delta c}$), in which the numbering is with reference to wild type IgG$_4$. In yet another embodiment, the Fc is human IgG$_4$ E233F234L235 to P233V234A235 with deletion G236 (IgG$_{4\Delta c}$). In another embodiment, the Fc is any human IgG$_4$ Fc (IgG$_4$, IgG$_{4\Delta b}$ or IgG$_{4\Delta c}$) containing hinge stabilizing mutation S228 to P228 (Aalberse et al., 2002, *Immunology* 105, 9-19).

In some embodiments, the antibody comprises a human heavy chain IgG$_2$ constant region comprising the following mutations: A330P331 to S330S331 (amino acid numbering with reference to the wild type IgG$_2$ sequence). *Eur. J. Immunol.*, 1999, 29:2613-2624. In still other embodiments, the constant region is aglycosylated for N-linked glycosylation. In some embodiments, the constant region is aglycosylated for N-linked glycosylation by mutating the oligosaccharide attachment residue and/or flanking residues that are part of the N-glycosylation recognition sequence in the constant region. For example, N-glycosylation site N297 may be mutated to, e.g., A, Q, K, or H. See, Tao et al., *J. Immunology* 143: 2595-2601, 1989; and Jefferis et al., *Immunological Reviews* 163:59-76, 1998. In some embodiments, the constant region is aglycosylated for N-linked glycosylation. The constant region may be aglycosylated for N-linked glycosylation enzymatically (such as removing carbohydrate by enzyme PNGase), or by expression in a glycosylation deficient host cell.

Other antibody modifications include antibodies that have been modified as described in PCT Publication No. WO 99/58572. These antibodies comprise, in addition to a binding domain directed at the target molecule, an effector domain having an amino acid sequence substantially homologous to all or part of a constant region of a human immunoglobulin heavy chain. These antibodies are capable of binding the target molecule without triggering significant complement dependent lysis, or cell-mediated destruction of the target. In some embodiments, the effector domain is capable of specifically binding FcRn and/or FcγRIIb. These are typically based on chimeric domains derived from two or more human immunoglobulin heavy chain CH2 domains. Antibodies modified in this manner are particularly suitable for use in chronic antibody therapy, to avoid inflammatory and other adverse reactions to conventional antibody therapy.

The disclosure also provides an antibody constant domain that may be further modified. It is known that variants of the Fc region, e.g., amino acid substitutions, insertions, and/or additions and/or deletions, enhance or diminish effector function. See, e.g., Presta et al, 2002, *Biochem. Soc. Trans.* 30:487-490; Strohl, 2009, *Curr. Opin. Biotechnol.* 20(6): 685-691; U.S. Pat. Nos. 5,624,821, 5,648,260, 5,885,573, 6,737,056, 7,317,091; PCT publication Nos. WO 99/58572, WO 00/42072, WO 04/029207, WO 2006/105338, WO 2008/022152, WO 2008/150494, WO 2010/033736; U.S. Patent Application Publication Nos. 2004/0132101, 2006/0024298, 2006/0121032, 2006/0235208, 2007/0148170, and 2015/0337053; Armour et al., 1999, *Eur. J. Immunol.* 29(8):2613-2624 (reduced ADCC and CDC); Shields et al., 2001, *J. Biol. Chem.* 276(9):6591-6604 (reduced ADCC and CDC); Idusogie et al., 2000, *J. Immunol.* 164(8):4178-4184 (increased ADCC and CDC); Steurer et al., 1995, *J. Immunol.* 155(3):1165-1174 (reduced ADCC and CDC); Idusogie et al., 2001, *J. Immunol.* 166(4):2571-2575 (increased ADCC and CDC); Lazar et al., 2006, *Proc. Natl. Acad. Sci. USA* 103(11): 4005-4010 (increased ADCC); Ryan et al., 2007, *Mol. Cancer. Ther.*, 6: 3009-3018 (increased ADCC): Richards et al., 2008, *Mol. Cancer Ther.* 7(8):2517-2527.

In some embodiments, the antibody comprises a modified constant region that has increased binding affinity for FcRn and/or an increased serum half-life as compared with the unmodified antibody.

In a process known as "germlining", certain amino acids in the VH and VL sequences can be mutated to match those found naturally in germline VH and VL sequences. In particular, the amino acid sequences of the framework regions in the VH and VL sequences can be mutated to match the germline sequences to reduce the risk of immunogenicity when the antibody is administered. Germline DNA sequences for human VH and VL genes are known in the art (see e.g., the "Vbase" human germline sequence database; see also Kabat, E. A., et al., 1991, Sequences of Proteins of Immunological Interest, Fifth Edition, U.S. Department of Health and Human Services, NIH Publication No. 91-3242; Tomlinson et al., 1992, J. Mol. Biol. 227:776-798; and Cox et al., 1994, Eur. J. Immunol. 24:827-836).

Another type of amino acid substitution that may be made is to remove potential proteolytic sites in the antibody. Such sites may occur in a CDR or framework region of a variable domain or in the constant region of an antibody. Substitution of cysteine residues and removal of proteolytic sites may decrease the risk of heterogeneity in the antibody product and thus increase its homogeneity. Another type of amino acid substitution is to eliminate asparagine-glycine pairs, which form potential deamidation sites, by altering one or both of the residues. In another example, the C-terminal lysine of the heavy chain of an anti-FXI antibody or anti-idiotype antibody of the disclosure can be cleaved or otherwise removed. In various embodiments of the disclosure, the heavy and light chains of the antibodies may optionally include a signal sequence.

Once DNA fragments encoding the VH and VL segments of the present disclosure are obtained, these DNA fragments can be further manipulated by standard recombinant DNA techniques, for example to convert the variable region genes to full-length antibody chain genes, to Fab fragment genes, or to a scFv gene. In these manipulations, a VL- or VH-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the VH region can be converted to a full-length heavy chain gene by operatively linking the VH-encoding DNA to another DNA molecule encoding heavy chain constant regions (CH1, CH2 and CH3). The sequences of human heavy chain constant region genes are known in the art (see e.g., Kabat, E. A., et al., 1991, Sequences of Proteins of Immunological Interest, Fifth Edition, U.S. Department of Health and Human Services. NIH Publication No. 91-3242) and DNA fragments encompassing these regions can be obtained by standard PCR amplification. The heavy chain constant region can be an $IgG_1$, $IgG_2$, $IgG_3$, $IgG_4$, IgA, IgE, IgM or IgD constant region, but most preferably is an $IgG_1$ or $IgG_2$ constant region. The IgG constant region sequence can be any of the various alleles or allotypes known to occur among different individuals, such as Gm(1), Gm(2), Gm(3), and Gm(17). These allotypes represent naturally occurring amino acid substitution in the IgG1 constant regions. For a Fab fragment heavy chain gene, the VH-encoding DNA can be operatively linked to another DNA molecule encoding only the heavy chain CH1 constant region. The CH1 heavy chain constant region may be derived from any of the heavy chain genes.

The isolated DNA encoding the VL region can be converted to a full-length light chain gene (as well as a Fab light chain gene) by operatively linking the VL-encoding DNA to another DNA molecule encoding the light chain constant region, CL. The sequences of human light chain constant region genes are known in the art (see e.g., Kabat. E. A., et al., 1991, Sequences of Proteins of Immunological Interest, Fifth Edition, U.S. Department of Health and Human Services, NIH Publication No. 91-3242) and DNA fragments encompassing these regions can be obtained by standard PCR amplification. The light chain constant region can be a kappa or lambda constant region. The kappa constant region may be any of the various alleles known to occur among different individuals, such as Inv(1), Inv(2), and Inv(3). The lambda constant region may be derived from any of the three lambda genes.

To create a scFv gene, the VH- and VL-encoding DNA fragments are operatively linked to another fragment encoding a flexible linker such that the VH and VL sequences can be expressed as a contiguous single-chain protein, with the VL and VH regions joined by the flexible linker (See e.g., Bird et al., 1988, Science 242:423-426; Huston et al., 1988, Proc. Natl. Acad. Sci. USA 85:5879-5883; McCafferty et al., 1990, Nature 348:552-554. Linkers of other sequences have been designed and used (Bird et al., 1988, supra). Linkers can in turn be modified for additional functions, such as attachment of drugs or attachment to solid supports. The single chain antibody may be monovalent, if only a single VH and VL are used, bivalent, if two VH and VL are used, or polyvalent, if more than two VH and VL are used. Bispecific or polyvalent antibodies may be generated that bind specifically to FXIa and to another molecule. In some embodiments, bispecific or polyvalent anti-idiotype antibodies may be generated that bind specifically to two or more anti-FXIa antibodies. The single chain variants can be produced either recombinantly or synthetically. For synthetic production of scFv, an automated synthesizer can be used. For recombinant production of scFv, a suitable plasmid containing polynucleotide that encodes the scFv can be introduced into a suitable host cell, either eukaryotic, such as yeast, plant, insect or mammalian cells, or prokaryotic, such as E. coli. Polynucleotides encoding the scFv of interest can be made by routine manipulations such as ligation of polynucleotides. The resultant scFv can be isolated using standard protein purification techniques known in the art.

Other forms of single chain antibodies, such as diabodies, are also encompassed. Diabodies are bivalent, bispecific antibodies in which VH and VL are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al., 1993, Proc. Natl. Acad Sci. USA 90:6444-6448; Poljak, R. J., et al., 1994, Structure 2:1121-1123).

Heteroconjugate antibodies, comprising two covalently joined antibodies, are also provided. Such antibodies have been used to target immune system cells to unwanted cells (U.S. Pat. No. 4,676,980), and for treatment of HIV infection (PCT Publication Nos. WO 91/00360 and WO 92/200373. EP 03089). Heteroconjugate antibodies may be made using any convenient cross-linking methods. Suitable cross-linking agents and techniques are well known in the art, and are described in U.S. Pat. No. 4,676,980.

Chimeric or hybrid antibodies also may be prepared in vitro using known methods of synthetic protein chemistry, including those involving cross-linking agents. For example, immunotoxins may be constructed using a disulfide exchange reaction or by forming a thioether bond. Examples of suitable reagents for this purpose include iminothiolate and methyl-4-mercaptobutyrimidate.

The disclosure also encompasses fusion proteins comprising one or more fragments or regions from the antibodies disclosed herein. In some embodiments, a fusion antibody may be made that comprises all or a portion of an anti-FXIa antibody of the disclosure linked to another polypeptide. In another embodiment, only the variable domains of the anti-FXIa antibody are linked to the polypeptide. In another embodiment, the VH domain of an anti-FXIa antibody is linked to a first polypeptide, while the VL domain of an anti-FXIa antibody is linked to a second polypeptide that associates with the first polypeptide in a manner such that the VH and VL domains can interact with one another to form an antigen-binding site. In another preferred embodiment, the VH domain is separated from the VL domain by a linker such that the VH and VL domains can interact with one another. The VH-linker-VL antibody is then linked to the polypeptide of interest. In some embodiments, a fusion antibody may be made that comprises all or a portion of an anti-idiotype antibody of the disclosure linked to another polypeptide. In another embodiment, only the variable domains of the anti-idiotype antibody are linked to the polypeptide. In another embodiment, the VH domain of an anti-idiotype antibody is linked to a first polypeptide, while the VL domain of an anti-idiotype antibody is linked to a second polypeptide that associates with the first polypeptide in a manner such that the VH and VL domains can interact with one another to form an antigen binding site. In another preferred embodiment, the VH domain is separated from the VL domain by a linker such that the VH and VL domains can interact with one another. The VH-linker-VL antibody is then linked to the polypeptide of interest. In addition, fusion antibodies can be created in which two (or more) single-chain antibodies are linked to one another. This is useful if one wants to create a divalent or polyvalent antibody on a single polypeptide chain, or if one wants to create a bispecific antibody.

In some embodiments, a fusion polypeptide is provided that comprises at least 10 contiguous amino acids of the variable light chain region shown in SEQ ID NOs: 7, 17, 21, 23, 25, 27, 31, 37, 39, 42, 46, 50, 54, 58, 62, 64, 68, or 97 and/or at least 10 amino acids of the variable heavy chain region shown in SEQ ID NOs: 1, 14, 18, 22, 24, 26, 28, 34, 38, 40, 43, 47, 51, 55, 59, 63, 65, or 96. In other embodiments, a fusion polypeptide is provided that comprises at least about 10, at least about 15, at least about 20, at least about 25, or at least about 30 contiguous amino acids of the variable light chain region and/or at least about 10, at least about 15, at least about 20, at least about 25, or at least about 30 contiguous amino acids of the variable heavy chain region. In another embodiment, the fusion polypeptide comprises one or more CDR(s). In still other embodiments, the fusion polypeptide comprises VH CDR3 and/or VL CDR3. For purposes of this disclosure, a fusion protein contains one or more antibodies and another amino acid sequence to which it is not attached in the native molecule, for example, a heterologous sequence or a homologous sequence from another region. Exemplary heterologous sequences include, but are not limited to a "tag" such as a FLAG tag or a 6His tag. Tags are well known in the art.

In some embodiments, a fusion polypeptide is provided that comprises at least 10 contiguous amino acids of the variable light chain region shown in SEQ ID NO 75 and/or at least 10 amino acids of the variable heavy chain region shown in SEQ ID NO: 69. In other embodiments, a fusion polypeptide is provided that comprises at least about 10, at least about 15, at least about 20, at least about 25, or at least about 30 contiguous amino acids of the variable light chain region and/or at least about 10, at least about 15, at least about 20, at least about 25, or at least about 30 contiguous amino acids of the variable heavy chain region. In another embodiment, the fusion polypeptide comprises one or more CDR(s). In still other embodiments, the fusion polypeptide comprises VH CDR3 and/or VL CDR3. For purposes of this disclosure, a fusion protein contains one or more antibodies and another amino acid sequence to which it is not attached in the native molecule, for example, a heterologous sequence or a homologous sequence from another region. Exemplary heterologous sequences include, but are not limited to a "tag" such as a FLAG tag or a 6His tag. Tags are well known in the art.

A fusion polypeptide can be created by methods known in the art, for example, synthetically or recombinantly. Typically, the fusion proteins of this disclosure are made by preparing and expressing a polynucleotide encoding them using recombinant methods described herein, although they may also be prepared by other means known in the art, including, for example, chemical synthesis.

In other embodiments, other modified antibodies may be prepared using nucleic acid molecules encoding an anti-FXIa antibody. In some embodiments, other modified antibodies may be prepared using nucleic acid molecules encoding an anti-idiotype antibody. For instance, "Kappa bodies" (Ill et al., 1997, *Protein Eng.* 10:949-57), "Minibodies" (Martin et al., 1994, *EMBO J.* 13:5303-9), "Diabodies" (Holliger et al., supra), or "Janusins" (Traunecker et al., 1991, *EMBO J.* 10:3655-3659 and Traunecker et al., 1992. *Int. J. Cancer* (Suppl.) 7:51-52) may be prepared using standard molecular biological techniques following the teachings of the specification.

For example, bispecific antibodies, monoclonal antibodies that have binding specificities for at least two different antigens, can be prepared using the antibodies disclosed herein. Methods for making bispecific antibodies are known in the art (see, e.g., Suresh et al., 1986, *Methods in Enzymology* 121:210). For example, bispecific antibodies or antigen-binding fragments can be produced by fusion of hybridomas or linking of Fab' fragments. See, e.g., Songsivilai & Lachmann, 1990, *Clin. Exp. Immunol.* 79:315-321, Kostelny et al., 1992, J. Immunol. 148:1547-1553. Traditionally, the recombinant production of bispecific antibodies was based on the coexpression of two immunoglobulin heavy chain-light chain pairs, with the two heavy chains having different specificities (Millstein and Cuello, 1983, *Nature* 305, 537-539). In addition, bispecific antibodies may be formed as "diabodies" or "Janusins." In some embodiments, the bispecific antibody binds to two different epitopes of FXIa. In some embodiments, the modified antibodies described above are prepared using one or more of the variable domains or CDR regions from an anti-FXIa antibody provided herein. In some embodiments, the bispecific antibody binds to two different epitopes of an anti-FXIa antibody. In some embodiments, a bispecific antibody binds two different anti-FXIa antibodies. In some embodiments, the modified antibodies described above are prepared using one or more of the variable domains or CDR regions from an anti-idiotype antibody provided herein.

According to one approach to making bispecific antibodies, antibody variable domains with the desired binding specificities (antibody-antigen combining sites) are fused to immunoglobulin constant region sequences. The fusion preferably is with an immunoglobulin heavy chain constant region, comprising at least part of the hinge, CH2 and CH3 regions. It is preferred to have the first heavy chain constant region (CH1), containing the site necessary for light chain binding, present in at least one of the fusions. DNAs encoding the immunoglobulin heavy chain fusions and, if desired, the immunoglobulin light chain, are inserted into separate expression vectors, and are cotransfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In one approach, the bispecific antibodies are composed of a hybrid immunoglobulin heavy chain with a first binding specificity in one arm, and a hybrid immunoglobulin heavy chain-light chain pair (providing a second binding specificity) in the other arm. This asymmetric structure, with an immunoglobulin light chain in only one half of the bispecific molecule, facilitates the separation of the desired bispecific compound from unwanted immunoglobulin chain combinations. This approach is described in PCT Publication No. WO 94/04690.

This disclosure also provides compositions comprising anti-FXIa antibodies conjugated (for example, linked) to an agent that facilitate coupling to a solid support (such as biotin or avidin). For simplicity, reference will be made generally to antibodies with the understanding that these methods apply to any of the FXIa binding embodiments described herein. This disclosure also provides compositions comprising anti-idiotype antibodies conjugated (for example, linked) to an agent that facilitate coupling to a solid support (such as biotin or avidin). For simplicity, reference will be made generally to antibodies with the understanding that these methods apply to any of the anti-FXIa antibody binding embodiments described herein. Conjugation generally refers to linking these components as described herein. The linking (which is generally fixing these components in proximate association at least for administration) can be achieved in any number of ways. For example, a direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

The antibodies can be bound to many different carriers. Carriers can be active and/or inert. Examples of well-known carriers include polypropylene, polystyrene, polyethylene, dextran, nylon, amylases, glass, natural and modified celluloses, polyacrylamides, agaroses and magnetite. The nature of the carrier can be either soluble or insoluble for purposes of the disclosure. Those skilled in the art will know of other suitable carriers for binding antibodies, or will be able to ascertain such, using routine experimentation.

An antibody or polypeptide of this disclosure may be linked to a labeling agent such as a fluorescent molecule, a radioactive molecule or any others labels known in the art. Labels are known in the art which generally provide (either directly or indirectly) a signal.

IV. Polynucleotides, Vectors, and Host Cells

The disclosure also provides polynucleotides encoding any of the antibodies, including antibody fragments and modified antibodies described herein, such as, e.g., antibodies having impaired effector function. In another aspect, the disclosure provides a method of making any of the polynucleotides described herein. Polynucleotides can be made and expressed by procedures known in the art. Accordingly, the disclosure provides polynucleotides or compositions, including pharmaceutical compositions, comprising polynucleotides, encoding any of the following anti-FXIa antibodies and antigen-binding fragments thereof: D4 VH (SEQ ID NO: 14), DEF VH (SEQ ID NO: 1), QCA11 VH (SEQ ID NO: 18), B1D2 VH (SEQ ID NO:22), B10H2 VH (SEQ ID NO:24), B10E6 VH (SEQ ID NO:26), B10F6 VH (SEQ ID NO:28), B10D8 VH (SEQ ID NO:34), B10B12 VH (SEQ ID NO:38), S1D4 VH (SEQ ID NO:40), S10H9 VH (SEQ ID NO:43), Clone 8 VH (SEQ ID NO:47), Clone 16 VH (SEQ ID NO:51), Clone 20 VH (SEQ ID NO:55), Clone 22 VH (SEQ ID NO:59), Clone 32 VH (SEQ ID NO:63), Clone 24 VH (SEQ ID NO:65), D4 VL (SEQ ID NO:17), DEF VL (SEQ ID NO:7), QCA11 VL (SEQ ID NO:21), B1D2 VL (SEQ ID NO:23), B10H2 VL (SEQ ID NO:25), B10E6 VL (SEQ ID NO:27), B10F6 VL (SEQ ID NO:31), B10D8 VL (SEQ ID NO:37), B10B12 VL (SEQ ID NO:39), S1D4 VL (SEQ ID NO:42), S10H9 VL (SEQ ID NO:46), Clone 8 VL (SEQ ID NO:50), Clone 16 VL (SEQ ID NO:54), Clone 20 VL (SEQ ID NO:58), Clone 22 VL (SEQ ID NO:62), Clone 32 VL (SEQ ID NO:64), or Clone 24 VL (SEQ ID NO:68), or any fragment or part thereof having the ability to bind FXIa. The disclosure further provides polynucleotides or compositions, including pharmaceutical compositions, comprising polynucleotides, encoding the following anti-idiotype antibody and antigen-binding fragments thereof: C4 VH (SEQ ID NO:69), or C4 VL (SEQ ID NO:75), or any fragment or part thereof having the ability to bind to an anti-FXIa antibody of the disclosure.

In one embodiment, the VH and VL domains, or antigen-binding fragment thereof, or full length HC or LC, are encoded by separate polynucleotides. Alternatively, both VH and VL, or antigen-binding fragment thereof, or HC and LC, are encoded by a single polynucleotide.

In another aspect, the disclosure provides polynucleotides and variants thereof encoding an anti-FXIa antibody, wherein such variant polynucleotides share at least 70%, at least 75%, at least 80%, at least 85%, at least 87%, at least 89%, at least 90%, at least 91%, at least 92%, at least 93%, at least 94%, at least 95%, at least 96%, at least 97%, at least 98%, or at least 99% sequence identity to any of the specific nucleic acid disclosed herein. In some embodiments, the polynucleotide has at least 70% sequence identity to SEQ ID NO:84, SEQ ID NO:85, SEQ ID NO:86, SEQ ID NO:87, SEQ ID NO:88, or SEQ ID NO:89.

In another aspect, the disclosure provides polynucleotides and variants thereof encoding an anti-idiotype antibody that specifically bind to the antigen-binding site of an anti-FXIa antibody or antigen-binding portion thereof of the disclosure, wherein such variant polynucleotides share at least 70%, at least 75%, at least 80%, at least 85%, at least 87%, at least 89%, at least 90%, at least 91%, at least 92%, at least 93%, at least 94%, at least 95%, at least 96%, at least 97%, at least 98%, or at least 99% sequence identity to any of the specific nucleic acid disclosed herein. In some embodiments, the polynucleotide has at least 70% sequence identity to SEQ ID NO:90 or SEQ ID NO:91.

Polynucleotides complementary to any such sequences are also encompassed by the present disclosure. Polynucleotides may be single-stranded (coding or antisense) or double-stranded, and may be DNA (genomic, cDNA or synthetic) or RNA molecules. RNA molecules include HnRNA molecules, which contain introns and correspond to a DNA molecule in a one-to-one manner, and mRNA molecules, which do not contain introns. Additional coding or non-coding sequences may, but need not, be present within a polynucleotide of the present disclosure, and a polynucleotide may, but need not, be linked to other molecules and/or support materials.

Polynucleotides may comprise a native sequence (i.e., an endogenous sequence that encodes an antibody or a fragment thereof) or may comprise a variant of such a sequence. Polynucleotide variants contain one or more substitutions, additions, deletions and/or insertions such that the immunoreactivity of the encoded polypeptide is not diminished, relative to a native immunoreactive molecule. The effect on the immunoreactivity of the encoded polypeptide may generally be assessed as described herein. Variants preferably exhibit at least about 70% identity, more preferably, at least about 80% identity, yet more preferably, at least about 90% identity, and most preferably, at least about 95% identity to a polynucleotide sequence that encodes a native antibody or a fragment thereof.

Two polynucleotide or polypeptide sequences are said to be "identical" if the sequence of nucleotides or amino acids in the two sequences is the same when aligned for maximum correspondence as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, or 40 to about 50, in which a sequence may be compared to a reference sequence of the same number of contiguous positions after the two sequences are optimally aligned.

Optimal alignment of sequences for comparison may be conducted using the MegAlign® program in the Lasergene® suite of bioinformatics software (DNASTAR®, Inc., Madison, Wis.), using default parameters. This program embodies several alignment schemes described in the following references: Dayhoff, M. O., 1978, A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3. pp. 345-358; Hein J., 1990. Unified Approach to Alignment and Phylogenes pp. 626-645 Methods in Enzymology vol. 183, Academic Press. Inc., San Diego, Calif.; Higgins, D. G, and Sharp, P. M., 1989, CABIOS 5:151-153; Myers, E. W. and Muller W., 1988, CABIOS 4:11-17; Robinson, E. D., 1971, Comb. Theor. 11:105; Santou, N., Nes. M., 1987, Mol. Biol. Evol. 4:406-425; Sneath, P. H. A, and Sokal, R. R., 1973, Numerical Taxonomy the Principles and Practice of Numerical Taxonomy, Freeman Press, San Francisco, Calif.; Wilbur, W. J, and Lipman, D. J., 1983, Proc. Natl. Acad Sci. USA 80:726-730.

Preferably, the "percentage of sequence identity" is determined by comparing two optimally aligned sequences over a window of comparison of at least 20 positions, wherein the portion of the polynucleotide or polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e., the window size) and multiplying the results by 100 to yield the percentage of sequence identity.

Variants may also, or alternatively, be substantially homologous to a native gene, or a portion or complement thereof. Such polynucleotide variants are capable of hybridizing under moderately stringent conditions to a naturally occurring DNA sequence encoding a native antibody (or a complementary sequence).

Suitable "moderately stringent conditions" include pre-washing in a solution of 5×SSC, 0.5% SDS, 1.0 mM EDTA (pH 8.0); hybridizing at 50° C.-65° C., 5×SSC, overnight; followed by washing twice at 65° C. for 20 minutes with each of 2×, 0.5× and 0.2×SSC containing 0.1% SDS.

As used herein, "highly stringent conditions" or "high stringency conditions" are those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C. The skilled artisan will recognize how to adjust the temperature, ionic strength, etc. as necessary to accommodate factors such as probe length and the like.

It will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present disclosure. Further, alleles of the genes comprising the polynucleotide sequences provided herein are within the scope of the present disclosure. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

The polynucleotides of this disclosure can be obtained using chemical synthesis, recombinant methods, or PCR. Methods of chemical polynucleotide synthesis are well known in the art and need not be described in detail herein. One of skill in the art can use the sequences provided herein and a commercial DNA synthesizer to produce a desired DNA sequence.

For preparing polynucleotides using recombinant methods, a polynucleotide comprising a desired sequence can be inserted into a suitable vector, and the vector in turn can be introduced into a suitable host cell for replication and amplification, as further discussed herein. Polynucleotides may be inserted into host cells by any means known in the art. Cells are transformed by introducing an exogenous polynucleotide by direct uptake, endocytosis, transfection, F-mating or electroporation. Once introduced, the exogenous polynucleotide can be maintained within the cell as a non-integrated vector (such as a plasmid) or integrated into the host cell genome. The polynucleotide so amplified can be isolated from the host cell by methods well known within the art. See, e.g., Sambrook et al., 1989.

Alternatively, PCR allows reproduction of DNA sequences. PCR technology is well known in the art and is described in U.S. Pat. Nos. 4,683,195, 4,800,159, 4,754,065 and 4,683,202, as well as PCR: The Polymerase Chain Reaction, Mullis et al. eds., Birkauswer Press, Boston, 1994.

RNA can be obtained by using the isolated DNA in an appropriate vector and inserting it into a suitable host cell. When the cell replicates and the DNA is transcribed into RNA, the RNA can then be isolated using methods well known to those of skill in the art, as set forth in Sambrook et al., 1989, supra, for example.

Suitable cloning vectors may be constructed according to standard techniques, or may be selected from a large number of cloning vectors available in the art. While the cloning vector selected may vary according to the host cell intended to be used, useful cloning vectors will generally have the ability to self-replicate, may possess a single target for a particular restriction endonuclease, and/or may carry genes for a marker that can be used in selecting clones containing the vector. Suitable examples include plasmids and bacterial viruses, e.g., pUC18, pUC19, Bluescript (e.g., pBS SK+) and its derivatives, mp18, mp19, pBR322, pMB9, ColE1, pCR1, RP4, phage DNAs, and shuttle vectors such as pSA3 and pAT28. These and many other cloning vectors are available from commercial vendors such as BioRad, Strategene, and Invitrogen.

Expression vectors are further provided. Expression vectors generally are replicable polynucleotide constructs that contain a polynucleotide according to the disclosure. It is implied that an expression vector must be replicable in the host cells either as episomes or as an integral part of the chromosomal DNA. Suitable expression vectors include but are not limited to plasmids, viral vectors, including adenoviruses, adeno-associated viruses, retroviruses, cosmids, and expression vector(s) disclosed in PCT Publication No. WO 87/04462. Vector components may generally include, but are not limited to, one or more of the following: a signal sequence; an origin of replication; one or more marker genes; suitable transcriptional controlling elements (such as promoters, enhancers and terminator). For expression (i.e., translation), one or more translational controlling elements are also usually required, such as ribosome binding sites, translation initiation sites, and stop codons.

The vectors containing the polynucleotides of interest and/or the polynucleotides themselves, can be introduced into the host cell by any of a number of appropriate means, including electroporation, transfection employing calcium chloride, rubidium chloride, calcium phosphate, DEAE-dextran, or other substances; microprojectile bombardment; lipofection; and infection (e.g., where the vector is an infectious agent such as vaccinia virus). The choice of introducing vectors or polynucleotides will often depend on features of the host cell.

The disclosure also provides host cells comprising any of the polynucleotides described herein. Any host cells capable of over-expressing heterologous DNAs can be used for the purpose of isolating the genes encoding the antibody, polypeptide or protein of interest. Non-limiting examples of mammalian host cells include but not limited to COS, HeLa, and CHO cells. See also PCT Publication No. WO 87/04462. Suitable non-mammalian host cells include prokaryotes (such as $E.\ coli$ or $B.\ subtillis$) and yeast (such as $S.\ cerevisae,\ S.\ pombe;$ or $K.\ lactis$). Preferably, the host cells express the cDNAs at a level of about 5 fold higher, more preferably, 10 fold higher, even more preferably, 20 fold higher than that of the corresponding endogenous antibody or protein of interest, if present, in the host cells. Screening the host cells for a specific binding to FXIa or anti-FXIa antibody is effected by an immunoassay or FACS. A cell overexpressing the antibody or protein of interest can be identified.

An expression vector can be used to direct expression of an anti-FXIa antibody or anti-idiotype antibody. One skilled in the art is familiar with administration of expression vectors to obtain expression of an exogenous protein in vivo. See, e.g., U.S. Pat. Nos. 6,436,908; 6,413,942; and 6,376, 471. Administration of expression vectors includes local or systemic administration, including injection, oral administration, particle gun or catheterized administration, and topical administration. In another embodiment, the expression vector is administered directly to the sympathetic trunk or ganglion, or into a coronary artery, atrium, ventrical, or pericardium.

Targeted delivery of therapeutic compositions containing an expression vector, or subgenomic polynucleotides can also be used. Receptor-mediated DNA delivery techniques are described in, for example, Findeis et al., *Trends Biotechnol.*, 1993, 11:202; Chiou et al., Gene Therapeutics: Methods And Applications Of Direct Gene Transfer, J. A. Wolff, ed., 1994; Wu et al., *J. Biol. Chem.*, 1988, 263:621; Wu et al., *J. Biol. Chem.*, 1994, 269:542; Zenke et al., *Proc. Natl. Acad. Sci. USA,* 1990, 87:3655; Wu et al., *J. Biol. Chem.,* 1991, 266:338. Therapeutic compositions containing a polynucleotide are administered in a range of about 100 ng to about 200 mg of DNA for local administration in a gene therapy protocol. Concentration ranges of about 500 ng to about 50 mg, about 1 μg to about 2 mg, about 5 μg to about 500 μg, and about 20 μg to about 100 μg of DNA can also be used during a gene therapy protocol. The therapeutic polynucleotides and polypeptides can be delivered using gene delivery vehicles. The gene delivery vehicle can be of viral or non-viral origin (see generally, Jolly, *Cancer Gene Therapy,* 1994, 1:51; Kimura, *Human Gene Therapy,* 1994, 5:845; Connelly, *Human Gene Therapy,* 1995, 1:185; and Kaplitt, *Nature Genetics,* 1994, 6:148). Expression of such coding sequences can be induced using endogenous mammalian or heterologous promoters. Expression of the coding sequence can be either constitutive or regulated.

Viral-based vectors for delivery of a desired polynucleotide and expression in a desired cell are well known in the art. Exemplary viral-based vehicles include, but are not limited to, recombinant retroviruses (see, e.g., PCT Publication Nos. WO 90/07936; WO 94/03622; WO 93/25698; WO 93/25234: WO 93/11230; WO 93/10218: WO 91/02805; U.S. Pat. Nos. 5,219,740 and 4,777,127: GB Patent No. 2,200,651; and EP Patent No. 0 345 242), alphavirus-based vectors (e.g., Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923: ATCC VR-1250: ATCC VR 1249; ATCC VR-532)), and adeno-associated virus (AAV) vectors (see, e.g., PCT Publication Nos. WO 94/12649, WO 93/03769; WO 93/19191, WO 94/28938; WO 95/11984 and WO 95/00655). Administration of DNA linked to killed adenovirus as described in Curiel, *Hum. Gene Ther.,* 1992, 3:147 can also be employed.

Non-viral delivery vehicles and methods can also be employed, including, but not limited to, polycationic condensed DNA linked or unlinked to killed adenovirus alone (see, e.g., Curiel, *Hum. Gene Ther.,* 1992, 3:147); ligand-linked DNA (see, e.g., Wu, *J. Biol. Chem.,* 1989, 264: 16985); eukaryotic cell delivery vehicles cells (see, e.g., U.S. Pat. No. 5,814,482; PCT Publication Nos. WO 95/07994: WO 96/17072; WO 95/30763; and WO 97/42338) and nucleic charge neutralization or fusion with cell membranes. Naked DNA can also be employed. Exemplary naked DNA introduction methods are described in PCT Publication No. WO 90/11092 and U.S. Pat. No. 5,580,859. Liposomes that can act as gene delivery vehicles are described in U.S. Pat. No. 5,422,120; PCT Publication Nos. WO 95/13796; WO 94/23697; WO 91/14445; and EP 0524968. Additional approaches are described in Philip, *Mol. Cell Biol.,* 1994, 14:2411, and in Woffendin, *Proc. Natl. Acad Sci.,* 1994, 91:1581.

V. Therapeutic Methods

In another aspect, therapeutic methods using the antibodies or antigen-binding fragments thereof are provided. In some embodiments, the therapeutic methods comprise the use of isolated antibodies, or antigen-binding fragments thereof, that specifically bind FXIa. In some embodiments, the therapeutic methods comprise the use of isolated antibodies, or antigen-binding fragments thereof, that specifically bind to the antigen-binding site of an anti-FXIa antibody or antigen-binding portion thereof (e.g., an anti-idiotype antibody that specifically binds to an anti-FXIa antibody described herein).

Therapeutic methods involve administering to a subject in need of treatment a therapeutically effective amount, or "effective amount," of an FXIa antibody, or antigen-binding portion, of the disclosure or of an anti-idiotype antibody, or antigen-binding portion thereof, that specifically binds to the antigen-binding site of an anti-FXIa antibody, or antigen-binding portion, of the disclosure are contemplated by the present disclosure. As used herein, a "therapeutically effective", or "effective," amount refers to an amount of an antibody or portion thereof that is of sufficient quantity to result in a decrease in severity of disease symptoms, an increase in frequency and duration of disease symptom-free periods, or a prevention of impairment or disability due to the disease affliction—either as a single dose or according to a multiple dose regimen, alone or in combination with other agents. Therapeutically effective or effective may also refer to decreasing an indication of disease that predicts clinically important events (e.g., for an anti-FXIa antibody, substantially prolonging APTT or decreasing the occurrence of deep venous thrombosis in the legs as measured by venography or ultrasound, and for an anti-idiotype antibody to an anti-FXIa antibody, returning APTT to normal). One of ordinary skill in the art would be able to determine such amounts based on such factors as the subject's size, the severity of the subject's symptoms, laboratory tests that indicate an effective dosing level (e.g., APTT), and the particular composition or route of administration selected. The subject may be a human or non-human animal (e.g., rabbit, rat, mouse, monkey or other lower-order primate).

An antibody or antigen-binding portion of the disclosure might be co-administered with known medicaments, and in some instances the antibody might itself be modified. Regarding co-administration with additional therapeutic agents, such agents can include an anticoagulant agent or a procoagulant agent. The antibody can be linked to the agent (as an immunocomplex) or can be administered separately from the agent. In the latter case (separate administration), the antibody can be administered before, after or concurrently with the agent or can be co-administered with other known therapies. Co-administration of the FXIa antibodies, or antigen binding fragments thereof, of the present disclosure with a therapeutic agent provides two agents which operate via different mechanisms may provide a therapeutic and perhaps synergistic effect to human disease.

To treat any of the foregoing disorders, pharmaceutical compositions for use in accordance with the present disclosure may be formulated in a conventional manner using one or more pharmaceutically acceptable carriers or excipients and administered as more fully discussed below.

Determining a therapeutically effective amount of an antibody or antigen-binding portion according to the present disclosure will largely depend on particular patient characteristics, route of administration, and the nature of the disorder being treated and is more fully discussed below.

Administration and dosing of the antibodies are more fully discussed elsewhere below.

Anti-FXIa Antibodies

According to the disclosure, an anti-FXIa antibody can be used to inhibit FXIa-mediated activity. The activity of an anti-FXIa antibody can be confirmed by bioassays, known to test the targeted biological activities. Some of the methods for characterizing an anti-FXIa antibody are described in detail in the Examples. Non-limiting exemplary tests include a fluorogenic peptide substrate assay, a thrombin generation assay, and an APTT test. Other tests are also possible within the knowledge of those of ordinary skill in the art.

The disclosure encompasses the use of an anti-FXIa antibody that binds FXIa as an anticoagulant. In certain embodiments, the anti-FXIa antibody binds to the catalytic domain of FXIa. In certain embodiments, the anti-FXIa antibody binds to the active site of the catalytic domain.

According to some embodiments, an anti-FXIa antibody reduces the activity of FXIa in a sample. In some embodiments, treatment with an anti-FXIa antibody reduces activity of FXIa in a sample at least 10%, 20%, 30%, 40%, 50%, 60%, 70%, 80%, 90%, 95%, or 99% in the presence of an anti-FXIa antibody compared to absence of treatment with an anti-FXIa antibody. In other embodiments, treatment with an anti-FXIa antibody reduces the activity of FXIa in a sample about 5%-10%, 10%-15%, 15%-20%, 20%-25%, 25%-30%, 30%-35%, 35%-40%, 40%-45%, 45%-50%, 50%-55%, 55%-60%, 60%-65%, 65%-70%, 70%-75%, 75%-80%, 80%-85%, 85%-90%, 90%-95%, or 95%-100%. These amounts are not meant to be limiting, and increments between the recited amounts are specifically envisioned as part of the disclosure.

According to some embodiments, reversing the effects of FXIa in a sample by administering an anti-FXIa antibody decreases the amount of thrombin produced in the sample. In some embodiments, treatment with an anti-FXIa antibody decreases thrombin production in a subject at least 10%, 20%, 30%, 40%, 50%, 60%, 70%, 80%, 90%, 95%, 100%, 1.5 fold, 2-fold, 3-fold, 4-fold, 5-fold, 6-fold, 7-fold, 10-fold, 15-fold, 20-fold, 25-fold, 30-fold, at least 50-fold, or more in the presence of an anti-FXIa antibody compared to the absence of an anti-FXIa antibody. Thrombin production in a sample can be determined using the thrombin generation assay (TGA) or other technique familiar to those of ordinary skill in the art. These amounts are not meant to be limiting, and increments between the recited amounts are specifically envisioned as part of the disclosure.

According to some embodiments, an anti-FXIa antibody decreases the amount of FXIa enzymatic activity observed in a fluorogenic substrate assay in a sample. n some embodiments, treatment with an anti-FXIa antibody decreases enzymatic cleavage of a fluorogenic substrate in a sample at least 10%, 20%, 30%, 40%, 50%, 60%, 70%, 80%, 90%, 95%, 100%, 1.5 fold, 2-fold, 3-fold, 4-fold, 5-fold, 6-fold, 7-fold, 10-fold, 15-fold, 20-fold, 25-fold, 30-fold, at least 50-fold, or more in the presence of an anti-FXIa antibody compared to the absence of an anti-FXIa antibody. These amounts are not meant to be limiting, and increments between the recited amounts are specifically envisioned as part of the disclosure.

According to the disclosure, the anti-FXIa antibody or antibodies selectively bind FXIa over other trypsin-like proteases by at least 5-fold, at least 6-fold, at least 7-fold, at least 10-fold, at least 15-fold, at least 20-fold, at least 25-fold, at least 30-fold, at least 50-fold, at least 100-fold, at least, 500-fold, at least 1.000-fold, at least 5,000-fold or at least 10,000-fold. These amounts are not meant to be limiting, and increments between the recited amounts are specifically envisioned as part of the disclosure.

In a clinical setting, anti-FXIa antibody effectiveness can be detected directly or by measuring the ability of subject blood to clot and detecting deviations from the expected degree of anti-coagulation. Blood clotting potential can be measured in ways familiar to those ordinarily skilled in the art (e.g., APTT).

In some embodiments, treatment with an anti-FXIa antibody is monitored using tests or assays performed on blood or plasma from a subject treated with an anti-FXIa antibody.

A blood sample can be taken from a subject at a predetermined time after treatment with an anti-FXIa antibody. The blood, or plasma prepared from it, is then subjected to one or more tests to determine certain hemostatic pharmacodynamic parameters. Tests for monitoring the effectiveness of treatment with an anti-FXIa antibody include tests that directly or indirectly measure the ability to clot or that measure the activity of an anti-FXIa antibody. Non-limiting exemplary tests include activated partial thromboplastin time, partial thromboplastin time, fluorogenic peptide substrate assay, thromboelastometry, thromboelastography, thrombin generation assay, level of prothrombin fragment 1+2, or level of thrombin-antithrombin III complex. Other tests are also possible within the knowledge of those of ordinary skill in the art.

According to some embodiments, an anti-FXIa antibody reduces coagulation in the subject. In some embodiments, treatment with an anti-FXIa antibody reduces coagulation in a subject at least 10%, 20%, 30%, 40%, 50%, 60%, 70%, 80%, 90%, 95%, or 99% in the presence of an anti-FXIa antibody compared to absence of an anti-FXIa antibody. In other embodiments, treatment with an anti-FXIa antibody reduces coagulation in a subject about 5%-10%, 10%-15%, 15%-20%, 20%-25%, 25%-30%, 30%-35%, 35%-40%, 40%-45%, 45%-50%, 50%-55%, 55%-60%, 60%-65%, 65%-70%, 70%-75%, 75%-80%, 80%-85%, 85%-90%, 90%-95%, or 95%-100%. These amounts are not meant to be limiting, and increments between the recited amounts are specifically envisioned as part of the disclosure.

According to some embodiments, an anti-FXIa antibody reduces the activity of FXIa in the subject. In some embodiments, treatment with an anti-FXIa antibody reduces activity of FXIa in a subject at least 10%, 20%, 30%, 40%, 50%, 60%, 70%, 80%, 90%, 95%, or 99% in the presence of an anti-FXIa antibody compared to absence of an anti-FXIa antibody. In other embodiments, treatment with an anti-FXIa antibody reduces the activity of FXIa in a subject about 5%-10%, 10%-15%, 15%-20%, 20%-25%, 25%-30%, 30%-35%, 35%-40%, 40%-45%, 45%-50%, 50%-55%, 55%-60%, 60%-65%, 65%-70%, 70%-75%, 75%-80%, 80%-85%, 85%-90%, 90%-95%, or 95%-100%. These amounts are not meant to be limiting, and increments between the recited amounts are specifically envisioned as part of the disclosure.

According to some embodiments, an anti-FXIa antibody decreases the amount of thrombin produced in the blood or plasma of the subject. In some embodiments, treatment with an anti-FXIa antibody decreases thrombin production in a subject at least 10%, 20%, 30%, 40%, 50%, 60%, 70%, 80%, 90%, 95%, 1000%, 1.5 fold, 2-fold, 3-fold, 4-fold, 5-fold, 6-fold, 7-fold, 10-fold, 15-fold, 20-fold, 25-fold, 30-fold, at least 50-fold, or more in the presence of an anti-FXIa antibody compared to the absence of an anti-FXIa antibody. Thrombin production in the blood or plasma of a subject can be determined using the thrombin generation assay (TGA) or other technique familiar to those of ordinary skill in the art. These amounts are not meant to be limiting, and increments between the recited amounts are specifically envisioned as part of the disclosure.

According to some embodiments, treatment with an anti-FXIa antibody decreases the amount of FXIa enzymatic activity observed in a fluorogenic substrate assay in a sample of blood or plasma of a subject. In some embodiments, treatment with an anti-FXIa antibody decreases enzymatic cleavage of a fluorogenic substrate in a sample at least 10%, 20%, 30%, 40%, 50%, 60%, 70%, 80%, 90%, 95%, 100%, 1.5 fold, 2-fold, 3-fold, 4-fold, 5-fold, 6-fold, 7-fold, 10-fold, 15-fold, 20-fold, 25-fold, 30-fold, at least 50-fold, or more in the presence of an anti-FXIa antibody compared to the absence of an anti-FXIa antibody. These amounts are not meant to be limiting, and increments between the recited amounts are specifically envisioned as part of the disclosure.

According to some embodiments, an anti-FXIa antibody decreases clotting by selective triggers in the subject. In some embodiments, treatment with an anti-FXIa antibody decreases clotting in a subject at least 10%, 20%, 30%, 40%, 50%, 60%, 70%, 80%, 90%, 95%, 100%, 1.5 fold, 2-fold, 3-fold, 4-fold, 5-fold, 6-fold, 7-fold, 10-fold, 15-fold, 20-fold, 25-fold, 30-fold, at least 50-fold, or more in the presence of an anti-FXIa antibody compared to the absence of an anti-FXIa antibody. These amounts are not meant to be limiting, and increments between the recited amounts are specifically envisioned as part of the disclosure.

According to some embodiments, an anti-FXIa antibody increases clotting time in the subject. In some embodiments, treatment with an anti-FXIa antibody increases clotting time in a subject at least 10%, 20%, 30%, 40%, 50%, 60%, 70%, 80%, 90%, 95%, 100%, 125%, 150% or greater in the presence of an anti-FXIa antibody compared to absence of treatment with an anti-FXIa antibody. In other embodiments, treatment with an anti-FXIa antibody increases clotting time in a subject about 5%-10%, 10%-15%, 15%-20%, 20%-25%, 25%-30%, 30%-35%, 35%-40%, 40%-45%, 45%-50%, 50%-55%, 55%-60%, 60%-65%, 65%-70%, 70%-75%, 75%-80%, 80%-85%, 85%-90%, 90%-95%, 95%-100%, 10%-25%, 25%-50%, 50%-75%, 75%-100%, 100%-125%, 125%-150%, or greater than 150%. In some embodiments, the increase in clotting time is measured by APTT These amounts are not meant to be limiting, and increments between the recited amounts are specifically envisioned as part of the disclosure.

In yet other embodiments, the methods of thromboelastometry or thromboelastography may be used to analyze clot formation or clotting time.

According to some embodiments, treatment with an anti-FXIa antibody decreases the level of prothrombin fragment 1+2 (PF1+2) in the blood or plasma of the subject. In some embodiments, treatment with an anti-FXIa antibody decreases PF1+2 in a subject at least 10%, 20%, 30%, 40%, 50%, 60%, 70%, 80%, 90%, 95%, 100%, 1.5-fold, 2-fold, 3-fold, 4-fold, 5-fold, 6-fold, 7-fold, 10-fold, 15-fold, 20-fold, 25-fold, 30-fold, at least 50-fold, or more in the presence of an anti-FXIa antibody compared to the absence of an anti-FXIa antibody. These amounts are not meant to be limiting, and increments between the recited amounts are specifically envisioned as part of the disclosure.

According to some embodiments, treatment with an anti-FXIa antibody decreases the level of thrombin-antithrombin III complex (TAT) in the blood or plasma of the subject. In some embodiments, treatment with an anti-FXIa antibody decreases TAT in a subject at least 10%, 20%, 30%, 40%, 50%, 60%, 70%, 80%, 90%, 95%, 100%, 1.5-fold, 2-fold, 3-fold, 4-fold, 5-fold, 6-fold, 7-fold, 10-fold, 15-fold, 20-fold, 25-fold, 30-fold, at least 50-fold, or more in the presence of an anti-FXIa antibody compared to the absence of an anti-FXIa antibody. These amounts are not meant to be limiting, and increments between the recited amounts are specifically envisioned as part of the disclosure.

According to some embodiments, treatment with an anti-FXIa antibody increases activated partial thromboplastin time (APTT) in the subject. The APTT test measures the time required for clotting of recalcified human plasma after addition of an intrinsic pathway activator such as ellagic acid or kaolin. In some embodiments, treatment with an anti-FXIa antibody increases activated partial thromboplastin time (APTT) by 20%, 50%, 100%, 150%, 200%, 250% or more. These amounts are not meant to be limiting, and increments between the recited amounts are specifically envisioned as part of the disclosure. In certain embodiments, treatment with an anti-FXIa antibody increases activated partial thromboplastin time (APTT) in a subject without prolonging prothrombin time (PT).

In some embodiments, the disclosed antibodies, or antigen-binding portions thereof, that specifically bind to FXIa can be used as anticoagulants. In some embodiments, the disclosed antibodies, or antigen-binding portions thereof, that specifically bind to FXIa can be used in the prevention, treatment, and/or amelioration of diseases, disorders or conditions caused by and/or associated with FXI activity. Such diseases, disorders or conditions include, but are not limited to, surgery or other type of interventional procedure: thrombotic or thromboembolic diseases; atrial fibrillation (AF): venous thromboembolism (VTE); VTE in the medically ill; VTE prophylaxis in the medically ill; VTE prophylaxis in knee or hip surgery; Afib in the renal disease population and/or patients previously identified as bleeders; acute coronary syndromes; use of extracorporeal circulations and devices in which blood contacts artificial surfaces; vascular grafts; myocardial infarction; acute myocardial infarction; congestive heart failure; pulmonary embolism; thrombosis; deep vein thrombosis; renal vein thrombosis; transient ischemic attack: thrombotic stroke; thromboembolic stroke; cardiogenic thromboembolism; atherosclerosis; inflammatory diseases: pulmonary hypertension; pulmonary and/or hepatic fibrosis; and sepsis; among others, as would be appreciated by one skilled in the art provided with the teachings disclosed herein. Additional uses include situations in which blood touches artificial surfaces, including mechanical heart valves, extracorporeal circulations including but not limited to extracorporeal membrane oxygenation, cardiopulmonary bypass, and hemodialysis: vascular grafts; catheters; wires; left ventricular assist devices (LVAD); transcatheter aortic valve replacement (TAVR); and and other devices introduced in to the heart and blood vessels. Examples of diseases and disorders are provided in WO2013167669, incorporated herein by reference.

In some embodiments, an anti-FXIa antibody or antigen-binding fragment thereof of the disclosure can be used as an anticoagulant in patients with mechanical heart valves. In some embodiments, an anti-FXIa antibody or antigen-binding fragment thereof of the disclosure can be used as an anticoagulant in atrial fibrillation patients with reduced kidney function or elevated bleeding risk. In some embodiments, an anti-FXIa antibody or antigen-binding fragment thereof of the disclosure can be used for VTE prophylaxis in the medically ill. In some embodiments, an anti-FXIa antibody or antigen-binding fragment thereof of the disclosure can be used for VTE prophylaxis in the surgically ill. In some embodiments, an anti-FXIa antibody or antigen-binding fragment thereof of the disclosure can be used as VTE prophylaxis in patients requiring knee or hip surgery. In some embodiments, an anti-FXIa antibody or antigen-binding fragment thereof of the disclosure can be used as an anticoagulant in patients fitted with an LVAD. In some embodiments, an anti-FXIa antibody or antigen-binding fragment thereof of the disclosure can be used as an anticoagulant in patients on extracorporeal membrane oxygenation support. In some embodiments, an anti-FXIa antibody or antigen-binding fragment thereof of the disclosure can be used as an anticoagulant in patients with undergoing cardiopulmonary bypass. In some embodiments, an anti-FXIa antibody or antigen-binding fragment thereof of the disclosure can be used as an anticoagulant in patients fitted with an indwelling catheter. In some embodiments, an anti-FXIa antibody or antigen-binding fragment thereof of the disclosure can be used as an anticoagulant in patients with a vascular graft.

In some embodiments, an anti-FXIa antibody or antigen-binding fragment thereof is used for the prevention of venous thrombosis and/or venous thromboembolism (VTE) in a patient undergoing major orthopedic surgery (e.g., total knee replacement, total hip replacement, or hip fracture surgery); in a patient hospitalized for medical illness and at increased risk for VTE; in a patient undergoing abdominal surgery; in a patient with a cancer associated with increased risk for VTE, such as pancreatic, gastric, or renal cell carcinoma; in a patient with genetic thrombophilia or another genetic disorder (e.g., Prader-Willi) that is associated with increased risk of venous thromboembolism; in a patient with a history of unprovoked pulmonary embolism or deep venous thrombosis; in a patient who would typically receive an inferior vena caval "umbrella" due to high risk for VTE but who is unable to receive standard anticoagulation therapy; or in a person with paralytic spinal cord injury or another trauma associated with elevated VTE risk.

In some embodiments, an anti-FXIa antibody or antigen-binding fragment thereof is used for the prevention of thromboembolism from the left atrium in a patient with atrial fibrillation. In some embodiments, the patient is intolerant of or unlikely to receive standard anticoagulants, including patients on hemodialysis, patients with end-stage renal disease, patients with a history of bleeding on standard anticoagulants or having multiple other risk factors for bleeding.

In some embodiments, an anti-FXIa antibody or antigen-binding fragment thereof is used for the prevention of arterial thrombi in a patient at elevated risk for myocardial infarction, including patients with acute coronary syndromes, patients with diffuse coronary disease and multiple risk factors (e.g., prior myocardial infarction and diabetes); in a patient with thromboembolic or thrombo-occlusive stroke (e.g., patients with severe carotid artery narrowing, transient ischemic attacks); or in a patient with acute limb ischemia.

In some embodiments, an anti-FXIa antibody or antigen-binding fragment thereof is used for the prevention of thrombus formation and embolization or device failure in a patient with an indwelling device that exposes artificial surfaces to blood, including patients with mechanical heart valves, left ventricular assist devices, transcatheter aortic valve replacements, indwelling catheters, vascular grafts, or vascular stents, including coronary, carotid, or peripheral arterial stents.

In some embodiments, an anti-FXIa antibody or antigen-binding fragment thereof is used for the prevention of activation of coagulation, consumption of coagulation factors, or clot formation in a patient connected to extracorporeal circulation, including hemodialysis machines, cardiopulmonary bypass, or extracorporeal membrane oxygenation.

In certain aspects of the disclosure, methods are provided for increasing anticoagulant activity in a subject comprising administering to said subject an anti-FXIa antibody as described herein, wherein the anticoagulant activity is increased compared with the anticoagulant activity in the subject prior to administration of the anti-FXIa antibody. In certain aspects of the disclosure, methods are provided for increasing clotting time in a subject, comprising administering to said subject an anti-FXIa antibody as described herein, wherein the clotting time is increased compared with the clotting time in the subject prior to administration of the anti-FXIa antibody.

In some embodiments, anti-FXIa antibodies as described herein for use in increasing anticoagulant activity in a subject are provided. In some embodiments, anti-FXIa antibodies as described herein for use in increasing clotting time in a subject are provided.

In some embodiments, use of an anti-FXIa antibody as described herein in the manufacture of a medicament for increasing anticoagulant activity in a subject is provided. In some embodiments, use of an antibody, or antigen-binding portion thereof, that specifically binds to the antigen-binding site of an anti-FXIa antibody as described herein in the manufacture of a medicament for increasing clotting time in a subject being administered the anti-FXIa antibody is provided.

Anti-Idiotype Antibodies that Specifically Bind to the Antigen-Binding Site of an Anti-FXIa Antibody According to the disclosure, an antibody, or antigen-binding portion thereof, that specifically binds to the antigen-binding site of an anti-FXIa antibody can be used to counteract an anti-FXIa antibody that binds FXIa. The activity of an antibody, or antigen-binding portion thereof, that specifically binds to the antigen-binding site of an anti-FXIa antibody can be confirmed by bioassays, known to test the targeted biological activities. Some of the methods for characterizing antibodies, or antigen-binding portions thereof, that specifically bind to the antigen-binding site of an anti-FXIa antibody are described in detail in the Examples. Non-limiting exemplary tests include a fluorogenic peptide substrate assay and a thrombin generation assay. Other tests are also possible within the knowledge of those of ordinary skill in the art.

The disclosure encompasses the use of an antibody, or antigen-binding portion thereof, that specifically binds to the antigen-binding site of an anti-FXIa antibody can be used to counteract an anti-FXIa antibody that binds FXIa. In certain embodiments, the anti-idiotype antibody is used to counteract an anti-FXIa antibody that binds to the catalytic domain of FXIa, e.g., an anti-FXIa antibody binds to the active site of the catalytic domain.

According to some embodiments, reversing the effects of an anti-FXIa antibody in a sample by administering an antibody, or antigen-binding portion thereof, that specifically binds to the antigen-binding site of an anti-FXIa antibody reduces the activity of an anti-FXIa antibody in the sample. In some embodiments, treatment with an antibody, or antigen-binding portion thereof, that specifically binds to the antigen-binding site of an anti-FXIa antibody reduces activity of the anti-FXIa antibody in a sample at least 10%, 20%, 30%, 40%, 50%, 60%, 70%, 80%, 90%, 95%, or 99% in the presence of an anti-FXIa antibody compared to absence of treatment with an antibody, or antigen-binding portion thereof, that specifically binds to the antigen-binding site of an anti-FXIa antibody. In other embodiments, treatment with an antibody, or antigen-binding portion thereof, that specifically binds to the antigen-binding site of an anti-FXIa antibody reduces the activity of a an anti-FXIa antibody in a sample about 5%-10%, 10%-15%, 15%-20%, 20%-25%, 25%-30%, 30%-35%, 35%-40%, 40%-45%, 45%-50%, 50%-55%, 55%-60%, 60%-65%, 65%-70%, 70%-75%, 75%-80%, 80%-85%, 85%-90%, 90%-95%, or 95%-100%. These amounts are not meant to be limiting, and increments between the recited amounts are specifically envisioned as part of the disclosure.

According to some embodiments, reversing the effects of an anti-FXIa antibody in a sample by administering an antibody, or antigen-binding portion thereof, that specifically binds to the antigen-binding site of an anti-FXIa antibody increases the amount of thrombin produced in the sample. In some embodiments, treatment with an antibody, or antigen-binding portion thereof, that specifically binds to the antigen-binding site of an anti-FXIa antibody increases thrombin production in a subject at least 10%, 20%, 30%, 40%, 50%, 60%, 70%, 80%, 90%, 95%, 100%, 1.5 fold, 2-fold, 3-fold, 4-fold, 5-fold, 6-fold, 7-fold, 10-fold, 15-fold, 20-fold, 25-fold, 30-fold, at least 50-fold, or more in the presence of an anti-FXIa antibody compared to the absence of an antibody, or antigen-binding portion thereof, that specifically binds to the antigen-binding site of an anti-FXIa antibody. Thrombin production in a sample can be determined using the thrombin generation assay (TGA) or other technique familiar to those of ordinary skill in the art. These amounts are not meant to be limiting, and increments between the recited amounts are specifically envisioned as part of the disclosure.

According to some embodiments, reversing the effects of an anti-FXIa antibody in a sample by administering an antibody, or antigen-binding portion thereof, that specifically binds to the antigen-binding site of an anti-FXIa antibody increases the amount of FXIa enzymatic activity observed in a fluorogenic substrate assay in the sample. In some embodiments, treatment with an antibody, or antigen-binding portion thereof, that specifically binds to the antigen-binding site of an anti-FXIa antibody increases enzymatic cleavage of a fluorogenic substrate in a sample at least 10%, 20%, 30%, 40%, 50%, 60%, 70%, 80%, 90%, 95%, 100%, 1.5 fold, 2-fold, 3-fold, 4-fold, 5-fold, 6-fold, 7-fold, 10-fold, 15-fold, 20-fold, 25-fold, 30-fold, at least 50-fold, or more in the presence of an anti-FXIa antibody compared to the absence of an antibody, or antigen-binding portion thereof, that specifically binds to the antigen-binding site of an anti-FXIa antibody. These amounts are not meant to be limiting, and increments between the recited amounts are specifically envisioned as part of the disclosure.

According to the methods of the disclosure, an antibody, or antigen-binding portion thereof, that specifically binds to the antigen-binding site of an anti-FXIa antibody is administered to a subject whose blood contains an anti-FXIa antibody. In some embodiments, an antibody, or antigen-binding portion thereof, that specifically binds to the antigen-binding site of an anti-FXIa antibody of the disclosure can be administered to a subject to reverse the effects of an anti-FXIa antibody where such anti-FXIa antibody occurs at therapeutic concentrations. In other embodiments, an antibody, or antigen-binding portion thereof, that specifically binds to the antigen-binding site of an anti-FXIa antibody of the disclosure can be administered to a subject to reverse the effects of an anti-FXIa antibody where such inhibitor occurs at supratherapeutic concentrations. A supratherapeutic concentration is one that is higher than that ordinarily considered required to safely achieve anti-coagulation in a particular subject or class of subjects. Supratherapeutic concentrations of an anti-FXIa antibody can result from accidental or intentional overdose. Supratherapeutic concentrations of an anti-FXIa antibody can also result from unexpected effects in particular subjects, such as an unexpectedly high sensitivity to these drugs, or unexpectedly slow rate of clearance, due for example to drug interactions or other factors. Determination of what would be a therapeutic concentration or supratherapeutic concentration of an anti-FXIa antibody in a particular subject or class of subjects is within the knowledge of those ordinarily skilled in the art.

According to the disclosure, an antibody, or antigen-binding portion thereof, that specifically binds to the antigen-binding site of an anti-FXIa antibody is used to counteract an anti-FXIa antibody or antibodies that selectively bind FXIa over other trypsin-like proteases by at least 5-fold, at least 6-fold, at least 7-fold, at least 10-fold, at least 15-fold, at least 20-fold, at least 25-fold, at least 30-fold, at least 50-fold, at least 100-fold, at least, 500-fold, at least 1,000-fold, at least 5,000-fold or at least 10,000-fold. These amounts are not meant to be limiting, and increments between the recited amounts are specifically envisioned as part of the disclosure.

The anti-FXIa antibody may bind an antibody, or antigen-binding portion thereof, that specifically binds to the antigen-binding site of an anti-FXIa antibody with a $K_i$ of about $2 \times 10^{-7}$ M or less. "$K_i$" refers to the inhibitor constant of a particular inhibitor-target interaction, which is the concentration required to produce half maximum inhibition. One can determine the $K_i$ by using methods known in the art. The disclosure contemplates, thus, counteracting an anti-FXIa antibody that binds with an antibody, or antigen-binding portion thereof, that specifically binds to the antigen-binding site of an anti-FXIa antibody with a $K_i$ of about $2 \times 10^{-8}$ M or less, about $1 \times 10^{-8}$ M or less, about $9 \times 10^{-9}$ M or less, about $8 \times 10^{-9}$ M or less, about $7 \times 10^{-9}$ M or less, about $6 \times 10^{-9}$ M or less, about $5 \times 10^{-9}$ M or less, about $4 \times 10^{-9}$ M or less, about $3 \times 10^{-9}$ M or less, about $2 \times 10^{-9}$ M or less, about $1 \times 10^{-9}$ M or less, about $9 \times 10^{-10}$ M or less, about $8 \times 10^{-10}$ M or less, about $7 \times 10^{-10}$ M or less, about $6 \times 10^{-10}$ M or less, about $5 \times 10^{-10}$ M or less, about $4 \times 10^{-10}$ M or less, about $3 \times 10^{-10}$ M or less, about $2 \times 10^{-10}$ M or less, about $1 \times 10^{-10}$ M or less, about $9 \times 10^{-11}$ M or less, about $8 \times 10^{-11}$ M or less, about $7 \times 10^{-11}$ M or less, about $6 \times 10^{-11}$ M or less, about $5 \times 10^{-11}$ M or less, about $4 \times 10^{-11}$ M or less, about $3 \times 10^{-11}$ M or less, about $2 \times 10^{-11}$ M or less, about $1 \times 10^{-11}$ M or less, about $9 \times 10^{-12}$ M or less, about $8 \times 10^{-12}$ M or less, about $7 \times 10^{-12}$ M or less, about $6 \times 10^{-12}$ M or less, about $5 \times 10^{-12}$ M or less, about $4 \times 10^{-12}$ M or less, about $3 \times 10^{-12}$ MN or less, about $2 \times 10^{-12}$ M or less, or about $1 \times 10^{-12}$ M or less, or less. The anti-FXIa antibody to be counteracted by an antibody, or antigen-binding portion thereof, that specifically binds to the antigen-binding site of an anti-FXIa antibody according to the methods of the disclosure may bind a wild-type FXIa with a $K_i$ at least 1.5 fold, at least 2-fold, at least 3-fold, at least 4-fold, at least 5-fold, at least 6-fold, at least 7-fold, at least 10-fold, at least 15-fold, at least 20-fold, at least 25-fold, at least 30-fold, or at least 50-fold less than it binds the antibody, or antigen-binding portion thereof, that specifically binds to the antigen-binding site of an anti-FXIa antibody. The anti-FXIa antibody may bind an FXIa dimer complex comprising a wild-type FXIa with about the same $K_i$. These amounts are not meant to be limiting, and increments between the recited amounts are specifically envisioned as part of the disclosure.

In one aspect, the disclosure provides methods for counteracting the effects of an anti-FXIa antibody in a subject who is bleeding (internally or externally) or is at risk of bleeding (e.g., in the course of a planned surgery) by administering antibody, or antigen-binding portion thereof, that specifically binds to the antigen-binding site of an anti-FXIa antibody. In some embodiments, the anti-FXIa antibody may be present in the subject at a therapeutic concentration or a higher concentration (i.e., a supratherapeutic concentration). In some embodiments, the therapeutic concentration may be an overdose in sensitive individuals.

The methods of the disclosure, thus, are useful for providing an antidote to an overdose of an anti-FXIa antibody. In various embodiments, the subject of treatment may be a human or a veterinary subject.

Anti-FXIa antibody overdose can be detected based on existence of symptoms or signs of excessively reduced clotting ability. Non-limiting examples include evidence of gastrointestinal bleeding, including dark tarry stools, bloody stools, and vomiting of blood. Other examples include nosebleeds, and increased tendency to, or severity of, bruising or bleeding from minor cuts and scrapes.

In a clinical setting, anti-FXIa antibody overdose can be detected directly or by measuring the ability of subject blood to clot and detecting deviations from the expected degree of anti-coagulation. Blood clotting potential can be measured in ways familiar to those ordinarily skilled in the art. For example, overdose may be suspected when a subject's activated partial thromboplastin time is excessively prolonged. In some embodiments, overdose is confirmed when the activated partial thromboplastin time is more than 2, 3, 4, or 5 fold, or greater than the activated partial thromboplastin time of a control sample untreated with an anti-FXIa antibody.

The antibody, or antigen-binding portion thereof, that specifically binds to the antigen-binding site of an anti-FXIa antibody may be administered whenever it is desired to counteract the effects of the anti-FXIa antibody, including but not limited to before a planned surgery, after an injury resulting in external or internal bleeding or after an anti-FXIa antibody overdose. According to the disclosure, the antibody, or antigen-binding portion thereof, that specifically binds to the antigen-binding site of an anti-FXIa antibody may be administered at least about 12 hours, at least about 6 hours, at least about 3 hours, at least about 2 hours, at least about 1 hour, at least about 30 minutes, at least about 10 minutes, or at least about 5 minutes of when the desired counteracting effect is needed, such as before a planned surgery, after an injury resulting in external or internal bleeding or after an anti-FXIa antibody overdose.

According to another embodiment, the disclosure provides a method of administering an antibody, or antigen-binding portion thereof, that specifically binds to the antigen-binding site of an anti-FXIa antibody to effect the urgent reversal of acquired coagulopathy due to an anti-FXIa antibody therapy in a subject with acute major bleeding. In some embodiments, subjects are adult human patients. In other embodiments, subjects are pediatric human patients.

In some embodiments, acute major bleeding is caused by trauma. In other embodiments, acute major bleeding occurs during surgery or other type of interventional procedure. Exemplary non-limiting interventional procedures include dental extractions, incisions, drainage, vascular surgery, appendectomy, herniotomy or hernioplasty, abdominal surgery, cholecystectomy, trephination (burr hole), lumbar puncture, cardiac pacemaker insertion, hip fracture surgery, uterine, kidney, prostate and bladder surgery, and others. In some embodiments, acute major bleeding may be menorrhagia. In still other embodiments, acute major bleeding can be spontaneous bleeding with no apparent cause.

Without limitation, sites of acute major bleeding include gastrointestinal bleeding, subcutaneous or intramuscular bleeding, bladder bleeding, hemarthrosis, subdural hematoma, nasal bleeding, peritoneal bleeding, uterine bleeding, and other sites of bleeding.

Effective treatment with antibodies, or antigen-binding portions thereof, that specifically bind to the antigen-binding site of an anti-FXIa antibody of the disclosure can reverse the effects of an anti-FXIa antibody. Successful reversal of such effects by an antibody, or antigen-binding portion thereof, that specifically binds to the antigen-binding site of an anti-FXIa antibody can be determined in a variety of ways and be measured or monitored using different assays, methods, or endpoints.

In some embodiments, treatment with an antibody, or antigen-binding portion thereof, that specifically binds to the antigen-binding site of an anti-FXIa antibody to reverse the effects of an anti-FXIa antibody is monitored using tests or assays performed on blood or plasma from a subject treated with an antibody, or antigen-binding portion thereof, that specifically binds to the antigen-binding site of an anti-FXIa antibody. A blood sample can be taken from a subject at a predetermined time after treatment with an antibody, or antigen-binding portion thereof, that specifically binds to the antigen-binding site of an anti-FXIa antibody. The blood, or plasma prepared from it, is then subjected to one or more tests to determine if certain hemostatic pharmacodynamic parameters have been normalized despite the presence of an anti-FXIa antibody. If normalization is found then the subject need not be further treated with an antibody, or antigen-binding portion thereof, that specifically binds to the antigen-binding site of an anti-FXIa antibody. If normalization is not found, however, then further treatment with an antibody, or antigen-binding portion thereof, that specifically binds to the antigen-binding site of an anti-FXIa antibody in accordance with the methods of the disclosure may be required to reverse the effect of an anti-FXIa antibody. Tests for monitoring the effectiveness of treatment with an antibody, or antigen-binding portion thereof, that specifically binds to the antigen-binding site of an anti-FXIa antibody include tests that directly or indirectly measure the ability to clot or that measure the activity of an anti-FXIa antibody. Non-limiting exemplary tests include fluorogenic peptide substrate assay, thromboelastometry, thromboelastography, thrombin generation assay, level of prothrombin fragment 1+2, level of thrombin-antithrombin III complex, and activated partial thromboplastin time. Other tests are also possible within the knowledge of those of ordinary skill in the art.

According to some embodiments, reversing the effects of an anti-FXIa antibody in a subject by administering an antibody, or antigen-binding portion thereof, that specifically binds to the antigen-binding site of an anti-FXIa antibody reduces bleeding in the subject. In some embodiments, treatment with an antibody, or antigen-binding portion thereof, that specifically binds to the antigen-binding site of an anti-FXIa antibody reduces bleeding in a subject at least 10%, 20%, 30%, 40%, 50%, 60%, 70%, 80%, 90%, 95%, or 99% in the presence of an anti-FXIa antibody compared to absence of treatment with an antibody, or antigen-binding portion thereof, that specifically binds to the antigen-binding site of an anti-FXIa antibody. In other embodiments, treatment with an antibody, or antigen-binding portion thereof, that specifically binds to the antigen-binding site of an anti-FXIa antibody reduces bleeding in a subject about 5%-10%, 10%-15%, 15%-20%, 20%-25%, 25%-30%, 30%-35%, 35%-40%, 40%-45%, 45%-50%, 50%-55%, 55%-60%, 60%-65/%, 65%-70%, 70%-75%, 75%-80%, 80%-85%, 85%-90%, 90%-95%, or 95%-100%. These amounts are not meant to be limiting, and increments between the recited amounts are specifically envisioned as part of the disclosure.

According to some embodiments, reversing the effects of an anti-FXIa antibody in a subject by administering an antibody, or antigen-binding portion thereof, that specifically binds to the antigen-binding site of an anti-FXIa antibody reduces the activity of an anti-FXIa antibody in the subject. In some embodiments, treatment with an antibody, or antigen-binding portion thereof, that specifically binds to the antigen-binding site of an anti-FXIa antibody reduces activity of the anti-FXIa antibody in a subject at least 10%, 20%, 30%, 40%, 50%, 60%, 70%, 80%, 90%, 95%, or 99% in the presence of an anti-FXIa antibody compared to absence of treatment with an antibody, or antigen-binding portion thereof, that specifically binds to the antigen-binding site of an anti-FXIa antibody. In other embodiments, treatment with an antibody, or antigen-binding portion thereof, that specifically binds to the antigen-binding site of an anti-FXIa antibody reduces the activity of an anti-FXIa antibody in a subject about 5%-10%, 10%-15%, 15%-20%, 20%-25%, 25%-30%, 30%-35%, 35%-40%, 40%-45%, 45%-50%, 50%-55%, 55%-60%, 60%-65%, 65%-70%, 70%-75%, 75%-80%, 80%-85%, 85%-90%, 90%-95%, or 95%-100%. These amounts are not meant to be limiting, and increments between the recited amounts are specifically envisioned as part of the disclosure.

According to some embodiments, reversing the effects of an anti-FXIa antibody in a subject by administering an antibody, or antigen-binding portion thereof, that specifically binds to the antigen-binding site of an anti-FXIa antibody increases the amount of thrombin produced in the blood or plasma of the subject. In some embodiments, treatment with an antibody, or antigen-binding portion thereof, that specifically binds to the antigen-binding site of an anti-FXIa antibody increases thrombin production in a subject at least 10%, 20%, 30%, 40%, 50%, 60%, 70%, 80%, 90%, 95%, 100%, 1.5 fold, 2-fold, 3-fold, 4-fold, 5-fold, 6-fold, 7-fold, 10-fold, 15-fold, 20-fold, 25-fold, 30-fold, at least 50-fold, or more in the presence of an anti-FXIa antibody compared to the absence of an antibody, or antigen-binding portion thereof, that specifically binds to the antigen-binding site of an anti-FXIa antibody. Thrombin production in the blood or plasma of a subject can be determined using the thrombin generation assay (TGA) or other technique familiar to those of ordinary skill in the art. These amounts are not meant to be limiting, and increments between the recited amounts are specifically envisioned as part of the disclosure.

According to some embodiments, reversing the effects of an anti-FXIa antibody in a subject by administering an antibody, or antigen-binding portion thereof, that specifically binds to the antigen-binding site of an anti-FXIa antibody increases the amount of FXIa enzymatic activity observed in a fluorogenic substrate assay in a sample of blood or plasma of a subject. In some embodiments, treatment with an antibody, or antigen-binding portion thereof, that specifically binds to the antigen-binding site of an anti-FXIa antibody increases enzymatic cleavage of a fluorogenic substrate in a sample at least 10%, 20%, 30%, 40%, 50%, 60%, 70%, 80%, 90%, 95%, 100%, 1.5 fold, 2-fold, 3-fold, 4-fold, 5-fold, 6-fold, 7-fold, 10-fold, 15-fold, 20-fold, 25-fold, 30-fold, at least 50-fold, or more in the presence of an anti-FXIa antibody compared to the absence of an antibody, or antigen-binding portion thereof, that specifically binds to the antigen-binding site of an anti-FXIa antibody molecule. These amounts are not meant to be limiting, and increments between the recited amounts are specifically envisioned as part of the disclosure.

According to some embodiments, reversing the effects of an anti-FXIa antibody in a subject by administering an antibody, or antigen-binding portion thereof, that specifically binds to the antigen-binding site of an anti-FXIa antibody increases clotting in the subject. In some embodiments, treatment with an antibody, or antigen-binding portion thereof, that specifically binds to the antigen-binding site of an anti-FXIa antibody increases clotting in a subject at least 10%, 20%, 30%, 40%, 50%, 60%, 70%, 80%, 90%, 95%, 100%, 1.5 fold, 2-fold, 3-fold, 4-fold, 5-fold, 6-fold, 7-fold, 10-fold, 15-fold, 20-fold, 25-fold, 30-fold, at least 50-fold, or more in the presence of an anti-FXIa antibody compared to the absence of an antibody, or antigen-binding portion thereof, that specifically binds to the antigen-binding site of an anti-FXIa antibody. These amounts are not meant to be limiting, and increments between the recited amounts are specifically envisioned as part of the disclosure.

According to some embodiments, reversing the effects of an anti-FXIa antibody in a subject by administering an antibody, or antigen-binding portion thereof, that specifically binds to the antigen-binding site of an anti-FXIa antibody reduces clotting time in the subject. In some embodiments, treatment with an antibody, or antigen-binding portion thereof, that specifically binds to the antigen-binding site of an anti-FXIa antibody reduces clotting time in a subject at least 10%, 20%, 30%, 40%, 50%, 60%, 70%, 80%, 90%, 95%, or 99% in the presence of an anti-FXIa antibody compared to absence of treatment with an antibody, or antigen-binding portion thereof, that specifically binds to the antigen-binding site of an anti-FXIa antibody. In other embodiments, treatment with an antibody, or antigen-binding portion thereof, that specifically binds to the antigen-binding site of an anti-FXIa antibody reduces clotting time in a subject about 5%-10%, 10%-15%, 15%-20%, 20%-25%, 25%-30%, 30%-35%, 35%-40%, 40%-45%, 45%-50%, 50%-55%, 55%-60%, 60%-65%, 65%-70%, 70%-75%, 75%-80%, 80%-85%, 85%-90%, 90%-95%, or 95%-100%. These amounts are not meant to be limiting, and increments between the recited amounts are specifically envisioned as part of the disclosure.

In yet other embodiments, the methods of thromboelastometry or thromboelastography may be used to analyze clot formation or clotting time.

According to some embodiments, reversing the effects of an anti-FXIa antibody in a subject by administering an antibody, or antigen-binding portion thereof, that specifically binds to the antigen-binding site of an anti-FXIa antibody increases the level of prothrombin fragment 1+2 (PF1+2) in the blood or plasma of the subject. In some embodiments, treatment with an antibody, or antigen-binding portion thereof, that specifically binds to the antigen-binding site of an anti-FXIa antibody increases PF1+2 in a subject at least 10%, 20%, 30%, 40%, 50%, 60%, 70%, 80%, 90%, 95%, 100%, 1.5-fold, 2-fold, 3-fold, 4-fold, 5-fold, 6-fold, 7-fold, 10-fold, 15-fold, 20-fold, 25-fold, 30-fold, at least 50-fold, or more in the presence of an anti-FXIa antibody compared to the absence of an antibody, or antigen-binding portion thereof, that specifically binds to the antigen-binding site of an anti-FXIa antibody. These amounts are not meant to be limiting, and increments between the recited amounts are specifically envisioned as part of the disclosure.

According to some embodiments, reversing the effects of an anti-FXIa antibody in a subject by administering an antibody, or antigen-binding portion thereof, that specifically binds to the antigen-binding site of an anti-FXIa antibody increases the level of thrombin-antithrombin III complex (TAT) in the blood or plasma of the subject. In some embodiments, treatment with an antibody, or antigen-binding portion thereof, that specifically binds to the antigen-binding site of an anti-FXIa antibody increases TAT in a subject at least 10%, 20%, 30%, 40%, 50%, 60%, 70%, 80%, 90%, 95%, 100%, 1.5-fold, 2-fold, 3-fold, 4-fold, 5-fold, 6-fold, 7-fold, 10-fold, 15-fold, 20-fold, 25-fold, 30-fold, at least 50-fold, or more in the presence of an anti-FXIa antibody compared to the absence of an antibody, or antigen-binding portion thereof, that specifically binds to the antigen-binding site of an anti-FXIa antibody. These amounts are not meant to be limiting, and increments between the recited amounts are specifically envisioned as part of the disclosure.

According to some embodiments, reversing the effects of an anti-FXIa antibody in a subject by administering an antibody, or antigen-binding portion thereof, that specifically binds to the antigen-binding site of an anti-FXIa antibody reduces activated partial thromboplastin time (APTT) in the subject. In some embodiments, treatment with an antibody, or antigen-binding portion thereof, that specifically binds to the antigen-binding site of an anti-FXIa antibody reduces activated partial thromboplastin time (APTT) in a subject to 1.0, 1.1, 1.2, 1.3, 1.4, 1.5, 1.6, 1.7, 1.8, 1.9, 2.0, 2.1, 2.2, 2.3, 2.4, or 2.5 fold or less of the normal range for the APTT test. In some embodiments, treatment with an antibody, or antigen-binding portion thereof, that specifically binds to the antigen-binding site of an anti-FXIa antibody reduces activated partial thromboplastin time (APTT) in a subject to less than 1.2 fold the APTT of a control sample untreated with an anti-FXIa antibody and an antibody, or antigen-binding portion thereof, that specifically binds to the antigen-binding site of an anti-FXIa antibody. These amounts are not meant to be limiting, and increments between the recited amounts are specifically envisioned as part of the disclosure.

In other embodiments, clinical endpoints can be relied upon to determine if hemostasis has been adequately restored in a subject treated with an antibody, or antigen-binding portion thereof, that specifically binds to the antigen-binding site of an anti-FXIa antibody to reverse the effects of an anti-FXIa antibody. For example, where a subject presents with acute bleeding, clinical hemostatic efficacy can be scored "very good" where prompt cessation of existing bleeding occurs after treatment with an antibody, or antigen-binding portion thereof, that specifically binds to the antigen-binding site of an anti-FXIa antibody; "satisfactory" where there is a 1-2 hr delay in bleeding cessation: "questionable" where there is a >2 hr delay in bleeding cessation; and "none" where an effect on bleeding is absent. Where treatment with an antibody, or antigen-binding portion thereof, that specifically binds to the antigen-binding site of an anti-FXIa antibody is determined to be less than satisfactory, then an additional dose of an antibody, or antigen-binding portion thereof, that specifically binds to the antigen-binding site of an anti-FXIa antibody can be administered to effect adequate hemostasis. In a further example, where a subject is undergoing an interventional procedure, clinical hemostatic efficacy can be scored "very good" where normal hemostasis is attained during the procedure; "satisfactory" where intraprocedural hemostasis is mildly abnormal as judged by quantity or quality of blood loss (e.g., slight oozing); "questionable" where intraprocedural hemostasis is moderately abnormal as judged by quantity or quality of blood loss (e.g., controllable bleeding); and "none" where intraprocedural hemostasis is severely abnormal as judged by quantity or quality of blood loss (e.g., severe refractory hemorrhage).

In some embodiments, the disclosed antibodies, or antigen-binding portions thereof, that specifically bind to the antigen-binding site of an anti-FXIa antibody can be used to decrease anticoagulant activity of an anti-FXIa antibody. In some embodiments, the disclosed antibodies, or antigen-binding portions thereof, that specifically bind to the antigen-binding site of an anti-FXIa antibody can be used in combination with an anti-FXIa antibody in the prevention, treatment, and/or amelioration of diseases, disorders or conditions caused by and/or associated with FXI activity. Such diseases, disorders or conditions include, but are not limited to, acute major bleeding caused by trauma; acute major bleeding during surgery or other type of interventional procedure: thrombotic or thromboembolic diseases; atrial fibrillation (AF): venous thromboembolism (VTE): VTE in the medically ill; VTE prophylaxis in the medically ill: VTE prophylaxis in knee or hip surgery; Afib in the renal disease population and/or patients previously identified as bleeders; acute coronary syndromes: use of extracorporeal circulations and devices in which blood contacts artificial surfaces; vascular grafts; myocardial infarction; acute myocardial infarction; congestive heart failure; pulmonary embolism; thrombosis; deep vein thrombosis; renal vein thrombosis; transient ischemic attack: thrombotic stroke; thromboembolic stroke; cardiogenic thromboembolism; atherosclerosis; inflammatory diseases: pulmonary hypertension; pulmonary and/or hepatic fibrosis; and sepsis; among others, as would be appreciated by one skilled in the art provided with the teachings disclosed herein. Additional uses include situations in which blood touches artificial surfaces, including mechanical heart valves, extracorporeal circulations, extracorporeal membrane oxygenation, left ventricular assist devices, cardiopulmonary bypass, vascular grafts, and catheters, wires, and other devices introduced in to the heart and blood vessels. Examples of diseases and disorders are provided in WO2013167669, incorporated herein by reference.

In certain aspects of the disclosure, methods are provided for decreasing anticoagulant activity in a subject being administered an anti-FXIa antibody, comprising administering to said subject an antibody, or antigen-binding portion thereof, that specifically binds to the antigen-binding site of an anti-FXIa antibody as described herein, wherein the anticoagulant activity is reduced compared with the anticoagulant activity in the subject prior to administration of the anti-FXIa antibody. In certain aspects of the disclosure, methods are provided for reducing clotting time in a subject being administered an anti-FXIa antibody, comprising administering to said subject an antibody, or antigen-binding portion thereof, that specifically binds to the antigen-binding site of an anti-FXIa antibody as described herein, wherein the clotting time is reduced compared with the clotting time in the subject prior to administration of the anti-FXIa antibody.

In some embodiments, the disclosure provides an antibody, or antigen-binding portion thereof, that specifically binds to the antigen-binding site of an anti-FXIa antibody as described herein for use in decreasing anticoagulant activity in a subject being administered an anti-FXIa antibody. In some embodiments, the disclosure provides an antibody, or antigen-binding portion thereof, that specifically binds to the antigen-binding site of an anti-FXIa antibody as described herein for use in reducing clotting time in a subject being administered an anti-FXIa antibody.

In some embodiments, the disclosure provides the use of an antibody, or antigen-binding portion thereof, that specifically binds to the antigen-binding site of an anti-FXIa antibody as described herein in the manufacture of a medicament for decreasing anticoagulant activity in a subject being administered an anti-FXIa antibody. In some embodiments, the disclosure provides the use of an antibody, or antigen-binding portion thereof, that specifically binds to the antigen-binding site of an anti-FXIa antibody as described herein in the manufacture of a medicament for reducing clotting time in a subject being administered an anti-FXIa antibody.

VI. Combination Therapies

Co-administration of an anti-FXIa antibody, or an anti-FXIa antibody and an anti-idiotype antibody that specifically binds to the antigen-binding site of the anti-FXIa antibody, or an antigen-binding portion thereof, as described herein with an additional therapeutic agent (combination therapy) encompasses administering a pharmaceutical composition comprising the anti-FXIa antibody of the disclosure or the anti-idiotype antibody, or antigen-binding portion thereof, as described herein and the additional therapeutic agent, as well as administering two or more separate pharmaceutical compositions. i.e., one comprising the anti-FXIa antibody of the disclosure or the anti-FXIa antibody and the anti-idiotype antibody, or an antigen-binding portion thereof, as described herein and the other(s) comprising the additional therapeutic agent(s). Co-administration or combination therapy further includes administering the anti-FXIa antibody of the disclosure or the anti-FXIa antibody and the anti-idiotype antibody, or antigen-binding portion thereof, and additional therapeutic agent(s) simultaneously or sequentially, or both. For instance, the anti-FXIa antibody of the disclosure or the anti-FXIa antibody and the anti-idiotype antibody, or antigen-binding portion thereof, as described herein may be administered once every three days, while the additional therapeutic agent is administered once daily at the same time as the anti-FXIa antibody of the disclosure or the anti-FXIa antibody and the anti-idiotype antibody, or antigen-binding portion thereof, as described herein, or at a different time. An anti-FXIa antibody of the disclosure, or antigen-binding portion thereof, or an anti-FXIa antibody and anti-idiotype antibody, or antigen-binding portion thereof, that specifically binds to the antigen-binding site of an anti-FXIa antibody as described herein may be administered prior to or subsequent to treatment with the additional therapeutic agent. Similarly, administration of an anti-FXIa antibody of the disclosure, or antigen-binding portion thereof, or the anti-FXIa antibody and the anti-idiotype antibody, or antigen-binding portion thereof, that specifically binds to the antigen-binding site of the anti-FXIa antibody as described herein may be part of a treatment regimen that includes other treatment modalities including surgery. The combination therapy may be administered to prevent recurrence of the condition. The combination therapy may be administered from multiple times hourly to weekly. The administrations may be on a schedule such as every 10 minutes, every 15 minutes, every 20 minutes, every 30 minutes, every hour, every two hours, every three hours, every four hours, three times daily, twice daily, once daily, once every two days, once every three days, once weekly, or may be administered continuously, e.g. via a minipump. The combination therapy may be administered, for example, via a parenteral route (e.g., intravenously, subcutaneously, intraperitoneally, or intramuscularly).

In another embodiment, the anti-FXIa antibody and the anti-idiotype antibody, or antigen-binding portion thereof, that specifically binds to the antigen-binding site of the anti-FXIa antibody as described herein may be co-administered with another procoagulant including another FXIa decoy molecule, Factor IX, Factor Xa, Factor XIIa, Factor VIII, Factor VIIa, FEIBA and prothrombin complex concentrate (PCC).

In some embodiments, the antibodies of the disclosure are given in combination with lipid lowering compounds; compounds suitable for the treatment of coronary diseases and/or compounds exhibiting vasodilatative activities; diuretics; inhibitors of calcium channels; inhibitors of the coagulation cascade; and anticoagulants like non-fractionated heparins, low molecular weight heparins, hirudin, bivalirudin and/or argatroban. Examples of suitable combination therapeutics are provided in WO2013167669, incorporated herein by reference.

In another embodiment, the anti-FXIa antibody and the anti-idiotype antibody, or antigen-binding portion thereof, that specifically binds to the antigen-binding site of the anti-FXIa antibody as described herein may be co-administered with another procoagulant including another FXIa decoy molecule, Factor IX, Factor Xa, Factor XIIa, Factor VIII, Factor VIIa, FEIBA and prothrombin complex concentrate (PCC).

Co-administration of an antibody of the disclosure with an additional therapeutic agent (combination therapy) encompasses administering a pharmaceutical composition comprising the antibody of the disclosure and the additional therapeutic agent, as well as administering two or more separate pharmaceutical compositions, i.e., one comprising the antibody and the other(s) comprising the additional therapeutic agent(s). Co-administration or combination therapy further includes administering the antibody of the disclosure and additional therapeutic agent(s) simultaneously or sequentially, or both. For instance, the antibody may be administered once every three days, while the additional therapeutic agent is administered once daily at the same as the antibody, or at a different time. An antibody of the disclosure may be administered prior to or subsequent to treatment with the additional therapeutic agent. Similarly, administration of an antibody of the disclosure may be part of a treatment regimen that includes other treatment modalities including surgery. The combination therapy may be administered to prevent recurrence of the condition. The combination therapy may be administered from multiple times hourly to weekly. The administrations may be on a schedule such as every 10 minutes, every 15 minutes, every 20 minutes, every 30 minutes, every hour, every two hours, every three hours, every four hours, three times daily, twice daily, once daily, once every two days, once every three days, once weekly, or may be administered continuously, e.g. via a minipump. The combination therapy may be administered, for example, via a parenteral route (e.g., intravenously, subcutaneously, intraperitoneally, or intramuscularly).

VII. Compositions

In one aspect, the disclosure provides pharmaceutical compositions comprising an effective amount of an anti-FXIa antibody described herein. Examples of such compositions, as well as how to formulate, are also described herein. In some embodiments, the composition comprises one or more anti-FXIa antibodies. In other embodiments, the anti-FXIa antibody recognizes FXIa. In other embodiments, the anti-FXIa antibody is a human antibody. In other embodiments, the anti-FXIa antibody is a humanized antibody. In some embodiments, the anti-FXIa antibody comprises a constant region that is capable of triggering a desired immune response, such as antibody-mediated lysis or ADCC. In other embodiments, the anti-FXIa antibody comprises a constant region that does not trigger an unwanted or undesirable immune response, such as antibody-mediated lysis or ADCC. In other embodiments, the anti-FXIa antibody comprises one or more CDR(s) of the antibody (such as one, two, three, four, five, or, in some embodiments, all six CDRs).

It is understood that the compositions can comprise more than one anti-FXIa antibody (e.g., a mixture of anti-FXIa antibodies that recognize different epitopes of FXIa). Other exemplary compositions comprise more than one anti-FXIa antibody that recognize the same epitope(s), or different species of anti-FXIa antibodies that bind to different epitopes of anti-FXIa. In some embodiments, the compositions comprise a mixture of anti-FXIa antibodies that recognize different variants of anti-FXIa.

The disclosure also provides pharmaceutical compositions comprising an effective amount of an anti-idiotype antibody that specifically binds to the antigen-binding site of an anti-FXIa antibody or antigen-binding portion thereof, as described herein. Examples of such compositions, as well as how to formulate, are also described herein. In some embodiments, the composition comprises one or more anti-idiotype antibodies. In other embodiments, the anti-idiotype antibody recognizes an anti-FXIa antibody of the disclosure. In other embodiments, the anti-FXIa antibody is a human antibody. In other embodiments, the anti-FXIa antibody is a humanized antibody. In some embodiments, the anti-idiotype antibody comprises a constant region that is capable of triggering a desired immune response, such as antibody-mediated lysis or ADCC. In other embodiments, the anti-FXIa antibody comprises a constant region that does not trigger an unwanted or undesirable immune response, such as antibody-mediated lysis or ADCC. In other embodiments, the anti-idiotype antibody comprises one or more CDR(s) of the antibody (such as one, two, three, four, five, or, in some embodiments, all six CDRs).

It is understood that the compositions can comprise more than one anti-idiotype antibody (e.g., a mixture of anti-idiotype antibodies that recognize different anti-FXIa antibodies or different epitopes on the same anti-FXIa antibody). Other exemplary compositions comprise more than one anti-idiotype antibody that recognize the same epitope(s), or different species of anti-idiotype antibodies that bind to different epitopes of an anti-FXIa antibody. In some embodiments, the compositions comprise a mixture of anti-idiotype antibodies that recognize different variants of an anti-FXIa antibody.

The compositions of the present disclosure can further comprise pharmaceutically acceptable carriers, excipients, or stabilizers (Remington: The Science and practice of Pharmacy 20th Ed., 2000, Lippincott Williams and Wilkins, Ed. K. E. Hoover), in the form of lyophilized formulations or aqueous solutions. Acceptable carriers, excipients, or stabilizers are nontoxic to recipients at the dosages and concentrations, and may comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol: alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine;

monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). Pharmaceutically acceptable excipients are further described herein.

The anti-FXIa antibody and compositions thereof or the anti-idiotype antibody and compositions thereof can also be used in conjunction with other agents that serve to enhance and/or complement the effectiveness of the agents.

The disclosure also provides compositions, including pharmaceutical compositions, comprising any of the polynucleotides of the disclosure. In some embodiments, the composition comprises an expression vector comprising a polynucleotide encoding the antibody as described herein. In other embodiments, the composition comprises an expression vector comprising a polynucleotide encoding any of the antibodies described herein. In still other embodiments, the composition comprises either or both of the polynucleotides comprising the sequence shown in SEQ ID NO: 84 and SEQ ID NO: 85, either or both of the polynucleotides shown in SEQ ID NO: 86 and SEQ ID NO: 87, or either or both of the polynucleotides shown in SEQ ID NO:88 and SEQ ID NO:89. In still other embodiments, the composition comprises either or both of the polynucleotides comprising the sequence shown in SEQ ID NO: 90 and SEQ ID NO: 91.

In another aspect, the polynucleotide can encode the VH, VL and/or both VH and VL of the anti-FXIa antibody of the disclosure. In another aspect, the polynucleotide can encode the VH, VL and/or both VH and VL of an anti-idiotype antibody of the disclosure. That is, the composition comprises a single polynucleotide or more than one polynucleotide encoding the antibody, or antigen-binding portion thereof, or the disclosure.

Pharmaceutical compositions of the disclosure also can be administered in combination therapy, such as, combined with other agents. For example, the combination therapy can include an anti-FXIa antibody, or antigen binding fragment thereof, of the present disclosure combined with at least one other therapy wherein the therapy may be surgery, immunotherapy, or drug therapy.

The pharmaceutical compounds of the disclosure may include one or more pharmaceutically acceptable salts. Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition of the disclosure also may include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like, and (3) metal chelating agents, such as citric acid, ethylenediamine tetraacetic acid (EDTA), sorbitol, tartaric acid, phosphoric acid, and the like.

Examples of suitable aqueous and non-aqueous carriers that may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Pharmaceutical compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be suitable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration.

Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

A pharmaceutical composition of the present disclosure may be prepared, packaged, or sold in a formulation suitable for ophthalmic administration. Such formulations may, for example, be in the form of eye drops including, for example, a 0.1 1.0% (w/w) solution or suspension of the active ingredient in an aqueous or oily liquid carrier. Such drops may further comprise buffering agents, salts, or one or more other of the additional ingredients described herein. Other ophthalmically-administrable formulations which are useful include those which comprise the active ingredient in microcrystalline form or in a liposomal preparation.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the disclosure are known in the art and described, for example in Remington's Pharmaceutical Sciences, Genaro, ed., Mack Publishing Co., Easton, Pa. (1985), which is incorporated herein by reference.

In one embodiment, the anti-FXIa antibody, or antigen binding fragment thereof, is administered in an intravenous formulation as a sterile aqueous solution containing 5 mg/ml, or more preferably, about 10 mg/ml, or yet more preferably, about 15 mg/ml, or even more preferably, about 20 mg/ml of antibody, with sodium acetate, polysorbate 80, and sodium chloride at a pH ranging from about 5 to 6. Preferably, the intravenous formulation is a sterile aqueous solution containing 5 or 10 mg/ml of antibody, with 20 mM sodium acetate, 0.2 mg/ml polysorbate 80, and 140 mM sodium chloride at pH 5.5. Further, a solution comprising an antibody, or antigen binding fragment thereof, can comprise, among many other compounds, histidine, mannitol, sucrose, trehalose, glycine, poly(ethylene) glycol, EDTA, methionine, and any combination thereof, and many other compounds known in the relevant art.

In one embodiment, a pharmaceutical composition of the present disclosure comprises the following components: 100 mg anti-FXIa antibody or antigen binding fragment of the present disclosure, 10 mM histidine, 5% sucrose, and 0.01% polysorbate 80 at pH 5.8. This composition may be provided as a lyophilized powder. When the powder is reconstituted at full volume, the composition retains the same formulation. Alternatively, the powder may be reconstituted at half volume, in which case the composition comprises 100 mg FXIa antibody or antigen binding fragment thereof of the present disclosure, 20 mM histidine, 10% sucrose, and 0.02% polysorbate 80 at pH 5.8.

In one embodiment, part of the dose is administered by an intravenous bolus and the rest by infusion of the antibody formulation. For example, a 0.01 mg/kg intravenous injection of the anti-FXIa antibody, or antigen binding fragment thereof, may be given as a bolus, and the rest of the antibody dose may be administered by intravenous injection. A predetermined dose of the anti-FXIa antibody, or antigen binding fragment thereof, may be administered, for example, over a period of an hour and a half to two hours to five hours.

In one embodiment, the anti-idiotype antibody, or antigen binding fragment thereof, is administered in an intravenous formulation as a sterile aqueous solution containing 5 mg/ml, or more preferably, about 10 mg/ml, or yet more preferably, about 15 mg/ml, or even more preferably, about 20 mg/ml of antibody, with sodium acetate, polysorbate 80, and sodium chloride at a pH ranging from about 5 to 6. Preferably, the intravenous formulation is a sterile aqueous solution containing 5 or 10 mg/ml of antibody, with 20 mM sodium acetate, 0.2 mg/ml polysorbate 80, and 140 mM sodium chloride at pH 5.5. Further, a solution comprising an antibody, or antigen binding fragment thereof, can comprise, among many other compounds, histidine, mannitol, sucrose, trehalose, glycine, poly(ethylene) glycol, EDTA, methionine, and any combination thereof, and many other compounds known in the relevant art.

In one embodiment, a pharmaceutical composition of the present disclosure comprises the following components: 100 mg anti-idiotype antibody or antigen binding fragment of the present disclosure, 10 mM histidine, 5% sucrose, and 0.01% polysorbate 80 at pH 5.8. This composition may be provided as a lyophilized powder. When the powder is reconstituted at full volume, the composition retains the same formulation. Alternatively, the powder may be reconstituted at half volume, in which case the composition comprises 100 mg anti-idiotype antibody or antigen binding fragment thereof of the present disclosure, 20 mM histidine, 10% sucrose, and 0.02% polysorbate 80 at pH 5.8.

In one embodiment, part of the dose is administered by an intravenous bolus and the rest by infusion of the antibody formulation. For example, a 0.01 mg/kg intravenous injection of the anti-idiotype antibody, or antigen binding fragment thereof, may be given as a bolus, and the rest of the antibody dose may be administered by intravenous injection. A predetermined dose of the anti-FXIa antibody, or antigen binding fragment thereof, may be administered, for example, over a period of an hour and a half to two hours to five hours.

With regard to a therapeutic agent, where the agent is, e.g., a small molecule, it can be present in a pharmaceutical composition in the form of a physiologically acceptable ester or salt, such as in combination with a physiologically acceptable cation or anion, as is well known in the art.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

In one embodiment the compositions of the disclosure are pyrogen-free formulations which are substantially free of endotoxins and/or related pyrogenic substances. Endotoxins include toxins that are confined inside a microorganism and are released when the microorganisms are broken down or die. Pyrogenic substances also include fever-inducing, thermostable substances (glycoproteins) from the outer membrane of bacteria and other microorganisms. Both of these substances can cause fever, hypotension and shock if administered to humans. Due to the potential harmful effects, it is advantageous to remove even low amounts of endotoxins from intravenously administered pharmaceutical drug solutions. The Food and Drug Administration ("FDA") has set an upper limit of 5 endotoxin units (EU) per dose per kilogram body weight in a single one hour period for intravenous drug applications (The United States Pharmacopeial Convention, Pharmacopeial Forum 26 (1):223 (2000)). When therapeutic proteins are administered in amounts of several hundred or thousand milligrams per kilogram body weight it is advantageous to remove even trace amounts of endotoxin. In one embodiment, endotoxin and pyrogen levels in the composition are less than 10 EU/mg, or less than 5 EU/mg, or less than 1 EU/mg, or less than 0.1 EU/mg, or less than 0.01 EU/mg, or less than 0.001 EU/mg. In another embodiment, endotoxin and pyrogen levels in the composition are less than about 10 EU/mg, or less than about 5 EU/mg, or less than about 1 EU/mg, or less than about 0.1 EU/mg, or less than about 0.01 EU/mg, or less than about 0.001 EU/mg.

In one embodiment, the disclosure comprises administering a composition wherein said administration is oral, parenteral, intramuscular, intranasal, vaginal, rectal, lingual, sublingual, buccal, intrabuccal, intravenous, cutaneous, subcutaneous or transdermal.

In another embodiment the disclosure further comprises administering a composition in combination with other therapies, such as surgery, chemotherapy, hormonal therapy, biological therapy, immunotherapy or radiation therapy.

VIII. Dosing and Administration

To prepare pharmaceutical or sterile compositions including an anti-FXIa antibody or antigen binding fragment thereof of the disclosure, or an anti-idiotype antibody or antigen binding fragment thereof of the disclosure, the antibody is mixed with a pharmaceutically acceptable carrier or excipient. Formulations of therapeutic and diagnostic agents can be prepared by mixing with physiologically acceptable carriers, excipients, or stabilizers in the form of, e.g., lyophilized powders, slurries, aqueous solutions, lotions, or suspensions (see, e.g., Hardman, et al. (2001) Goodman and Gilman's The Pharmacological Basis of Therapeutics, McGraw-Hill, New York, N.Y.; Gennaro (2000) Remington: The Science and Practice of Pharmacy, Lippincott. Williams, and Wilkins, New York, N.Y.; Avis, et al. (eds.) (1993) Pharmaceutical Dosage Forms: Parenteral Medications, Marcel Dekker, NY; Lieberman, et al. (eds.) (1990) Pharmaceutical Dosage Forms: Tablets, Marcel Dekker, NY; Lieberman, et al. (eds.) (1990) Pharmaceutical Dosage Forms: Disperse Systems, Marcel Dekker, NY: Weiner and Kotkoskie (2000) Excipient Toxicity and Safety, Marcel Dekker, Inc., New York, N.Y.).

Selecting an administration regimen for a therapeutic depends on several factors, including the serum or tissue turnover rate of the entity, the level of symptoms, the immunogenicity of the entity, and the accessibility of the target cells in the biological matrix. In certain embodiments, an administration regimen maximizes the amount of therapeutic delivered to the patient consistent with an acceptable level of side effects. Accordingly, the amount of biologic delivered depends in part on the particular entity and the severity of the condition being treated. Guidance in selecting appropriate doses of antibodies, cytokines, and small molecules are available (see, e.g., Wawrzynczak, 1996, Antibody Therapy, Bios Scientific Pub. Ltd, Oxfordshire, UK; Kresina (ed.), 1991. Monoclonal Antibodies. Cytokines and Arthritis, Marcel Dekker, New York, N.Y.; Bach (ed.), 1993, Monoclonal Antibodies and Peptide Therapy in Autoimmune Diseases, Marcel Dekker, New York, N.Y.; Baert, et al., 2003, New Engl. J. Med. 348:601-608; Milgrom, et al., 1999, New Engl. J. Med. 341:1966-1973; Slamon, et al., 2001, New Engl. J. Med. 344:783-792; Beniaminovitz, et al., 2000, New Engl. J. Med. 342:613-619; Ghosh, et al., 2003, New Engl. J. Med. 348:24-32: Lipsky, et al., 2000, New Engl. J. Med. 343:1594-1602).

Determination of the appropriate dose is made by the clinician, e.g., using parameters or factors known or suspected in the art to affect treatment or predicted to affect treatment. Generally, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced.

Actual dosage levels of the active ingredients in the pharmaceutical compositions of the present disclosure may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present disclosure employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

In some embodiments, an anti-idiotype antibody or antigen binding fragment thereof of the disclosure is administered to a subject who is being administered an anti-FXIa antibody of the disclosure. In some embodiments, the anti-FXIa antibody is selected from: D4, DEF, QCA11, B1D2, B10H2, B0E6, B10F6, B10D8, B10B12, S1D4, S10H9, Clone 8, Clone 16, Clone 20, Clone 22, Clone 32, or Clone 24. In some embodiments, the anti-FXIa antibody is DEF. In some embodiments, the anti-FXIa antibody is DEF and the anti-idiotype antibody is C4.

Compositions comprising anti-FXIa antibodies or antigen binding fragments thereof of the disclosure, or anti-idiotype antibodies or antigen binding fragments thereof of the disclosure, can be provided by continuous infusion, or by doses at intervals of, e.g., one day, one week, or 1-7 times per week. Doses may be provided intravenously, subcutaneously, topically, orally, nasally, rectally, intramuscular, intracerebrally, or by inhalation. A specific dose protocol is one involving the maximal dose or dose frequency that avoids significant undesirable side effects. A total weekly dose may be at least 0.05 µg/kg body weight, at least 0.2 µg/kg, at least 0.5 µg/kg, at least 1 µg/kg, at least 10 µg/kg, at least 100 µg/kg, at least 0.2 mg/kg, at least 1.0 mg/kg, at least 2.0 mg/kg, at least 10 mg/kg, at least 15 mg/kg, at least 20 mg/kg, at least 25 mg/kg, or at least 50 mg/kg (see, e.g., Yang, et al., 2003, New Engl. J. Med. 349:427-434; Herold, et al., 2002, New Engl. J. Med. 346:1692-1698; Liu, et al., 1999. J. Neurol. Neurosurg. Psych. 67:451-456; Portielji, et al., 2003, Cancer. Immunol. Immunother. 52: 133-144). The dose may be at least 15 µg, at least 20 µg, at least 25 µg, at least 30 µg, at least 35 µg, at least 40 µg, at least 45 µg, at least 50 µg, at least 55 µg, at least 60 µg, at least 65 µg, at least 70 µg, at least 75 µg, at least 80 µg, at least 85 µg, at least 90 µg, at least 95 µg, or at least 100 µg. The doses administered to a subject may number at least 1, 2, 3, 4, 5, 6, 7, 8, 9, 10, 11, or 12, or more.

For anti-FXIa antibodies or antigen binding fragments thereof of the disclosure, or anti-idiotype antibodies or antigen binding fragments thereof of the disclosure, the dosage administered to a patient may be 0.0001 mg/kg to 100 mg/kg of the patient's body weight. The dosage may be between 0.0001 mg/kg and 20 mg/kg, 0.0001 mg/kg and 10 mg/kg, 0.0001 mg/kg and 5 mg/kg, 0.0001 and 2 mg/kg, 0.0001 and 1 mg/kg, 0.0001 mg/kg and 0.75 mg/kg, 0.0001 mg/kg and 0.5 mg/kg, 0.0001 mg/kg to 0.25 mg/kg, 0.0001 to 0.15 mg/kg, 0.0001 to 0.10 mg/kg, 0.001 to 0.5 mg/kg, 0.01 to 0.25 mg/kg or 0.01 to 0.10 mg/kg of the patient's body weight.

The dosage of the anti-FXIa antibody, or antigen binding fragment thereof, or the anti-idiotype antibody, or antigen binding fragment thereof, may be calculated using the patient's weight in kilograms (kg) multiplied by the dose to be administered in mg/kg. The dosage of the antibodies of the disclosure may be 150 µg/kg or less, 125 µg/kg or less, 100 µg/kg or less, 95 µg/kg or less, 90 µg/kg or less, 85 µ/kg or less, 80 µ/kg or less, 75 µ/kg or less, 70 µ/kg or less, 65 µ/kg or less, 60 µ/kg or less, 55 µ/kg or less, 50 µ/kg or less, 45 µ/kg or less, 40 µ/kg or less, 35 µ/kg or less, 30 µ/kg or less, 25 µ/kg or less, 20 µ/kg or less, 15 µ/kg or less, 10 µ/kg or less, 5 µ/kg or less, 2.5 µ/kg or less, 2 µ/kg or less, 1.5 µ/kg or less, 1 µ/kg or less, 0.5 µ/kg or less, or 0.1 µ/kg or less of a patient's body weight.

A unit dose of the anti-FXIa antibodies or antigen binding fragments thereof of the disclosure, or the anti-idiotype antibodies or antigen binding fragments thereof of the disclosure, may be 0.1 mg to 200 mg, 0.1 mg to 175 mg, 0.1 mg to 150 mg, 0.1 mg to 125 mg, 0.1 mg to 100 mg, 0.1 mg to 75 mg, 0.1 mg to 50 mg, 0.1 mg to 30 mg, 0.1 mg to 20 mg, 0.1 mg to 15 mg, 0.1 mg to 12 mg, 0.1 mg to 10 mg, 0.1 mg to 8 mg, 0.1 mg to 7 mg, 0.1 mg to 5 mg, 0.1 to 2.5 mg, 0.25 mg to 20 mg, 0.25 to 15 mg, 0.25 to 12 mg, 0.25 to 10 mg, 0.25 to 8 mg, 0.25 mg to 7 m g, 0.25 mg to 5 mg, 0.5 mg to 2.5 mg, 1 mg to 20 mg, 1 mg to 15 mg, 1 mg to 12 mg, 1 mg to 10 mg, 1 mg to 8 mg, 1 mg to 7 mg, 1 mg to 5 mg, or 1 mg to 2.5 mg.

The dosage of the anti-FXIa antibodies or antigen binding fragments thereof of the disclosure, or the anti-idiotype antibodies or antigen binding fragments thereof of the disclosure, may achieve a serum titer of at least 0.1 µg/ml, at least 0.5 µg/ml, at least 1 µg/ml, at least 2 µg/ml, at least 5 µg/ml, at least 6 µg/ml, at least 10 µg/ml, at least 15 µg/ml, at least 20 µg/ml, at least 25 µg/ml, at least 50 µg/ml, at least 100 µg/ml, at least 125 µg/ml, at least 150 v, at least 175 µg/ml, at least 200 µg/ml, at least 225 µg/ml, at least 250 µg/ml, at least 275 µg/ml, at least 300 µg/ml, at least 325 µg/ml, at least 350 µg/ml, at least 375 µg/ml/ml, or at least 400 µg/ml/ml in a subject. Alternatively, the dosage of the antibodies of the disclosure may achieve a serum titer of at least 0.1 µg/ml, at least 0.5 µg/ml, at least 1 µg/ml, at least, 2 µg/ml, at least 5 µg/ml, at least 6 µg/ml, at least 10 µg/ml, at least 15 µg/ml, at least 20 µg/ml, at least 25 µg/ml, at least 50 µg/ml, at least 100 µg/ml, at least 125 µg/ml, at least 150 µg/ml, at least 175 µg/ml, at least 200 µg/ml, at least 225 µg/ml, at least 250 µg/ml, at least 275 µg/ml, at least 300 µg/ml, at least 325 µg/ml, at least 350 µg/ml, at least 375 µg/ml, or at least 400 µg/ml in the subject.

Doses of anti-FXIa antibodies or antigen binding fragments thereof of the disclosure, or anti-idiotype antibodies or antigen binding fragments thereof of the disclosure, may be repeated and the administrations may be separated by at least 1 day, 2 days, 3 days, 5 days, 10 days, 15 days, 30 days, 45 days, 2 months, 75 days, 3 months, or at least 6 months.

An effective amount for a particular patient may vary depending on factors such as the condition being treated, the overall health of the patient, the method route and dose of administration and the severity of side effects (see, e.g., Maynard, et al., 1996. A Handbook of SOPs for Good Clinical Practice, Interpharm Press, Boca Raton. Fla.; Dent, 2001, Good Laboratory and Good Clinical Practice, Urch Publ, London, UK).

The route of administration may be by, e.g., topical or cutaneous application, injection or infusion by intravenous, intraperitoncal, intracerebral, intramuscular, intraocular, intraarterial, intracerebrospinal, intralesional, or by sustained release systems or an implant (see, e.g., Sidman et al., 1983, Biopolymers 22:547-556; Langer, et al., 1981, J. Biomed. Mater. Res. 15: 167-277; Langer, 1982, Chem. Tech. 12:98-105; Epstein, et al., 1985, Proc. Natl. Acad. Sci. USA 82:3688-3692; Hwang, et al., 1980, Proc. Natl. Acad. Sci. USA 77:4030-4034; U.S. Pat. Nos. 6,350,466 and 6,316, 024). Where necessary, the composition may also include a solubilizing agent and a local anesthetic such as lidocaine to ease pain at the site of the injection. In addition, pulmonary administration can also be employed, e.g., by use of an inhaler or nebulizer, and formulation with an aerosolizing agent. See, e.g., U.S. Pat. Nos. 6,019,968, 5,985,320, 5,985, 309, 5,934,272, 5,874,064, 5,855,913, 5,290,540, and 4,880, 078; and PCT Publication Nos. WO 92/19244, WO 97/32572, WO 97/44013, WO 98/31346, and WO 99/66903, each of which is incorporated herein by reference their entirety. In one embodiment, the anti-FXIa antibody or antigen binding fragment thereof, or a composition of the disclosure is administered using Alkermes AIR™ pulmonary drug delivery technology (Alkermes, Inc., Cambridge, Mass.). In one embodiment, the anti-idiotype antibody or antigen binding fragment thereof, or a composition of the disclosure is administered using Alkermes AIR™ pulmonary drug delivery technology (Alkermes, Inc., Cambridge, Mass.).

A composition of the present disclosure may also be administered via one or more routes of administration using one or more of a variety of methods known in the art. As will be appreciated by the skilled artisan, the route and/or mode of administration will vary depending upon the desired results. Selected routes of administration for antibodies of the disclosure include intravenous, intramuscular, intradermal, intraperitoneal, subcutaneous, spinal or other parenteral routes of administration, for example by injection or infusion. Parenteral administration may represent modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Alternatively, a composition of the disclosure can be administered via a non-parenteral route, such as a topical, epidermal or mucosal route of administration, for example, intranasally, orally, vaginally, rectally, sublingually or topically.

If the anti-FXIa antibodies or antigen binding fragments thereof of the disclosure, or anti-idiotype antibodies or antigen binding fragments thereof of the disclosure, are administered in a controlled release or sustained release system, a pump may be used to achieve controlled or sustained release (see Langer, supra; Sefton, 1987, CRC Crit. Ref. Biomed. Eng. 14:20; Buchwald et al., 1980, Surgery 88:501; Saudek et al., 1989, N. Engl. J. Med. 321:514).

Polymeric materials can be used to achieve controlled or sustained release of the therapies of the disclosure (see e.g., Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984): Ranger and Peppas, 1983, J. Macromol. ScL Rev. Macromol. Chem. 23:61; see also Levy et al, 1985, Science 11 225:190; During et al., 19Z9, Ann. Neurol. 25:351; Howard et al, 1989, J. Neurosurg. 71: 105); U.S. Pat. Nos. 5,679,377; 5,916,597; 5,912,015; 5,989,463; 5,128,326; PCT Publication No. WO 99/15154; and PCT Publication No. WO 99/20253. Examples of polymers used in sustained release formulations include, but are not limited to, poly(2-hydroxy ethyl methacrylate), poly(methyl methacrylate), poly (acrylic acid), poly(ethylene-co-vinyl acetate), poly(methacrylic acid), polyglycolides (PLG), polyanhydrides, poly (N-vinyl pyrrolidone), polyvinyl alcohol), polyacrylamide, polyethylene glycol), polylactides (PLA), polyoeactide-coglycolides) (PLGA), and polyorthoesters. In one embodiment, the polymer used in a sustained release formulation is inert, free of leachable impurities, stable on storage, sterile, and biodegradable. A controlled or sustained release system can be placed in proximity of the prophylactic or therapeutic target, thus requiring only a fraction of the systemic dose (see, e.g., Goodson, in Medical Applications of Controlled Release, supra, vol. 2, pp. 115-138 (1984)).

Controlled release systems are discussed in the review by Langer, 1990, Science 249:1527-1533. Any technique known to one of skill in the art can be used to produce sustained release formulations comprising one or more antibodies of the disclosure or conjugates thereof. See, e.g., U.S. Pat. No. 4,526,938, International Patent Publication Nos. WO 91/05548, WO 96/20698, Ning et al., 1996, "Intratumoral Radioimmunotheraphy of a Human Colon Cancer Xenograft Using a Sustained-Release Gel," *Radiotherapy and Oncology* 59:179-189, Song et al., 1995, "Antibody Mediated Lung Targeting of Long-Circulating Emulsions," *PDA Journal of Pharmaceutical Science and Technology* 50:372-397, Cleek et ah, 1997, "Biodegradable Polymeric Carriers for a bFGF Antibody for Cardiovascular Application," *Pro. ML Symp. Control. Rel. Bioact. Mater.* 24:853-854, and Lam et al., 1997. "Microencapsulation of Recombinant Humanized Monoclonal Antibody for Local Delivery," *Proc. ML Symp. Control Rel. Bioact. Mater.* 24: 759-160, each of which is incorporated herein by reference in their entirety.

If the anti-FXIa antibody or antigen binding fragment thereof of the disclosure, or the anti-idiotype antibody or antigen binding fragment thereof of the disclosure, is administered topically, it can be formulated in the form of an ointment, cream, transdermal patch, lotion, gel, shampoo, spray, aerosol, solution, emulsion, or other form well-known to one of skill in the art. See, e.g., Remington's Pharmaceutical Sciences and Introduction to Pharmaceutical Dosage Forms, 19th ed., Mack Pub. Co., Easton. Pa. (1995). For non-sprayable topical dosage forms, viscous to semi-solid or solid forms comprising a carrier or one or more excipients compatible with topical application and having a dynamic viscosity, in some instances, greater than water are typically employed. Suitable formulations include, without limitation, solutions, suspensions, emulsions, creams, ointments, powders, liniments, salves, and the like, which are, if desired, sterilized or mixed with auxiliary agents (e.g., preservatives, stabilizers, wetting agents, buffers, or salts) for influencing various properties, such as, for example, osmotic pressure. Other suitable topical dosage forms include sprayable aerosol preparations wherein the active ingredient, in some instances, in combination with a solid or liquid inert carrier, is packaged in a mixture with a pressurized volatile (e.g., a gaseous propellant, such as freon) or in a squeeze bottle. Moisturizers or humectants can also be added to pharmaceutical compositions and dosage forms if desired. Examples of such additional ingredients are well-known in the art.

If the composition comprising the anti-FXIa antibody or antigen binding fragment thereof of the disclosure, or the anti-idiotype antibody or antigen binding fragment thereof of the disclosure, is administered intranasally, it can be formulated in an aerosol form, spray, mist or in the form of drops. In particular, prophylactic or therapeutic agents for use according to the present disclosure can be conveniently delivered in the form of an aerosol spray presentation from pressurized packs or a nebuliser, with the use of a suitable propellant (e.g., dichlorodifluoromethane, trichlorofluoromethane, dichlorotetrafluoroethane, carbon dioxide or other suitable gas). In the case of a pressurized aerosol the dosage unit may be determined by providing a valve to deliver a metered amount. Capsules and cartridges (composed of, e.g., gelatin) for use in an inhaler or insufflator may be formulated containing a powder mix of the compound and a suitable powder base such as lactose or starch.

Methods for co-administration or treatment with a second therapeutic agent, e.g., a cytokine, steroid, chemotherapeutic agent, antibiotic, or radiation, are well known in the art (see, e.g., Hardman, et al. (eds.) (2001) Goodman and Gilman's The Pharmacological Basis of Therapeutics, 10 th ed., McGraw-Hill, New York, N.Y.; Poole and Peterson (eds.) (2001) Pharmacotherapeutics for Advanced Practice: A Practical Approach, Lippincott, Williams and Wilkins, Phila., Pa.; Chabner and Longo (eds.) (2001) Cancer Chemotherapy and Biotherapy, Lippincott. Williams and Wilkins. Phila., Pa.). An effective amount of therapeutic may decrease the symptoms by at least 10 percent; by at least 20 percent; at least about 30 percent; at least 40 percent, or at least 50 percent.

In certain embodiments, the anti-FXIa antibodies or antigen binding fragments thereof of the disclosure, or the anti-idiotype antibodies or antigen binding fragments thereof of the disclosure, can be formulated to ensure proper distribution in vivo. For example, the blood-brain barrier (BBB) excludes many highly hydrophilic compounds. To ensure that the therapeutic compounds of the disclosure cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., V. V. Ranade, 1989, *J. Clin. Pharmacol.* 29:685). Exemplary targeting moieties include folate or biotin (see, e.g., U.S. Pat. No. 5,416,016); mannosides (Umezawa et al., *Biochem. Biophys. Res. Commun.* 153: 1038); antibodies (P. G. Bloeman et al., 1995, *FEBS Lett.* 357: 140; M. Owais et al., 1995, Antimicrob. Agents Chemother. 39: 180); surfactant protein A receptor (Briscoc et al. (1995) *Am. J. Physiol.* 1233: 134); and p120 (Schreier et al. (1994) *J. Biol. Chem.* 269:9090); see also K. Keinanen; M. L. Laukkanen, 1994, *FEBS Lett.* 346:123; Killion; Fidler, 1994; *Immunomethods* 4:273.

The disclosure provides protocols for the administration of pharmaceutical composition comprising anti-FXIa antibodies or antigen binding fragments thereof of the disclosure, alone or in combination with other therapies to a subject in need thereof. The disclosure provides protocols for the administration of pharmaceutical composition comprising anti-idiotype antibodies or antigen binding fragments thereof of the disclosure, alone or in combination with other therapies to a subject in need thereof. The therapies (e.g., prophylactic or therapeutic agents) of the combination therapies of the present disclosure can be administered concomitantly or sequentially to a subject. The therapy (e.g., prophylactic or therapeutic agents) of the combination therapies of the present disclosure can also be cyclically administered. Cycling therapy involves the administration of a first therapy (e.g., a first prophylactic or therapeutic agent) for a period of time, followed by the administration of a second therapy (e.g., a second prophylactic or therapeutic agent) for a period of time and repeating this sequential administration, i.e., the cycle, in order to reduce the development of resistance to one of the therapies (e.g., agents) to avoid or reduce the side effects of one of the therapies (e.g., agents), and/or to improve, the efficacy of the therapies.

The therapies (e.g., prophylactic or therapeutic agents) of the combination therapies of the disclosure can be administered to a subject concurrently. The term "concurrently" is not limited to the administration of therapies (e.g., prophylactic or therapeutic agents) at exactly the same time, but rather it is meant that a pharmaceutical composition comprising anti-FXIa antibodies or antigen binding fragments thereof of the disclosure, or anti-idiotype antibodies or antigen binding fragments thereof of the disclosure, are administered to a subject in a sequence and within a time interval such that the antibodies of the disclosure or conjugates thereof can act together with the other therapy(ies) to provide an increased benefit than if they were administered otherwise. For example, each therapy may be administered to a subject at the same time or sequentially in any order at different points in time; however, if not administered at the same time, they should be administered sufficiently close in time so as to provide the desired therapeutic or prophylactic effect. Each therapy can be administered to a subject separately, in any appropriate form and by any suitable route. In various embodiments, the therapies (e.g., prophylactic or therapeutic agents) are administered to a subject less than 15 minutes, less than 30 minutes, less than 1 hour apart, at about 1 hour apart, at about 1 hour to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, 24 hours apart, 48 hours apart, 72 hours apart, or 1 week apart. In other embodiments, two or more therapies (e.g., prophylactic or therapeutic agents) are administered to a within the same patient visit.

The prophylactic or therapeutic agents of the combination therapies can be administered to a subject in the same pharmaceutical composition. Alternatively, the prophylactic or therapeutic agents of the combination therapies can be administered concurrently to a subject in separate pharmaceutical compositions. The prophylactic or therapeutic agents may be administered to a subject by the same or different routes of administration.

IX. Kits

In another aspect, kits comprising any or all of the antibodies described herein are provided. In some embodiments, kits of the disclosure include one or more containers comprising an anti-FXIa antibody described herein and instructions for use in accordance with any of the methods of the disclosure described herein. In some embodiments, kits of the disclosure include one or more containers comprising an anti-idiotype antibody described herein and instructions for use in accordance with any of the methods of the disclosure described herein. In some embodiments, kits of the disclosure include one or more containers comprising an anti-FXIa antibody described herein and one or more containers comprising an anti-idiotype antibody described herein and instructions for use in accordance with any of the methods of the disclosure described herein. Generally, these instructions comprise a description of administration of the antibody for the above described therapeutic treatments. In some embodiments, kits are provided for producing a single-dose administration unit. In certain embodiments, the kit can contain both a first container having a dried protein and a second container having an aqueous formulation. In certain embodiments, kits containing an applicator, e.g., single and multi-chambered prefilled syringes (e.g., liquid syringes and lyosyringes), are included.

The instructions relating to the use of an anti-FXIa antibody and/or anti-idiotype antibody generally include information as to dosage, dosing schedule, and route of administration for the intended treatment. The containers may be unit doses, bulk packages (e.g., multi-dose packages) or sub-unit doses. Instructions supplied in the kits of the disclosure are typically written instructions on a label or package insert (e.g., a paper sheet included in the kit), but machine-readable instructions (e.g., instructions carried on a magnetic or optical storage disk) are also acceptable.

The kits of this disclosure are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is an anti-FXIa antibody of the disclosure or an anti-idiotype antibody of the disclosure. The container may further comprise a second pharmaceutically active agent.

Kits may optionally provide additional components such as buffers and interpretive information. Normally, the kit comprises a container and a label or package insert(s) on or associated with the container.

In some embodiments, a kit comprising one or more anti-FXIa antibodies and/or anti-idiotype antibodies is used in a therapeutic method as described herein (e.g., in Section V above). In some embodiments, a kit comprising an anti-FXIa antibody and/or an anti-idiotype antibody against an anti-FXIa antibody as described herein is used in a method for inhibiting the intrinsic pathway of coagulation in a subject. In some embodiments, a kit comprising an anti-FXIa antibody and/or an anti-idiotype antibody against an anti-FXIa antibody as described herein is used in a method for increasing clotting time in a subject.

The disclosure also provides diagnostic kits comprising any or all of the antibodies described herein. The diagnostic kits comprising anti-FXIa antibodies are useful for, for example, detecting the presence of FXIa in a sample. In some embodiments, a diagnostic kit can be used to identify an individual with a latent disease, disorder or condition that may put them at risk of developing FXIa-mediated disease, disorder or condition. In some embodiments, a diagnostic kit can be used to detect the presence and/or level of FXIa in an individual suspected of having a FXIa mediated disease. The diagnostic kits comprising anti-idiotype antibodies are useful for, for example, detecting the presence of an anti-FXIa antibody in a sample. In some embodiments, a diagnostic kit can be used to identify an individual with who is at risk for bleeding disorders. In some embodiments, a diagnostic kit can be used to detect the presence and/or level of anti-FXIa antibody in an individual being administered the anti-FXIa antibody.

Diagnostic kits of the disclosure include one or more containers comprising an anti-FXIa antibody described herein and instructions for use in accordance with any of the methods of the disclosure described herein. Generally, these instructions comprise a description of use of the anti-FXIa antibody to detect the presence of FXIa in individuals at risk for, or suspected of having, an FXIa mediated disease. In some embodiments, an exemplary diagnostic kit can be configured to contain reagents such as, for example, an anti-FXIa antibody, a negative control sample, a positive control sample, and directions for using the kit.

In some embodiments, diagnostic kits of the disclosure include one or more containers comprising an anti-idiotype antibody described herein and instructions for use in accordance with any of the methods of the disclosure described herein. Generally, these instructions comprise a description of use of the anti-idiotype antibody to detect the presence of an anti-FXIa antibody in individuals at risk for developing a bleeding disorder. In some embodiments, an exemplary diagnostic kit can be configured to contain reagents such as, for example, an anti-idiotype antibody, a negative control sample, a positive control sample, and directions for using the kit.

X. Examples

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Example 1. Production and Selection of Anti-FXIa mAbs

Anti-FXIa scFvs were selected from an antibody phage display library. The antigen used to screen the library, human FXIa (Haematologic Technologies Inc.), was biotinylated with Sulfo-NHS-LC-Biotin (Pierce) according to the manufacturer's protocol. This biotinylated FXIa was immobilized on streptavidin-coated magnetic Dynabeads M-280 (Invitrogen) and used to select binders from a scFv antibody phage display library, using standard methods. Four rounds of selection were performed with decreasing concentrations of the target (FXIa) as follows, 150 nM ($1^{st}$ round), 75 nM ($2^{nd}$ round), 30 nM ($3^{rd}$ round) and 5 nM ($4^{th}$ round). To obtain antibodies specific to FXIa that did not substantially bind the zymogen, all selections were performed in the presence of 300 nM human FXI. A total of 6000 clones were screened by FXI/FXIa ELISA from the $3^{rd}$ and $4^{th}$ round outputs, resulting in 166 FXIa specific hits that exhibited binding to FXIa, but did not detectably bind FXI.

After sequencing, 13 unique clones specific to human factor XIa were identified. These clones bound FXIa and also inhibited FXIa in an in vitro activity assay. After testing these scFv clones for cross-reactivity to cynomolgus monkey ("cyno") FXIa by ELISA, 11 clones moved forward. After reformatting, 7 reformatted IgGs retained binding selectivity to FXIa and exhibited cyno cross-reactivity. In this ELISA binding assay, a series of wells were coated with either 1 µg of FXIa or 1 µg of FXI. After the necessary incubation time, the wells were washed, blocked, and then the anti-FXIa mAbs were added at various concentrations. After a series of washes, an anti-human IgG HRP secondary (Southern Biotech) was added for the standard incubation period, followed by additional washes, addition of developing solutions, with the specific binding signal then measured on a spectrophotometer at 450 nM OD. To measure the inhibitory activity of the mAbs against FXIa, an in vitro assay was run that involved a 5 minute pre-incubation of the mAbs at various concentrations with either 200 pM human FXI or 200 pM cyno FXIa in the standard assay buffer (50 mM Tris-Hcl, pH 7.4, 250 mM NaCl, 1 mM EDTA). This was followed by addition of 100 µM of a fluorogenic peptide (SN-59, Haematological Technologies) to start the reaction. The plate was then read in a SpectraMax® plate reader at 37° C. for 30 minutes. Settings: excitation 353 nM, emission 470 nM. Data was collected in one minute intervals. Instrument determined Vmax values taken from the linear part of each reaction curve were then plotted for the determination of $IC_{50}$ values.

Results

Figure 1C:
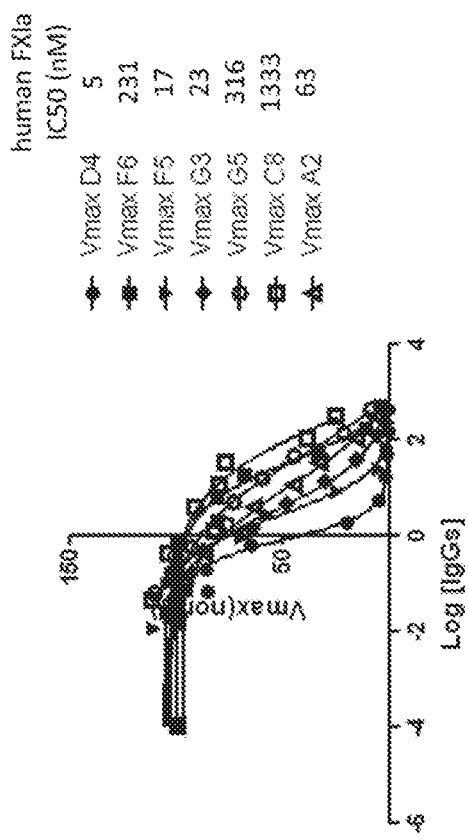
Figure 1D:
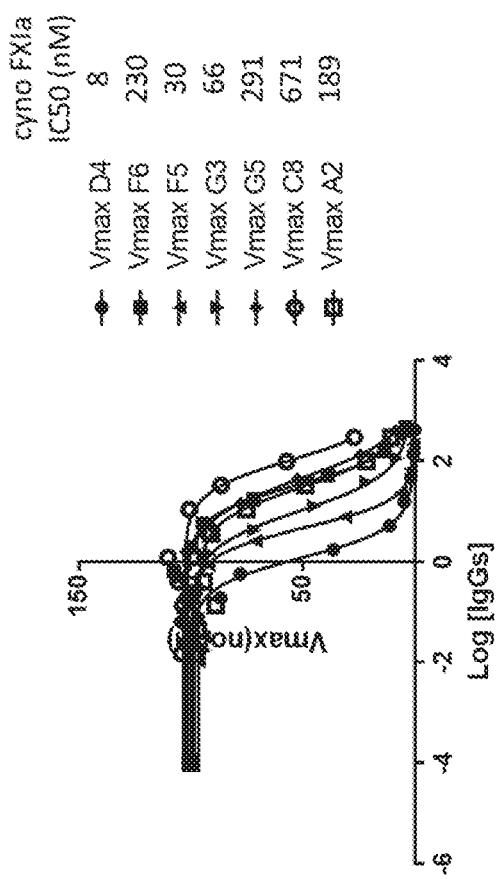

After reformatting to IgG, seven out of the original eleven positive scFv clones retained binding selectivity to human (FIG. 1A) and cyno FXIa (FIG. 1B). These seven anti-FXIa mAbs also inhibit human FXIa (FIG. 1C) and cyno FXIa (FIG. 1D) activity with a range of $IC_{50}$ values in an in vitro assay involving a fluorogenic peptide substrate that is cleaved by FXIa.

Example 2. Binding of Anti-FXIa Clones to FXIa/D4 mAb Complexes

Antibody epitope binning data was collected using an Octet QK384 instrument (ForteBio). Biotinylated blood-derived FXIa (Haematologic Technologies Inc.) was diluted in phosphate-buffered saline with 0.1% bovine serum albumin (PBS-BSA) and loaded onto streptavidin-conjugated Octet® biosensors (ForteBio). Biosensors were then washed in PBS to remove unbound FXIa and loaded to saturation with 500 nM D4 IgG in PBS-BSA. Each sensor was subsequently dipped into a second antibody (500 nM IgG in PBS-BSA) including the commercially available mouse anti-FXI clone AHXI-5061 (Haematologic Technologies Inc.) to assess if concurrent binding to the FXIa-D4 complex is possible. Data is reported as the change in response (nm) for the second antibody clone binding to the FXIa-D4 complex.

Results

Figure 2:
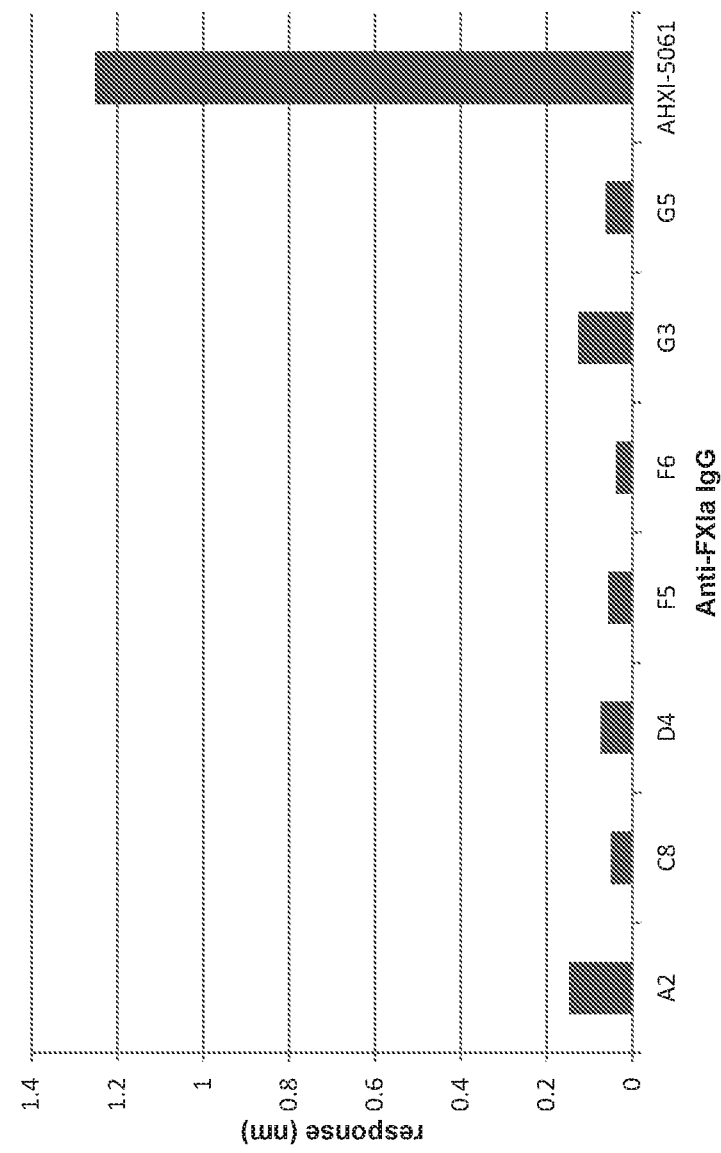
FIG. 2 depicts the epitope binning data for seven anti-FXIa mAbs, as determined by measuring the binding of anti-FXIa clones to FXIa/D4 complexes. Binding of mouse anti-FXI clone AHXI-5061 was also tested.

All 7 anti-FXIa mAbs tested bind the same or an overlapping epitope on FXIa, as indicated by the lack of increased response signal when D4 anti-FXIa mAb is bound first (FIG. 2). Binding signal with mouse anti-FXI clone AHXI-5061, which binds a different FXI/FXIa epitope, illustrates an increased signal seen when an additional IgG binding event occurs at the same time that D4 mAb is bound.

Example 3. Generating Improved Versions of the D4 Anti-FXIa mAb

Error prone PCR (ep-PCR) based random mutagenesis was performed on the D4 scFv gene in order to optimize this antibody. The amplified D4 scFv DNA from ep-PCR was cloned into a proprietary parental vector and generated a 2e10 scFv phage library. After rescuing the library, 3 rounds of selection were performed. In the $1^{st}$ round, 900 pM of human FXIa (hu-FXIa) on streptavidin magnetic beads was used to capture binding phage for 1 hour at room temperature. In the 2$^{nd}$ round, 90 pM of antigen was reacted with output phage from the 1$^{st}$ round in solution for 1 hour followed by streptavidin magnetic beads capture. In the final round, 9 pM of hu-FXIa on streptavidin magnetic beads was reacted with output phage from the 2$^{nd}$ round for 5 minutes and the washed beads were incubated with soluble FXIa overnight. A total of 500 colonies from the 3$^{rd}$ round were picked and tested in the following assays: 1) direct binding ELISA, 2) competition ELISA in the presence of excess parental D4 scFv and 3) Homogeneous Time-Resolved Fluorescence (HTRF) assay in the scFv format. Of the total clones screened, 367 were ELISA positive and 87 clones were identified as likely higher affinity clones than parental D4 based on competition ELISA and HTRF assay using D4 scFv as the competitor. Of these 87 clones, 70 clones were identified as unique and all of these unique clones were reformatted into full length human IgG followed by HTRF assay in order to assess its affinity by competition with D4 IgG. All 70 clones were also tested as inhibitors in the human FXIa fluorogenic peptide assay. Nine clones (QCA11, B1D2, B10H2, B10E6, B10F6, B10D8, B10B12, S1D4 and S10H9) were selected based on their HTRF assay result. ELISA signal and their IC$_{50}$ in the fluorogenic peptide assay. Sequence alignment of these 9 clones identified several position hot spots: W50R, N52D, N54D and G56D in the heavy chain CDR2 and Q6K in light chain framework 1. These hot spots were then used to generate 32 IgGs (clone 1 through clone 32 including clone 8, 16, 20, 22, 24 and 32 as shown in the amino acid alignment table) having different combinations of these 5 mutations, followed by ELISA, Biacore™ and in vitro FXIa activity assays run as previously described. Clone 24 containing N51D, N53D and G55D mutations in heavy chain CDR2 and Q6K in light chain framework 1 was the IgG with the highest affinity of about 10 pM. Clone 24 had a possible deamination site in the CDRH2, thus 54S was changed to 54E and this new clone was named "DEF." DEF showed the same affinity and potency in in vitro assays as clone 24.

Results

Figure 3B:
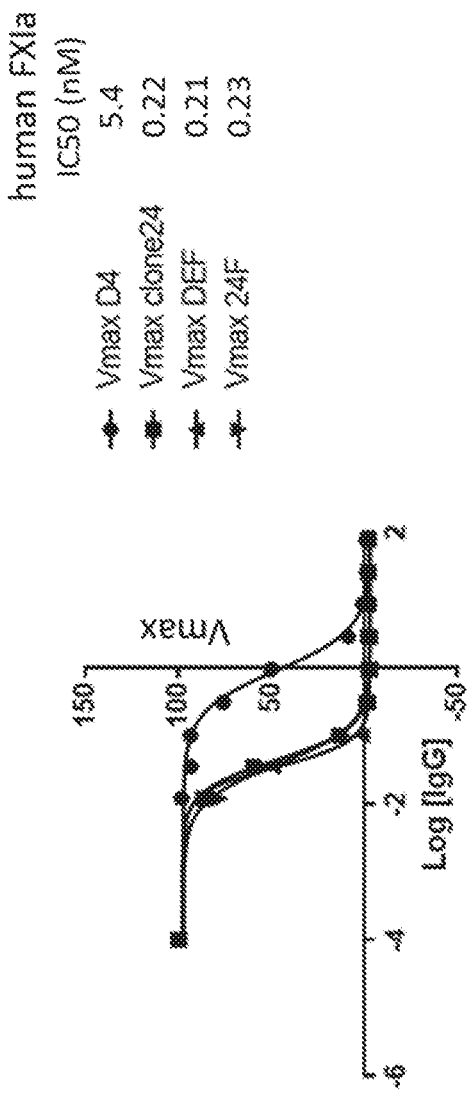
Figure 3C:
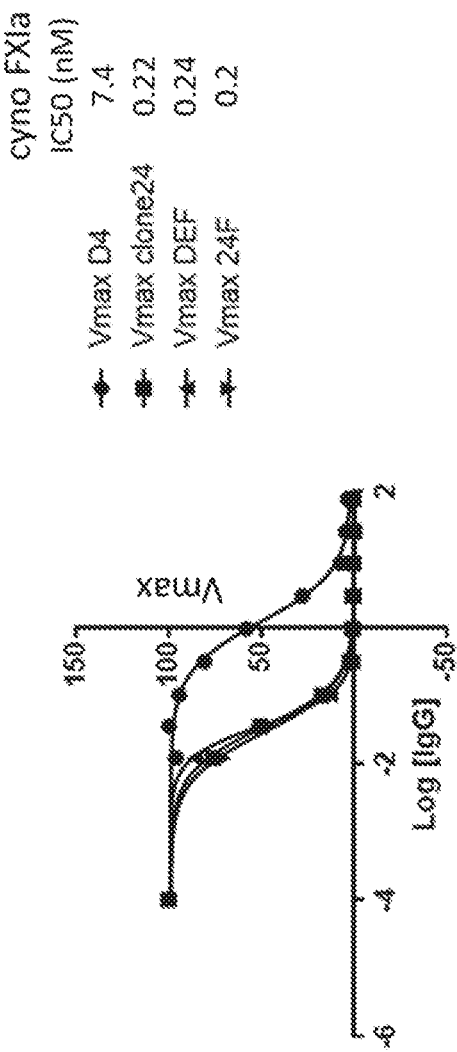
Figure 3D:
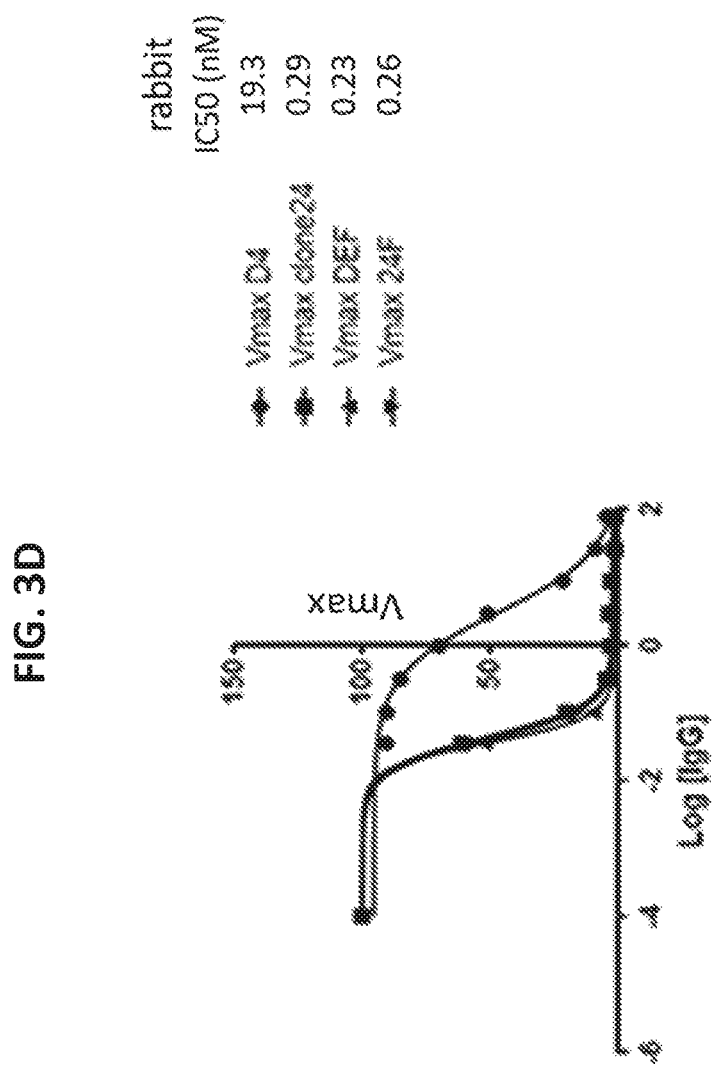

Increased binding affinity and potency was achieved via selective substitutions in original D4 anti-FXIa mAb. Affinity for human FXIa increases as follows: clone 24>B11>D4 mAb (FIG. 3A). Anti-FXIa potency against the human (FIG. 3B), cyno (FIG. 3C), and rabbit (FIG. 3D) FXIa enzymes increases with a similar trend seen across all three species tested: DEF=24F=clone 24>>D4 mAb. Clone 24F is an effector null version of clone 24 that differs from Clone 24 at 3 residues in the Fc region (SEQ ID NO: 82).

A human DNA Insert encoding the IgG heavy chain of DEF was deposited under ATCC accession number PTA-122090. A human DNA Insert encoding the IgG light chain of DEF was deposited under ATCC accession number PTA-122091. The deposits were made under terms in accordance with the Budapest Treaty with the American Type Culture Collection (ATCC), 10801 University Blvd., Manassas, Va. 20110-2209.

Example 4. Anti-FXIa mAb Binding Kinetics

Biotinylated FXIa was captured on a streptavidin-coated Biacore™ chip and the binding response versus time for D4 IgG, B11 IgG, C24 Fab and DEF Fab measured over a series of antibody/Fab concentrations. Representative background subtracted Biacore™ sensorgrams overlaid with the kinetic curve fits are shown. Basic methods in brief: blood-derived FXIa and FXI (Haematologic Technologies Inc.) were biotin labeled via primary amines and immobilized on a CAP chip using a Biacore™ T200 instrument (GE Healthcare). IgG binding experiments were performed at 25° C. using a 50 μl/min flow rate in 0.01 M HEPES pH 7.4, 0.15 M NaCl and 0.005% v/v surfactant P20 (HBS-P) buffer. After each antibody injection, the chip surface was regenerated with a mixture of 6 M guanidine HCl and 0.25 M NaOH, and new FXIa/FXI was captured. Fab binding experiments were performed at 37° C. using a 50 μl/min flow rate in HBS-P. All data was analyzed using the Biacore™ T200 Evaluation software. Kinetic constants for at least three experiments were obtained and reported as the mean. The table of values for affinity measurements for IgGs and Fabs shows overall affinity of Fab or IgG for human FXIa target, as well as rate constants (FIG. 4B). No binding was seen with immobilized human FXI in similar experiments (data not shown) consistent with FXIA/FXI ELISA data (see Example 2).

Results

Figure 4A:
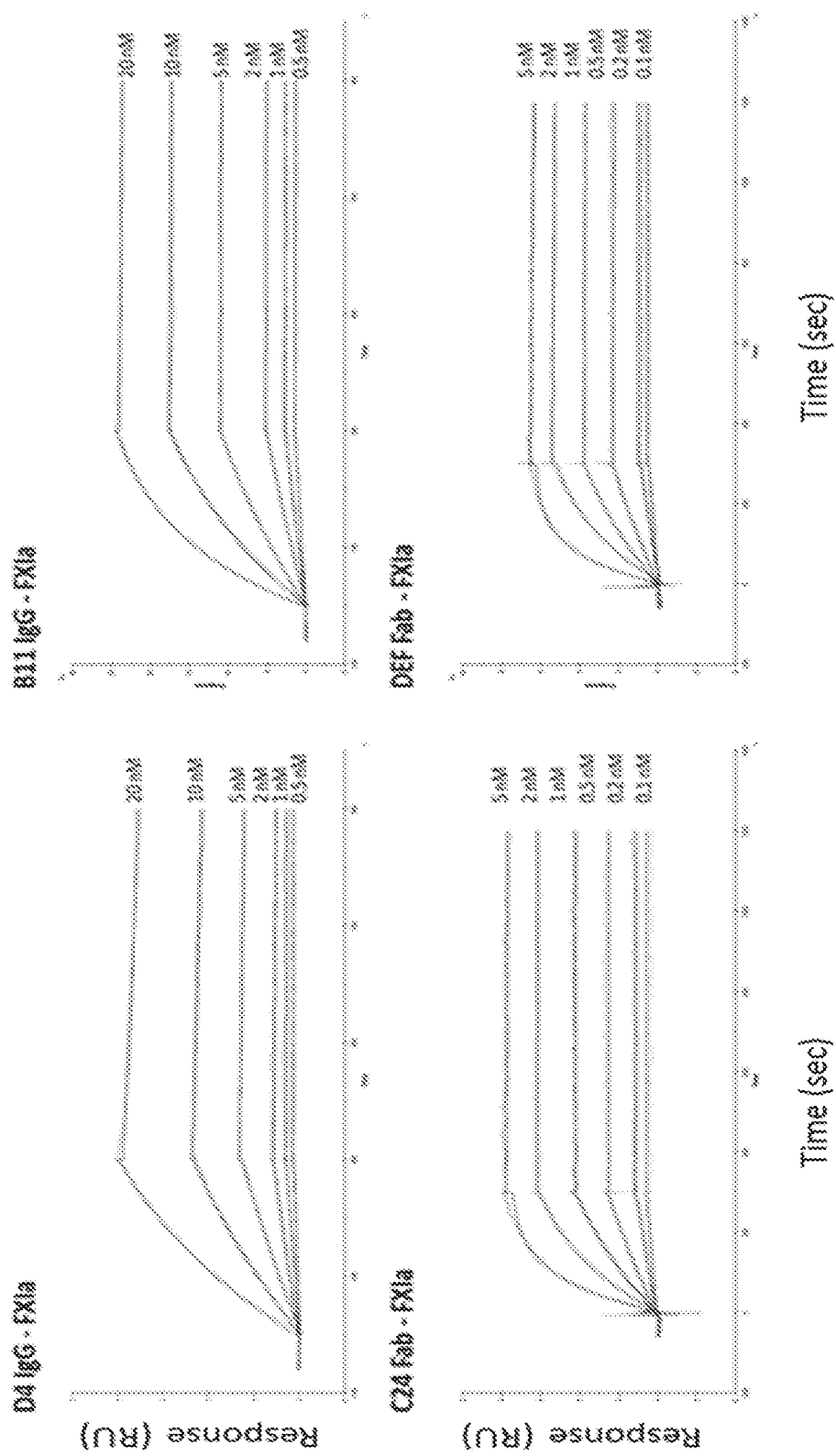

Significant increases in overall affinity to human FXIa were achieved by making selected amino acid substitutions to original D4 mAb molecule. Greater than 25-fold affinity (KD) increase was seen with 24 and DEF Fabs over that of original D4 mAb (FIG. 4A and FIG. 4B).

Figure 5A:
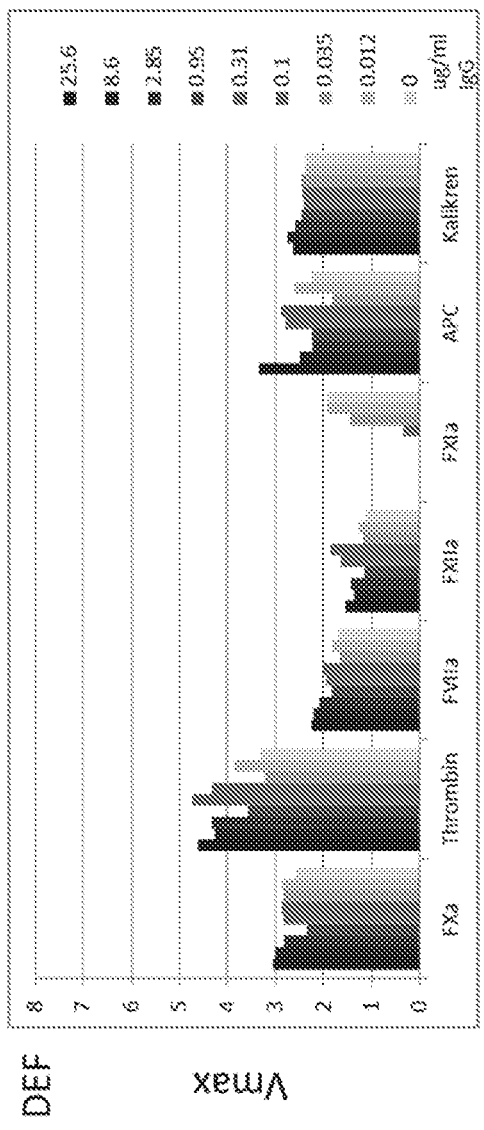
FIG. 5A-5B show the effect of anti-FXIa mAbs DEF (A) and 24F (B) on the activity of FXIa and other serine proteases on the coagulation cascade in an in vitro assay.
Figure 5B:
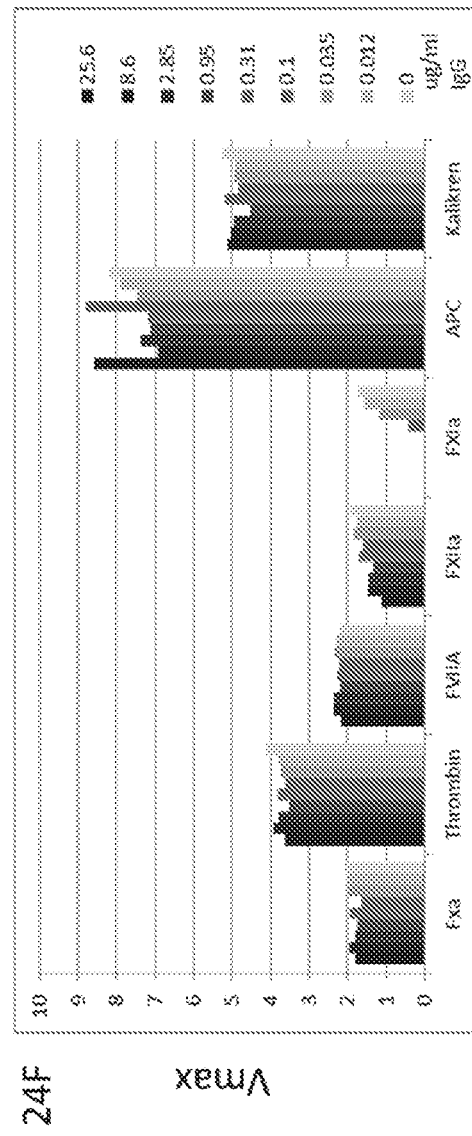

Example 5. Anti-FXIa mAbs do not Inhibit Other Serine Proteases on the Coagulation Cascade The effects of anti-FXIa mAbs DEF and 24F on serine proteases of the coagulation cascade were tested in an assay as shown in FIGS. 5A-B. The following standard conditions were used for all reactions regardless of enzyme tested: 50 μl diluted enzyme (as indicated below), 8 μl SN59 peptide (final reaction concentration is 100 μM), 92 μl Standard Assay buffer, 50 μl test IgG (DEF or clone 24F) or buffer (no IgG wells). Final IgG concentration of first dilution is 25.6 μg/ml, seven 3-fold serial dilutions were tested). Set up and order of addition: Pre-incubate the DEF or 24 IgG at concentrations shown (in FIG. 5A and FIG. 5B) for 5 minutes with the various enzymes in standard assay buffer prior to the addition of the SN-59 peptide substrate which starts the reaction. The plate was then read in a fluorescent SpectraMax® plate reader at 37° C. for 30 minutes. Settings: excitation 353 nM, emission 470 nM. Data was collected in one minute intervals. Instrument determined Vmax values taken from the linear part of each reaction curve were then plotted as shown. Hematological Technologies Inc. (HTI) was the supplier for majority of human enzymes used in this screen. Final enzyme concentrations were as follows: FXa (HCXA-0060, HTI) was 2 μg/ml. Thrombin (HCT-0020, HTI) was 5 μg/ml. FVIIa (HCVIIA-0031, HTI) was 5 μg/ml with Tissue Factor (RTF-0300, HTI) was 0.5 μg/ml and added phospholipid (PC) at 12 μM. FXIIa (HFXIIa1212a, Enzyme Research) was 0.9 μg/ml. FXIa (HCXIA-0160, HTI) was 0.2 μg/ml. APC (HCAPC-0080, HTI) was 1.2 μg/ml. Kallikrein-1 (KLK1) (JNV-367, Reagent Protein) was 2.5 μg/ml. All enzymes were of human origin. As shown in FIG. 5A-B, anti-FXIa mAbs did not inhibit other serine proteases on the coagulation cascade or other related proteases tested. Vmax data plots show the high selectivity of anti-FXIa mAb DEF (FIG. 5A) and clone 24F (FIG. 5B) for inhibition of FXIa only in these in vitro assay comparisons.

Figure 5C:
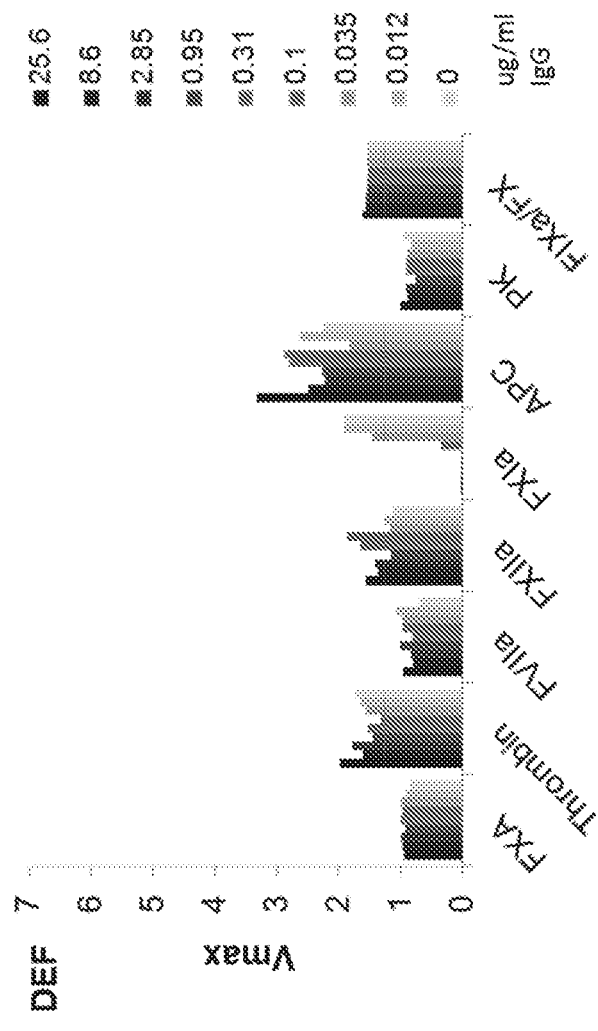
FIG. 5C-5D show the effect of anti-FXIa mAbs DEF (C) and 24 (D) on the activity of FXIa and other serine proteases on the coagulation cascade in an in vitro assay.
Figure 5D:
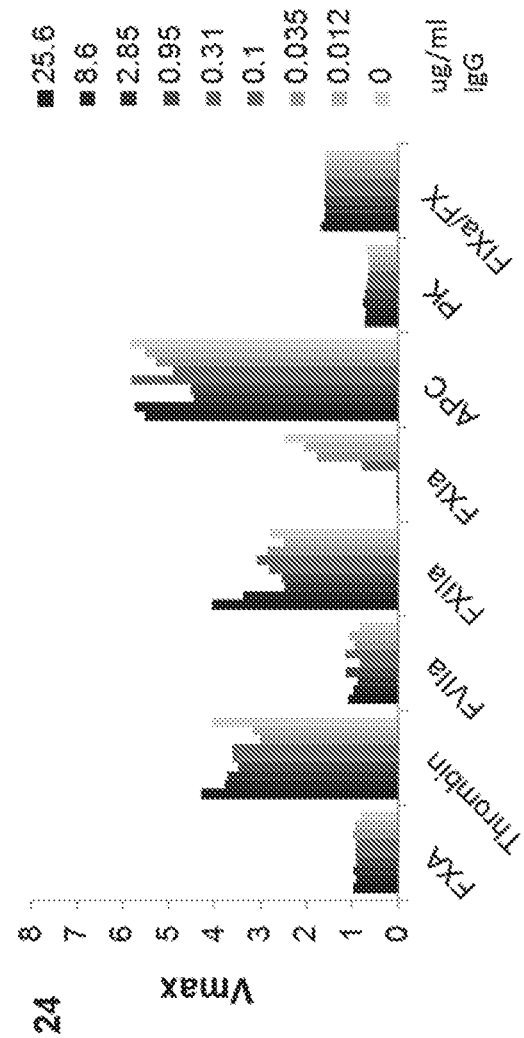

The effects of anti-FXIa mAbs DEF and clone 24 on serine proteases of the coagulation cascade were tested in an assay as shown in FIGS. 5C-D. The following standard conditions were used for all reactions regardless of enzyme tested: 50 μl diluted enzyme (as indicated below), 8 μl fluorogenic peptide (final reaction concentration is 100 μM), 92 μl Standard Assay buffer, 50 μl test IgG (DEF or clone 24)

or buffer (no IgG wells). Hematological Technologies Inc. (HTI) was the supplier of human enzymes and fluorogenic substrates used in this screen, unless otherwise indicated. Final IgG concentration of first dilution is 25.6 µg/ml, with seven 3-fold serial dilutions tested. Set up and order of addition: Pre-incubate the DEF or clone 24 IgG at concentrations shown (in FIG. 5A and FIG. 5B) for 5 minutes with the various enzymes in standard assay buffer. The following fluorogenic substrates were then added at a final concentration of 100 µM to start the reaction: SN-59 for FXIIa, FXIa, APC and PK; SN-17A for Thrombin and FVIIa; and SN-7 for FXa. The plate was then read in a fluorescent SpectraMax® plate reader at 37° C. for 30 minutes. Settings: excitation 353 nM, emission 470 nM. Data was collected in one minute intervals. Instrument determined Vmax values taken from the linear part of each reaction curve were then plotted as shown. Final enzyme concentrations were as follows: FXa (HCXA-0060, HTI) was 2 µg/ml. Thrombin (HCT-0020, HTI) was 5 µg/ml. FVIIa (HCVIIA-0031, HTI) was 5 µg/ml with Tissue Factor (RTF-0300, HTI) was 0.5 µg/ml and added phospholipid (PC) at 12 µM. FXIIa (HFXIIa1212a, Enzyme Research) was 0.9 µg/ml. FXIa (HCXIA-0160, HTI) was 0.2 µg/ml. APC (HCAPC-0080) at 1.2 µg/ml: and plasma kallikrein (PK; KLKB1; 2497-SE, R&D Systems) at 4 µg/ml. The latter was purchased as zymogen and activated with thermolysin according to R&D's instructions. Thermolysin alone had no detectable activity in the SN-59 hydrolysis assay. Due to low efficiency of small peptide substrate cleavage by FIXa, the activity against FIXa was assessed by using a coupled assay involving FIXa activation of FX in the presence of FVIIIa and phospholipid and the FXa chromogenic substrate SXa-11 (Biophen FIXa, Ref A221812, Aniara; used according to supplier protocol). All enzymes were of human origin. As shown in FIG. 5C-D, anti-FXIa mAbs did not inhibit other serine proteases on the coagulation cascade or other related proteases tested. Vmax data plots show the high selectivity of anti-FXIa mAb DEF (FIG. 5C) and clone 24 (FIG. 5D) for inhibition of FXIa only in these in vitro assay comparisons.

Figure 6F:
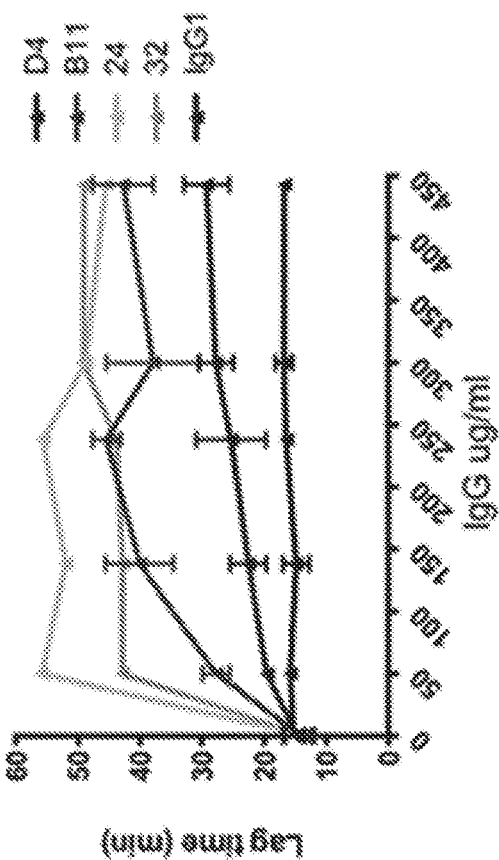
Figure 6E:
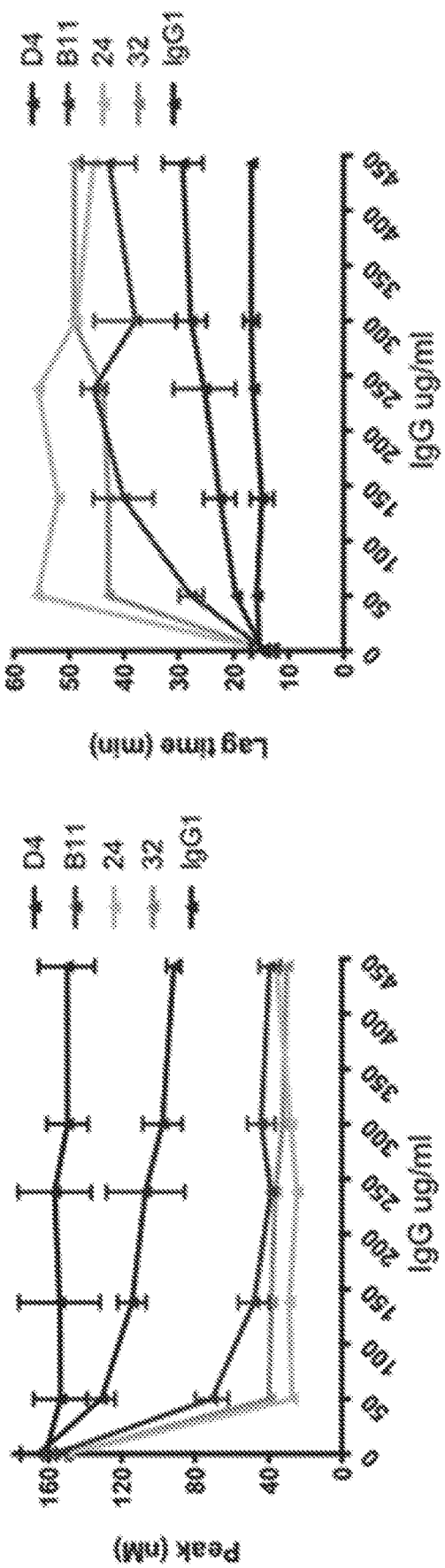

Example 6. Effects of Anti-FXIa mAbs in FXIIa-Triggered Human Plasma Reactions that Measure Thrombin Generation Readout Thrombin generation was measured using a fluorogenic thrombin substrate on a multi-well automated fluorescent plate reader (ThrombinoSCOPE, Maastricht, the Netherlands) according to the manufacturer's protocol. Briefly, 5 µL of anti-FXIa antibody or IgG ctrl (from 5 µg/mL to 443 µg/mL of D4, B11, 24, 32, and IgG1 ctrl) was mixed with 20 µL PBS-60 nM human Factor XIIa (Enzyme Research Laboratories. South Bend, Ind., USA)-PC/PS (Phospholipid-TGT, DiaPharma, West Chester, Ohio, USA) in a 96-well plate. Finally, 75 µL human Plasma (Triclinical Reference Plasma, TCoag, Wicklow, Ireland) was added. Due to lot to lot variability for the PC/PS reagent, for each lot the concentration was adjusted to achieve a ~10 min Lag Time and ~125 nM Thrombin Peak. Finally, clotting was triggered with the addition of calcium chloride buffer and a fluorogenic thrombin substrate. The amount of thrombin generated in the reaction was measured over time and plotted as to peak activity, and time to peak.
Results Anti-FXIa mAbs inhibit FXIa in the more complex setting of human plasma. In this assay, FXIIa was used to trigger the start of the coagulation process, and readout was at the level of thrombin generation, which was the final activation step on the coagulation cascade. Higher affinity clones (as previously determined by ELISA and Biacore™ measurements and shown above in FIGS. 2 and 3) were more potent in this assay (Clone 24>B11>D4; FIGS. 6A, 6B, 6C, 6E and 6F). Potency was measured by decreases in peak thrombin activity (FIG. 6E) and in delays (lag time) to peak thrombin activity (FIG. 6F). These results indicate that anti-FXIa mAbs are active against FXIa in human plasma, even when, under these conditions, it is being continuously generated by FXIIa-mediated conversion of FXI to FXIa. The ctrl IgG has no effect in this assay (FIGS. 6D, 6E and 6F).

Figure 7:
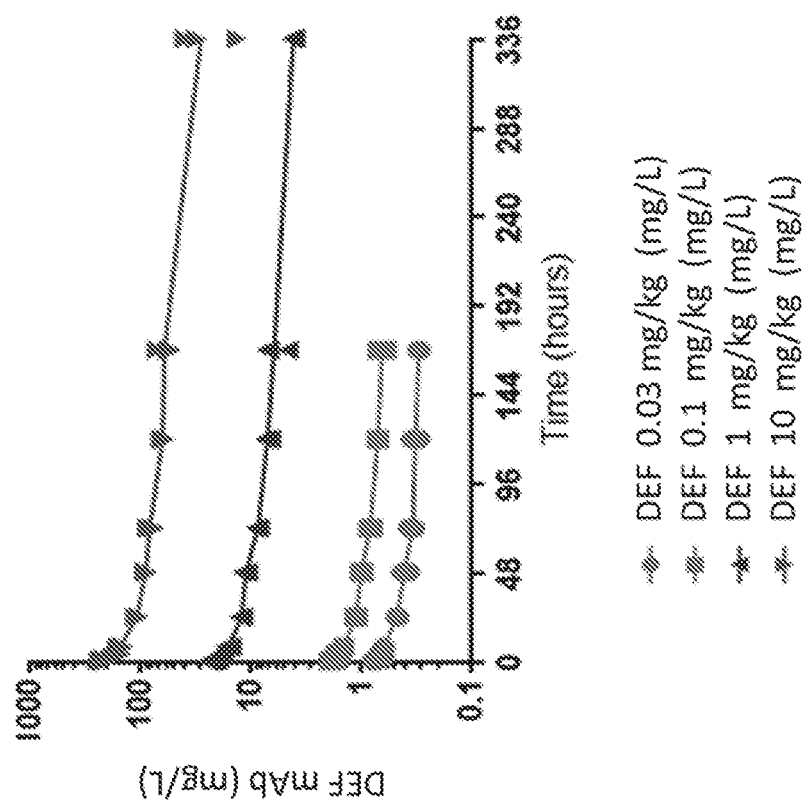
FIG. 7 shows the results of a single dose intravenous bolus pharmacokinetic (PK) study with DEF in New Zealand white rabbits.

Example 7. Single Dose i.v. Bolus Pharmacokinetic (PK) Study with DEF in New Zealand White Rabbits All procedures performed on these animals were in accordance with regulations and established guidelines and were reviewed and approved by an Institutional Animal Care and Use Committee or through an ethical review process. Three animals in each dosing group received an intravenous (i.v) bolus injection of either 10, 1, 0.1 or 0.03 mg/kg of the DEF IgG, or with 1 or 0.1 mg/kg of the Ctrl IgG. The following sampling times of 0.02, 1, 2, 4, 8 24, 48 120 and 168 hours were used to collect 0.5 ml of blood, half of which was processed to serum (for PK determination) and half for plasma (for pharmacodynamics (PD) markers). Serum IgG levels were determined by ELISA using standard protocols for detecting human IgG. The concentration of DEF measured in serum for all doses and times was plotted to evaluate the PK.
Results DEF exhibits normal human IgG PK in rabbits, with typical exposure seen at all concentrations tested over time (FIG. 7). Values were near to, or identical with, that measured with the negative control IgG (data not shown).

Figure 8:
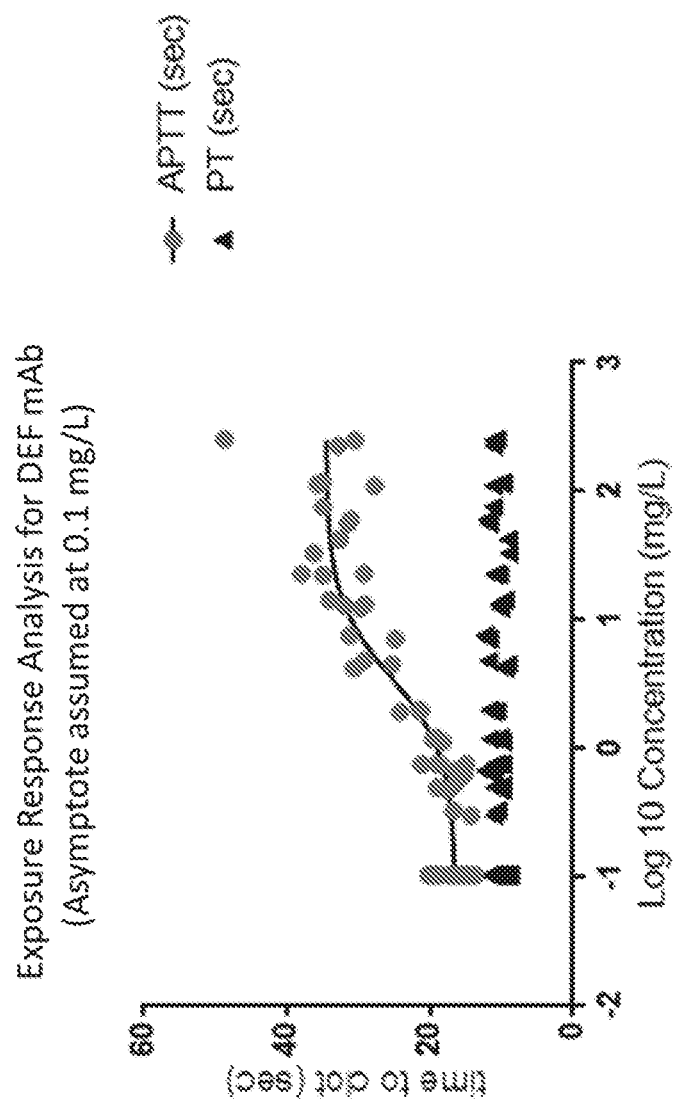
FIG. 8 shows a plot of activated partial thromboplastin time (APTT) and prothrombin time (PT) clotting times versus DEF plasma concentration in New Zealand white rabbits injected with different doses of DEF.

Example 8. Injection of Different Doses of DEF in New Zealand White Rabbits Reveals Concentration Dependent and Selective Prolongation of APTT Clotting Times with No Effect on PT Clotting Times Three animals in each dosing group received an i.v bolus injection of either 10, 1, 0.1 or 0.03 mg/kg DEF IgG, or with 1 or 0.1 mg/kg Ctrl IgG. The following sampling times of 0.02, 1, 2, 4, 8, 24, 48, 120 and 168 hours were used to collect 0.5 ml of blood, half of which was processed to serum (for PK determination) and half for plasma (for PD markers). Serum samples were analyzed for DEF concentration (plotted on X-axis in mg/L) and plasma samples (pre-dose, 30 min, 24 hr, 7 d and 14 d post-dose) were analyzed for drug effects on time to clotting (plotted on the Y-axis in seconds) for both the APTT and the PT coagulation assays (FIG. 8). The PT and APTT assays were run on the plasma by CRO (Covance) using standard assay formats. The PK was determined on serum by standard ELISA format.
Results Rabbit PK/PD (APTT, PT) summary data shows that DEF IgG prolongs time to clotting in a dose dependent fashion in the APTT coagulation assay, but has no effect on clotting time in the PT coagulation assay (FIG. 8). Negative control IgG had no effect on either APTT or PT readouts over time or dose tested (data not shown).

Example 9. Effects of Anti-FXa mAb DEF in Rabbit Model of Venous Thromboembolism (VTE) with Effects Monitored at Level of Thrombus Formation (Thrombus Weight) and at Level of Plasma PD Readout (APTT and PT Assays to Measure Clotting Time Effects All procedures performed on these animals were in accordance with regulations and established guidelines and were reviewed and approved by an Institutional Animal Care and Use Committee or through an ethical review process. Rabbits were anesthetized according to established protocols. Six animals in each dosing group received an i.v bolus injection of either 10, 3, 1, 0.1 or 0.03 mg/kg of DEF IgG, 10 mg/kg of the negative control IgG, 1.5 mg/kg Rivaroxaban, 0.045 mg/kg Rivaroxaban, or a 10% DMA/30% PEG400/60% Water vehicle control. Furthermore, for the Rivaroxaban treated animals, the i.v. bolus injection was supplemented by a continuous i.v. infusion of Rivaroxaban to maintain proper dosing throughout the duration of the study due to short half-life concerns. For all treatment groups, 30 minutes after bolus injection, a sheath of the appropriate size was placed in the left femoral vein. Then a wire of approximately 14 cm with 8 strands of cotton thread attached to it (each 3 cm long) was inserted into the femoral vein. Fluoroscopy was used for guidance of the wire with the threads towards the target area in the vena cava. The device remained in the inferior vena cava for 90 minutes during which clots formed on the cotton threads. After 90 minutes the device was removed by surgical dissection, cut from the wire, and the clot-containing cotton threads were weighed after having been blotted dry. Prior to IgG dosing, and also prior to surgical removal of threads, a blood sample was drawn for preparation of serum (PK) and plasma (for PD biomarkers APTT and PT). Data is plotted to show dose-dependent effects of DEF on clot weight reduction, APTT prolongation, and PT prolongation.

Results

Figure 9B:
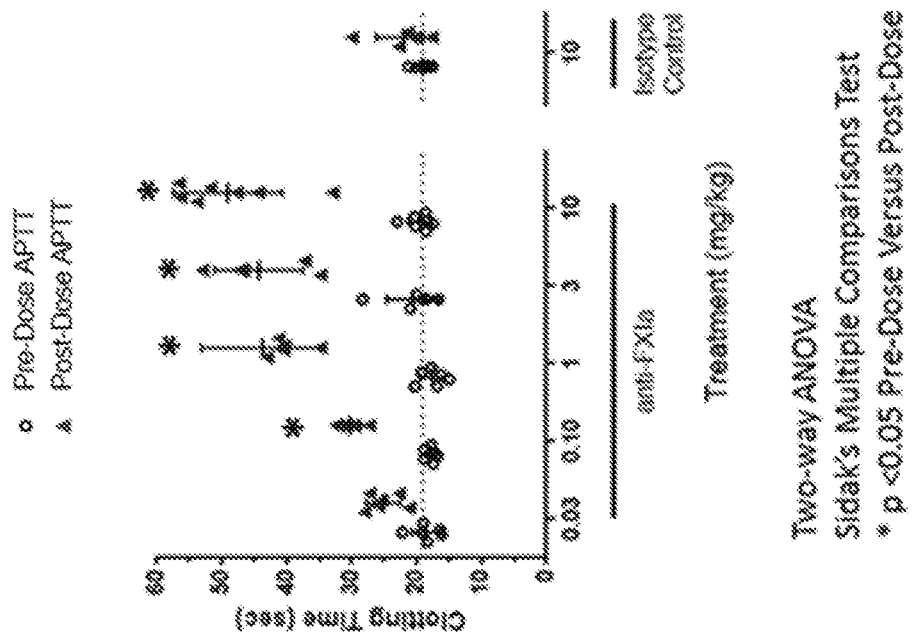
FIG. 9A-9F show the dose-dependent inhibition of anti-FXIa mAb DEF (FIG. 9A-9C) on thrombus weight (A), APTT (B), and PT (C) in a rabbit venous thromboembolism (VTE) model in comparison to the effects of rivaroxaban and both IgG and vehicle controls (FIG. 9D-9F) on thrombus weight (D), APTT (E), and PT (F).
Figure 9A:
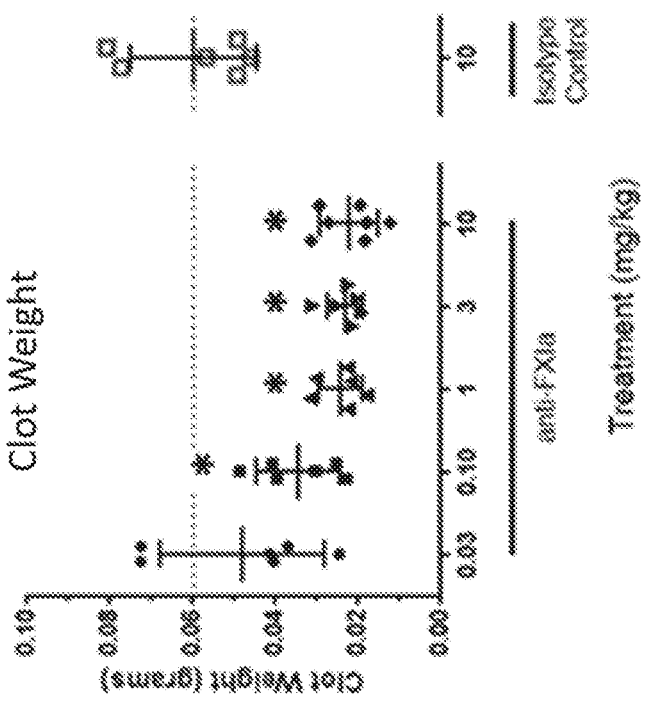
Figure 9D:
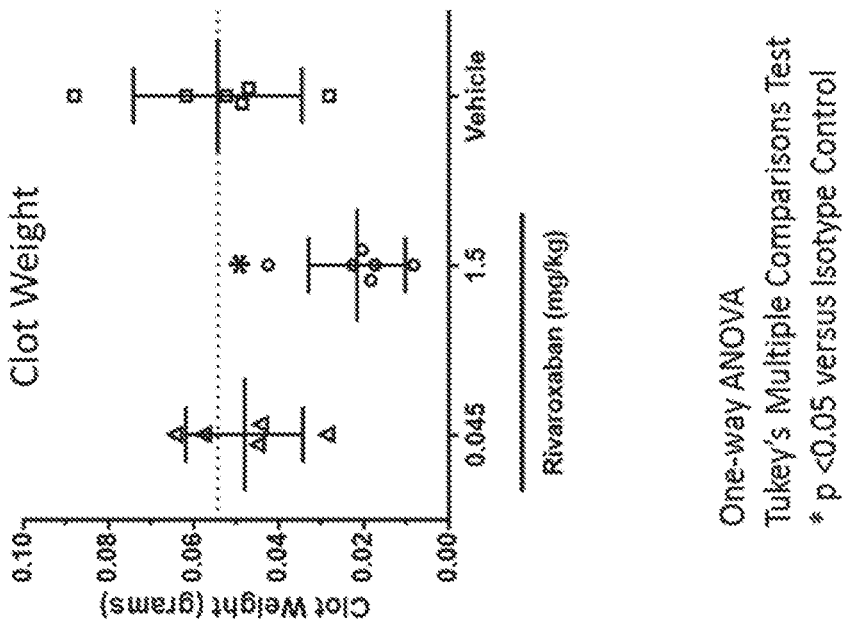
Figure 9C:
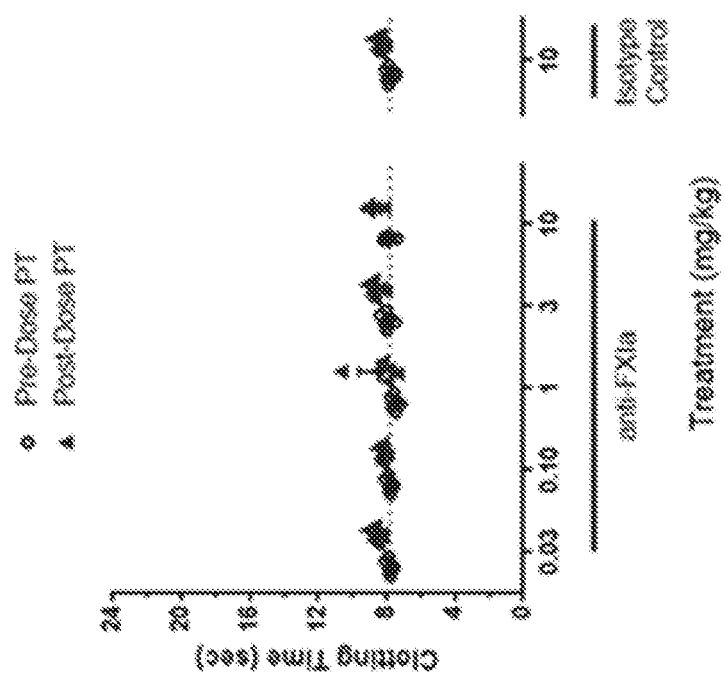
Figure 9E:
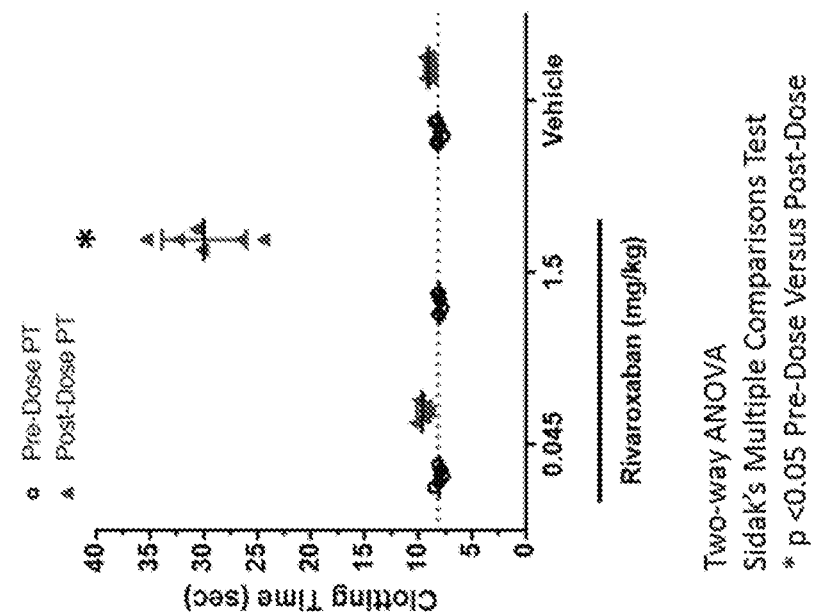
Figure 9F:
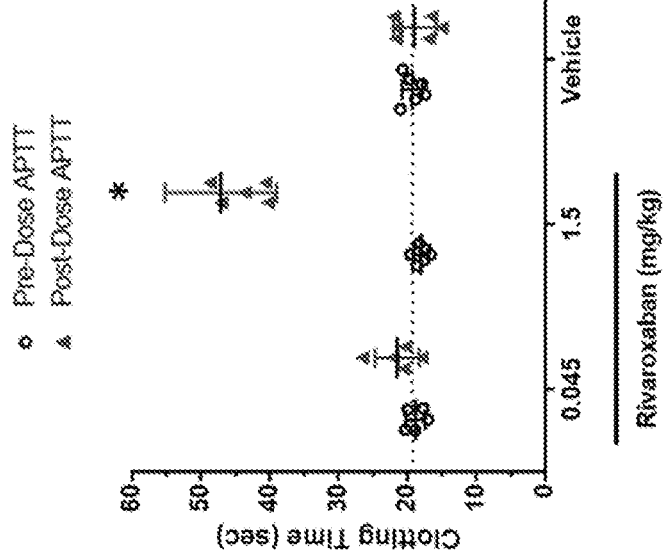

The anti-FXIa mAb DEF dose dependently decreased thrombus/clot weight (FIG. 9A), dose dependently prolonged time to clotting in the APTT assay (FIG. 9B), but had no effect at any dose on clotting times measured in the PT assay of coagulation (FIG. 9C). In contrast, the 1.5 mg/kg dose of Rivaroxaban decreased thrombus/clot weight (FIG. 9D), but prolonged time to clotting in both the APTT (FIG. 9E) and PT (FIG. 9F) assays of coagulation. DEF treatment is thus distinguished by having no effects on PT values, but can confer equivalent thrombus/clot weight reduction to that seen with Rivaroxaban at the 1.5 mg/kg dose. No effects were seen for the 0.045 mg/kg Rivaroxaban dose on any read outs measured. Both the IgG control (FIGS. 9A, 9B and 9C) and the DMA/PEG400/water vehicle control for rivaroxaban (FIGS. 9D, 9E and 9F) had no effects on any readouts measured (all panels).

Example 10. Rabbit Cuticle Bleeding Study Comparing Effects of DEF mAb to Rivaroxaban and Controls All procedures performed on these animals were in accordance with regulations and established guidelines and were reviewed and approved by an Institutional Animal Care and Use Committee or through an ethical review process. Rabbits were anesthetized according to established protocols. After anesthesia and cannulation etc., both front paws were shaved to remove fur that would otherwise contaminate saline and wick it out of the tube. Pre dosing bleeds were performed on the middle digit of the left front paw. Post dosing bleeds were performed on the same digit on the right front paw. There were four dosing groups of 10 animals each. Ten animals in each dosing group received either an i.v bolus injection of either 10 mg/kg DEF IgG, 10 mg/kg control IgG, 1.5 mg/kg of Rivaroxaban, or a 10% DMA/30% PEG400/60% water vehicle control. Furthermore, for the Rivaroxaban treated animals, the i.v. bolus injection was supplemented by a continuous i.v. infusion of Rivaroxaban to maintain proper dosing throughout the duration of the study due to short half-life concerns.

Nails were transilluminated with white light to visualize the quick and cut with a razor blade so as to transect the cuticle approximately 1 mm proximal to the apex of the quick. The nail was then immediately immersed in a saline solution in 10×75 mm 3 ml polystyrene (clear) tube. The tube with saline was stored at 37° C. before the cut. The nail was kept in the solution and time to cessation of flow was measured. If bleeding did not stop, the procedure was stopped at 20 min and logged as >20 min. At the end of the blood collection the tube is capped and inverted 5 times and centrifuged at 200 to 250×g for 15 min. The blood cell pellet was resuspended in 3 mL erythrocyte lysis buffer (8.3 g/L NH4Cl, 1.0 g/LKHCO3, and 0.037 g/L EDTA in water). After at least 15 min of lysis time, hemoglobin (Hb) concentration was measured at OD 575 nM using a Spectrophotometer) and expressed as arbitrary absorbance units.

As indicated above, baseline cuticle bleeding times were performed prior to dosing. After cessation of bleeding, animals were then dosed i.v. at t=0 min with DEF IgG, inactive control IgG, Rivaroxaban, or vehicle. 30 minutes later a second cuticle cut was made and bleeding times recorded and blood loss measured. In addition, blood samples obtained before dosing and at the end of the study were used for serum PK determinations of Ab and Rivaroxaban levels and plasma was used to determine PD markers (via standard APTT and PT coagulation assays). Data is plotted to show effects of dosing with DEF IgG, ctrl IgG, Rivaroxaban, and vehicle on total blood loss, APTT prolongation, and PT prolongation.

Results

Figure 10A:
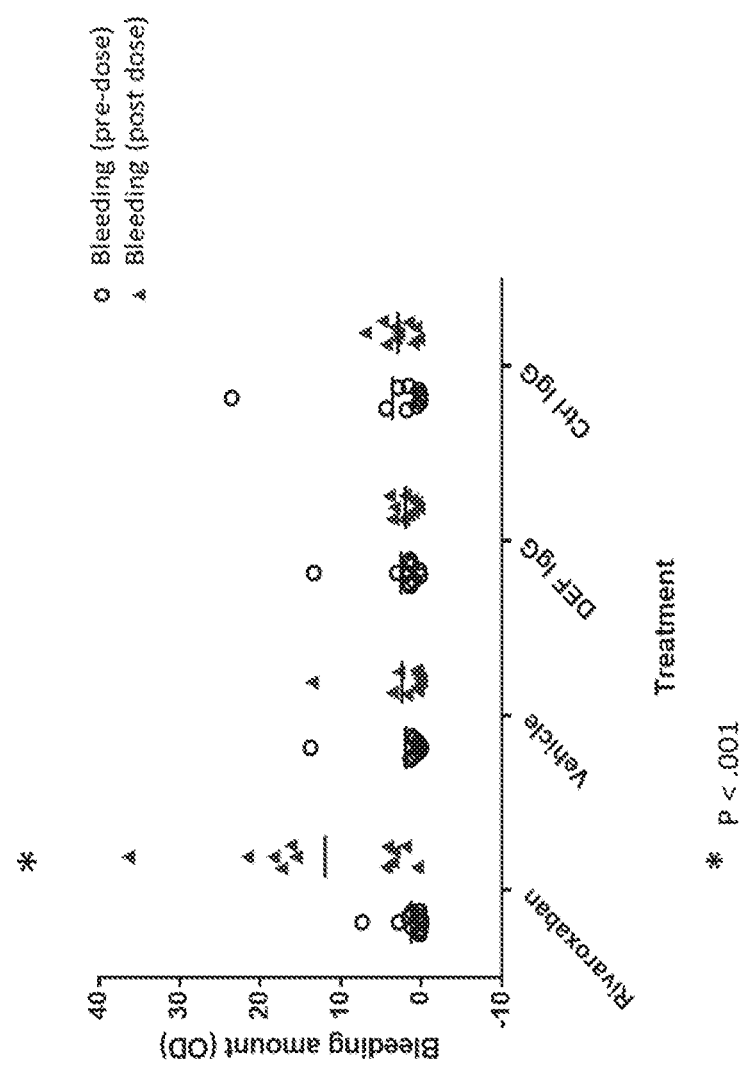
Figure 10C:
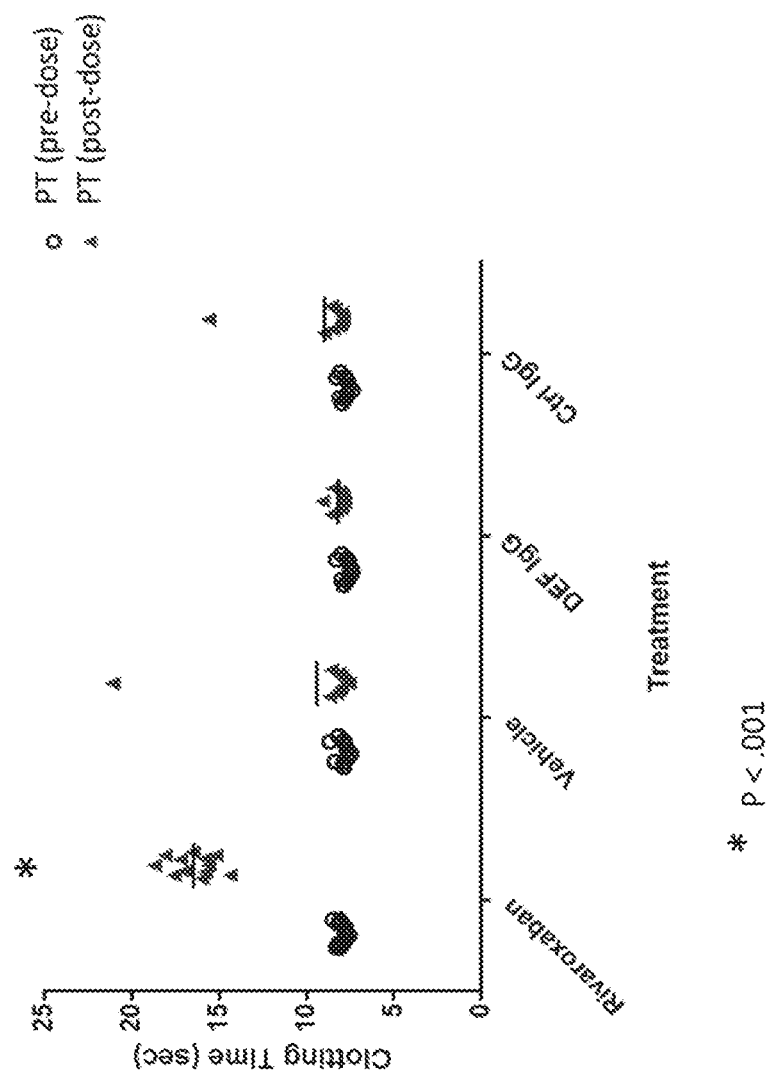

The anti-FXIa mAb DEF at 10 mg/kg had no effect on total blood loss following cuticle cutting (FIG. 10A), induced a significant prolongation in time to clotting as measured in the APTT coagulation assay (FIG. 10B), but had no effect on time to clotting as measured in the PT assay of coagulation (FIG. 10C). In contrast, Rivaroxaban at 1.5 mg/kg significantly increased total blood loss following cuticle cutting (FIG. 10A), and induced a significant prolongation in time to clotting in the both the APTT (FIG. 10B) and PT (FIG. 10C) coagulation assays. Both the IgG control and the DMA/PEG400/water vehicle control had no effects on any readouts measured (FIGS. 10A-10C). Combining the results from FIG. 8 and FIG. 9, we conclude that the DEF IgG can reduce thrombus/clot weight (anti-thrombotic effect) while at the same time have little or no effect on injury-induced blood loss (hemostatic effect) as measured in these rabbit studies.

Figure 11:
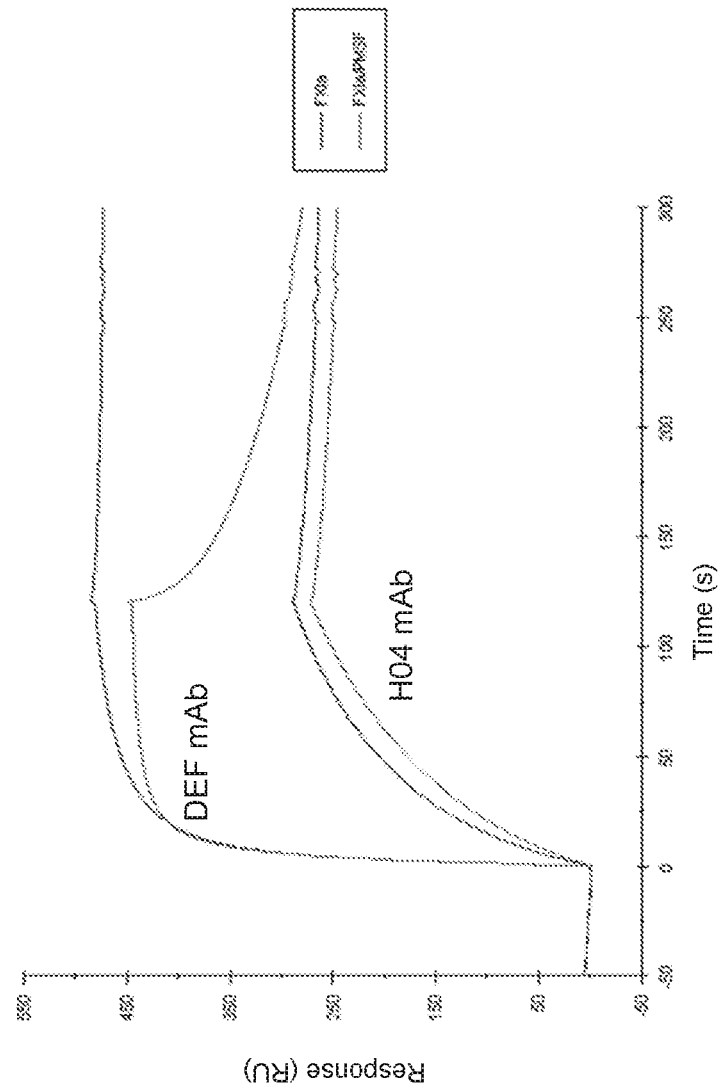
FIG. 11 shows the effect of PMSF modification of FXIa catalytic serine residue on the binding affinity of anti-FXIa mAbs DEF and H04 for FXIa.

Example 11. Anti-FXIa mAb has an Increased Off-Rate when Bound to FXIa Inhibited with PMSF Biotinylated FXIa was incubated with 1 mM PMSF prior to capture on a streptavidin-coated Biacore™ chip. The binding of 100 nM DEF IgG or H04 IgG (e.g., as described in WO 2013/167669 A1) was observed over 120 sec followed by 120 sec dissociation phase. Blood-derived FXIa (Haematologic Technologies Inc.) was biotin labeled via primary amines and immobilized on a CAP chip using a Biacore™ T200 instrument (GE Healthcare). The binding experiment was performed at 25° C. using a 50 μl/min flow rate in 0.01 M HEPES pH 7.4, 0.15 M NaCl and 0.005% v/v surfactant P20 (HBS-P) buffer. After the antibody injection the chip surface was regenerated with a mixture of 6 M guanidine HCl and 0.25 M NaOH, and new FXIa captured. The data was background subtracted using the signal from the adjacent streptavidin coupled flow cell and buffer-only injections over the FXIa surface using Biacore™ T200 Evaluation software (GE Healthcare).
Results A significant increase in the DEF mAb dissociation rate but not that of the anti-FXIa H04 mAb (described in WO 2013/167669, incorporated herein by reference) was observed when the FXIa was pre-bound to the serine protease inhibitor PMSF compared to FXIa alone (FIG. 11). PMSF covalently binds to the active site serine, irreversibly inhibiting the protease. The ability of PMSF to partially disrupt DEF mAb binding to FXIa indicates that the binding epitope overlaps with the catalytic serine and/or adjacent residues within the active site cleft. This was not observed for the H04 mAb, which binds to both FXIa and FXIa-PMSF with similar kinetics, suggesting that the H04 mAb binding epitope is distinct from that of the DEF mAb.

Example 12. Multiple Dose PK Study with DEF in Cynomolgus Monkeys

Figure 12:
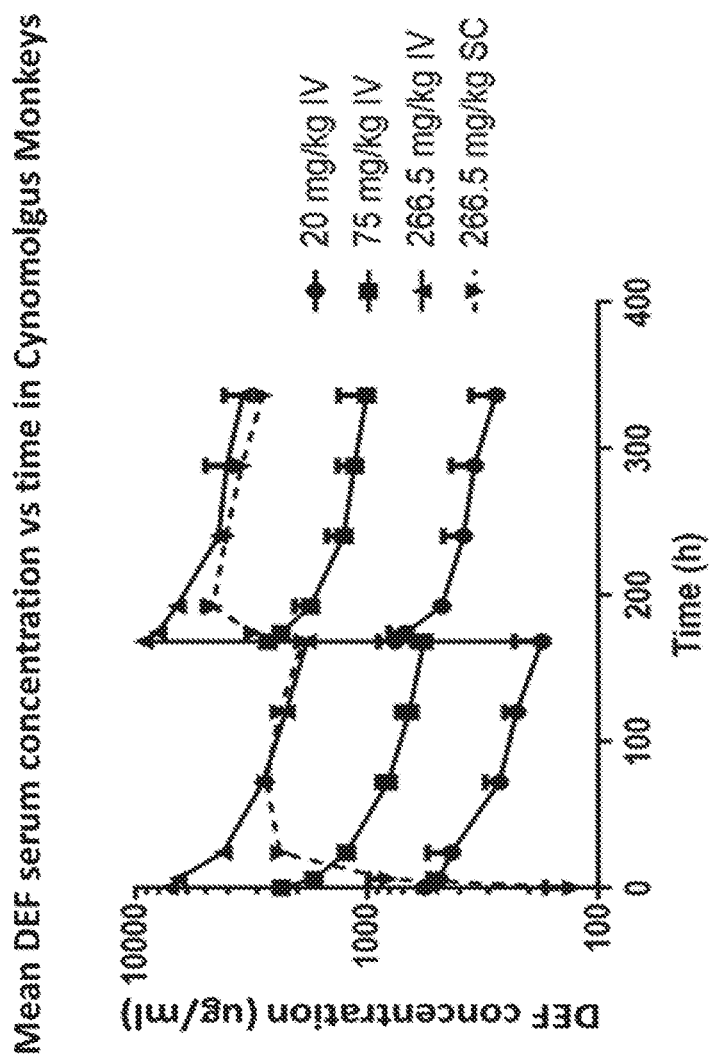
FIG. 12 shows the PK of DEF IgG in cynomolgus monkeys.

As part of an exploratory toxicology and PK study in cynomolgus monkeys, two animals (one female, one male) in each dose group were dosed with either 20, 75, or 266.5 mg/kg DEF i.v. or 266.4 mg/kg DEF s.c. on days 1, 8 and 15 with necropsy occurring on day 15. Daily observations were made over the course of this study, and no test article-related mortality, clinical signs, effects on body weight or food consumption, hematology or clinical chemistry parameters, or microscopic observations were observed. Additionally, over the course of this study multiple blood samples were drawn for preparation of serum (PK) and plasma (PD makers). Serum IgG levels were determined by ELISA using standard protocols for detecting human IgG. Sampling times were at 0.08, 6, 24, 168, 168.08, 174, 192, 240, 280, 288 and 336 hours. The concentration of DEF measured in serum for all doses and times was plotted to evaluate the PK.
Results DEF exhibits normal human IgG pharmacokinetics (PK) in cynomolgus monkeys, with typical exposure seen at all concentrations tested over time (FIG. 12). Antibody accumulation was observed after day 8 in all DEF dose groups. The exposure ratios of Day 8 vs Day 1 ranged from 1.36x-1.64x. Given the apparent typical antibody pharmacokinetics observed in this study, ADA measurements were not performed. Due to the small sample size, comparisons of DEF antibody exposure between males and females were not performed. Following i.v. administration of DEF, systemic exposures (assessed by $C_{max}$ and AUC) on Day 1 and Day 8 increased proportionally as dose increased from 20 to 266.5 mg/kg. Comparison of $AUC_{(0-168h)}$ in the i.v, and s.c. 266.5 mg/kg dose groups shows that subcutaneously administered DEF is 61% bioavailable, and reached $T_{max}$ 72 hours after the first dose. Overall exposure after subcutaneous dosing, expressed as $AUC_{(0-168h)}$, was 74% of that seen via the intravenous route. Due to uncertainties arising from the short study duration and dosing regimen, antibody half-life was not calculated.

Figure 13B:
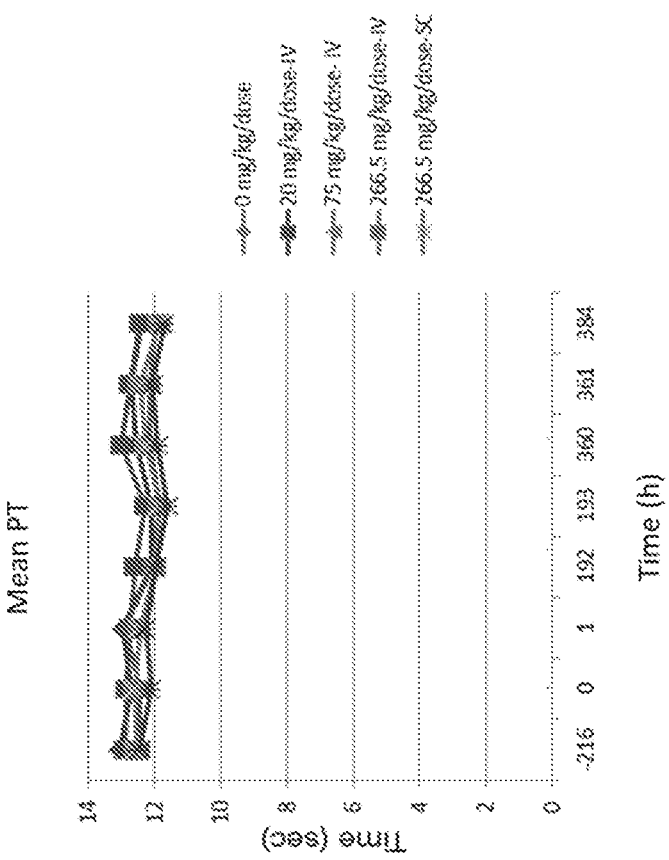
FIG. 13A-13B show the effect of high dose DEF exposure on APTT and PT coagulation time in cynomolgus monkeys.
Figure 13A:
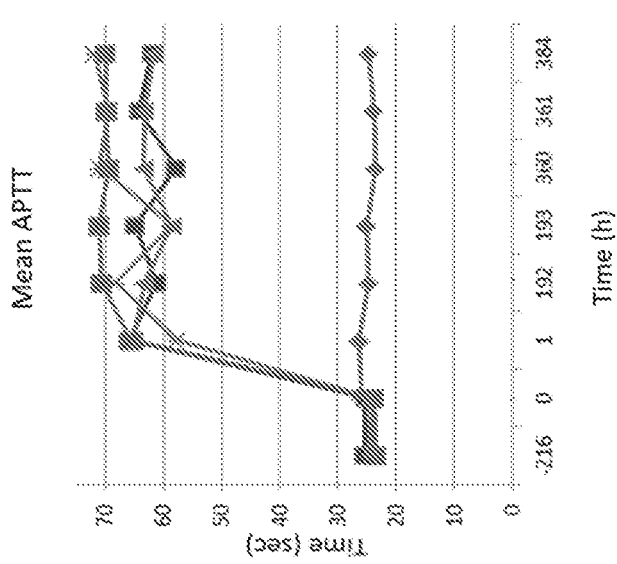

Example 13. Prolongation of APTT, but not PT, Coagulation Times Seen in 15 Day Study of Cynomolgus Monkeys Treated with High Doses of DEF IgG As part of an exploratory toxicology and PK study in cynomolgus monkeys, two animals (one female, one male) in each group were dosed with either 20, 75, or 266.5 mk/kg DEF i.v or 266.4 mg/kg DEF s.c. on days 1, 8 and 15 with necropsy occurring on day 16. Daily observations were made over the course of this study, and no test article-related mortality, clinical signs, effects on body weight or food consumption, hematology or clinical chemistry parameters, or microscopic observations were observed. Additionally, over the course of this study, multiple blood samples were drawn for plasma preparation and assessment of coagulation parameters. These samples were collected on Day −9 and then just before dosing and 1 h after dosing on days 1, 8, and 15, and then just prior to necropsy on Day 16. The Day −9 and just prior to dosing on Day 1 are used to determine a base line value. Plasma samples were analyzed for drug effects on time to clotting (plotted on the Y-axis in seconds) in both the APTT and the PT coagulation assays. The APTT and PT assays were performed using standard assay formats.
Results DEF IgG prolongs clotting time in APTT coagulation assay (FIG. 13A) but has no effects on clotting time in PT coagulation assay (FIG. 13B) in cynomolgus monkeys treated with high doses of DEF IgG over course of 15 days. Even at the high concentrations of DEF IgG dosing used in this toxicology study, the only evident sign of treatment in these animals was the expected pharmacological change of APTT prolongation. This result is significant as it has previously been shown in earlier rabbit studies (see, e.g., as described in Examples 8-9) that APTT prolongation was associated with anti-thrombotic protection but not with increased bleeding risk. Rather, PT prolongation was associated with bleeding risk. Thus, the essential mechanism of DEF action (intrinsic pathway inhibition reflected as selective APTT prolongation) is the same in rabbits and in this non-human primate model, and thus likely to translate to humans as well.

Example 14. Identification of an Anti-Idiotype Antibody to DEF

Figure 14:
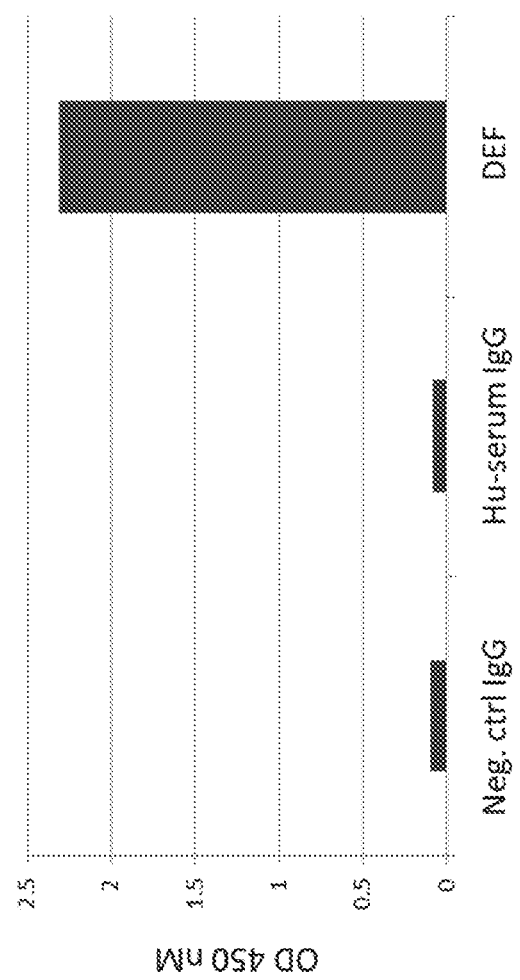
FIG. 14 shows the binding selectivity of C4 mAb, an anti-idiotype antibody to DEF.

The antigen DEF is an IgG1 human antibody specific for FXIa. DEF was chemically biotinylated using biotin-LC-NHS (Pierce; Cat. NO: 21347), according to the manufacturer's protocol. This biotinylated DEF was immobilized on streptavidin-coated magnetic Dynabeads M-280 (Invitrogen, Cat. No: 11206D) and used to select binders from a scFv antibody phage display library (WyHN5 kappa and lambda), using standard methods. Prior to each round of selection, phage antibody library was absorbed to streptavidin-coated Dynabeads M-280 in order to deplete streptavidin binders. The phage selection was performed in the presence of 500 nM of human serum IgG, using decreasing concentrations of the antigen (DEF) and increasing number of washes with PBS containing 0.1% Tween20 (PBST), as follows: $1^{st}$ round 100 nM/5×PBST/2×PBS, $2^{nd}$ round 10 nM/10×PBST/5×PBS and $3^{rd}$ round 1 nM/15×PBST/5× PBS. A total of 3,000 clones were picked from the $3^{rd}$ round output colonies and tested in ELISA assay for DEF, Human-IgG and streptavidin binding. This selection and screening gave a single specific anti-DEF hit. After sequencing, the unique clone (C4) specific to DEF was reformatted into a fully human IgG1. In order to evaluate the specificity of full length C4 IgG against DEF, ELISA assay was performed as follows. 1 µg/ml of biotinylated control antibody, human serum IgG or DEF were added on to ELISA plate on which 10 mg/ml of streptavidin was previously coated overnight. After blocking and washing, 100 ng/ml of C4 IgG was added to each well and incubated at room temperature for 1 hour. After washing and treating with anti-human IgG-HRPO, enzyme substrate (TMB) was added to develop the color. The signal was read at 450 nm after stopping the reaction by adding 0.16M sulfuric acid.
Results The reformatted C4 mAb binds selectivity to DEF. ELISA data shows no binding to a negative control IgG, no binding to human serum IgG, but strong binding to DEF IgG (FIG. 14).

Example 15. Binding Kinetics for the Anti-DEF mAb C4

Figures 15A, 15B:
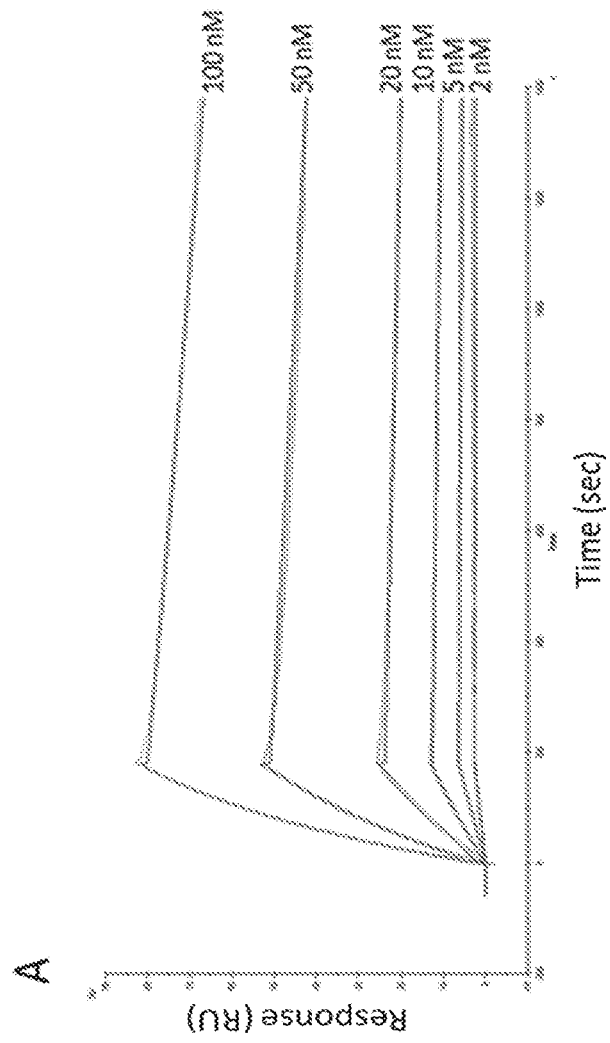
FIG. 15A-15B show the DEF Fab binding kinetics for C4 mAb.

For C4-DEF binding experiments, C4 IgG was captured by anti-human IgG (Fc) antibody amine coupled to a CM5 chip using a Biacore™ T200 instrument (GE Healthcare). The anti-human IgG capture chip surface was prepared using a Biacore™ Human Antibody Capture Kit according to the manufactures directions (GE Healthcare). DEF Fab binding experiments were performed at 25° C. using a 30 µl/min flow rate in 0.01 M HEPES pH 7.4, 0.15 M NaCl and 0.005% v/v surfactant P20 (HBS-P) buffer. After each cycle, the chip surface was regenerated with 3 M $MgCl_2$ and new C4 antibody captured. DEF Fab samples ranging from 2-100 nM were injected over the surface for 3 minutes and the dissociation monitored for a further 20 minutes. Data was analyzed using the Biacore™ T200 Evaluation software and the results reported as the mean of two experiments.
Results The affinity of the C4 mAb for the DEF mAb has a Kd of 3 nM. Representative background subtracted Biacore™ sensorgrams overlaid with the kinetic curve fits are shown (FIG. 15A) along with the measured kinetic rate constants in the Table (FIG. 15B).

Figure 16:
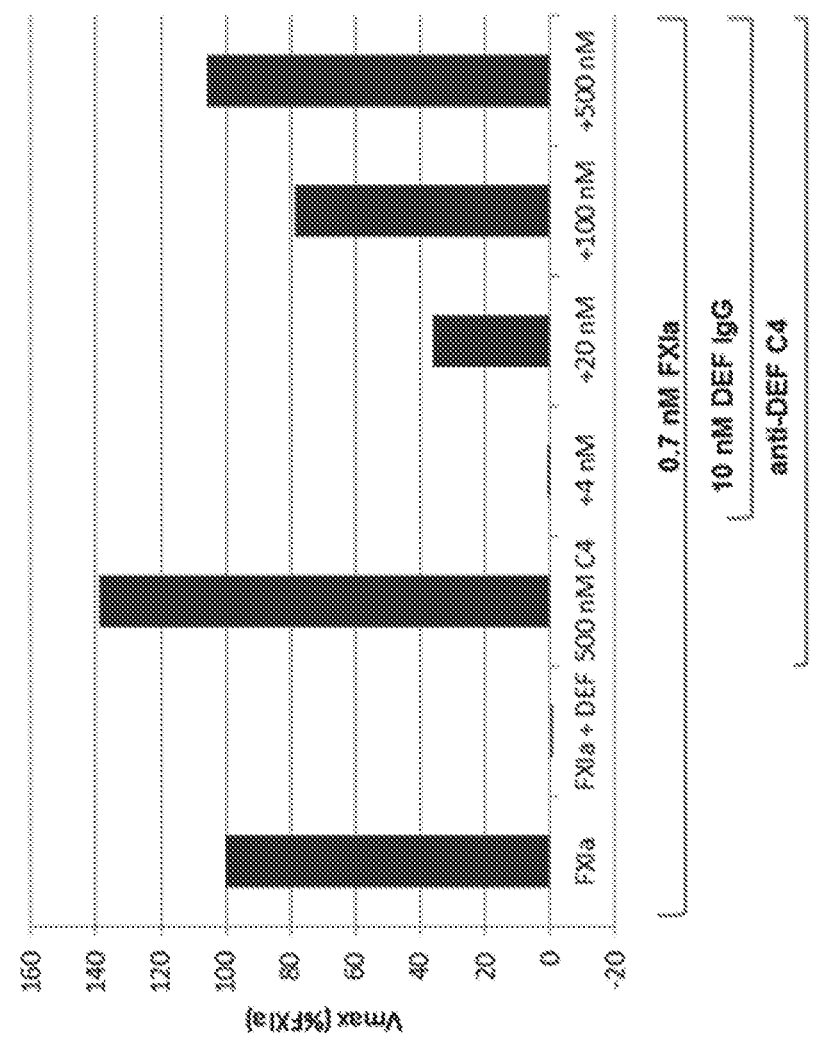
FIG. 16 shows the reversal effect of C4 mAb on the inhibitory effects of anti-FXIa mAb DEF in an m vitro FXIa assay.

Example 16. Effects of the C4 mAb to Reverse Inhibitory Effects of Anti-FXIa mAb DEF in an In Vitro FXIa Assay DEF IgG and anti-DEF C4 IgG (4/20/100/500 nM) were premixed and incubated for 20 min in the FXIa assay buffer. Following this time 0.7 nM FXIa was incubated for further 5 min. The reaction was then initiated by adding the fluorogenic peptide substrate which starts the reaction. The plate was immediately inserted into and read on a fluorescent plate reader at 37° C. for 30 minutes. Excitation setting was 352 nM, emission setting was 470 nM. Data were collected every 1 minute on a SpectraMax®, 3 instrument. The Vmax data was then plotted for the individual conditions tested.
Results Excess C4 mAb (at approximately 2-10-fold that of DEF concentration) can reverse the inhibitory effects of anti-FXIa mAb DEF in a human FXIa activity assay in vitro (FIG. 16). It is predicted that even only partial restoration of FXIa function will probably be sufficient to reverse anticoagulant effects.

Figure 17:
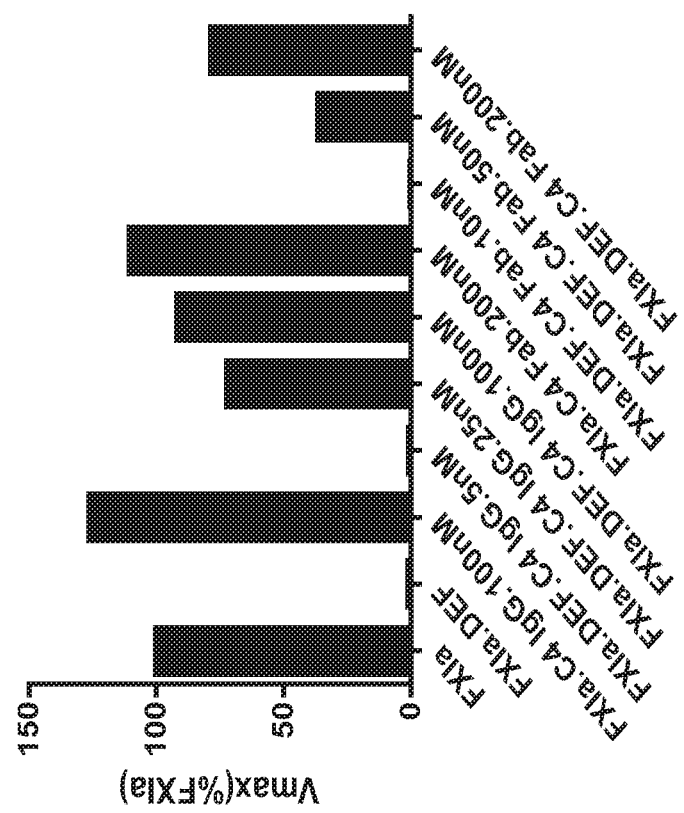
FIG. 17 shows the reversal effect of C4 mAb on the inhibitory effects of anti-FXIa mAb DEF in an in vitro FXIa assay.

Example 17. Effects of the C4 mAb to Reverse Inhibitory Effects of Anti-FXIa mAb DEF in an In Vitro FXIa Assay 10 nM DEF antibody was premixed and incubated with the indicated concentrations of either the C4 IgG or C4 Fab for 10 min in the FXIa assay buffer. Following this time 0.5 nM FXIa was added and incubated for an additional 5 min. The reaction was then initiated by adding the fluorogenic peptide substrate which starts the reaction. The plate was immediately inserted into and read on a fluorescent plate reader at 37 C for 30 minutes. Excitation setting was 352 nM, emission setting was 470 nM. Data were collected every 1 minute on a Spectramax 3 instrument. The Vmax (% FXIa alone) data was then plotted for the individual conditions tested. Control FXIa assay reactions containing no DEF or with only C4 mAb or C4 Fab are also shown.
Results Excess C4 Fab (at approximately 5-20-fold that of DEF concentration) can reverse the inhibitory effects of anti-FXIa mAb DEF in a human FXIa activity assay in vitro (FIG. 17). The greater activity of C4 IgG compared to C4 Fab may be a result of their bivalent and monovalent structures, respectively. It is predicted that even only partial restoration of FXIa function will probably be sufficient to reverse anticoagulant effects.

Figure 18A:
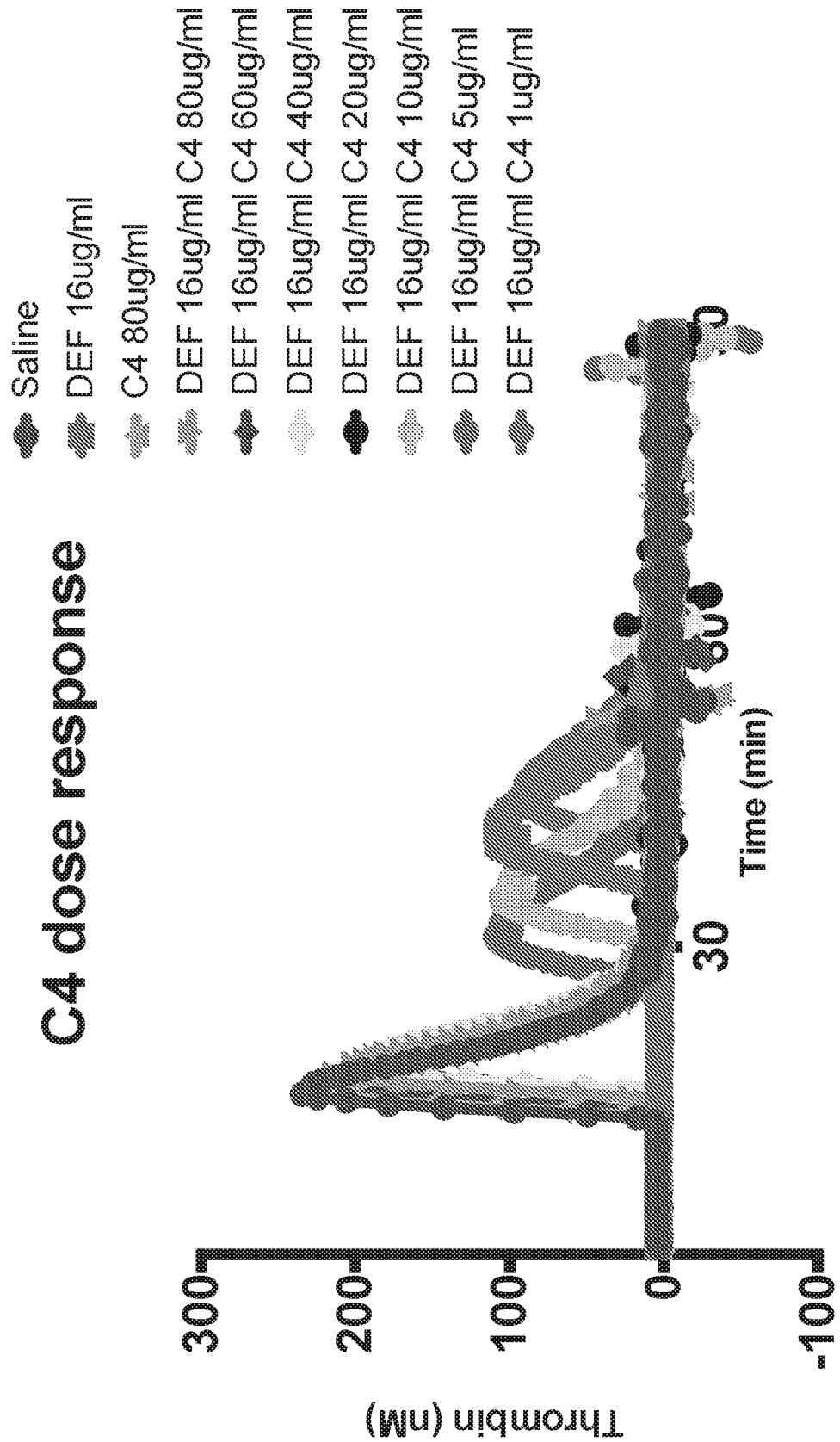
FIG. 18A, FIG. 18B, and FIG. 18C show the effect of C4 mAb on the inhibitory effects of anti-FXIa mAb DEF in human plasma in a FXIIa-triggered thrombin generation assay.
Figure 18C:
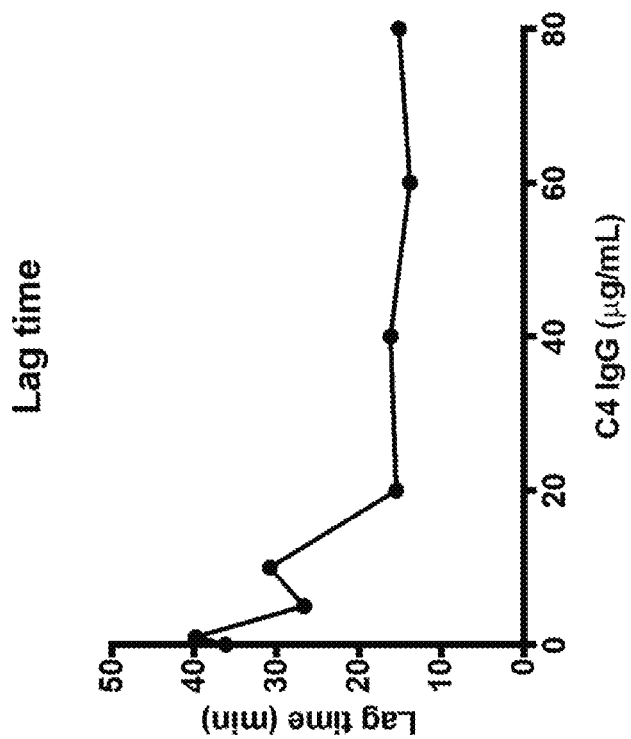
Figure 18B:
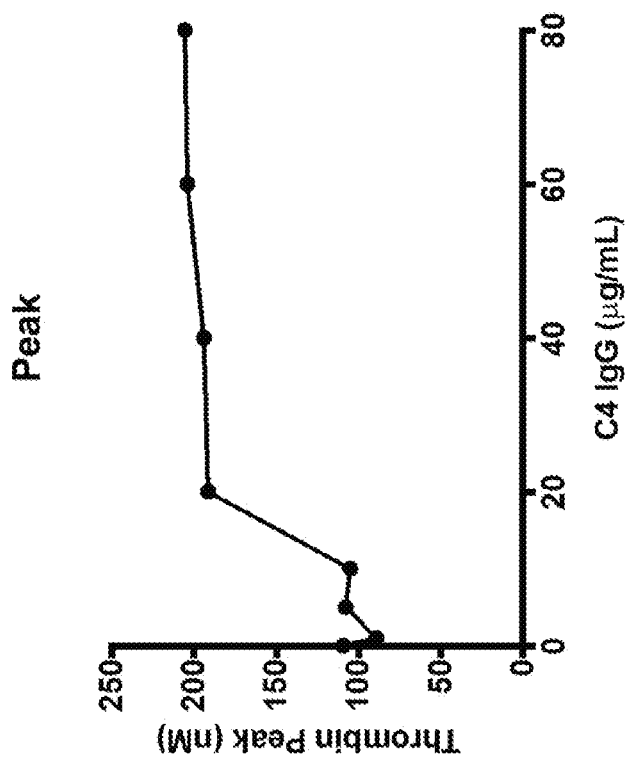

Example 18. Reversal Effects of the Anti-DEF mAb C4 on the Anti-FXIa mAb DEF in a FXIIa-Triggered Human Plasma Reaction that Measures Downstream Thrombin Generation as a Readout Thrombin generation was measured using a fluorogenic thrombin substrate on a multiwell automated fluorescent plate reader (ThrombinoSCOPE, Maastricht, the Netherlands) according to the manufacturer's protocol. Briefly, 5 µL of anti-FXIa DEF antibody (16 µg/ml) was added in combination with different ratios of the anti DEF C4 IgG (1, 5, 10, 20, 40, 60, 80 µg/ml) and mixed with 20 µL PBS-60 nM human Factor XIIa (Enzyme Research Laboratories, South Bend, Ind. USA)-PC/PS (Phospholipid-TGT, DiaPharma, West Chester, Ohio, USA) in a 96-well plate. Finally, 75 µL human Plasma (Triclinical Reference Plasma. TCoag, Wicklow, Ireland) was added. Due to lot-to-lot variability for the PC/PS reagent, for each lot, the concentration was adjusted to achieve a ~10 min Lag Time and ~125 nM Thrombin Peak. Finally, clotting was triggered with the addition of calcium chloride buffer and a fluorogenic thrombin substrate. The amount of thrombin generated in the reaction was measured over time.
Results The C4 mAb reverses the inhibitory effects of the anti-FXIa mAb DEF on FXIIa-triggered thrombin generation in a human plasma assay. Reversal of DEF effects are seen for all doses at or above 20 µg/ml of the C4 mAb, indicating that the reversal properties are first evident in this assay at an ~1:1 ratio with the DEF mAb (FIGS. 18A-C).

Example 19. C4 mAb Reverses Effects of Anti-FXIa mAb DEF in In Vivo Rabbit Dosing Experiment All procedures performed on these animals were in accordance with regulations and established guidelines and were reviewed and approved by an Institutional Animal Care and Use Committee or through an ethical review process. Rabbits were anesthetized according to established protocols. A 90-minute in-life rabbit study was then carried out involving the following procedures. Five rabbits were treated, with all animals being treated the same. At time 0 each animal received a 1 mg/kg bolus injection of the DEF IgG, 30 minutes later each animal then received a bolus injection of 3 mg/kg ctrl IgG, 30 minutes after that each animal then received a bolus injection of 3 mg/kg ctrl C4 IgG. Just prior to each bolus injection, and 30 minutes after the final (C4 IgG) injection, blood was drawn to make plasma for APTT and PT clotting time assays. Data is plotted to show the sequential effects of DEF, ctrl IgG, and C4 IgG injection on APTT and PT coagulation times.

Results

Figure 19B:
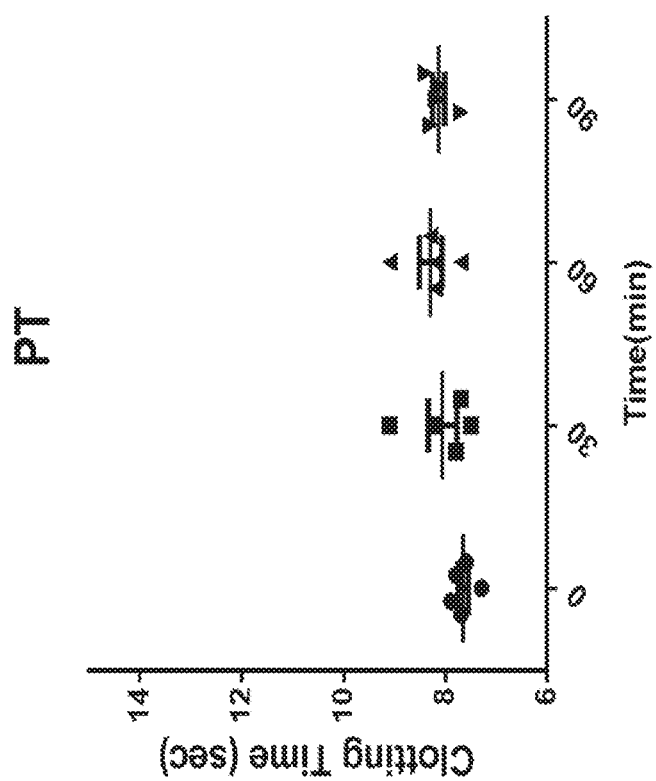
FIG. 19A-19B show the effect of C4 mAb on anti-FXIa mAb DEF in an in vivo rabbit dosing experiment followed by ex vivo APTT and PT assays.
Figure 19A:
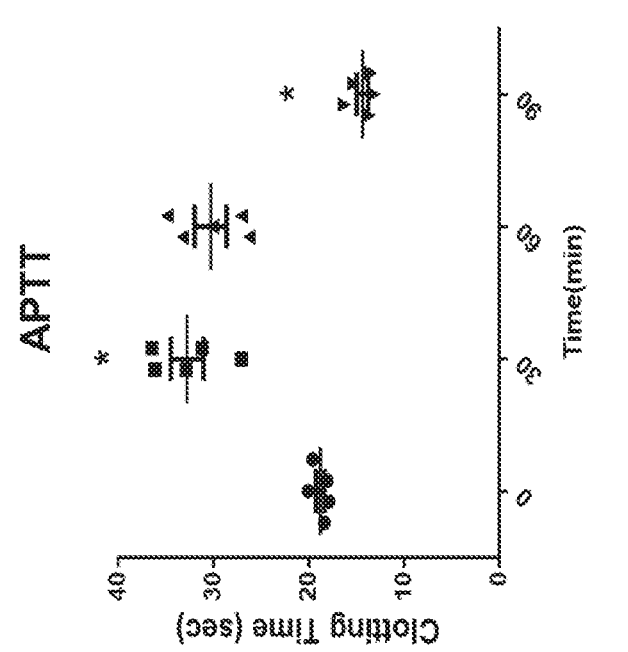

The results of this sequential dosing experiment in the live rabbit show that the C4 mAb reverses the effects of the DEF mAb, as measured in the ex vivo APTT assay, 30 minutes after dosing with C4 (FIG. 19A). This result provides further evidence that dosing of the C4 mAb could quickly reverse the effects of DEF dosing in vivo were any DEF-related adverse bleeding events to occur. No effects on PT coagulation times were seen between pre- and post-dose samples, as expected (FIG. 19B).

Example 20. Effects of Anti-FXIa Antibody C24 on FeCl$_3$-Triggered Carotid Artery Thrombosis in Human FXI-Reconstituted FXI-Deficient Mice A mouse model known to be FXI-dependent was utilized for an initial determination of whether Clone 24 ("C24") antibody could alter thrombosis in vivo. FXI-deficient mice are protected against FeCl$_3$-induced carotid artery occlusion, a commonly used assay of injury-induced arterial thrombosis. See, Rosen et al., *Thrombosis and haemostasis* 87, 774-776 (2002); Wang et al., *Journal of thrombosis and haemostasis: JTH* 3, 695-702 (2005). Because our antibodies did not cross react with mouse FXIa, a FXI-humanized mouse analogous to that reported by Geng et al. (*Blood* 121, 3962-3969 (2013)) was established, but by administration of human FXI protein rather than hydrodynamic transduction. Administration of human FXI (0.25 mg/kg i.v.) to FXI-deficient mice rescued FXIIa-driven thrombin generation in plasma to wild-type values and provided a concentration of human FXI in plasma as measured by ELISA of ~1.5 µg/ml, ~30% of the level in human plasma, for the duration of the thrombosis protocol.

FXI-knockout mice received an i.v. bolus injection via tail vein of 0.25 mg/kg purified human FXI and 0.5, 2, 4, 12, 35 mg/kg C24 (a fully human IgG1 monoclonal antibody) or control IgG1 at the same concentrations. Fifteen minutes later, the mice were anesthetized. The left common carotid artery was exposed and a flow probe (model MA0.5PSB, Transonic Systems Inc., Ithaca, N.Y.) was placed around the artery proximal to the bifurcation (Wang et al., *Journal of thrombosis and haemostasis: JTH* 3, 695-702 (2005); Cornelissen et al., *Proceedings of the National Academy of Sciences of the United States of America* 107, 18605-18610 (2010)). Filter papers soaked in a 250 mM ferric chloride (FeCl$_3$) solution were placed above and below the artery for 3 minutes then removed. Arterial flow was measured continuously using a TS420 flow meter (Transonic Systems inc., Ithaca, N.Y.) connected to an ADinstruments Powerlab 4/30 and Chart software. Monitoring was continued until the artery was occluded (defined as no flow for ≥1 minutes) or for 20 minutes if no occlusion occurred. Data are plotted as % of vessels remaining open as a function of time after injury. Human FXI preparations had no detectable (<1%) FXIa activity in the SN-59 hydrolysis assay.

Results

Figure 20:
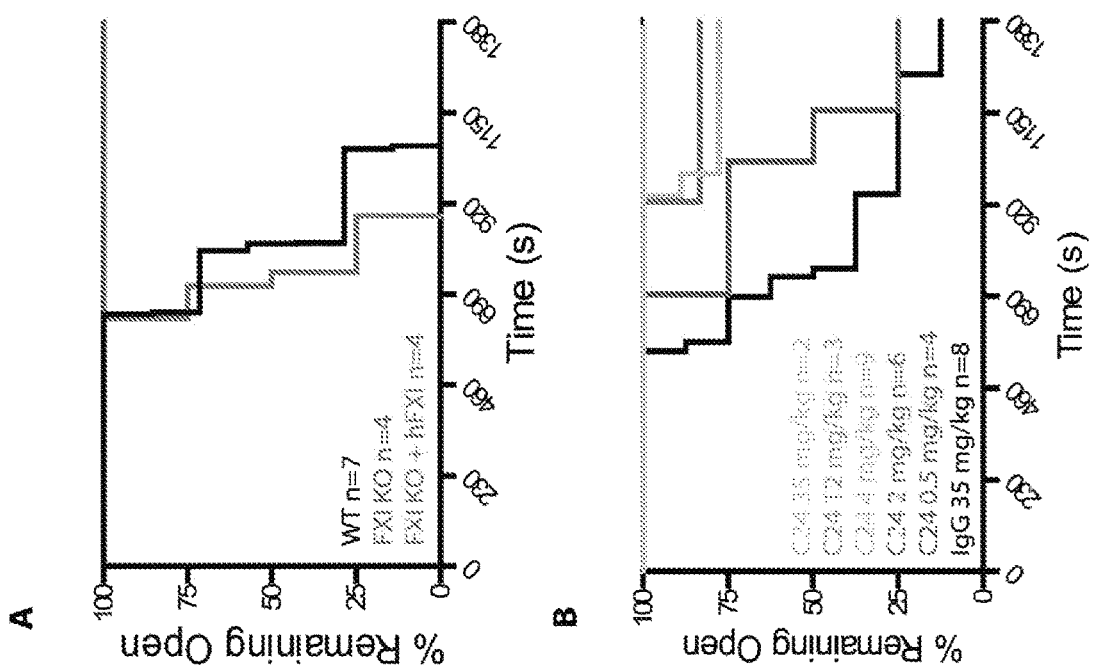
FIG. 20A-20B show the effect on $FeCl_3$-triggered carotid artery thrombosis in human FXI-reconstituted FXI-deficient mice. (A) Blood flow after carotid injury with 250 mM v/v $FeCl_3$ in FXI-deficient mice injected with vehicle (blue) or human FXI at 0.25 mg/kg (red) or in age-matched wild-type mice from the same colony (black). % of vessels remaining open as a function of time after injury is shown. (B) Human FXI-reconstituted FXI-deficient mice were injected with C24 at 0.5 (blue), 2 (red), 4 (green), 12 (orange) and 35 (gray) mg/kg i.v. or with the same doses of control IgG1. The % of vessels remaining open as a function of time after injury was determined as in (A). Carotids in mice injected with all doses of control IgG1 had median occlusion times similar to wild-type mice; only 35 mg/kg IgG1 data are shown (black) to avoid clutter. The rate of occlusion was decreased in human FXI-reconstituted FXI null mice treated with C24 at 2 mg/kg and higher doses when compared to the rate in mice treated with control IgG1 by Log-Rank Analysis (Mantel Cox) (p=0.01).

Reconstitution of FXI-deficient mice with human FXI restored carotid occlusion after application of FeCl$_3$ (4% w/v; 250 mM) (FIG. 20A). 4/4, 0/4, and 4/4 carotids were occluded by the end of the protocol in wild-type, FXI-deficient, and FXI-humanized mice, respectively. Median time to occlusion was similar in wild-type and FXI-humanized mice (850 vs. 740 sec). In FXI-humanized mice that received control IgG1 at 35 mg/kg i.v., the highest dose tested, 7/8 carotids were occluded by the end of the protocol and median time to occlusion was 750 sec, a rate indistinguishable from that seen in wild-type or FXI-humanized mice. By contrast, only 3/19 carotids occluded in FXI-humanized mice that received C24 at 2 mg/kg i.v. or above (FIG. 20B). At 0.5 mg/kg, C24 prolonged median time to occlusion to 1100 sec, and at 2 mg/kg and above, median times to occlusion were greater than 1380 sec, the end of the protocol. Achieving substantial inhibition of carotid occlusion at C24 dose of 2 mg/kg (FIG. 20B) supported further exploration of its activity in vivo. In summary, inhibition of human FXIa function by the active-site directed FXIa antibody C24 decreased or prevented arterial thrombosis in this mouse model.

Example 21. IgG Potency is Improved in Human FXIa Activity, Assay by Addition of Q→K FW1 Substitution into Related IgG Sequences Table 2 below illustrates how IgG potency is improved in human FXIa activity assay by the addition of a Q→K substitution in framework 1 of the D4 IgG, and others, to generate related sequences.

TABLE 2

| IgG | CDR2 subs | FW1 Sub | Fc | other sub | in vitro IC50 (nM) |
|---|---|---|---|---|---|
| D4 | WNNG | DIVMTQSPSSLSASVGDRVTI TC (wt) | wt | S54 | 5.4 |
| B10B12 | WNNG | Q → K | wt | S54 | 0.74 |
| clone16 | RDDD | wt | wt | S54 | 0.57 |
| clone32 | RDDD | Q → K | wt | S54 | 0.28 |
| B10D8 | WDND | wt | wt | S54 | 1.4 |
| clone22 | WDND | Q → K | wt | S54 | 0.38 |
| DEW | WDDD | wt | Fc- | S54E | 0.36 |
| DEF | WDDD | Q → K | Fc- | S54E | 0.21 |
| clone8 | WDDD | wt | wt | S54 | 0.73 |
| clone24 | WDDD | Q → K | wt | S54 | 0.22 |

Example 22. Anti-FXIa Binding to FXIa is Inhibited by the Serine Protease Inhibitors PMSF and PPACK The binding of the anti-FXIa C24 Fab to FXIa in the presence of the serine protease inhibitors PMSF and PPACK (also known as FPRCK) (Haematologic Technologies Inc.) was evaluated by surface plasmon resonance as described in Example 4. Binding analysis was performed at 37° C. with concentrations of C24 Fab ranging from 0.1-5 nM. Biotinylated FXIa protein (Haematologic Technologies Inc.) was diluted into the HBS-P buffer and incubated at room temperature with or without 1 mM PMSF or 0.2 mM PPACK for at least 30 minutes. For each experiment, equivalent amounts of FXIa+/− inhibitor was captured on two different Biacore chip flow cells, and the C24 Fab passed over for 3 minutes and allowed to dissociate for a further 20 minutes. The reported response is the C24 Fab binding to FXIa+/− inhibitor with dual reference subtraction to remove any background signal from the adjacent streptavidin-only control flow cell and buffer only injections.

Results

Figure 21:
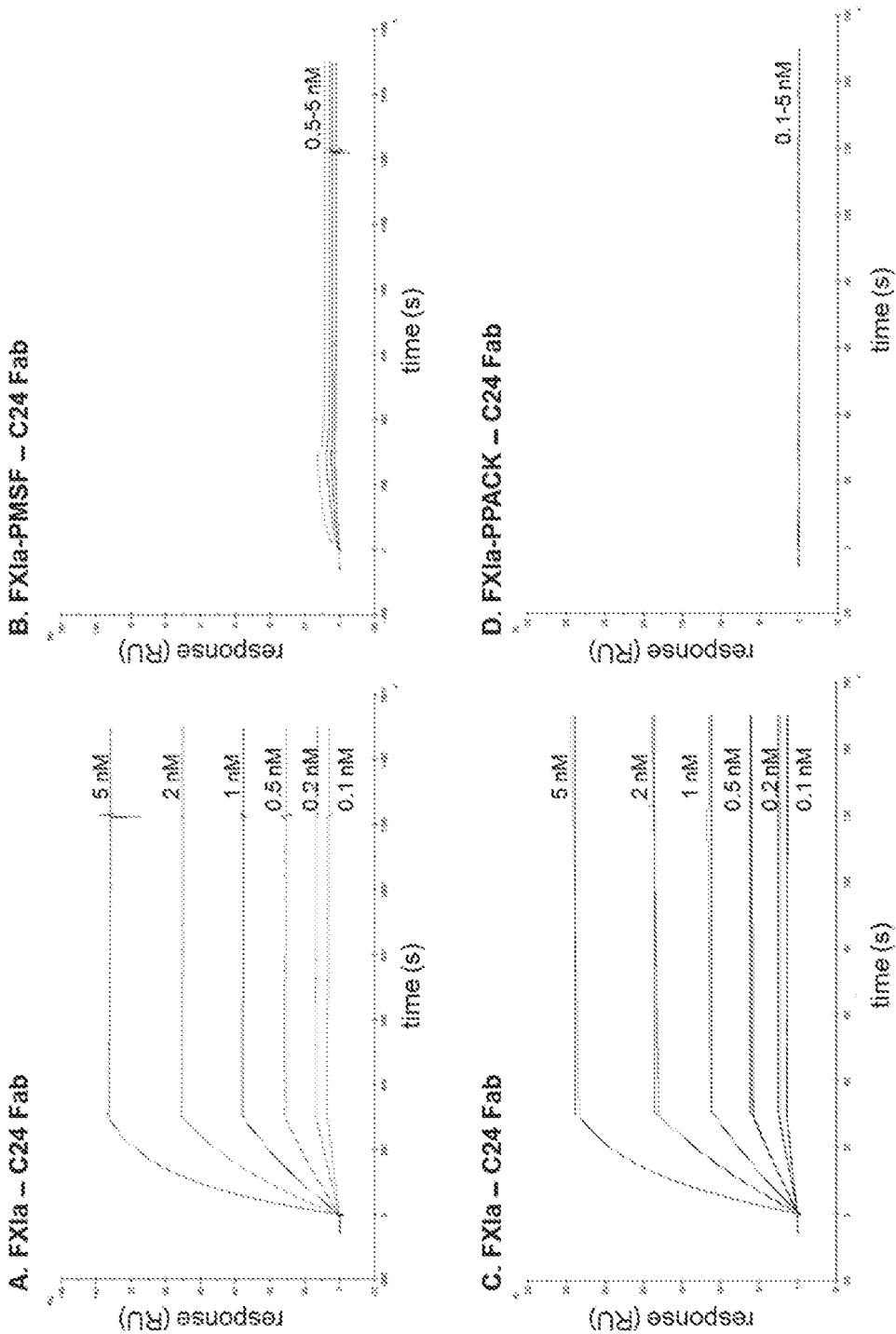
FIG. 21A-D show the Biacore™ binding analysis for C24 Fab to FXIa−/+PMSF (A, B) and FXIa−/+PPACK (C, D).

A significant loss of C24 Fab binding was observed when FXIa is inhibited with either PMSF (FIG. 21A-B) or PPACK (FIG. 21C-D). For the FXIa-PMSF complex, a small amount of C24 DEF binding was observed which may be reflective of incomplete inhibition of FXIa by PMSF. No binding was observed at concentrations up to 5 nM C24 Fab for the FXIa-PPACK complex. These results suggest that the C24 Fab binding epitope may be in close proximity to the active site and thus sterically blocked by these active site inhibitors.

Example 23. Crystal Structure of the DEF Fab Bound to the Human FXIa Catalytic Domain Complex Formation and Crystallization The FXIa catalytic domain was produced using a gene fragment synthesized to encode a mammalian signal peptide derived from mouse IgG followed by the catalytic domain of human FXI (i.e., Ile370 to Ala606), and a C-terminal 6-His tag. The catalytic domain active site Ser was substituted with an Ala (Ser557Ala), the unpaired Cys with a Ser (Cys482Ser), and the Asn residues of the two predicted N-linked glycosylation sites, identified by the consensus sequence Asn-X-Ser, were substituted with Gln residues to inhibit N-linked glycosylation ("glyco-"). This gene was subcloned into a mammalian expression vector and transiently expressed by Expi293F cells (Life Technologies, CA, USA). The DEF Fab was expressed by co-transfecting two mammalian expression plasmids, one encoding the Fab heavy chain with a C-terminal 6-His tag and the second the light chain, into Expi293F cells. Supernatants were harvested 3 days post transfection and the recombinant proteins captured on HisTrap columns (GE Healthcare Bio-Sciences, PA, USA). Purified FXIa protein was mixed with DEF Fab in a 1.5-fold molar excess and concentrated in a centrifugal filter unit at 4° C. The complex was purified using a Superdex 200 gel filtration column (GE Healthcare Bio-Sciences) equilibrated in 10 mM Tris (pH8.0), 150 mM sodium chloride buffer (TBS) on an AKTA Avant FPLC instrument (GE Healthcare Bio-Sciences). Fractions corresponding to peaks in 280 nm absorbance were run on SDS-PAGE under reducing and non-reducing conditions. Fractions containing the DEF Fab—FXIa catalytic domain complex were pooled and concentrated for crystallization trials.

Purified DEF Fab-FXIa catalytic domain complex was concentrated to 25.7 mg/ml. A 0.25 µl drop of protein sample was mixed with 0.25 µl of reservoir solution (1.86 M ammonium sulfate, 8 mM CoCl$_2$, 30 mM K/Na phosphate, pH 6.5) and crystallized in hanging-drop configuration over 100 µl of reservoir solution at 20° C. Crystals appeared overnight and grew to full size in 1 week. Crystals were harvested and cryoprotected with a saturated ammonium sulfate solution containing 8 mM CoCl$_2$, 30 mM K/Na phosphate, pH 6.5 and 3% glycerol and then flash frozen in liquid nitrogen.

Data Collection and Processing

Two datasets were collected from a single crystal at 100 K using synchrotron radiation (APS GM/CAT beamline 23-IDB, Chicago, Ill.). A native dataset was collected at λ=1.033 Å with 180° rotation. An additional dataset was collected near the cobalt K-edge (λ=1.606 Å) in order to maximize the cobalt anomalous signal present in the crystallization solution. The two datasets were processed with XDS, scaled and merged with Aimless and a resolution cutoff of 1.8 Å and 2.5 Å for the native and derivative datasets respectively, was applied accordingly to the CC$_{1/2}$ criterion (Diederichs and Karplus, 2013; Karplus and Diederichs, 2012). Crystals belong to the 1422 space group.

Structure Determination and Refinement

The complex structure of the DEF Fab-FXIa catalytic domain complex was solved by molecular replacement using the Fab fragment of the human germline antibody 5-51/O12 (PDB code: 4KMT) as search model. Once the Fab fragment was placed, the electron density for the missing FXIa catalytic domain was clearly visible. It was finally placed with a second MR round using the PDB code 3SOS as search model. Iterative rounds of model building using, COOT (Emsley and Cowtan, 2004), and refinement using REFMAC5 (Collaborative Computational Project, 1994) and PHENIX (Adams et al., 2010) were carried out to improve the electron density map.

To help assign the residual positive peaks, an anomalous map was generated using the dataset collected at cobalt K-edge. The wavelength used was sufficient to get a strong signal from the sulfur ions, helping us to model 4 sulfate anions and 2 cobalt cations. Data set and refinement statistics are summarized in Table 3.

X-Ray Structure-Based Epitope Mapping

The complex of DEF Fab and FXIa crystallized as 1 copy of the complex per asymmetric unit. Residues of the DEF Fab (paratope) in contact with FXIa (epitope) were determined with PISA (Protein Interactions. Surfaces and Assemblies) (E. Krissinel and K. Henrick, *J. Mol. Biol.*, 2007, 372, 774-797) and are listed in Table 4 below.

Results

Figure 22:
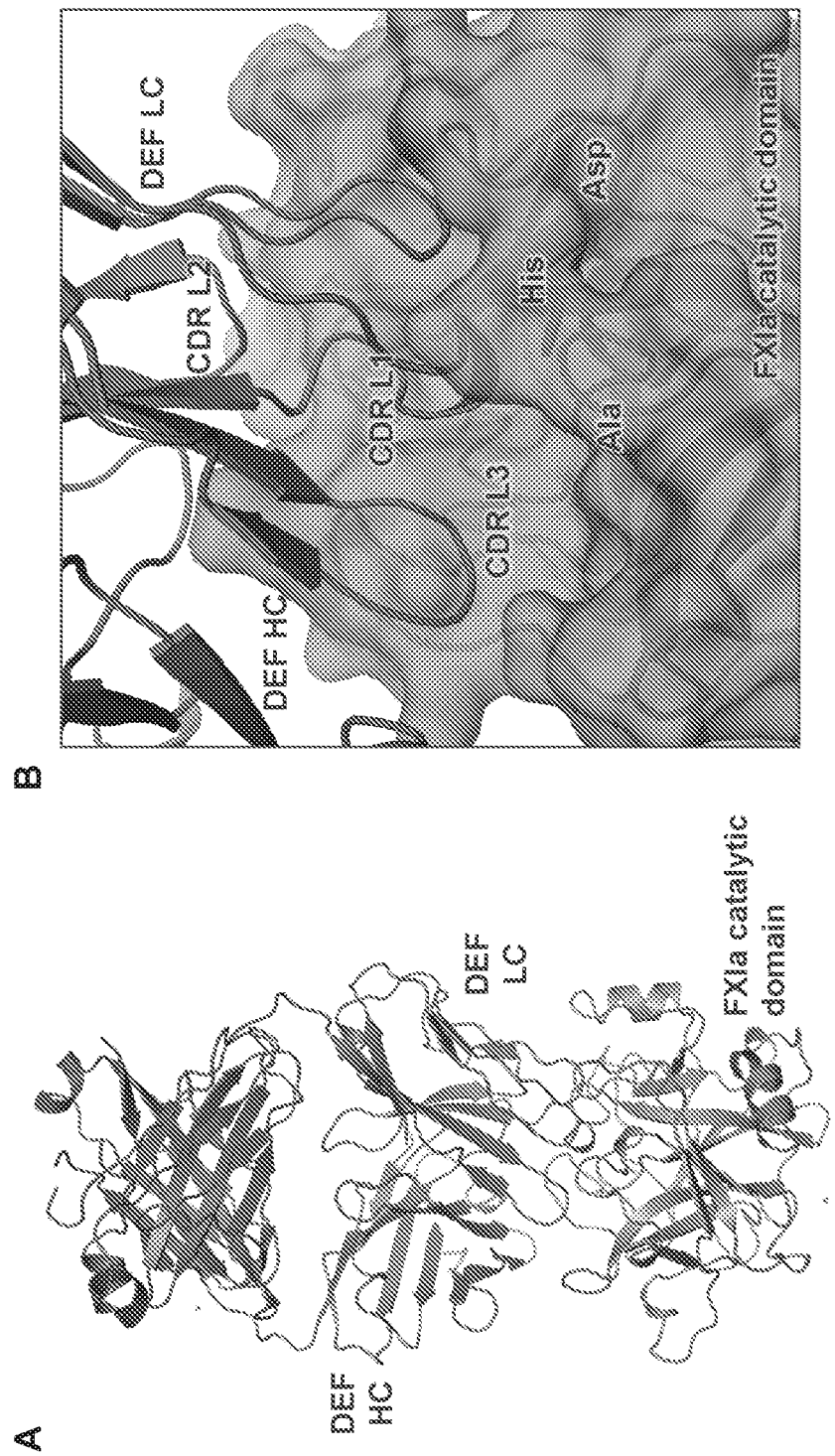
FIG. 22A-B show the crystal structure of the DEF Fab binding to the FXIa catalytic domain. (A) The DEF Fab interacts with the FXIa catalytic domain predominantly via the light chain CDRs. (B) The DEF Fab light chain makes contacts surrounding the active site of the FXIa. The catalytic triad residues, Ala (Ser557Ala mutant), His and Asp, are highlighted.
Figure 23:
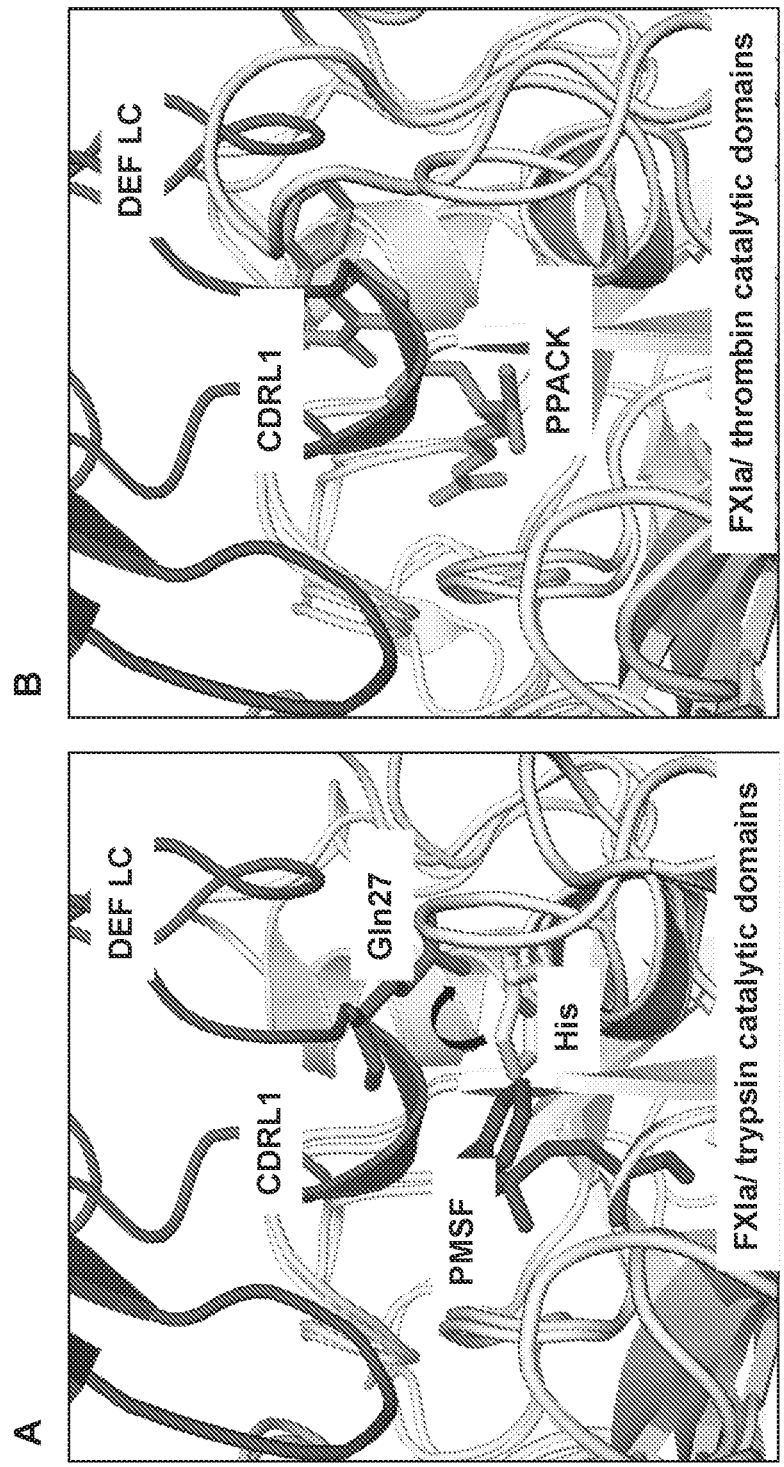
FIG. 23A-B show the overlay of inhibitor bound serine protease catalytic domains with the FXIa catalytic domain. (A) Trypsin-PMSF (PDB 1PQA) and (B) thrombin-PPACK (PDB 1Z8I) superimposed on the FXIa catalytic domain—DEF Fab complex. In the trypsin-PMSF structure the active site His takes on an alternate conformation (arrow), which would in turn create a steric clash for the DEF CDR L1 Gln27.

The FXIa catalytic domain—DEF Fab complex crystal structure was determined to 1.8 Å (Table 3). The total interface area between FXIa and DEF Fab light chain is 976.4 Å$^2$ and the total interface between FXIa and DEF Fab heavy chain is 276.6 Å$^2$. The DEF Fab acts as a direct competitive inhibitor blocking the active site of FXIa. The DEF Fab recognizes FXIa predominantly via the light chain CDR L1 and CDR L3, additional hydrogen bonds are made by the light chain variable region, the CDR H1 and CDR H3 (Table 4, FIG. 22). The interaction with the FXIa catalytic domain is focused around the active site. Specifically the FXIa epitope is formed by the following residues: His 27, Tyr 47, Met 87, Ala 88, Ser 90, Asp 93, Tyr 134, Arg 138, Asp 182, Asp 139, Lys 185, Ser 207, and Gly 211, with the numbering convention starting with Ile1 at the NH2-terminal (i.e., numbered with respect to SEQ ID NO: 100). CDR L1 is in close proximately to Ala 188, corresponding to Ser 188 in catalytic triad of the active site in wild-type human Factor XIa. Such proximity is consistent with our experimental results showing that the C24 Fab loses binding affinity for FXIa when it is bound to the serine protease inhibitors PMSF and PPACK (Example 22). A superimposition of published serine protease catalytic domain structures bound to PMSF (PDB 1PQA) or PPACK (PDB 1Z8I)

on the FXIa catalytic domain illustrates that the inhibitors may sterically impede the Fab from binding to FXIa through blocking the CDRL1 loop interactions (FIG. 23).

TABLE 3

Data set and refinement statistics for DEF Fab - FXIa complex

|  | FXIa cat. domain - DEF Fab complex (native) | FXIa cat. domain - DEF Fab complex (derivative) |
|---|---|---|
| Data Collection |  |  |
| Space group | I422 | I422 |
| Cell dimensions a/b/c (Å) | 136.09/136.09/175.99 | 136.61/136.61/176.31 |
| α/β/γ (°) | 90.0/90.0/90.0 | 90.0/90.0/90.0 |
| Resolution (Å) | 64.94-1.80 (1.86-1.80) | 107.99-2.50 (2.59-2.50) |
| Rsym (%) | 5.4 | 3.4 |
| I/σ I | 12.99 (0.83) | 25.77 (3.30) |
| Correlation Coefficient | 0.99 (0.28) | 0.99 (0.92) |
| Completeness (%) | 100 (98.0) | 100 (100) |
| Redundancy | 5.7 (5.4) | 15.9 (14.6) |
| Unique reflections | 75924 (7371) | 28898 (2817) |
| Wilson B-factor | 34.35 | 47.30 |
| Refinement |  |  |
| Rwork/Rfree (%) | 18.8/22.8 |  |
| No. of chains in AU | 3 |  |
| No. of protein residues | 653 |  |
| No. of ligand atoms | 19 |  |
| No. of water atoms | 618 |  |
| RMSD bond lengths (Å) | 0.008 |  |
| RMSD angles (°) | 1.19 |  |
| Ramachandran best/disallowed regions (%) | 98.0/0.0 |  |

TABLE 4

Contact residues at the FXIa - DEF Fab interface

| DEF FAB Light chain | DEF FAB Heavy chain | FXIa | Type (H-bond/Salt bridge) |
|---|---|---|---|
| Tyr 94 |  | His 27 | H-bond |
| Ala 25 |  | Tyr 47 | H-bond |
| Thr 69 |  | Met 87 | H-bond |
| Set 67 |  | Ala 88 | H-bond |
| Gln 27 |  | Ser 90 | H-bond |
| Gln 27 |  | Asp 93 | H-bond |
| Asp 92 |  | Tyr 134 | H-bond |
| Ile 93 |  |  |  |
| Asp 32 |  | Arg 138 | Salt bridge |
|  | Leu 99 |  | H-bond |
|  | Tyr 33 |  | H-bond |
| Arg 30 |  | Asp 182 | Salt bridge |
|  | Tyr 33 | Asp 139 | H-bond |
| His 91 |  | Lys 185 | H-bond |
| Asp 32 |  |  | Salt bridge |
| Gln 27 |  | Ser 207 | H-bond |
| Arg 30 |  | Gly 211 | H-bond |

Example 24. Effect of Anti-FXIa Antibodies on FXIIa-Induced Thrombin Generation, APTT in Human Plasma and Intrinsic Pathway-Triggered Clotting in Whole Human Blood Thrombin generation in platelet-poor plasma was measured using a fluorogenic thrombin substrate and a multi-well automated fluorescent plate reader (ThrombinoSCOPE, Maastricht, the Netherlands). 5 µL of anti-FXIa or IgG control (Mab 8.8) antibody solution was mixed with 20 µL phosphate-buffered saline containing 60 nM human FXIIa (Enzyme Research Laboratories, South Bend, Ind., USA) and PC/PS (Phospholipid-TGT, DiaPharma, West Chester, Ohio, USA) in a 96-well plate. 75 µL citrated platelet-poor human plasma (Triclinical Reference Plasma, TCoag, Wicklow, Ireland) was added, and coagulation was triggered with the addition of 20 µL calcium chloride buffer and fluorogenic thrombin substrate according to the ThrombinoSCOPE manufacturer's protocol. Thrombin activity was measured as velocity of fluorogenic peptide hydrolysis as a function of time. Total thrombin activity generated (commonly called endogenous thrombin potential, ETP), peak activity, and time to onset of thrombin generation (lag time) and time to peak activity were measured. The final concentrations of the antibodies tested (D4, B11, 24, DEF, and IgG1 ctrl) ranged from 5 µg/mL to 443 µg/mL. Due to lot-to-lot variability, the concentration of each lot of PC/PS reagent was adjusted to achieve a ~15 min lag to onset and ~150 nM peak thrombin activity.

APTT was measured using standard pooled human platelet-poor plasma and a Triniclot aPTT kit (Parsippany, N.J.) according to manufacturer instructions.

For whole blood clotting, whole blood was collected in 3.8% citrate a blood:citrate ratio of 9:1 (v/v). 5 µl of C24, control IgG1, or saline control was added to 300 µl of citrated whole blood. Samples were preincubated at 37° C. for 5 minutes, and clotting was initiated by addition of 7 µl of INTEM reagent (ellagic acid/phospholipid; TEM systems, Inc., Durham, N.C.) and 20 µl STARTEM reagent (0.2M CaCl$_2$ in Hepes buffer, pH 7.4). Time to clotting was measured using a semi-automated coagulation analyzer (KC4 Delta; Tcoag, Wicklow, Ireland).

Results

Figure 24:
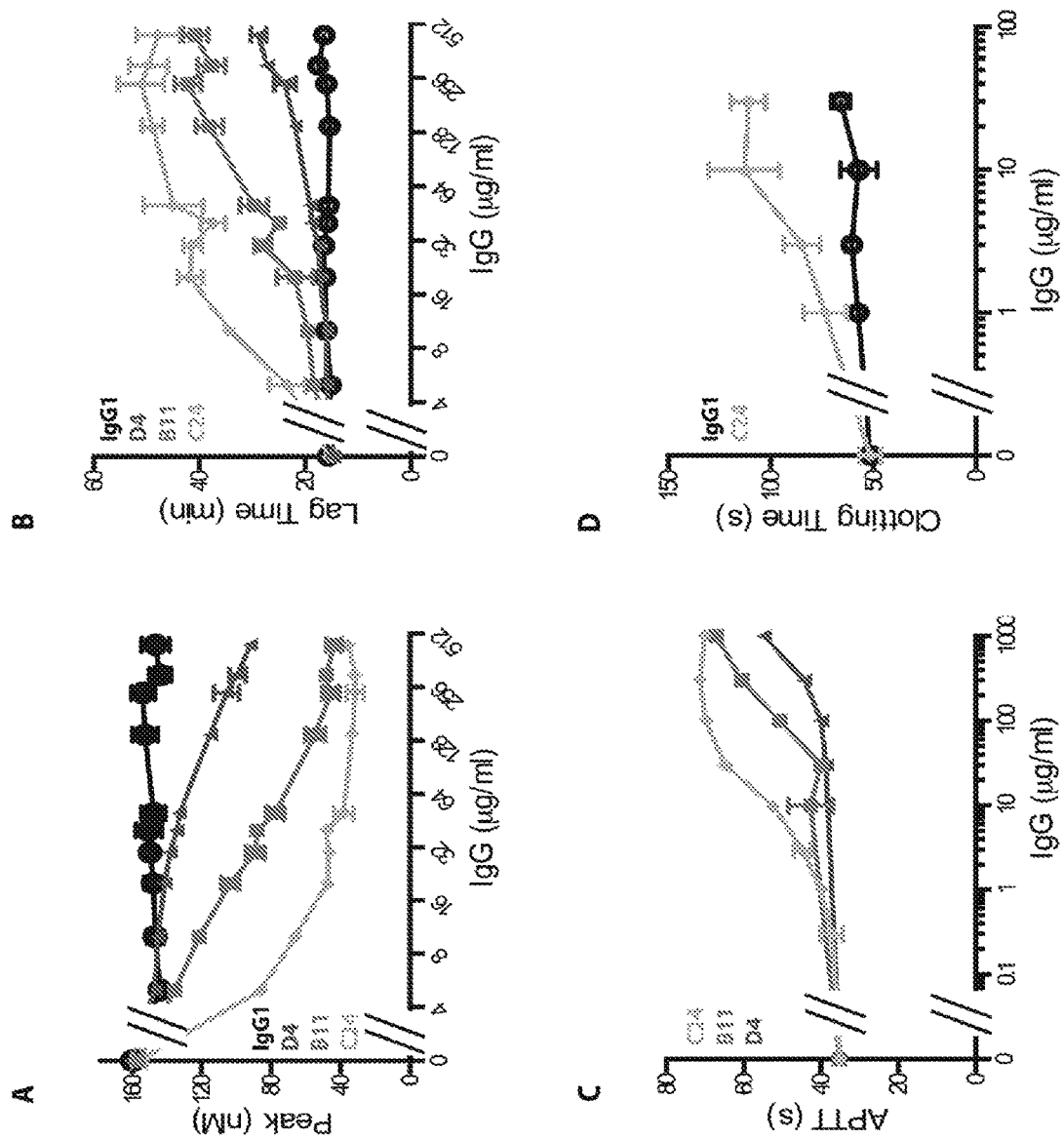
FIG. 24A-D show the effects of anti-FXIa antibodies on FXIIa-induced thrombin generation, APTT in human plasma, and intrinsic pathway-triggered clotting in whole blood. (A-B) FXIIa-triggered thrombin activity as a function of time was determined in the presence of the indicated concentrations of anti-FXIa antibodies D4 (blue), B11 (red), C24 (green) or control IgG1 (black). Peak thrombin activity (A) and lag to onset of thrombin generation (B) are shown (mean+/−SEM; n=3-5). Note substantial reduction in peak thrombin generation and prolongation of time to onset of thrombin generation in samples containing C24 at 4 ug/ml or greater. (C) APTT assay as a function of antibody concentration (mean+/−SEM; n=2). Control IgG1 had no effect in this assay. Note prolongation of APTT in samples containing C24 at 10 ug/ml or greater. (D) Effect of C24 or control IgG1 on intrinsic pathway-triggered clotting of whole blood. Time to clot is shown (mean+/−SEM; n=3-4). Note prolongation of time to clotting in whole human blood in samples containing C24.

As shown in FIG. 24A and FIG. 24B, FXIIa-triggered thrombin activity as a function of time was determined in the presence of the indicated concentrations of anti-FXIa antibodies D4 (blue), B11 (red), C24 (green) or control IgG1 (black). Peak thrombin activity (A) and lag to onset of thrombin generation (B) are shown (mean+/-SEM; n=3-5). There was a substantial reduction in peak thrombin generation and prolongation of time to onset of thrombin generation in samples containing C24 at 4 ug/ml or greater. FIG. 24C shows an APTT assay as a function of antibody concentration (mean+/-SEM; n=2). Control IgG1 had no effect in this assay. There was a prolongation of APTT in samples containing C24 at 10 ug/ml or greater. FIG. 24D shows the effect of C24 or control IgG1 on intrinsic pathway-triggered clotting of whole blood. Time to clot is shown (mean+/-SEM; n=3-4). There was a prolongation of time to clotting in whole human blood in samples containing C24.

TABLE 5

Sequence Listing Table
CDR amino acid sequences are underlined (Chothia) or in bold (Kabat).

| | | |
|---|---|---|
| DEF_VH AA | SEQ ID NO: 1 | EVQLVQSGAEVKKPGASVKVSCKAS<u>GYTFTGYYMH</u>WVRQAPGQGLEWMGWIDPDEGDTNYAQKFQGRVTMTRDTSISTAYMELSRLRSDDTAVYYCARLASGFRDYWGQGTLVTVSS |
| DEF_HCDR1 Kabat AA | SEQ ID NO: 2 | GYYMH |
| DEF_HCDR2 Kabat AA | SEQ ID NO: 3 | WIDPDEGDTNYAQKFQG |
| DEF_HCDR3 Kabat/Chothia AA | SEQ ID NO: 4 | LASGFRDY |
| DEF_HCDR1 Chothia AA | SEQ ID NO: 5 | GYTFTGYYMH |
| DEF_HCDR2 Chothia AA | SEQ ID NO: 6 | WIDPDEGD |
| DEF_VL AA | SEQ ID NO: 7 | DIVMTKSPSSLSASVGDRVTITCRASQGIRNDLGWYQQKPGKAPKRLIYAASSLQSGVPSRFSGSGSGTEFTLTISSLQPEDFATYYCLQHDIYASTFGPGTKVDIKR |
| DEF_LCDR1 Kabat AA | SEQ ID NO: 8 | RASQGIRNDLG |
| DEF_LCDR2 Kabat AA | SEQ ID NO: 9 | YAASSLQS |
| DEF_LCDR3 Kabat AA | SEQ ID NO: 10 | LQHDIYAST |
| DEF_LCDR1 Chothia AA | SEQ ID NO: 11 | ASQGIRNDL |
| DEF_LCDR2 Chothia AA | SEQ ID NO: 12 | YAASS |
| DEF_LCDR3 Chothia AA | SEQ ID NO: 13 | QHDIYAST |
| D4_VH AA | SEQ ID NO: 14 | EVQLVQSGAEVKKPGASVKVSCKAS<u>GYTFTGYYMH</u>WVRQAPGQGLEWMGWINPNSGGTNYAQKFQGRVTMTRDTSISTAYMELSRLRSDDTAVYYCARLASGFRDYWGQGTLVTVSS |
| D4_HCDR2 Kabat AA | SEQ ID NO: 15 | WINPNSGGTNYAQKFQG |
| D4_HCDR2 Chothia AA | SEQ ID NO: 16 | WINPNSGG |
| D4_VL AA | SEQ ID NO: 17 | DIVMTQSPSSLSASVGDRVTITCRASQGIRNDLGWYQQKPGKAPKRLIYAASSLQSGVPSRFSGSGSGTEFTLTISSLQPEDFATYYCLQHDIYASTFGPGTKVDIKR |
| QCA11_VH AA | SEQ ID NO: 18 | EVQLVQSGAEVKKPGASVKVSCKAS<u>GYTFTGYYMH</u>WVRQAPGQGLEWMGRINPNSGDTNYAQKFQGRVTMTRDTSISTAYMELSRLRSDDTAVYYCARLASGFRDYWGQGTLVTVSS |
| QCA11_HCDR2 Kabat AA | SEQ ID NO: 19 | RINPNSGDTNYAQKFQG |
| QCA11_HCDR2 Chothia AA | SEQ ID NO: 20 | RINPNSGD |
| QCA11_VL AA | SEQ ID NO: 21 | DIVMTQSPSSLSASVGDRVTITCRASQGIRNDLGWYQQKPGKAPKRLIYAASSLQSGVPSRFSGSGSGTEFTLTISSLQPEDFATYYCLQHDIYASTFGPGTKVDIKR |
| B1D2_VH AA | SEQ ID NO: 22 | EVQLVQSGAEVKKPGASVKVSCKAS<u>GYTFTGYYMH</u>WVRQAPGQGLEWMGWINPNSGGTNYAQKFQGRVTMTRDTSISTAYMELSRLSSDDTAVYYCARLASGFRDYWGQGTLVTVSS |
| B1D2_VL AA | SEQ ID NO: 23 | DIVMTQSPSSLSASVGDRVTITCRASQGIRNDLGWYQQKPGKAPKRLIYAASSLQSGVPSRFSGSGSGTEFTLTISSLQPEDFATYYCLQHDIYASTFGPGTKVDIKR |

TABLE 5-continued

Sequence Listing Table
CDR amino acid sequences are underlined (Chothia) or in bold (Kabat).

```
B10H2_VH AA    SEQ ID NO: 24   EVQLVQSGAEVKKPGASVKVSCKASGYTFTGYYMHWVRQAPGQGLEWMG
                               WINPNSGGTNYAQKFQGRVTMTRDTSISTAYMELSRLRSDDTAVYYCAR
                               LASGFRDYWGQGLTVTVSS

B10H2_VL AA    SEQ ID NO: 25   DIVMTQSPSSLSASVGDRVTITCRASQGIRNDLGWYQQKPGKAPKRLIY
                               AASSLQSGVPSRFSGSVSGTEFTLTISSLQPEDLATYYCLQHDIYASTF
                               GPGTKVDIKR

B10E6_VH AA    SEQ ID NO: 26   EVLQVQSGAEVKKPGASVKVSCKASGYTFTGYYMHWVRQAPGQGLEWMG
                               WINPNSGGTNYAQKFQGRVTMTRDTSISTAYMELSRLRSDDTAVYYCAR
                               LASGFRDYWGQGTLVTVSS

B10E6_VL AA    SEQ ID NO: 27   DIVMTQSPSSLSASVGDRVTITCRASQGIRNDLGWYQQKPGKAPKRLIY
                               AASSLQSGVPSRFSGSGSGTEFTLTISSLQPEDFATYYCLQHDIYASTF
                               GPGTKVDIKR

B10F6_VH AA    SEQ ID NO: 28   EVQLVQSGAEVKKPGASVKVSCKASGYTFTGYYMHWVRQAPGQGLEWMG
                               RINPNSGGTNYAQKFQGRVTMTRDTSISTAYMELSRLRSDDTAVYYCAR
                               LASGFRDYWGQGTLVTVSS

B10F6_HCD      SEQ ID NO: 29   RINPNSGGTNYAQKFQG
R2 Kabat AA

B10F6_HCD R2   SEQ ID NO: 30   RINPNSGG
Chothia AA

B10F6_VL AA    SEQ ID NO: 31   DIVMTQSPSSLSASVGDRVTITCRASLGIRNDLGWYQQKPGKAPKRLIY
                               AASSLQSGVPSRFSGSGSGTEFSLTISSLQPEDFATYYCLQHDIYASTF
                               GPGTKVDIKR

B10F6_LCDR     SEQ ID NO: 32   RASLGIRNDLG
1 Kabat AA

B10F6_LCDR     SEQ ID NO: 33   ASLGIRNDL
1 Chothia AA

B10D8_VH AA    SEQ ID NO: 34   EVLQVQSGAEVKKPGASVKVSCKASGYTFTGYYMHWVRQAPGQGLEWMG
                               WIDPNSGDTNYAQKFQGRVTMTRDTSISTAYMELSRLRSDDTAVYYCAR
                               LASGFRDYWGQGTLVTVSS

B10D8_HCD      SEQ ID NO: 35   WIDPNSGDTNYAQKFQG
R2 Kabat AA

B10D8_HCD      SEQ ID NO: 36   WIDPNSGD
R2 Chothia AA

B10D8_VL AA    SEQ ID NO: 37   DIVMTQSPSSLSASVGDRVTITCRASQGIRNDLGWYQQKPGKAPKRLIY
                               AASSLQSGVPSRFSGSGSGTEFTLTISSLQPEDFATYYCLQHDIYASTF
                               GPGTKVDIKR

B10B12_VH AA   SEQ ID NO: 38   EVQLVQSGAEVKKPGASVKVSCKASGYTFTGYYMHWVRQAPGQGLEWMG
                               WINPNSGGTNYAQKFQGRVTMTRDTSISTAYMELSRLRSDDTAVYYCAR
                               LASGFRDYWGQGTLVTVSS

B10B12_VL AA   SEQ ID NO: 39   DIVMTKSPSSLSASVGDRVTITCRASQGIRNDLGWYQQKPGKAPKRLIY
                               AASSLQSGVPSRFSGSGSGTEFTLTISSLQPEDFATYYCLQHDIYASTF
                               GPGTKVDIKR

S1D4_VH AA     SEQ ID NO: 40   EVQLVQSGAEVKKPGASVKVSCKASGYTFTGYYMHWVRQAPGQGLEWMG
                               WINPNSGGTNYAPKFQGRVTMTRDTSISTAYMELSRLRSDDTAVYYCAR
                               LASGFRDYWGQGTLVTVSS

S1D4_HCD4      SEQ ID NO: 41   WINPNSGGTNYAPKFQG
2 Kabat AA

S1D4_VL AA     SEQ ID NO: 42   DIVMTQSPSSLSASVGDRVTITCRASQGIRNDLGWYQQKPGKAPKRLIY
                               AASSLQSGVPSRFSGSASGTEFTLTISSLQPEDFATYYCLQHDIYASTF
                               GPGTKVDIKR

S10H9_VH AA    SEQ ID NO: 43   EVQLVQSGAEVKKPGASVKVSCKASGYTFTGYYMHWVRQAPGQGLEWMG
                               WIDPDSGGTNYAQKFQGRVTMTRDTSISTAYMELSRLRSDDTAVYYCAR
                               LASGFRDYWGHGTLVTVSS
```

TABLE 5-continued

Sequence Listing Table
CDR amino acid sequences are underlined (Chothia) or in bold (Kabat).

| Name | SEQ ID NO | Sequence |
|---|---|---|
| S10H9_HCDR2 Kabat AA | SEQ ID NO: 44 | WIDPDSGGTNYAQKFQG |
| S10H9_HCDR2 Chothia AA | SEQ ID NO: 45 | WIDPDSGG |
| S10H9_VL AA | SEQ ID NO: 46 | DIVMTQSPSSLSASVGDRVTITCRASQGIRNDLGWYQQKPGKAPKRLIY AASSLQSGVPSRFSGSGSGTEFTLTISSLQPEDFATYYCLQHDIYASTF GPGTKVDIKR |
| Clone 8_VH AA | SEQ ID NO: 47 | EVQLVQSGAEVKKPGASVKVSCKAS<u>GYTFTGYYMH</u>WVRQAPGQGLEWMG <u>WIDPDSGDTNYAQKFQG</u>RVTMTRDTSISTAYMELSRLRSDDTAVYYCAR LASGFRDYWGQGTLVTVSS |
| Clone 8_HCDR2 Kabat AA | SEQ ID NO: 48 | WIDPDSGDTNYAQKFQG |
| Clone 8_HCDR2 Chothia AA | SEQ ID NO: 49 | WIDPDSG |
| Clone 8_VL AA | SEQ ID NO: 50 | DIVMTQSPSSLSASVGDRVTITCRASQGIRNDLGWYQQKPGKAPKRLIY AASSLQSGVPSRFSGSGSGTEFTLTISSLQPEDFATYYCLQHDIYASTF GPGTKVDIKR |
| Clone 16_VH AA | SEQ ID NO: 51 | EVQLVQSGAEVKKPGASVKVSCKAS<u>GYTFTGYYMH</u>WVRQAPGQGLEWMG <u>RIDPDSGDTNYAQKFQG</u>RVTMTRDTSISTAYMELSRLRSDDTAVYYCAR LASGFRDYWGQGTLVTVSS |
| Clone 16_HCDR2 Kabat AA | SEQ ID NO: 52 | RIDPDSGDTNYAQKFQG |
| Clone 16_HCDR2 Chothia AA | SEQ ID NO: 53 | RIDPDSGD |
| Clone 16_VL AA | SEQ ID NO: 54 | DIVMTQSPSSLSASVGDRVTITCRASQGIRNDLGWYQQKPGKAPKRLIY AASSLQSGVPSRFSGSGSGTEFTLTISSLQPEDFATYYCLQHDIYASTF GPGTKVDIKR |
| Clone 20_VH AA | SEQ ID NO: 55 | EVQLVQSGAEVKKPGASVKVSCKAS<u>GYTFTGYYMH</u>WVRQAPGQGLEWMG <u>WINPDSGDTNYAQKFQG</u>RVTMTRDTSISTAYMELSRLRSDDTAVYYCAR LASGFRDYWGQGTLVTVSS |
| Clone 20_HCDR2 Kabat AA | SEQ ID NO: 56 | WINPDSGDTNYAQKFQG |
| Clone 20_HCDR2 Chothia AA | SEQ ID NO: 57 | WINPDSGD |
| Clone 20_VL AA | SEQ ID NO: 58 | DIVMTKSPSSLSASVGDRVTITCRASQGIRNDLGWYQQKPGKAPKRLIY AASSLQSGVPSRFSGSGSGTEFTLTISSLQPEDFATYYCLQHDIYASTF GPGTKVDIKR |
| Clone 22_VH AA | SEQ ID NO: 59 | EVLQVQSGAEVKKPGASVKVSCKAS<u>GYTFTGYYMH</u>WVRQAPGQGLEWMG <u>WIDPNSGDTNYAQKFQG</u>RVTMTRDTSISTAYMELSRLRSDDTAVYYCAR LASGFRDYWGQGTLVTVSS |
| Clone 22_HCDR2 Kabat AA | SEQ ID NO: 60 | WIDPNSGDTNYAQKFQG |
| Clone 22_HCDR2 Chothia AA | SEQ ID NO: 61 | WIDPNSGD |
| Clone 22_VL AA | SEQ ID NO: 62 | DIVMTKSPSSLSASVGDRVTITCRASQGIRNDLGWYQQKPGKAPKRLIY AASSLQSGVPSRFSGSGSGTEFTLTISSLQPEDFATYYCLQHDIYASTF GPGTKVDIKR |

TABLE 5-continued

Sequence Listing Table
CDR amino acid sequences are underlined (Chothia) or in bold (Kabat).

| | | |
|---|---|---|
| Clone 32_VH AA | SEQ ID NO: 63 | EVLQVQSGAEVKKPGASVKVSCKAS<u>GYTFTGYYMH</u>WVRQAPGQGLEWMG<u>RIDPDSGD</u>TNYAQKFQGRVTMTRDTSISTAYMELSRLRSDDTAVYYCARLASGFRDYWGQGTLVTVSS |
| Clone 32_VL AA | SEQ ID NO: 64 | DIVMTKSPSSLSASVGDRVTITCRASQGRINDLGWYQQKPGKAPKRLIYAASSLQSGVPSRFSGSGSGTEFTLTISSLQPEDFATYYCLQHDIYASTFGPGTKVDIKR |
| Clone 24_VH AA | SEQ ID NO: 65 | EVQLVQSGAEVKKPGASVKVSCKAS<u>GYTFTGYYMH</u>WVRQAPGQGLEWMG<u>WIDPDSGD</u>TNYAQKFQGRVTMTRDTSISTAYMELSRLRSDDTAVYYCARLASGFRDYWGQGTLVTVSS |
| Clone 24_HCDR2 Kabat AA | SEQ ID NO: 66 | WIDPDSGDTNYAQKFQG |
| Clone 24_HCDR2 Chothia AA | SEQ ID NO: 67 | WIDPDSGD |
| Clone 24_VL AA | SEQ ID NO: 68 | DIVMTKSPSSLSASVGDRVTITCRASQGIRNDLGWYQQKPGKAPKRLIYAASSLQSGVPSRFSGSGSGTEFTLTISSLQPEDFATYYCLQHDIYASTFGPGTKVDIKR |
| C4_VH AA | SEQ ID NO: 69 | QVQLVQSGAEVKKPGASVKVSCKAS<u>GYTFTSYYMH</u>WVRQAPGQGLEWMG<u>IINPSGGS</u>TSYAQKFQGRVTMTRDTSTSTVYMELSSLRSEDTAVYYCARDTIPGIAVAGTDYWGQGTLVTVSS |
| C4_HCDR1 Kabat AA | SEQ ID NO: 70 | SYYMH |
| C4_HCDR2 Kabat AA | SEQ ID NO: 71 | IINPSGGSTSYAQKFQG |
| C4_HCDR3 Kabat/Chothia AA | SEQ ID NO: 72 | DTIPGIAVAGTDY |
| C4_HCDR1 Chothia AA | SEQ ID NO: 73 | GYTFTSYYMH |
| C4_HCDR2 Chothia AA | SEQ ID NO: 74 | IINPSGGS |
| C4_VL AA | SEQ ID NO: 75 | QSVLTQPPSVSAAPGQKVTSICSGSTSNIGNNYVSWYQQVPGTPPKLLIYDNDKRPSGIPDRFSGSKSGTSATLDITGLQTGDEADYYCGTWHSGLYVVVFGGGTKLTVL |
| C4_LCDR1 Kabat AA | SEQ ID NO: 76 | SGSTSNIGNNYVS |
| C4_LCDR2 Kabat AA | SEQ ID NO: 77 | YDNDKRPS |
| C4_LCDR3 Kabat AA | SEQ ID NO: 78 | GTWHSGLYVVV |
| C4_LCDR1 Chothia AA | SEQ ID NO: 79 | GSTSNIGNNYV |
| C4_LCDR2 Chothia AA | SEQ ID NO: 80 | YDNDK |
| C4_LCDR3 Chothia AA | SEQ ID NO: 81 | TWHSGLYVVV |
| HC Constant Region AA | SEQ ID NO: 82 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGAPSVFLFPPKPKDTLMISRTPEVTCVVVDVSHEDPEVKFNWYDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |

TABLE 5-continued

Sequence Listing Table
CDR amino acid sequences are underlined (Chothia) or in bold (Kabat).

| | | |
|---|---|---|
| LC Constant Region AA | SEQ ID NO: 83 | TVAASPVFIFPPSDEQLKSGTASVVCLLNNFYPREAKQVWKVDNALQSG NSQESVTEQDSKDSTYSLSSTLTLSKADYEKHKVYACEVTHQGLSSPVT KSFNRGEC |
| DEF_VH NT | SEQ ID NO: 84 | GAGGTCCAGCTGGTGCAGTCTGGGGCTGAGGTGAAGAAGCCTGGGGCCT CAGTGAAGGTCTCCTGCAAGGCTTCTGGATACACCTTCACCGGCTACTA TATGCACTGGGTGCGACAGGCCCCTGGACAAGGGCTTGAGTGGATGGGA TGGATCgACCCTgACgaaGGTGaCACAAACTATGCACAGAAGTTTCAGG GCAGGGTCACCATGACCAGGGACACGTCCATCAGCACAGCCTACATGGA GCTGAGCAGGCTGAGATCTGACGACACGGCCGTGTATTACTGTGCGAGA TTAGCTAGTGGCTTTCGTGACTACTGGGGCCAGGGAACCCTGGTCACCG TCTCGAGC |
| DEF_VL NT | SEQ ID NO: 85 | GACATCGTGATGACCaAGTCTCCATCCTCCCTGTCTGCtTCTGTAGGAG ACAGAGTCACCATCACTTGCCGGGCAAGTCAGGGCATTAGAAATGATTT AGGCTGGTATCAGCAGAAACCAGGGAAAGCCCCTAAGCGCCTCATCTAT GCTGCATCCAGTTTGCAAAGTGGGGTCCCATCAAGGTTCAGCGGCAGTG GATCTGGGACAGAATTCACTCTCACAATCAGCAGCCTGCAGCCTGAAGA TTTTGCAACTTATTACTGTCTACAGCATGATATTTACGCTAGCACTTTC GGCCCTGGGACCAAAGTGGATATCAAACGT |
| D4_VH NT | SEQ ID NO: 86 | GAGGTCCAGCTGGTGCAGTCTGGGGCTGAGGTGAAGAAGCCTGGGGCCT CAGTGAAGGTCTCCTGCAAGGCTTCTGGATACACCTTCACCGGCTACTA TATGCACTGGGTGCGACAGGCCCCTGGACAAGGGCTTGAGTGGATGGGA TGGATCAACCCTAACAGTGGTGGCACAAACTATGCACAGAAGTTTCAGG GCAGGGTCACCATGACCAGGGACACGTCCATCAGCACAGCCTACATGGA GCTGAGCAGGCTGAGATCTGACGACACGGCCGTGTATTACTGTGCGAGA TTAGCTAGTGGCTTTCGTGACTACTGGGGCCAGGGAACCCTGGTCACCG TCTCGAGC |
| D4_VL NT | SEQ ID NO: 87 | GACATCGTGATGACCCAGTCTCCATCCTCCCTGTCTGCATCTGTAGGAG ACAGAGTCACCATCACTTGCCGGGCAAGTCAGGGCATTAGAAATGATTT AGGCTGGTATCAGCAGAAACCAGGGAAAGCCCCTAAGCGCCTCATCTAT GCTGCATCCAGTTTGCAAAGTGGGGTCCCATCAAGGTTCAGCGGCAGTG GATCTGGGACAGAATTCACTCTCACAATCAGCAGCCTGCAGCCTGAAGA TTTTGCAACTTATTACTGTCTACAGCATGATATTTACGCTAGCACTTTC GGCCCTGGGACCAAAGTGGATATCAAACGT |
| Clone 24_VH NT | SEQ ID NO: 88 | GAGGTCCAGCTGGTGCAGTCTGGGGCTGAGGTGAAGAAGCCTGGGGCCT CAGTGAAGGTCTCCTGCAAGGCTTCTGGATACACCTTCACCGGCTACTA TATGCACTGGGTGCGACAGGCCCCTGGACAAGGGCTTGAGTGGATGGGA TGGATCgACCCTgACAGTGGTGaCACAAACTATGCACAGAAGTTTCAGG GCAGGGTCACCATGACCAGGGACACGTCCATCAGCACAGCCTACATGGA GCTGAGCAGGCTGAGATCTGACGACACGGCCGTGTATTACTGTGCGAGA TTAGCTAGTGGCTTTCGTGACTACTGGGGCCAGGGAACCCTGGTCACCG TCTCGAGC |
| Clone 24_VL NT | SEQ ID NO: 89 | GACATCGTGATGACCaAGTCTCCATCCTCCCTGTCTGCtTCTGTAGGAG ACAGAGTCACCATCACTTGCCGGGCAAGTCAGGGCATTAGAAATGATTT AGGCTGGTATCAGCAGAAACCAGGGAAAGCCCCTAAGCGCCTCATCTAT GCTGCATCCAGTTTGCAAAGTGGGGTCCCATCAAGGTTCAGCGGCAGTG GATCTGGGACAGAATTCACTCTCACAATCAGCAGCCTGCAGCCTGAAGA TTTTGCAACTTATTACTGTCTACAGCATGATATTTACGCTAGCACTTTC GGCCCTGGGACCAAAGTGGATATCAAACGT |
| C4_VH NT | SEQ ID NO: 90 | CAGGTCCAGCTGGTACAGTCTGGGGCTGAGGTGAAGAAGCCTGGGGCCT CAGTGAAGGTTTCCTGCAAGGCATCTGGATACACCTTCACCAGCTACTA TATGCACTGGGTGCGACAGGCCCCTGGACAAGGGCTTGAGTGGATGGGA ATAATCAACCCTAGTGGTGGTAGCACAAGCTACGCACAGAAGTTCCAGG GCAGAGTCACCATGACCAGGGACACGTCCACGAGCACAGTCTACATGGA GCTGAGCAGCCTGAGATCTGAGGACACGGCCGTGTATTACTGTGCGAGA GACACTATTCCGGGTATAGCAGTGGCTGGTACGGACTACTGGGCCAGGG AACCCTGGTCACCGTCTCGAGC |
| C4_VL NT | SEQ ID NO: 91 | CAGTCTGTCTTGACGCAGCCGCCCTCAGTGTCTGCGGCCCCAGGACAGA AGGTCACCATCTCCTGCTCTGGAAGCACCTCCAACATTGGCAATAATTA TGTATCCTGGTACCAGCAGGTCCCAGGAACACCCCCAAACTCCTCATT TATGACAATGATAAGCGACCCTCAGGGATTCCTGACCGATTCTCTGGCT CCAAGTCTGGCACGTCAGCCACCCTGGACATCACCGGACTCCAGACTGG GGACGAGGCCGATTATTACTGCGGAACATGGCATAGTGGCCTGTATGTC GTGGTGTTCGGCGAGGGACCAAGCTGACCGTCCTA |
| HC Constant Region NT | SEQ ID NO: 92 | GCCTCCACCAAGGGCCCATCGGTCTTCCCCCTGGCACCCTCCTCCAAGA GCACCTCTGGGGGCACAGCGGCCCTGGGCTGCCTGGTCAAGGACTACTT CCCCGAACCGGTGACGGTGTCGTGGAACTCAGGCGCCCTGACCAGCGGC GTGCACACCTTCCCGGCTGTCCTACAGTCCTCAGGACTCTACTCCCTCA |

TABLE 5-continued

Sequence Listing Table
CDR amino acid sequences are underlined (Chothia) or in bold (Kabat).

| | | |
|---|---|---|
| | | GCAGCGTGGTGACCGTGCCCTCCAGCAGCTTGGGCACCCAGACCTACAT<br>CTGCAACGTGAATCACAAGCCCAGCAACACCAAGGTGGACAAGAAAGTT<br>GAGCCCAAATCTTGTGACAAAACTCACACATGCCCACCGTGCCCAGCAC<br>CTGAAGCCGCTGGGGCACCGTCAGTCTTCCTCTTCCCCCCAAAACCCAA<br>GGACACCCTCATGATCTCCCGGACCCCTGAGGTCACATGCGTGGTGGTG<br>GACGTGAGCCACGAAGACCCTGAGGTCAAGTTCAACTGGTACGTGGACG<br>GCGTGGAGGTGCATAATGCCAAGACAAAGCCGCGGGAGGAGCAGTACAA<br>CAGCACGTACCGTGTGGTCAGCGTCCTCACCGTCCTGCACCAGGACTGG<br>CTGAATGGCAAGGAGTACAAGTGCAAGGTCTCCAACAAAGCCCTCCCAG<br>CCCCCATCGAGAAAACCATCTCCAAAGCCAAAGGGCAGCCCCGAGAACC<br>ACAGGTGTACACCCTGCCCCCATCCCGGGAGGAGATGACCAAGAACCAG<br>GTCAGCCTGACCTGCCTGGTCAAAGGCTTCTATCCCAGCGACATCGCCG<br>TGGAGTGGGAGAGCAATGGGCAGCCGGAGAACAACTACAAGACCACGCC<br>TCCCGTGCTGGACTCCGACGGCTCCTTCTTCCTCTATAGCAAGCTCACC<br>GTGGACAAGAGCAGGTGGCAGCAGGGGAACGTCTTCTCATGCTCCGTGA<br>TGCATGAGGCTCTGCACAACCACTACACGCAGAAGAGCCTCTCCCTGTC<br>TCCGGGTAAA |
| LC Constant Region NT | SEQ ID NO: 93 | ACTGTGGCTGCACCATCTGTCTTCATCTTCCCGCCATCTGATGAGCAGT<br>TGAAATCTGGAACTGCCTCTGTTGTGTGCCTGCTGAATAACTTCTATCC<br>CAGAGAGGCCAAAGTACAGTGGAAGGTGGATAACGCCCTCCAATCGGGT<br>AACTCCCAGGAGAGTGTCACAGAGCAGGACAGCAAGGACAGCACCTACA<br>GCCTCAGCAGCACCCTGACGCTGAGCAAAGCAGACTACGAGAAACACAA<br>AGTCTACGCCTGCGAAGTCACCCATCAGGGCCTGAGCTCGCCCGTCACA<br>AAGAGCTTCAACAGGGGAGAGTGT |
| HCDR2 Kabat consensus AA | SEQ ID NO: 94 | $X_1$I $X_2$P $X_2$ $X_3$G $X_4$TNYA X5KFQG<br>$X_1$ = W or R<br>$X_2$ = N or D<br>$X_3$ = s or e<br>$X_4$ = g or d<br>$X^5$ = q or p |
| HCDR2 Chothia consensus AA | SEQ ID NO: 95 | $X_1$I $X_2$P $X_2$ $X_3$G $X_4$<br>$X_1$ = W or R<br>$X_2$ = N or D<br>$X_3$ = s or e<br>$X_4$ = g or d |
| VH Consensus aa | SEQ ID NO: 96 | QVQLVQSGAEVKKPGASVKVSCKAS<u>GYTFTGYYMH</u>WVRQAPGQGLEWMG<br>$X_1$I$X_2$P$X_2$$X_3$G$X_4$<u>TNYA$X_5$KFQG</u>RVTMTRDTSISTAYMELSRLX$_6$SDD<br>TAVYYCAR<u>LASGFRDY</u>WG X$_7$GTLVTVSS<br>$X_1$ = W or R<br>$X_2$ = N or D<br>$X_3$ = s or e<br>$X_4$ = g or d<br>$X_5$ = q or p<br>$X_6$ = R or S<br>$X_7$ = Q or H |
| VL consensus aa | SEQ ID NO: 97 | DIVMTX1SPSSLSASVGDRVTITCRAS<u>X$_2$GIRNDL</u>GWYQQKPGKAPKRL<br>IYAASSLQSGVPSRFSGSX$_3$SGTEFLX$_4$LTISSLQPEDX$_5$ATYYC<u>LQHDI<br>YAST</u>FGPGTKVDIKR<br>$X_1$ = Q or K<br>$X_2$ = Q or L<br>$X_3$ = G or V OR A<br>$X_4$ = T or S<br>$X_5$ = F or L |
| Human Factor XIa | SEQ ID NO: 98 | MIFLYQVVHFILFTSVSGECVTQLLKDTCFEGGDITTVFTPSAKYCQVV<br>CTYHPRCLLFTFTAESPSEDPTRWFTCVLKDSVTETLPRVNRTAAISGY<br>SFKQCSHQISACNKDIYVDLDMKGINYNSSVAKSAQECQERCTDDVHCH<br>FFTYATRQFPSLEHRNICLLKHTQTGTPTRITKLDKVVSGFSLKSCALS<br>NLACIRDIFPNTVFADSNIDSVMAPDAFVCGRICTHHPGCLFFTFFSQE<br>WPKESQRNLCLLKTSESGLPSTRIKKSKALSGFSLQSCRHSIPVFCHSS<br>FYHDTDFLGEELDIVAAKSHEACQKLCTNAVRCQFFTYTPAQASCNEGK<br>GKCYLKLSSNGSPTKILHGRGGISGYTLRLCKMDNECTTKIKPRIVGGT<br>ASVRGEWPWQVTLHTTSPTQRHLCGGSIIGNQWILTAAHCFYGVESPKI<br>LRVYSGILNQSEIKEDTSFFGVQEIIHDQYKMAESGYDIALLKLETTVN<br>YTDSQRPICLPSKGDRNVIYTDCWVTGWGYRKLRDKIQNTLQKAKIPLV<br>TNEECQKRYRGHKITHKMICAGYREGGKDACKGDSGGPLSCKHNEVWHL<br>VGITSWGEGCAQRERPGVYTNVVEYVDWILEKTQAV |
| Human FXI catalytic domain | SEQ ID NO: 99 | MGWSCIILFLVATATGVHSIVGGTASVRGEWPWQVTLHTTSPTQRHLCG<br>GSIIGNQWILTAAHCFYGVESPKILRVYSGILQQSEIKEDTSFFGVQEI<br>IIHDQYKMAESGYDIALLKLETTVQYTDSQRPISLPSKGDRNVIYTDCW |

TABLE 5-continued

Sequence Listing Table
CDR amino acid sequences are underlined (Chothia) or in bold (Kabat).

| | | |
|---|---|---|
| S557A glyco- | | VTGWGYRKLRDKIQNTLQKAKIPLVTNEECQKRYRGHKITHKMICAGYR EGGKDACKGDAGGPLSCKHNEVWHLVGITSWGEGCAQRERPGVYTNVVE YVDWILEKTQAHHHHHH |
| Human FXI catalytic domain S557A glyco-mature peptide | SEQ ID NO: 100 | IVGGTAVFRGEWPWQVTLHTTSPTQRHLCGGSIIGNQWILTAAHCFYGV ESPKILRVYSGILQQSEIKEDTSFFGVQEIIIHDQYKMAESGYDIALLK LETTVQYTDSQRPISLPSKGDRNVIYTDCWVTGWGYRKLRDKIQNTLQK AKIPLVTNEECQKRYRGHKITHKMICAGYREGGKDACKGDAGGPLSCKH NEVWHLVGITSWGEGCAQRERPGVYTNVVEYVDWILEKTQAHHHHHH |
| DEF_FAB_HEAVY | SEQ ID NO: 101 | EVQLVQSGAEVKKPGASVKVSCKASGYTFTGYYMHWVRQAPGQGLEWMG WIDPDEGDTNYAQKFQGRVTMTRDTSISTAYMELSRLRSDDTAVYYCAR LASGFRDYWGQGTLVTVSSASTKGPSVFPLAPSSKSTSGGTAALGCLVK DYFPEPVTVSWNSGALTSGVHTFPAVLQSSGLYSLSSVVTVPSSSLGTQ TYICNVNHKPSNTKVDKKVEPKSCGGSHHHHHH |
| DEF_FAB_LIGHT | SEQ ID NO: 102 | DIVMTKSPSSLSASVGDRVTITCRASQGIRNDLGQYQQKPGKAPKRLIY AASSLQSGVPSRFSGSGSGTEFTLTISSLQPEDFATYYCLQHDIYASTF GPGTKVDIKTVAAPSVFIFPPSDEQLKSGTASVVCLLNNFYPREAKVQW KVDNALQSGNSQESVTEQDSKDSTYSLSSTLTLSKADYEKHKVYACEVT HQGLSSPVTKSFNRGEC |
| HC Constant Region AA | SEQ ID NO: 103 | ASTKGPSVFPLAPSSKSTSGGTAALGCLVKDYFEPEVTVSWNSGALTSG VHTFPAVLQSSLGYSLSSVVTVPSSSLGTQTYICNVNHKPSNTKVDKKV EPKSCDKTHTCPPCPAPELLGGPSVFLFPPKPKDTLMISRTPEVTCVVV DVSHEDPEVKFNWYVDGVEVHNAKTKPREEQYNSTYRVVSVLTVLHQDW LNGKEYKCKVSNKALPAPIEKTISKAKGQPREPQVYTLPPSREEMTKNQ VSLTCLVKGFYPSDIAVEWESNGQPENNYKTTPPVLDSDGSFFLYSKLT VDKSRWQQGNVFSCSVMHEALHNHYTQKSLSLPGK |

Although the disclosed teachings have been described with reference to various applications, methods, kits, and compositions, it will be appreciated that various changes and modifications can be made without departing from the teachings herein and the claimed invention below. The foregoing examples are provided to better illustrate the disclosed teachings and are not intended to limit the scope of the teachings presented herein. While the present teachings have been described in terms of these exemplary embodiments, the skilled artisan will readily understand that numerous variations and modifications of these exemplary embodiments are possible without undue experimentation. All such variations and modifications are within the scope of the current teachings.

All publications, patents, patent applications or other documents cited herein are hereby incorporated by reference in their entirety for all purposes to the same extent as if each individual publication, patent, patent application, or other document was individually indicated to be incorporated by reference for all purposes.

What is claimed is:

1. An isolated monoclonal antibody, or an antigen-binding portion thereof, that specifically binds the Factor XIa catalytic domain, wherein the antibody or antigen-binding portion comprises HCDR1-3 and LCDR1-3 comprising the amino acid sequences of:
   a) SEQ ID NOs: 2, 3, 4, 8, 9, and 10, respectively; or
   b) SEQ ID NOs: 5, 6, 4, 11, 12, and 13, respectively.

2. The isolated monoclonal antibody or an antigen-binding portion thereof of claim 1, wherein the antibody comprises: a heavy chain variable domain (VH) comprising the amino acid sequence of SEQ ID NO: 1 or a light chain variable domain (VL) comprising the amino acid sequence of SEQ ID NO: 7.

3. The isolated monoclonal antibody or antigen-binding portion of claim 1, wherein the antibody specifically binds to the active site of the catalytic domain of Factor XIa.

4. The isolated monoclonal antibody or antigen-binding portion of claim 1, wherein the antibody is chimeric, humanized, or human.

5. The isolated monoclonal antibody or antigen-binding portion of claim 4, wherein the antibody comprises a human IgG heavy chain constant region.

6. The isolated monoclonal antibody or antigen-binding portion of claim 5, wherein the antibody comprises a human IgG$_1$ heavy chain constant region.

7. The isolated monoclonal antibody or antigen-binding portion of claim 1, wherein the antibody comprises a heavy chain constant domain comprising the amino acid sequence of SEQ ID NO: 82 and/or a light chain constant domain comprising the amino acid sequence of SEQ ID NO: 83.

8. A pharmaceutical composition comprising the isolated monoclonal antibody or antigen-binding portion of claim 1, and a pharmaceutically acceptable excipient.

9. The isolated monoclonal antibody or an antigen-binding portion thereof of claim 1, wherein the antibody comprises: a heavy chain variable domain (VH) comprising the amino acid sequence of SEQ ID NO: 1 and a light chain variable domain (VL) comprising the amino acid sequence of SEQ ID NO: 7.

10. An isolated monoclonal antibody, or an antigen-binding portion thereof, that specifically binds the Factor XIa catalytic domain, wherein the antibody or antigen-binding portion comprises HCDR1-3 and LCDR1-3 comprising the amino acid sequences of:
   a) SEQ ID NOs: 2, 15, 4, 8, 9, and 10, respectively;
   b) SEQ ID NOs: 5, 16, 4, 11, 12, and 13, respectively;
   c) SEQ ID NOs: 2, 66, 4, 8, 9, and 10, respectively;
   d) SEQ ID NOs: 5, 67, 4, 11, 12, and 13, respectively;
   e) SEQ ID NOs: 2, 35, 4, 8, 9, and 10, respectively; or
   f) SEQ ID NOs: 1, 36, 4, 11, 12, and 13, respectively.

11. The isolated monoclonal antibody or an antigen-binding portion thereof of claim 10, wherein the antibody comprises: a heavy chain variable domain (VH) comprising the amino acid sequence of SEQ ID NO: 14 and a light chain variable domain (VL) comprising the amino acid sequence of SEQ ID NO: 17.

12. The isolated monoclonal antibody or an antigen-binding portion thereof of claim 10, wherein the antibody comprises: a heavy chain variable domain (VH) comprising the amino acid sequence of SEQ ID NO: 65 and a light chain variable domain (VL) comprising the amino acid sequence of SEQ ID NO: 68.

13. The isolated monoclonal antibody or an antigen-binding portion thereof of claim 10, wherein the antibody comprises: a heavy chain variable domain (VH) comprising the amino acid sequence of SEQ ID NO: 34 and a light chain variable domain (VL) comprising the amino acid sequence of SEQ ID NO: 37.

14. The isolated monoclonal antibody or antigen-binding portion of claim 10, wherein the antibody specifically binds to the active site of the catalytic domain of Factor XIa.

15. The isolated monoclonal antibody or antigen-binding portion of claim 10, wherein the antibody is chimeric, humanized, or human.

16. The isolated monoclonal antibody or antigen-binding portion of claim 14, wherein the antibody comprises a human IgG heavy chain constant region.

17. The isolated monoclonal antibody or antigen-binding portion of claim 15, wherein the antibody comprises a human $IgG_1$ heavy chain constant region.

18. The isolated monoclonal antibody or antigen-binding portion of claim 10, wherein the antibody comprises a heavy chain constant domain comprising the amino acid sequence of SEQ ID NO: 82 and/or a light chain constant domain comprising the amino acid sequence of SEQ ID NO: 83.

19. A pharmaceutical composition comprising the isolated monoclonal antibody or antigen-binding portion of claim 10, and a pharmaceutically acceptable excipient.

* * * * *

SEQUENCE LISTING

```
<160> NUMBER OF SEQ ID NOS: 103

<210> SEQ ID NO 1
<211> LENGTH: 117
<212> TYPE: PRT
<213> ORGANISM: Artificial Sequence
<220> FEATURE:
<223> OTHER INFORMATION: Synthetic construct

<400> SEQUENCE: 1

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asp Pro Asp Glu Gly Asp Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80
```

```
Met Glu Leu Ser Arg Leu Arg Ser Asp Asp Thr Ala Val Tyr Tyr Cys
            85                  90                  95

Ala Arg Leu Ala Ser Gly Phe Arg Asp Tyr Trp Gly Gln Gly Thr Leu
        100                 105                 110

Val Thr Val Ser Ser
        115

<210> SEQ ID NO 2
<211> LENGTH: 5
<212> TYPE: PRT
<213> ORGANISM: Artificial Sequence
<220> FEATURE:
<223> OTHER INFORMATION: Synthetic Construct

<400> SEQUENCE: 2

Gly Tyr Tyr Met His
1               5

<210> SEQ ID NO 3
<211> LENGTH: 17
<212> TYPE: PRT
<213> ORGANISM: Artificial Sequence
<220> FEATURE:
<223> OTHER INFORMATION: Synthetic Construct

<400> SEQUENCE: 3

Trp Ile Asp Pro Asp Glu Gly Asp Thr Asn Tyr Ala Gln Lys Phe Gln
1               5                   10                  15

Gly

<210> SEQ ID NO 4
<211> LENGTH: 8
<212> TYPE: PRT
<213> ORGANISM: Artificial Sequence
<220> FEATURE:
<223> OTHER INFORMATION: Synthetic Construct

<400> SEQUENCE: 4

Leu Ala Ser Gly Phe Arg Asp Tyr
1               5

<210> SEQ ID NO 5
<211> LENGTH: 10
<212> TYPE: PRT
<213> ORGANISM: Artificial Sequence
<220> FEATURE:
<223> OTHER INFORMATION: Synthetic Construct

<400> SEQUENCE: 5

Gly Tyr Thr Phe Thr Gly Tyr Tyr Met His
1               5                   10

<210> SEQ ID NO 6
<211> LENGTH: 8
<212> TYPE: PRT
<213> ORGANISM: Artificial Sequence
<220> FEATURE:
<223> OTHER INFORMATION: Synthetic Construct

<400> SEQUENCE: 6

Trp Ile Asp Pro Asp Glu Gly Asp
1               5

<210> SEQ ID NO 7
<211> LENGTH: 108
```

<212> TYPE: PRT
<213> ORGANISM: Artificial Sequence
<220> FEATURE:
<223> OTHER INFORMATION: Synthetic Construct

<400> SEQUENCE: 7

Asp Ile Val Met Thr Lys Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asp Ile Tyr Ala Ser
                85                  90                  95

Thr Phe Gly Pro Gly Thr Lys Val Asp Ile Lys Arg
            100                 105

<210> SEQ ID NO 8
<211> LENGTH: 11
<212> TYPE: PRT
<213> ORGANISM: Artificial Sequence
<220> FEATURE:
<223> OTHER INFORMATION: Synthetic Construct

<400> SEQUENCE: 8

Arg Ala Ser Gln Gly Ile Arg Asn Asp Leu Gly
1               5                   10

<210> SEQ ID NO 9
<211> LENGTH: 8
<212> TYPE: PRT
<213> ORGANISM: Artificial Sequence
<220> FEATURE:
<223> OTHER INFORMATION: Synthetic Construct

<400> SEQUENCE: 9

Tyr Ala Ala Ser Ser Leu Gln Ser
1               5

<210> SEQ ID NO 10
<211> LENGTH: 9
<212> TYPE: PRT
<213> ORGANISM: Artificial Sequence
<220> FEATURE:
<223> OTHER INFORMATION: Synthetic Construct

<400> SEQUENCE: 10

Leu Gln His Asp Ile Tyr Ala Ser Thr
1               5

<210> SEQ ID NO 11
<211> LENGTH: 9
<212> TYPE: PRT
<213> ORGANISM: Artificial Sequence
<220> FEATURE:
<223> OTHER INFORMATION: Synthetic Construct

<400> SEQUENCE: 11

Ala Ser Gln Gly Ile Arg Asn Asp Leu
1               5

<210> SEQ ID NO 12
<211> LENGTH: 5
<212> TYPE: PRT
<213> ORGANISM: Artificial Sequence
<220> FEATURE:
<223> OTHER INFORMATION: Synthetic Construct

<400> SEQUENCE: 12

Tyr Ala Ala Ser Ser
1               5

<210> SEQ ID NO 13
<211> LENGTH: 8
<212> TYPE: PRT
<213> ORGANISM: Artificial Sequence
<220> FEATURE:
<223> OTHER INFORMATION: Synthetic Construct

<400> SEQUENCE: 13

Gln His Asp Ile Tyr Ala Ser Thr
1               5

<210> SEQ ID NO 14
<211> LENGTH: 117
<212> TYPE: PRT
<213> ORGANISM: Artificial Sequence
<220> FEATURE:
<223> OTHER INFORMATION: Synthetic Construct

<400> SEQUENCE: 14

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Leu Ala Ser Gly Phe Arg Asp Tyr Trp Gly Gln Gly Thr Leu
            100                 105                 110

Val Thr Val Ser Ser
        115

<210> SEQ ID NO 15
<211> LENGTH: 17
<212> TYPE: PRT
<213> ORGANISM: Artificial Sequence
<220> FEATURE:
<223> OTHER INFORMATION: Synthetic Construct

<400> SEQUENCE: 15

Trp Ile Asn Pro Asn Ser Gly Gly Thr Asn Tyr Ala Gln Lys Phe Gln
1               5                   10                  15

Gly

<210> SEQ ID NO 16
<211> LENGTH: 8

```
<212> TYPE: PRT
<213> ORGANISM: Artificial Sequence
<220> FEATURE:
<223> OTHER INFORMATION: Synthetic Construct

<400> SEQUENCE: 16

Trp Ile Asn Pro Asn Ser Gly Gly
1               5

<210> SEQ ID NO 17
<211> LENGTH: 108
<212> TYPE: PRT
<213> ORGANISM: Artificial Sequence
<220> FEATURE:
<223> OTHER INFORMATION: Synthetic Construct

<400> SEQUENCE: 17

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asp Ile Tyr Ala Ser
                85                  90                  95

Thr Phe Gly Pro Gly Thr Lys Val Asp Ile Lys Arg
            100                 105

<210> SEQ ID NO 18
<211> LENGTH: 117
<212> TYPE: PRT
<213> ORGANISM: Artificial Sequence
<220> FEATURE:
<223> OTHER INFORMATION: Synthetic Construct

<400> SEQUENCE: 18

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Arg Ile Asn Pro Asn Ser Gly Asp Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Leu Ala Ser Gly Phe Arg Asp Tyr Trp Gly Gln Gly Thr Leu
            100                 105                 110

Val Thr Val Ser Ser
        115

<210> SEQ ID NO 19
<211> LENGTH: 17
<212> TYPE: PRT
```

<213> ORGANISM: Artificial Sequence
<220> FEATURE:
<223> OTHER INFORMATION: Synthetic Construct

<400> SEQUENCE: 19

Arg Ile Asn Pro Asn Ser Gly Asp Thr Asn Tyr Ala Gln Lys Phe Gln
1               5                   10                  15

Gly

<210> SEQ ID NO 20
<211> LENGTH: 8
<212> TYPE: PRT
<213> ORGANISM: Artificial Sequence
<220> FEATURE:
<223> OTHER INFORMATION: Synthetic Construct

<400> SEQUENCE: 20

Arg Ile Asn Pro Asn Ser Gly Asp
1               5

<210> SEQ ID NO 21
<211> LENGTH: 108
<212> TYPE: PRT
<213> ORGANISM: Artificial Sequence
<220> FEATURE:
<223> OTHER INFORMATION: Synthetic Construct

<400> SEQUENCE: 21

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asp Ile Tyr Ala Ser
                85                  90                  95

Thr Phe Gly Pro Gly Thr Lys Val Asp Ile Lys Arg
            100                 105

<210> SEQ ID NO 22
<211> LENGTH: 117
<212> TYPE: PRT
<213> ORGANISM: Artificial Sequence
<220> FEATURE:
<223> OTHER INFORMATION: Synthetic Construct

<400> SEQUENCE: 22

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

```
Met Glu Leu Ser Arg Leu Ser Ser Asp Asp Thr Ala Val Tyr Tyr Cys
                85                  90                  95

Ala Arg Leu Ala Ser Gly Phe Arg Asp Tyr Trp Gly Gln Gly Thr Leu
            100                 105                 110

Val Thr Val Ser Ser
        115

<210> SEQ ID NO 23
<211> LENGTH: 108
<212> TYPE: PRT
<213> ORGANISM: Artificial Sequence
<220> FEATURE:
<223> OTHER INFORMATION: Synthetic Construct

<400> SEQUENCE: 23

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asp Ile Tyr Ala Ser
                85                  90                  95

Thr Phe Gly Pro Gly Thr Lys Val Asp Ile Lys Arg
            100                 105

<210> SEQ ID NO 24
<211> LENGTH: 117
<212> TYPE: PRT
<213> ORGANISM: Artificial Sequence
<220> FEATURE:
<223> OTHER INFORMATION: Synthetic Construct

<400> SEQUENCE: 24

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Leu Ala Ser Gly Phe Arg Asp Tyr Trp Gly Gln Gly Thr Leu
            100                 105                 110

Val Thr Val Ser Ser
        115

<210> SEQ ID NO 25
<211> LENGTH: 108
<212> TYPE: PRT
```

<213> ORGANISM: Artificial Sequence
<220> FEATURE:
<223> OTHER INFORMATION: Synthetic Construct

<400> SEQUENCE: 25

```
Asp Ile Val Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
50                  55                  60

Ser Val Ser Gly Thr Glu Phe Thr Leu Thr Ile Ser Ser Leu Gln Pro
65                  70                  75                  80

Glu Asp Leu Ala Thr Tyr Tyr Cys Leu Gln His Asp Ile Tyr Ala Ser
                85                  90                  95

Thr Phe Gly Pro Gly Thr Lys Val Asp Ile Lys Arg
            100                 105
```

<210> SEQ ID NO 26
<211> LENGTH: 117
<212> TYPE: PRT
<213> ORGANISM: Artificial Sequence
<220> FEATURE:
<223> OTHER INFORMATION: Synthetic Construct

<400> SEQUENCE: 26

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Leu Ala Ser Gly Phe Arg Asp Tyr Trp Gly Gln Gly Thr Leu
            100                 105                 110

Val Thr Val Ser Ser
        115
```

<210> SEQ ID NO 27
<211> LENGTH: 108
<212> TYPE: PRT
<213> ORGANISM: Artificial Sequence
<220> FEATURE:
<223> OTHER INFORMATION: Synthetic Construct

<400> SEQUENCE: 27

```
Asp Ile Val Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45
```

Tyr Ala Ala Ser Ser Leu Gln Ser Gly Val Pro Ser Arg Phe Ser Gly
            50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Asp Ile Tyr Ala Ser
                 85                  90                  95

Thr Phe Gly Pro Gly Thr Lys Val Asp Ile Lys Arg
            100                 105

<210> SEQ ID NO 28
<211> LENGTH: 117
<212> TYPE: PRT
<213> ORGANISM: Artificial Sequence
<220> FEATURE:
<223> OTHER INFORMATION: Synthetic Construct

<400> SEQUENCE: 28

Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Gly Tyr
                 20                  25                  30

Tyr Met His Trp Val Arg Gln Ala Pro Gly Gln Gly Leu Glu Trp Met
             35                  40                  45

Gly Arg Ile Asn Pro Asn Ser Gly Gly Thr Asn Tyr Ala Gln Lys Phe
 50                  55                  60

Gln Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Leu Ala Ser Gly Phe Arg Asp Tyr Trp Gly Gln Gly Thr Leu
            100                 105                 110

Val Thr Val Ser Ser
        115

<210> SEQ ID NO 29
<211> LENGTH: 17
<212> TYPE: PRT
<213> ORGANISM: Artificial Sequence
<220> FEATURE:
<223> OTHER INFORMATION: Synthetic Construct

<400> SEQUENCE: 29

Arg Ile Asn Pro Asn Ser Gly Gly Thr Asn Tyr Ala Gln Lys Phe Gln
 1               5                  10                  15

Gly

<210> SEQ ID NO 30
<211> LENGTH: 8
<212> TYPE: PRT
<213> ORGANISM: Artificial Sequence
<220> FEATURE:
<223> OTHER INFORMATION: Synthetic Construct

<400> SEQUENCE: 30

Arg Ile Asn Pro Asn Ser Gly Gly
 1               5

<210> SEQ ID NO 31
<211> LENGTH: 108
<212> TYPE: PRT

```
<213> ORGANISM: Artificial Sequence
<220> FEATURE:
<223> OTHER INFORMATION: Synthetic Construct

<400> SEQUENCE: 31

Asp Ile Val Met Thr Gln Ser Pro Ser Ser Leu Ser Ala Ser Val Gly
1               5                   10                  15

Asp Arg Val Thr Ile Thr Cys Arg Ala Ser Leu Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
50                  55                  60

Ser Gly Ser Gly Thr Glu Phe Ser Leu Thr Ile Ser Ser Leu Gln Pro
65                  70                  75                  80

Glu Asp Phe Ala Thr Tyr Tyr Cys Leu Gln His Asp Ile Tyr Ala Ser
                85                  90                  95

Thr Phe Gly Pro Gly Thr Lys Val Asp Ile Lys Arg
            100                 105

<210> SEQ ID NO 32
<211> LENGTH: 11
<212> TYPE: PRT
<213> ORGANISM: Artificial Sequence
<220> FEATURE:
<223> OTHER INFORMATION: Synthetic Construct

<400> SEQUENCE: 32

Arg Ala Ser Leu Gly Ile Arg Asn Asp Leu Gly
1               5                   10

<210> SEQ ID NO 33
<211> LENGTH: 9
<212> TYPE: PRT
<213> ORGANISM: Artificial Sequence
<220> FEATURE:
<223> OTHER INFORMATION: Synthetic Construct

<400> SEQUENCE: 33

Ala Ser Leu Gly Ile Arg Asn Asp Leu
1               5

<210> SEQ ID NO 34
<211> LENGTH: 117
<212> TYPE: PRT
<213> ORGANISM: Artificial Sequence
<220> FEATURE:
<223> OTHER INFORMATION: Synthetic Construct

<400> SEQUENCE: 34

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asp Pro Asn Ser Gly Asp Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
```

```
                    85                  90                  95
Ala Arg Leu Ala Ser Gly Phe Arg Asp Tyr Trp Gly Gln Gly Thr Leu
            100                 105                 110

Val Thr Val Ser Ser
        115

<210> SEQ ID NO 35
<211> LENGTH: 17
<212> TYPE: PRT
<213> ORGANISM: Artificial Sequence
<220> FEATURE:
<223> OTHER INFORMATION: Synthetic Construct

<400> SEQUENCE: 35

Trp Ile Asp Pro Asn Ser Gly Asp Thr Asn Tyr Ala Gln Lys Phe Gln
1               5                   10                  15

Gly

<210> SEQ ID NO 36
<211> LENGTH: 8
<212> TYPE: PRT
<213> ORGANISM: Artificial Sequence
<220> FEATURE:
<223> OTHER INFORMATION: Synthetic Construct

<400> SEQUENCE: 36

Trp Ile Asp Pro Asn Ser Gly Asp
1               5

<210> SEQ ID NO 37
<211> LENGTH: 108
<212> TYPE: PRT
<213> ORGANISM: Artificial Sequence
<220> FEATURE:
<223> OTHER INFORMATION: Synthetic Construct

<400> SEQUENCE: 37

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asp Ile Tyr Ala Ser
                85                  90                  95

Thr Phe Gly Pro Gly Thr Lys Val Asp Ile Lys Arg
            100                 105

<210> SEQ ID NO 38
<211> LENGTH: 117
<212> TYPE: PRT
<213> ORGANISM: Artificial Sequence
<220> FEATURE:
<223> OTHER INFORMATION: Synthetic Construct

<400> SEQUENCE: 38

Glu Val Gln Leu Val Gln Ser Gly Ala Glu Val Lys Lys Pro Gly Ala
1               5                   10                  15
```

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
 50                  55                  60

Gln Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                85                  90                  95

Ala Arg Leu Ala Ser Gly Phe Arg Asp Tyr Trp Gly Gln Gly Thr Leu
                100                 105                 110

Val Thr Val Ser Ser
        115

<210> SEQ ID NO 39
<211> LENGTH: 108
<212> TYPE: PRT
<213> ORGANISM: Artificial Sequence
<220> FEATURE:
<223> OTHER INFORMATION: Synthetic Construct

<400> SEQUENCE: 39

Asp Ile Val Met Thr Lys Ser Pro Ser Ser Leu Ser Ala Ser Val Gly
1               5                   10                  15

Asp Arg Val Thr Ile Thr Cys Arg Ala Ser Gln Gly Ile Arg Asn Asp
                20                  25                  30

Leu Gly Trp Tyr Gln Gln Lys Pro Gly Lys Ala Pro Lys Arg Leu Ile
            35                  40                  45

Tyr Ala Ala Ser Ser Leu Gln Ser Gly Val Pro Ser Arg Phe Ser Gly
 50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asp Ile Tyr Ala Ser
                85                  90                  95

Thr Phe Gly Pro Gly Thr Lys Val Asp Ile Lys Arg
                100                 105

<210> SEQ ID NO 40
<211> LENGTH: 117
<212> TYPE: PRT
<213> ORGANISM: Artificial Sequence
<220> FEATURE:
<223> OTHER INFORMATION: Synthetic Construct

<400> SEQUENCE: 40

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Pro Lys Phe
 50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys

```
                        85                  90                  95
Ala Arg Leu Ala Ser Gly Phe Arg Asp Tyr Trp Gly Gln Gly Thr Leu
                100                 105                 110

Val Thr Val Ser Ser
        115

<210> SEQ ID NO 41
<211> LENGTH: 17
<212> TYPE: PRT
<213> ORGANISM: Artificial Sequence
<220> FEATURE:
<223> OTHER INFORMATION: Synthetic Construct

<400> SEQUENCE: 41

Trp Ile Asn Pro Asn Ser Gly Gly Thr Asn Tyr Ala Pro Lys Phe Gln
1               5                   10                  15

Gly

<210> SEQ ID NO 42
<211> LENGTH: 108
<212> TYPE: PRT
<213> ORGANISM: Artificial Sequence
<220> FEATURE:
<223> OTHER INFORMATION: Synthetic Construct

<400> SEQUENCE: 42

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Ala Ser Gly Thr Glu Phe Thr Leu Thr Ile Ser Ser Leu Gln Pro
65                  70                  75                  80

Glu Asp Phe Ala Thr Tyr Tyr Cys Leu Gln His Asp Ile Tyr Ala Ser
                85                  90                  95

Thr Phe Gly Pro Gly Thr Lys Val Asp Ile Lys Arg
            100                 105

<210> SEQ ID NO 43
<211> LENGTH: 117
<212> TYPE: PRT
<213> ORGANISM: Artificial Sequence
<220> FEATURE:
<223> OTHER INFORMATION: Synthetic Construct

<400> SEQUENCE: 43

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asp Pro Asp Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80
```

Met Glu Leu Ser Arg Leu Arg Ser Asp Asp Thr Ala Val Tyr Tyr Cys
                85                  90                  95

Ala Arg Leu Ala Ser Gly Phe Arg Asp Tyr Trp Gly His Gly Thr Leu
            100                 105                 110

Val Thr Val Ser Ser
        115

<210> SEQ ID NO 44
<211> LENGTH: 17
<212> TYPE: PRT
<213> ORGANISM: Artificial Sequence
<220> FEATURE:
<223> OTHER INFORMATION: Synthetic Construct

<400> SEQUENCE: 44

Trp Ile Asp Pro Asp Ser Gly Gly Thr Asn Tyr Ala Gln Lys Phe Gln
1               5                   10                  15

Gly

<210> SEQ ID NO 45
<211> LENGTH: 8
<212> TYPE: PRT
<213> ORGANISM: Artificial Sequence
<220> FEATURE:
<223> OTHER INFORMATION: Synthetic Construct

<400> SEQUENCE: 45

Trp Ile Asp Pro Asp Ser Gly Gly
1               5

<210> SEQ ID NO 46
<211> LENGTH: 108
<212> TYPE: PRT
<213> ORGANISM: Artificial Sequence
<220> FEATURE:
<223> OTHER INFORMATION: Synthetic Construct

<400> SEQUENCE: 46

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asp Ile Tyr Ala Ser
                85                  90                  95

Thr Phe Gly Pro Gly Thr Lys Val Asp Ile Lys Arg
            100                 105

<210> SEQ ID NO 47
<211> LENGTH: 117
<212> TYPE: PRT
<213> ORGANISM: Artificial Sequence
<220> FEATURE:
<223> OTHER INFORMATION: Synthetic Construct

<400> SEQUENCE: 47

Glu Val Gln Leu Val Gln Ser Gly Ala Glu Val Lys Lys Pro Gly Ala

```
            1               5                  10                 15
          Ser Val Lys Val Ser Cys Lys Ala Ser Gly Tyr Thr Phe Thr Gly Tyr
                          20                  25                 30

Tyr Met His Trp Val Arg Gln Ala Pro Gly Gln Gly Leu Glu Trp Met
                          35                  40                 45

Gly Trp Ile Asp Pro Asp Ser Gly Asp Thr Asn Tyr Ala Gln Lys Phe
                          50                  55                 60

Gln Gly Arg Val Thr Met Thr Arg Asp Thr Ser Ile Ser Thr Ala Tyr
          65                70                  75                 80

Met Glu Leu Ser Arg Leu Arg Ser Asp Asp Thr Ala Val Tyr Tyr Cys
                          85                  90                 95

Ala Arg Leu Ala Ser Gly Phe Arg Asp Tyr Trp Gly Gln Gly Thr Leu
                          100                 105                110

Val Thr Val Ser Ser
                  115

<210> SEQ ID NO 48
<211> LENGTH: 17
<212> TYPE: PRT
<213> ORGANISM: Artificial Sequence
<220> FEATURE:
<223> OTHER INFORMATION: Synthetic Construct

<400> SEQUENCE: 48

Trp Ile Asp Pro Asp Ser Gly Asp Thr Asn Tyr Ala Gln Lys Phe Gln
1               5                  10                 15

Gly

<210> SEQ ID NO 49
<211> LENGTH: 7
<212> TYPE: PRT
<213> ORGANISM: Artificial Sequence
<220> FEATURE:
<223> OTHER INFORMATION: Synthetic Construct

<400> SEQUENCE: 49

Trp Ile Asp Pro Asp Ser Gly
1               5

<210> SEQ ID NO 50
<211> LENGTH: 108
<212> TYPE: PRT
<213> ORGANISM: Artificial Sequence
<220> FEATURE:
<223> OTHER INFORMATION: Synthetic Construct

<400> SEQUENCE: 50

Asp Ile Val Met Thr Gln Ser Pro Ser Ser Leu Ser Ala Ser Val Gly
1               5                  10                 15

Asp Arg Val Thr Ile Thr Cys Arg Ala Ser Gln Gly Ile Arg Asn Asp
                20                  25                 30

Leu Gly Trp Tyr Gln Gln Lys Pro Gly Lys Ala Pro Lys Arg Leu Ile
                35                  40                 45

Tyr Ala Ala Ser Ser Leu Gln Ser Gly Val Pro Ser Arg Phe Ser Gly
                50                  55                 60

Ser Gly Ser Gly Thr Glu Phe Thr Leu Thr Ile Ser Ser Leu Gln Pro
65                  70                  75                 80

Glu Asp Phe Ala Thr Tyr Tyr Cys Leu Gln His Asp Ile Tyr Ala Ser
                85                  90                 95
```

```
Thr Phe Gly Pro Gly Thr Lys Val Asp Ile Lys Arg
        100                 105
```

<210> SEQ ID NO 51
<211> LENGTH: 117
<212> TYPE: PRT
<213> ORGANISM: Artificial Sequence
<220> FEATURE:
<223> OTHER INFORMATION: Synthetic Construct

<400> SEQUENCE: 51

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Arg Ile Asp Pro Asp Ser Gly Asp Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Leu Ala Ser Gly Phe Arg Asp Tyr Trp Gly Gln Gly Thr Leu
            100                 105                 110

Val Thr Val Ser Ser
        115
```

<210> SEQ ID NO 52
<211> LENGTH: 17
<212> TYPE: PRT
<213> ORGANISM: Artificial Sequence
<220> FEATURE:
<223> OTHER INFORMATION: Synthetic Construct

<400> SEQUENCE: 52

```
Arg Ile Asp Pro Asp Ser Gly Asp Thr Asn Tyr Ala Gln Lys Phe Gln
1               5                   10                  15

Gly
```

<210> SEQ ID NO 53
<211> LENGTH: 8
<212> TYPE: PRT
<213> ORGANISM: Artificial Sequence
<220> FEATURE:
<223> OTHER INFORMATION: Synthetic Construct

<400> SEQUENCE: 53

```
Arg Ile Asp Pro Asp Ser Gly Asp
1               5
```

<210> SEQ ID NO 54
<211> LENGTH: 108
<212> TYPE: PRT
<213> ORGANISM: Artificial Sequence
<220> FEATURE:
<223> OTHER INFORMATION: Synthetic Construct

<400> SEQUENCE: 54

```
Asp Ile Val Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
```

20                  25                  30

Leu Gly Trp Tyr Gln Gln Lys Pro Gly Lys Ala Pro Lys Arg Leu Ile
            35                  40                  45

Tyr Ala Ala Ser Ser Leu Gln Ser Gly Val Pro Ser Arg Phe Ser Gly
 50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asp Ile Tyr Ala Ser
                85                  90                  95

Thr Phe Gly Pro Gly Thr Lys Val Asp Ile Lys Arg
            100                 105

<210> SEQ ID NO 55
<211> LENGTH: 117
<212> TYPE: PRT
<213> ORGANISM: Artificial Sequence
<220> FEATURE:
<223> OTHER INFORMATION: Synthetic Construct

<400> SEQUENCE: 55

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
            35                  40                  45

Gly Trp Ile Asn Pro Asp Ser Gly Asp Thr Asn Tyr Ala Gln Lys Phe
 50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Leu Ala Ser Gly Phe Arg Asp Tyr Trp Gly Gln Gly Thr Leu
            100                 105                 110

Val Thr Val Ser Ser
        115

<210> SEQ ID NO 56
<211> LENGTH: 17
<212> TYPE: PRT
<213> ORGANISM: Artificial Sequence
<220> FEATURE:
<223> OTHER INFORMATION: Synthetic Construct

<400> SEQUENCE: 56

Trp Ile Asn Pro Asp Ser Gly Asp Thr Asn Tyr Ala Gln Lys Phe Gln
1               5                   10                  15

Gly

<210> SEQ ID NO 57
<211> LENGTH: 8
<212> TYPE: PRT
<213> ORGANISM: Artificial Sequence
<220> FEATURE:
<223> OTHER INFORMATION: Synthetic Construct

<400> SEQUENCE: 57

Trp Ile Asn Pro Asp Ser Gly Asp
1               5

<210> SEQ ID NO 58
<211> LENGTH: 108
<212> TYPE: PRT
<213> ORGANISM: Artificial Sequence
<220> FEATURE:
<223> OTHER INFORMATION: Synthetic Construct

<400> SEQUENCE: 58

```
Asp Ile Val Met Thr Lys Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asp Ile Tyr Ala Ser
                85                  90                  95

Thr Phe Gly Pro Gly Thr Lys Val Asp Ile Lys Arg
            100                 105
```

<210> SEQ ID NO 59
<211> LENGTH: 117
<212> TYPE: PRT
<213> ORGANISM: Artificial Sequence
<220> FEATURE:
<223> OTHER INFORMATION: Synthetic Construct

<400> SEQUENCE: 59

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asp Pro Asn Ser Gly Asp Thr Asn Tyr Ala Gln Lys Phe
50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Leu Ala Ser Gly Phe Arg Asp Tyr Trp Gly Gln Gly Thr Leu
            100                 105                 110

Val Thr Val Ser Ser
        115
```

<210> SEQ ID NO 60
<211> LENGTH: 17
<212> TYPE: PRT
<213> ORGANISM: Artificial Sequence
<220> FEATURE:
<223> OTHER INFORMATION: Synthetic Construct

<400> SEQUENCE: 60

```
Trp Ile Asp Pro Asn Ser Gly Asp Thr Asn Tyr Ala Gln Lys Phe Gln
1               5                   10                  15

Gly
```

<210> SEQ ID NO 61
<211> LENGTH: 8
<212> TYPE: PRT
<213> ORGANISM: Artificial Sequence
<220> FEATURE:
<223> OTHER INFORMATION: Synthetic Construct

<400> SEQUENCE: 61

Trp Ile Asp Pro Asn Ser Gly Asp
1               5

<210> SEQ ID NO 62
<211> LENGTH: 108
<212> TYPE: PRT
<213> ORGANISM: Artificial Sequence
<220> FEATURE:
<223> OTHER INFORMATION: Synthetic Construct

<400> SEQUENCE: 62

Asp Ile Val Met Thr Lys Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asp Ile Tyr Ala Ser
                85                  90                  95

Thr Phe Gly Pro Gly Thr Lys Val Asp Ile Lys Arg
            100                 105

<210> SEQ ID NO 63
<211> LENGTH: 117
<212> TYPE: PRT
<213> ORGANISM: Artificial Sequence
<220> FEATURE:
<223> OTHER INFORMATION: Synthetic Construct

<400> SEQUENCE: 63

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Arg Ile Asp Pro Asp Ser Gly Asp Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Leu Ala Ser Gly Phe Arg Asp Tyr Trp Gly Gln Gly Thr Leu
            100                 105                 110

Val Thr Val Ser Ser
            115

<210> SEQ ID NO 64
<211> LENGTH: 108
<212> TYPE: PRT
<213> ORGANISM: Artificial Sequence
<220> FEATURE:
<223> OTHER INFORMATION: Synthetic Construct

<400> SEQUENCE: 64

```
Asp Ile Val Met Thr Lys Ser Pro Ser Ser Leu Ser Ala Ser Val Gly
1               5                   10                  15

Asp Arg Val Thr Ile Thr Cys Arg Ala Ser Gln Gly Ile Arg Asn Asp
                20                  25                  30

Leu Gly Trp Tyr Gln Gln Lys Pro Gly Lys Ala Pro Lys Arg Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asp Ile Tyr Ala Ser
                85                  90                  95

Thr Phe Gly Pro Gly Thr Lys Val Asp Ile Lys Arg
            100                 105
```

<210> SEQ ID NO 65
<211> LENGTH: 117
<212> TYPE: PRT
<213> ORGANISM: Artificial Sequence
<220> FEATURE:
<223> OTHER INFORMATION: Synthetic Construct

<400> SEQUENCE: 65

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
            35                  40                  45

Gly Trp Ile Asp Pro Asp Ser Gly Asp Thr Asn Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Leu Ala Ser Gly Phe Arg Asp Tyr Trp Gly Gln Gly Thr Leu
            100                 105                 110

Val Thr Val Ser Ser
        115
```

<210> SEQ ID NO 66
<211> LENGTH: 17
<212> TYPE: PRT
<213> ORGANISM: Artificial Sequence
<220> FEATURE:
<223> OTHER INFORMATION: Synthetic Construct

<400> SEQUENCE: 66

```
Trp Ile Asp Pro Asp Ser Gly Asp Thr Asn Tyr Ala Gln Lys Phe Gln
1               5                   10                  15

Gly
```

```
<210> SEQ ID NO 67
<211> LENGTH: 8
<212> TYPE: PRT
<213> ORGANISM: Artificial Sequence
<220> FEATURE:
<223> OTHER INFORMATION: Synthetic Construct

<400> SEQUENCE: 67

Trp Ile Asp Pro Asp Ser Gly Asp
1               5

<210> SEQ ID NO 68
<211> LENGTH: 108
<212> TYPE: PRT
<213> ORGANISM: Artificial Sequence
<220> FEATURE:
<223> OTHER INFORMATION: Synthetic Construct

<400> SEQUENCE: 68

Asp Ile Val Met Thr Lys Ser Pro Ser Ser Leu Ser Ala Ser Val Gly
1               5                  10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asp Ile Tyr Ala Ser
                85                  90                  95

Thr Phe Gly Pro Gly Thr Lys Val Asp Ile Lys Arg
            100                 105

<210> SEQ ID NO 69
<211> LENGTH: 122
<212> TYPE: PRT
<213> ORGANISM: Artificial Sequence
<220> FEATURE:
<223> OTHER INFORMATION: Synthetic Construct

<400> SEQUENCE: 69

Gln Val Gln Leu Val Gln Ser Gly Ala Glu Val Lys Lys Pro Gly Ala
1               5                  10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Thr Ile Pro Gly Ile Ala Val Ala Gly Thr Asp Tyr Trp
            100                 105                 110

Gly Gln Gly Thr Leu Val Thr Val Ser Ser
        115                 120
```

<210> SEQ ID NO 70
<211> LENGTH: 5
<212> TYPE: PRT
<213> ORGANISM: Artificial Sequence
<220> FEATURE:
<223> OTHER INFORMATION: Synthetic Construct

<400> SEQUENCE: 70

Ser Tyr Tyr Met His
1               5

<210> SEQ ID NO 71
<211> LENGTH: 17
<212> TYPE: PRT
<213> ORGANISM: Artificial Sequence
<220> FEATURE:
<223> OTHER INFORMATION: Synthetic Construct

<400> SEQUENCE: 71

Ile Ile Asn Pro Ser Gly Gly Ser Thr Ser Tyr Ala Gln Lys Phe Gln
1               5                   10                  15

Gly

<210> SEQ ID NO 72
<211> LENGTH: 13
<212> TYPE: PRT
<213> ORGANISM: Artificial Sequence
<220> FEATURE:
<223> OTHER INFORMATION: Synthetic Construct

<400> SEQUENCE: 72

Asp Thr Ile Pro Gly Ile Ala Val Ala Gly Thr Asp Tyr
1               5                   10

<210> SEQ ID NO 73
<211> LENGTH: 10
<212> TYPE: PRT
<213> ORGANISM: Artificial Sequence
<220> FEATURE:
<223> OTHER INFORMATION: Synthetic Construct

<400> SEQUENCE: 73

Gly Tyr Thr Phe Thr Ser Tyr Tyr Met His
1               5                   10

<210> SEQ ID NO 74
<211> LENGTH: 8
<212> TYPE: PRT
<213> ORGANISM: Artificial Sequence
<220> FEATURE:
<223> OTHER INFORMATION: Synthetic Construct

<400> SEQUENCE: 74

Ile Ile Asn Pro Ser Gly Gly Ser
1               5

<210> SEQ ID NO 75
<211> LENGTH: 110
<212> TYPE: PRT
<213> ORGANISM: Artificial Sequence
<220> FEATURE:
<223> OTHER INFORMATION: Synthetic Construct

<400> SEQUENCE: 75

Gln Ser Val Leu Thr Gln Pro Pro Ser Val Ser Ala Ala Pro Gly Gln
1               5                   10                  15

```
Lys Val Thr Ile Ser Cys Ser Gly Ser Thr Ser Asn Ile Gly Asn Asn
                20                  25                  30

Tyr Val Ser Trp Tyr Gln Gln Val Pro Gly Thr Pro Lys Leu Leu
            35                  40                  45

Ile Tyr Asp Asn Asp Lys Arg Pro Ser Gly Ile Pro Asp Arg Phe Ser
        50                  55                  60

Gly Ser Lys Ser Gly Thr Ser Ala Thr Leu Asp Ile Thr Gly Leu Gln
65                  70                  75                  80

Thr Gly Asp Glu Ala Asp Tyr Tyr Cys Gly Thr Trp His Ser Gly Leu
                85                  90                  95

Tyr Val Val Val Phe Gly Gly Gly Thr Lys Leu Thr Val Leu
            100                 105                 110

<210> SEQ ID NO 76
<211> LENGTH: 13
<212> TYPE: PRT
<213> ORGANISM: Artificial Sequence
<220> FEATURE:
<223> OTHER INFORMATION: Synthetic Construct

<400> SEQUENCE: 76

Ser Gly Ser Thr Ser Asn Ile Gly Asn Asn Tyr Val Ser
1               5                   10

<210> SEQ ID NO 77
<211> LENGTH: 8
<212> TYPE: PRT
<213> ORGANISM: Artificial Sequence
<220> FEATURE:
<223> OTHER INFORMATION: Synthetic Construct

<400> SEQUENCE: 77

Tyr Asp Asn Asp Lys Arg Pro Ser
1               5

<210> SEQ ID NO 78
<211> LENGTH: 11
<212> TYPE: PRT
<213> ORGANISM: Artificial Sequence
<220> FEATURE:
<223> OTHER INFORMATION: Synthetic Construct

<400> SEQUENCE: 78

Gly Thr Trp His Ser Gly Leu Tyr Val Val Val
1               5                   10

<210> SEQ ID NO 79
<211> LENGTH: 11
<212> TYPE: PRT
<213> ORGANISM: Artificial Sequence
<220> FEATURE:
<223> OTHER INFORMATION: Synthetic Construct

<400> SEQUENCE: 79

Gly Ser Thr Ser Asn Ile Gly Asn Asn Tyr Val
1               5                   10

<210> SEQ ID NO 80
<211> LENGTH: 5
<212> TYPE: PRT
<213> ORGANISM: Artificial Sequence
<220> FEATURE:
<223> OTHER INFORMATION: Synthetic Construct
```

```
<400> SEQUENCE: 80

Tyr Asp Asn Asp Lys
1               5

<210> SEQ ID NO 81
<211> LENGTH: 10
<212> TYPE: PRT
<213> ORGANISM: Artificial Sequence
<220> FEATURE:
<223> OTHER INFORMATION: Synthetic Construct

<400> SEQUENCE: 81

Thr Trp His Ser Gly Leu Tyr Val Val Val
1               5                   10

<210> SEQ ID NO 82
<211> LENGTH: 330
<212> TYPE: PRT
<213> ORGANISM: Artificial Sequence
<220> FEATURE:
<223> OTHER INFORMATION: Synthetic Construct

<400> SEQUENCE: 82

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
                100                 105                 110

Pro Ala Pro Glu Ala Ala Gly Ala Pro Ser Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270
```

```
Asn Tyr Lys Thr Thr Pro Pro Val Leu Asp Ser Asp Gly Ser Phe Phe
            275                 280                 285
Leu Tyr Ser Lys Leu Thr Val Asp Lys Ser Arg Trp Gln Gln Gly Asn
        290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330

<210> SEQ ID NO 83
<211> LENGTH: 106
<212> TYPE: PRT
<213> ORGANISM: Artificial Sequence
<220> FEATURE:
<223> OTHER INFORMATION: Synthetic Construct

<400> SEQUENCE: 83

Thr Val Ala Ala Pro Ser Val Phe Ile Phe Pro Pro Ser Asp Glu Gln
1               5                   10                  15
Leu Lys Ser Gly Thr Ala Ser Val Val Cys Leu Leu Asn Asn Phe Tyr
            20                  25                  30
Pro Arg Glu Ala Lys Val Gln Trp Lys Val Asp Asn Ala Leu Gln Ser
        35                  40                  45
Gly Asn Ser Gln Glu Ser Val Thr Gln Asp Ser Lys Asp Ser Thr
    50                  55                  60
Tyr Ser Leu Ser Ser Thr Leu Thr Leu Ser Lys Ala Asp Tyr Glu Lys
65                  70                  75                  80
His Lys Val Tyr Ala Cys Glu Val Thr His Gln Gly Leu Ser Ser Pro
                85                  90                  95
Val Thr Lys Ser Phe Asn Arg Gly Glu Cys
            100                 105

<210> SEQ ID NO 84
<211> LENGTH: 351
<212> TYPE: DNA
<213> ORGANISM: Artificial Sequence
<220> FEATURE:
<223> OTHER INFORMATION: Synthetic Construct

<400> SEQUENCE: 84
gaggtccagc tggtgcagtc tggggctgag gtgaagaagc tggggcctc  agtgaaggtc      60 tcctgcaagg cttctggata caccttcacc ggctactata tgcactgggt gcgacaggcc    120
cctggacaag gcttgagtg gatgggatgg atcgaccctg acgaaggtga cacaaactat    180
gcacagaagt tcagggcag ggtcaccatg accagggaca cgtccatcag cacagcctac    240
atggagctga gcaggctgag atctgacgac acggccgtgt attactgtgc gagattagct    300
agtggctttc gtgactactg gggccaggga accctggtca ccgtctcgag c            351

<210> SEQ ID NO 85
<211> LENGTH: 324
<212> TYPE: DNA
<213> ORGANISM: Artificial Sequence
<220> FEATURE:
<223> OTHER INFORMATION: Synthetic Construct

<400> SEQUENCE: 85
gacatcgtga tgaccaagtc tccatcctcc ctgtctgctt ctgtaggaga cagagtcacc     60
atcacttgcc gggcaagtca gggcattaga aatgatttag ctggtatca gcagaaacca    120
```

```
gggaaagccc ctaagcgcct catctatgct gcatccagtt tgcaaagtgg ggtcccatca      180
aggttcagcg gcagtggatc tgggacagaa ttcactctca caatcagcag cctgcagcct      240
gaagattttg caacttatta ctgtctacag catgatattt acgctagcac tttcggccct      300
gggaccaaag tggatatcaa acgt                                             324
```

<210> SEQ ID NO 86
<211> LENGTH: 351
<212> TYPE: DNA
<213> ORGANISM: Artificial Sequence
<220> FEATURE:
<223> OTHER INFORMATION: Synthetic Construct

<400> SEQUENCE: 86

```
gaggtccagc tggtgcagtc tggggctgag gtgaagaagc ctggggcctc agtgaaggtc      60
tcctgcaagg cttctggata caccttcacc ggctactata tgcactgggt gcgacaggcc     120
cctggacaag gcttgagtg gatgggatgg atcaaccctm acagtggtgg cacaaactat      180
gcacagaagt tcagggcag ggtcaccatg accaggaca cgtccatcag cacagcctac       240
atggagctga gcaggctgag atctgacgac acggccgtgt attactgtgc gagattagct      300
agtggctttc gtgactactg gggccaggga accctggtca ccgtctcgag c              351
```

<210> SEQ ID NO 87
<211> LENGTH: 324
<212> TYPE: DNA
<213> ORGANISM: Artificial Sequence
<220> FEATURE:
<223> OTHER INFORMATION: Synthetic Construct

<400> SEQUENCE: 87

```
gacatcgtga tgacccagtc tccatcctcc ctgtctgcat ctgtaggaga cagagtcacc      60
atcacttgcc gggcaagtca gggcattaga aatgatttag gctggtatca gcagaaacca     120
gggaaagccc ctaagcgcct catctatgct gcatccagtt tgcaaagtgg ggtcccatca     180
aggttcagcg gcagtggatc tgggacagaa ttcactctca caatcagcag cctgcagcct    240
gaagattttg caacttatta ctgtctacag catgatattt acgctagcac tttcggccct    300
gggaccaaag tggatatcaa acgt                                             324
```

<210> SEQ ID NO 88
<211> LENGTH: 351
<212> TYPE: DNA
<213> ORGANISM: Artificial Sequence
<220> FEATURE:
<223> OTHER INFORMATION: Synthetic Construct

<400> SEQUENCE: 88

```
gaggtccagc tggtgcagtc tggggctgag gtgaagaagc ctggggcctc agtgaaggtc      60
tcctgcaagg cttctggata caccttcacc ggctactata tgcactgggt gcgacaggcc     120
cctggacaag gcttgagtg gatgggatgg atcgaccctg acagtggtga cacaaactat      180
gcacagaagt tcagggcag ggtcaccatg accagggaca cgtccatcag cacagcctac     240
atggagctga gcaggctgag atctgacgac acggccgtgt attactgtgc gagattagct     300
agtggctttc gtgactactg gggccaggga accctggtca ccgtctcgag c              351
```

<210> SEQ ID NO 89
<211> LENGTH: 324
<212> TYPE: DNA
<213> ORGANISM: Artificial Sequence

```
<220> FEATURE:
<223> OTHER INFORMATION: Synthetic Construct

<400> SEQUENCE: 89
gacatcgtga tgaccaagtc tccatcctcc ctgtctgctt ctgtaggaga cagagtcacc    60
atcacttgcc gggcaagtca gggcattaga aatgatttag gctggtatca gcagaaacca   120
gggaaagccc ctaagcgcct catctatgct gcatccagtt tgcaaagtgg ggtcccatca   180
aggttcagcg gcagtggatc tgggacagaa ttcactctca caatcagcag cctgcagcct   240
gaagattttg caacttatta ctgtctacag catgatattt acgctagcac tttcggccct   300
gggaccaaag tggatatcaa acgt                                          324

<210> SEQ ID NO 90
<211> LENGTH: 366
<212> TYPE: DNA
<213> ORGANISM: Artificial Sequence
<220> FEATURE:
<223> OTHER INFORMATION: Synthetic Construct

<400> SEQUENCE: 90
caggtccagc tggtacagtc tggggctgag gtgaagaagc ctggggcctc agtgaaggtt    60
tcctgcaagg catctggata caccttcacc agctactata tgcactgggt gcgacaggcc   120
cctggacaag gcttgagtg gatgggaata atcaaccta gtggtggtag cacaagctac    180
gcacagaagt tccagggcag agtcaccatg accagggaca cgtccacgag cacagtctac   240
atggagctga gcagcctgag atctgaggac acggccgtgt attactgtgc gagagacact   300
attccgggta tagcagtggc tggtacggac tactggggcc agggaaccct ggtcaccgtc   360
tcgagc                                                              366

<210> SEQ ID NO 91
<211> LENGTH: 330
<212> TYPE: DNA
<213> ORGANISM: Artificial Sequence
<220> FEATURE:
<223> OTHER INFORMATION: Synthetic Construct

<400> SEQUENCE: 91
cagtctgtct tgacgcagcc gccctcagtg tctgcggccc caggacagaa ggtcaccatc    60
tcctgctctg gaagcacctc caacattggc aataattatg tatcctggta ccagcaggtc   120
ccaggaacac cccccaaact cctcatttat gacaatgata agcgaccctc agggattcct   180
gaccgattct ctggctccaa gtctggcacg tcagccaccc tggacatcac cggactccag   240
actggggacg aggccgatta ttactgcgga acatggcata gtggcctgta tgtcgtggtg   300
ttcggcggag ggaccaagct gaccgtccta                                    330

<210> SEQ ID NO 92
<211> LENGTH: 990
<212> TYPE: DNA
<213> ORGANISM: Artificial Sequence
<220> FEATURE:
<223> OTHER INFORMATION: Synthetic Construct

<400> SEQUENCE: 92
gcctccacca agggcccatc ggtcttcccc ctggcaccct cctccaagag cacctctggg    60
ggcacagcgg ccctgggctg cctggtcaag gactacttcc ccgaaccggt gacggtgtcg   120
tggaactcag gcgccctgac cagcggcgtg cacaccttcc cggctgtcct acagtcctca   180
```

```
ggactctact ccctcagcag cgtggtgacc gtgccctcca gcagcttggg cacccagacc    240
tacatctgca acgtgaatca caagcccagc aacaccaagg tggacaagaa agttgagccc    300
aaatcttgtg acaaaactca cacatgccca ccgtgcccag cacctgaagc cgctggggca    360
ccgtcagtct tcctcttccc cccaaaaccc aaggacaccc tcatgatctc ccggacccct    420
gaggtcacat gcgtggtggt ggacgtgagc cacgaagacc ctgaggtcaa gttcaactgg    480
tacgtggacg gcgtggaggt gcataatgcc aagacaaagc cgcggaggga gcagtacaac    540
agcacgtacc gtgtggtcag cgtcctcacc gtcctgcacc aggactggct gaatggcaag    600
gagtacaagt gcaaggtctc caacaaagcc ctcccagccc ccatcgagaa aaccatctcc    660
aaagccaaag ggcagccccg agaaccacag gtgtacaccc tgcccccatc ccgggaggag    720
atgaccaaga accaggtcag cctgacctgc ctggtcaaag gcttctatcc cagcgacatc    780
gccgtggagt gggagagcaa tgggcagccg gagaacaact acaagaccac gcctcccgtg    840
ctggactccg acggctcctt cttcctctat agcaagctca ccgtggacaa gagcaggtgg    900
cagcagggga acgtcttctc atgctccgtg atgcatgagg ctctgcacaa ccactacacg    960
cagaagagcc tctccctgtc tccgggtaaa                                    990

<210> SEQ ID NO 93
<211> LENGTH: 318
<212> TYPE: DNA
<213> ORGANISM: Artificial Sequence
<220> FEATURE:
<223> OTHER INFORMATION: Synthetic Construct

<400> SEQUENCE: 93
actgtggctg caccatctgt cttcatcttc ccgccatctg atgagcagtt gaaatctgga     60
actgcctctg ttgtgtgcct gctgaataac ttctatccca gagaggccaa agtacagtgg    120
aaggtggata acgccctcca atcgggtaac tcccaggaga gtgtcacaga gcaggacagc    180
aaggacagca cctacagcct cagcagcacc ctgacgctga gcaaagcaga ctacgagaaa    240
cacaaagtct acgcctgcga agtcacccat cagggcctga gctcgcccgt cacaaagagc    300
ttcaacaggg gagagtgt                                                 318

<210> SEQ ID NO 94
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (1)..(1)
<223> OTHER INFORMATION: Xaa = Trp or Arg
<220> FEATURE:
<221> NAME/KEY: VARIANT
<222> LOCATION: (3)..(3)
<223> OTHER INFORMATION: Xaa = Asn or Asp
<220> FEATURE:
<221> NAME/KEY: VARIANT
<222> LOCATION: (5)..(5)
<223> OTHER INFORMATION: Xaa = Asn or Asp
<220> FEATURE:
<221> NAME/KEY: VARIANT
<222> LOCATION: (6)..(6)
<223> OTHER INFORMATION: Xaa = Ser or Glu
<220> FEATURE:
<221> NAME/KEY: VARIANT
<222> LOCATION: (8)..(8)
<223> OTHER INFORMATION: Xaa = Gly or Asp
<220> FEATURE:
<221> NAME/KEY: VARIANT
```

<222> LOCATION: (13)..(13)
<223> OTHER INFORMATION: Xaa = Gln or Pro

<400> SEQUENCE: 94

Xaa Ile Xaa Pro Xaa Xaa Gly Xaa Thr Asn Tyr Ala Xaa Lys Phe Gln
1               5                   10                  15

Gly

<210> SEQ ID NO 95
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (1)..(1)
<223> OTHER INFORMATION: Xaa = Trp or Arg
<220> FEATURE:
<221> NAME/KEY: VARIANT
<222> LOCATION: (3)..(3)
<223> OTHER INFORMATION: Xaa = Asn or Asp
<220> FEATURE:
<221> NAME/KEY: VARIANT
<222> LOCATION: (5)..(5)
<223> OTHER INFORMATION: Xaa = Asn or Asp
<220> FEATURE:
<221> NAME/KEY: VARIANT
<222> LOCATION: (6)..(6)
<223> OTHER INFORMATION: Xaa = Ser or Glu
<220> FEATURE:
<221> NAME/KEY: VARIANT
<222> LOCATION: (8)..(8)
<223> OTHER INFORMATION: Xaa = Gly or Asp

<400> SEQUENCE: 95

Xaa Ile Xaa Pro Xaa Xaa Gly Xaa
1               5

<210> SEQ ID NO 96
<211> LENGTH: 117
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (50)..(50)
<223> OTHER INFORMATION: Xaa = Trp or Arg
<220> FEATURE:
<221> NAME/KEY: VARIANT
<222> LOCATION: (52)..(52)
<223> OTHER INFORMATION: Xaa = Asn or Asp
<220> FEATURE:
<221> NAME/KEY: VARIANT
<222> LOCATION: (54)..(54)
<223> OTHER INFORMATION: Xaa = Asn or Asp
<220> FEATURE:
<221> NAME/KEY: VARIANT
<222> LOCATION: (55)..(55)
<223> OTHER INFORMATION: Xaa =  Ser or Glu
<220> FEATURE:
<221> NAME/KEY: VARIANT
<222> LOCATION: (57)..(57)
<223> OTHER INFORMATION: Xaa =  Gly or Asp
<220> FEATURE:
<221> NAME/KEY: VARIANT
<222> LOCATION: (62)..(62)
<223> OTHER INFORMATION: Xaa =  Gln or Pro
<220> FEATURE:
<221> NAME/KEY: VARIANT
<222> LOCATION: (87)..(87)
<223> OTHER INFORMATION: Xaa =  Arg or Ser
<220> FEATURE:

```
<221> NAME/KEY: VARIANT
<222> LOCATION: (109)..(109)
<223> OTHER INFORMATION: Xaa = Gln or His

<400> SEQUENCE: 96
```

| | | | | | | | | | | | | | | | |
|---|---|---|---|---|---|---|---|---|---|---|---|---|---|---|---|
| Glu | Val | Gln | Leu | Val | Gln | Ser | Gly | Ala | Glu | Val | Lys | Lys | Pro | Gly | Ala |
| 1 | | | | 5 | | | | | 10 | | | | | 15 | |
| Ser | Val | Lys | Val | Ser | Cys | Lys | Ala | Ser | Gly | Tyr | Thr | Phe | Thr | Gly | Tyr |
| | | | 20 | | | | | 25 | | | | | 30 | | |
| Tyr | Met | His | Trp | Val | Arg | Gln | Ala | Pro | Gly | Gln | Gly | Leu | Glu | Trp | Met |
| | | 35 | | | | | 40 | | | | | 45 | | | |
| Gly | Xaa | Ile | Xaa | Pro | Xaa | Xaa | Gly | Xaa | Thr | Asn | Tyr | Ala | Xaa | Lys | Phe |
| 50 | | | | | 55 | | | | | 60 | | | | | |
| Gln | Gly | Arg | Val | Thr | Met | Thr | Arg | Asp | Thr | Ser | Ile | Ser | Thr | Ala | Tyr |
| 65 | | | | | 70 | | | | | 75 | | | | | 80 |
| Met | Glu | Leu | Ser | Arg | Leu | Xaa | Ser | Asp | Asp | Thr | Ala | Val | Tyr | Tyr | Cys |
| | | | | 85 | | | | | 90 | | | | | 95 | |
| Ala | Arg | Leu | Ala | Ser | Gly | Phe | Arg | Asp | Tyr | Trp | Gly | Xaa | Gly | Thr | Leu |
| | | | 100 | | | | | 105 | | | | | 110 | | |
| Val | Thr | Val | Ser | Ser | | | | | | | | | | | |
| | | | 115 | | | | | | | | | | | | |

```
<210> SEQ ID NO 97
<211> LENGTH: 108
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (6)..(6)
<223> OTHER INFORMATION: Xaa = Gln or Lys
<220> FEATURE:
<221> NAME/KEY: VARIANT
<222> LOCATION: (27)..(27)
<223> OTHER INFORMATION: Xaa = Gln or Leu
<220> FEATURE:
<221> NAME/KEY: VARIANT
<222> LOCATION: (66)..(66)
<223> OTHER INFORMATION: Xaa = Gly, Val or Ala
<220> FEATURE:
<221> NAME/KEY: VARIANT
<222> LOCATION: (72)..(72)
<223> OTHER INFORMATION: Xaa = Thr or Ser
<220> FEATURE:
<221> NAME/KEY: VARIANT
<222> LOCATION: (83)..(83)
<223> OTHER INFORMATION: Xaa = Phe or Leu

<400> SEQUENCE: 97
```

| | | | | | | | | | | | | | | | |
|---|---|---|---|---|---|---|---|---|---|---|---|---|---|---|---|
| Asp | Ile | Val | Met | Thr | Xaa | Ser | Pro | Ser | Ser | Leu | Ser | Ala | Ser | Val | Gly |
| 1 | | | | 5 | | | | | 10 | | | | | 15 | |
| Asp | Arg | Val | Thr | Ile | Thr | Cys | Arg | Ala | Ser | Xaa | Gly | Ile | Arg | Asn | Asp |
| | | | 20 | | | | | 25 | | | | | 30 | | |
| Leu | Gly | Trp | Tyr | Gln | Gln | Lys | Pro | Gly | Lys | Ala | Pro | Lys | Arg | Leu | Ile |
| | | 35 | | | | | 40 | | | | | 45 | | | |
| Tyr | Ala | Ala | Ser | Ser | Leu | Gln | Ser | Gly | Val | Pro | Ser | Arg | Phe | Ser | Gly |
| 50 | | | | | 55 | | | | | 60 | | | | | |
| Ser | Xaa | Ser | Gly | Thr | Glu | Phe | Xaa | Leu | Thr | Ile | Ser | Ser | Leu | Gln | Pro |
| 65 | | | | | 70 | | | | | 75 | | | | | 80 |
| Glu | Asp | Xaa | Ala | Thr | Tyr | Tyr | Cys | Leu | Gln | His | Asp | Ile | Tyr | Ala | Ser |
| | | | | 85 | | | | | 90 | | | | | 95 | |
| Thr | Phe | Gly | Pro | Gly | Thr | Lys | Val | Asp | Ile | Lys | Arg | | | | |

<210> SEQ ID NO 98
<211> LENGTH: 625
<212> TYPE: PRT
<213> ORGANISM: Homo sapiens

<400> SEQUENCE: 98

```
Met Ile Phe Leu Tyr Gln Val Val His Phe Ile Leu Phe Thr Ser Val
1               5                   10                  15

Ser Gly Glu Cys Val Thr Gln Leu Leu Lys Asp Thr Cys Phe Glu Gly
            20                  25                  30

Gly Asp Ile Thr Thr Val Phe Thr Pro Ser Ala Lys Tyr Cys Gln Val
        35                  40                  45

Val Cys Thr Tyr His Pro Arg Cys Leu Leu Phe Thr Phe Thr Ala Glu
    50                  55                  60

Ser Pro Ser Glu Asp Pro Thr Arg Trp Phe Cys Val Leu Lys Asp
65              70                  75                  80

Ser Val Thr Glu Thr Leu Pro Arg Val Asn Arg Thr Ala Ala Ile Ser
            85                  90                  95

Gly Tyr Ser Phe Lys Gln Cys Ser His Gln Ile Ser Ala Cys Asn Lys
            100                 105                 110

Asp Ile Tyr Val Asp Leu Asp Met Lys Gly Ile Asn Tyr Asn Ser Ser
        115                 120                 125

Val Ala Lys Ser Ala Gln Glu Cys Gln Glu Arg Cys Thr Asp Asp Val
    130                 135                 140

His Cys His Phe Phe Thr Tyr Ala Thr Arg Gln Phe Pro Ser Leu Glu
145                 150                 155                 160

His Arg Asn Ile Cys Leu Leu Lys His Thr Gln Thr Gly Thr Pro Thr
                165                 170                 175

Arg Ile Thr Lys Leu Asp Lys Val Val Ser Gly Phe Ser Leu Lys Ser
            180                 185                 190

Cys Ala Leu Ser Asn Leu Ala Cys Ile Arg Asp Ile Phe Pro Asn Thr
            195                 200                 205

Val Phe Ala Asp Ser Asn Ile Asp Ser Val Met Ala Pro Asp Ala Phe
    210                 215                 220

Val Cys Gly Arg Ile Cys Thr His His Pro Gly Cys Leu Phe Phe Thr
225                 230                 235                 240

Phe Phe Ser Gln Glu Trp Pro Lys Glu Ser Gln Arg Asn Leu Cys Leu
                245                 250                 255

Leu Lys Thr Ser Glu Ser Gly Leu Pro Ser Thr Arg Ile Lys Lys Ser
            260                 265                 270

Lys Ala Leu Ser Gly Phe Ser Leu Gln Ser Cys Arg His Ser Ile Pro
        275                 280                 285

Val Phe Cys His Ser Ser Phe Tyr His Asp Thr Asp Phe Leu Gly Glu
    290                 295                 300

Glu Leu Asp Ile Val Ala Ala Lys Ser His Glu Ala Cys Gln Lys Leu
305                 310                 315                 320

Cys Thr Asn Ala Val Arg Cys Gln Phe Phe Thr Tyr Thr Pro Ala Gln
                325                 330                 335

Ala Ser Cys Asn Glu Gly Lys Gly Lys Cys Tyr Leu Lys Leu Ser Ser
            340                 345                 350

Asn Gly Ser Pro Thr Lys Ile Leu His Gly Arg Gly Gly Ile Ser Gly
            355                 360                 365
```

Tyr Thr Leu Arg Leu Cys Lys Met Asp Asn Glu Cys Thr Thr Lys Ile
    370                 375                 380

Lys Pro Arg Ile Val Gly Gly Thr Ala Ser Val Arg Gly Glu Trp Pro
385                 390                 395                 400

Trp Gln Val Thr Leu His Thr Thr Ser Pro Thr Gln Arg His Leu Cys
                    405                 410                 415

Gly Gly Ser Ile Ile Gly Asn Gln Trp Ile Leu Thr Ala Ala His Cys
                420                 425                 430

Phe Tyr Gly Val Glu Ser Pro Lys Ile Leu Arg Val Tyr Ser Gly Ile
                435                 440                 445

Leu Asn Gln Ser Glu Ile Lys Glu Asp Thr Ser Phe Phe Gly Val Gln
450                 455                 460

Glu Ile Ile Ile His Asp Gln Tyr Lys Met Ala Glu Ser Gly Tyr Asp
465                 470                 475                 480

Ile Ala Leu Leu Lys Leu Glu Thr Thr Val Asn Tyr Thr Asp Ser Gln
                485                 490                 495

Arg Pro Ile Cys Leu Pro Ser Lys Gly Asp Arg Asn Val Ile Tyr Thr
                500                 505                 510

Asp Cys Trp Val Thr Gly Trp Gly Tyr Arg Lys Leu Arg Asp Lys Ile
                515                 520                 525

Gln Asn Thr Leu Gln Lys Ala Lys Ile Pro Leu Val Thr Asn Glu Glu
530                 535                 540

Cys Gln Lys Arg Tyr Arg Gly His Lys Ile Thr His Lys Met Ile Cys
545                 550                 555                 560

Ala Gly Tyr Arg Glu Gly Gly Lys Asp Ala Cys Lys Gly Asp Ser Gly
                565                 570                 575

Gly Pro Leu Ser Cys Lys His Asn Glu Val Trp His Leu Val Gly Ile
                580                 585                 590

Thr Ser Trp Gly Glu Gly Cys Ala Gln Arg Glu Arg Pro Gly Val Tyr
                595                 600                 605

Thr Asn Val Val Glu Tyr Val Asp Trp Ile Leu Glu Lys Thr Gln Ala
                610                 615                 620

Val
625

<210> SEQ ID NO 99
<211> LENGTH: 262
<212> TYPE: PRT
<213> ORGANISM: Artificial Sequence
<220> FEATURE:
<223> OTHER INFORMATION: Synthetic Construct

<400> SEQUENCE: 99

Met Gly Trp Ser Cys Ile Ile Leu Phe Leu Val Ala Thr Ala Thr Gly
1               5                   10                  15

Val His Ser Ile Val Gly Gly Thr Ala Ser Val Arg Gly Glu Trp Pro
                20                  25                  30

Trp Gln Val Thr Leu His Thr Thr Ser Pro Thr Gln Arg His Leu Cys
            35                  40                  45

Gly Gly Ser Ile Ile Gly Asn Gln Trp Ile Leu Thr Ala Ala His Cys
        50                  55                  60

Phe Tyr Gly Val Glu Ser Pro Lys Ile Leu Arg Val Tyr Ser Gly Ile
65                  70                  75                  80

Leu Gln Gln Ser Glu Ile Lys Glu Asp Thr Ser Phe Phe Gly Val Gln
                85                  90                  95

```
Glu Ile Ile Ile His Asp Gln Tyr Lys Met Ala Glu Ser Gly Tyr Asp
                100                 105                 110

Ile Ala Leu Leu Lys Leu Glu Thr Thr Val Gln Tyr Thr Asp Ser Gln
            115                 120                 125

Arg Pro Ile Ser Leu Pro Ser Lys Gly Asp Arg Asn Val Ile Tyr Thr
        130                 135                 140

Asp Cys Trp Val Thr Gly Trp Gly Tyr Arg Lys Leu Arg Asp Lys Ile
145                 150                 155                 160

Gln Asn Thr Leu Gln Lys Ala Lys Ile Pro Leu Val Thr Asn Glu Glu
                165                 170                 175

Cys Gln Lys Arg Tyr Arg Gly His Lys Ile Thr His Lys Met Ile Cys
            180                 185                 190

Ala Gly Tyr Arg Glu Gly Gly Lys Asp Ala Cys Lys Gly Asp Ala Gly
        195                 200                 205

Gly Pro Leu Ser Cys Lys His Asn Glu Val Trp His Leu Val Gly Ile
210                 215                 220

Thr Ser Trp Gly Glu Gly Cys Ala Gln Arg Glu Arg Pro Gly Val Tyr
225                 230                 235                 240

Thr Asn Val Val Glu Tyr Val Asp Trp Ile Leu Glu Lys Thr Gln Ala
                245                 250                 255

His His His His His His
            260

<210> SEQ ID NO 100
<211> LENGTH: 243
<212> TYPE: PRT
<213> ORGANISM: Artificial Sequence
<220> FEATURE:
<223> OTHER INFORMATION: Synthetic Construct

<400> SEQUENCE: 100

Ile Val Gly Gly Thr Ala Ser Val Arg Gly Glu Trp Pro Trp Gln Val
1               5                   10                  15

Thr Leu His Thr Thr Ser Pro Thr Gln Arg His Leu Cys Gly Gly Ser
                20                  25                  30

Ile Ile Gly Asn Gln Trp Ile Leu Thr Ala Ala His Cys Phe Tyr Gly
            35                  40                  45

Val Glu Ser Pro Lys Ile Leu Arg Val Tyr Ser Gly Ile Leu Gln Gln
        50                  55                  60

Ser Glu Ile Lys Glu Asp Thr Ser Phe Phe Gly Val Gln Glu Ile Ile
65                  70                  75                  80

Ile His Asp Gln Tyr Lys Met Ala Glu Ser Gly Tyr Asp Ile Ala Leu
                85                  90                  95

Leu Lys Leu Glu Thr Thr Val Gln Tyr Thr Asp Ser Gln Arg Pro Ile
                100                 105                 110

Ser Leu Pro Ser Lys Gly Asp Arg Asn Val Ile Tyr Thr Asp Cys Trp
            115                 120                 125

Val Thr Gly Trp Gly Tyr Arg Lys Leu Arg Asp Lys Ile Gln Asn Thr
        130                 135                 140

Leu Gln Lys Ala Lys Ile Pro Leu Val Thr Asn Glu Glu Cys Gln Lys
145                 150                 155                 160

Arg Tyr Arg Gly His Lys Ile Thr His Lys Met Ile Cys Ala Gly Tyr
                165                 170                 175

Arg Glu Gly Gly Lys Asp Ala Cys Lys Gly Asp Ala Gly Gly Pro Leu
            180                 185                 190
```

-continued

```
Ser Cys Lys His Asn Glu Val Trp His Leu Val Gly Ile Thr Ser Trp
            195                 200                 205

Gly Glu Gly Cys Ala Gln Arg Glu Arg Pro Gly Val Tyr Thr Asn Val
        210                 215                 220

Val Glu Tyr Val Asp Trp Ile Leu Glu Lys Thr Gln Ala His His His
225                 230                 235                 240

His His His

<210> SEQ ID NO 101
<211> LENGTH: 229
<212> TYPE: PRT
<213> ORGANISM: Artificial Sequence
<220> FEATURE:
<223> OTHER INFORMATION: Synthetic Construct

<400> SEQUENCE: 101

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asp Pro Asp Glu Gly Asp Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Leu Ala Ser Gly Phe Arg Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Gly Gly Ser His
    210                 215                 220

His His His His
225

<210> SEQ ID NO 102
<211> LENGTH: 213
<212> TYPE: PRT
<213> ORGANISM: Artificial Sequence
<220> FEATURE:
<223> OTHER INFORMATION: Synthetic Construct

<400> SEQUENCE: 102

Asp Ile Val Met Thr Lys Ser Pro Ser Ser Leu Ser Ala Ser Val Gly
1               5                   10                  15
```

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
 50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asp Ile Tyr Ala Ser
                85                  90                  95

Thr Phe Gly Pro Gly Thr Lys Val Asp Ile Lys Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 103
<211> LENGTH: 330
<212> TYPE: PRT
<213> ORGANISM: Artificial Sequence
<220> FEATURE:
<223> OTHER INFORMATION: Synthetic Construct

<400> SEQUENCE: 103

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

-continued

```
Tyr Val Asp Gly Val Glu Val His Asn Ala Lys Thr Lys Pro Arg Glu
            165             170             175

Glu Gln Tyr Asn Ser Thr Tyr Arg Val Val Ser Val Leu Thr Val Leu
            180             185             190

His Gln Asp Trp Leu Asn Gly Lys Glu Tyr Lys Cys Lys Val Ser Asn
            195             200             205

Lys Ala Leu Pro Ala Pro Ile Glu Lys Thr Ile Ser Lys Ala Lys Gly
            210             215             220

Gln Pro Arg Glu Pro Gln Val Tyr Thr Leu Pro Pro Ser Arg Glu Glu
225             230             235             240

Met Thr Lys Asn Gln Val Ser Leu Thr Cys Leu Val Lys Gly Phe Tyr
            245             250             255

Pro Ser Asp Ile Ala Val Glu Trp Glu Ser Asn Gly Gln Pro Glu Asn
            260             265             270

Asn Tyr Lys Thr Thr Pro Pro Val Leu Asp Ser Asp Gly Ser Phe Phe
            275             280             285

Leu Tyr Ser Lys Leu Thr Val Asp Lys Ser Arg Trp Gln Gln Gly Asn
            290             295             300

Val Phe Ser Cys Ser Val Met His Glu Ala Leu His Asn His Tyr Thr
305             310             315             320

Gln Lys Ser Leu Ser Leu Ser Pro Gly Lys
            325             330
```